(12) United States Patent
Bonfanti et al.

(10) Patent No.: US 10,822,349 B2
(45) Date of Patent: *Nov. 3, 2020

(54) MACROCYCLIC PURINES FOR THE TREATMENT OF VIRAL INFECTIONS

(71) Applicant: JANSSEN SCIENCES IRELAND UNLIMITED COMPANY, Co Cork (IE)

(72) Inventors: Jean-François Bonfanti, Andé (FR); Jérôme Michel Claude Fortin, Igoville (FR); Frédéric Marc Maurice Doublet, Isneauville (FR); Pierre Jean-Marie Bernard Raboisson, Wavre (BE); Eric Pierre Alexandre Arnoult, Le Vaudreuil (FR)

(73) Assignee: JANSSEN SCIENCES IRELAND UNLIMITED COMPANY, Ringaskiddy (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/404,638

(22) Filed: May 6, 2019

(65) Prior Publication Data

US 2019/0330234 A1    Oct. 31, 2019

Related U.S. Application Data

(63) Continuation of application No. 14/408,681, filed as application No. PCT/EP2013/064763 on Jul. 12, 2013, now Pat. No. 10,280,180.

(30) Foreign Application Priority Data

Jul. 13, 2012 (EP) ..................................... 12176330

(51) Int. Cl.
  *C07D 498/22* (2006.01)
  *C07D 487/16* (2006.01)
  *C07D 498/16* (2006.01)
  *C07D 487/22* (2006.01)

(52) U.S. Cl.
  CPC ......... *C07D 498/22* (2013.01); *C07D 487/16* (2013.01); *C07D 487/22* (2013.01); *C07D 498/16* (2013.01)

(58) Field of Classification Search
  None
  See application file for complete search history.

(56) References Cited

U.S. PATENT DOCUMENTS

| | | |
|---|---|---|
| 6,028,076 A | 2/2000 | Hirota et al. |
| 6,329,381 B1 | 12/2001 | Kurimoto et al. |
| 6,376,501 B1 | 4/2002 | Isobe et al. |
| 6,458,798 B1 | 10/2002 | Fujita et al. |
| 6,503,908 B1 | 1/2003 | Maw |
| 6,583,148 B1 | 6/2003 | Kelley et al. |
| 6,951,866 B2 | 10/2005 | Fujita et al. |
| 7,030,118 B2 | 4/2006 | Lombardo et al. |
| 7,091,232 B2 | 8/2006 | Chow et al. |
| 7,498,409 B2 | 3/2009 | Vlach et al. |
| 7,524,852 B2 | 4/2009 | Arai et al. |
| 7,531,547 B2 | 5/2009 | Dillon et al. |
| 7,754,728 B2 | 7/2010 | Isobe et al. |
| 7,923,554 B2 | 4/2011 | Hoornaert et al. |
| 8,012,964 B2 | 9/2011 | Kurimoto et al. |
| 8,022,077 B2 | 9/2011 | Simmen et al. |
| 8,455,458 B2 | 6/2013 | Marcum et al. |
| 8,486,952 B2 | 7/2013 | Boy et al. |
| 8,637,525 B2 | 1/2014 | Boy et al. |
| 8,916,575 B2 | 12/2014 | McGowan et al. |
| 9,133,192 B2 | 9/2015 | McGowan et al. |
| 9,284,304 B2 | 3/2016 | McGowan et al. |
| 9,365,571 B2 | 6/2016 | McGowan et al. |
| 9,376,448 B2 | 6/2016 | Charifson et al. |
| 9,416,114 B2 | 8/2016 | Gembus et al. |
| 9,422,250 B2 | 8/2016 | McGowan |
| 9,499,549 B2 | 8/2016 | McGowan et al. |
| 9,556,176 B2 | 1/2017 | Bonfanti et al. |
| 9,556,199 B2 | 1/2017 | McGowan et al. |
| 9,598,378 B2 | 3/2017 | McGowan et al. |
| 9,663,474 B2 | 5/2017 | Last et al. |
| 9,878,996 B2 | 1/2018 | Silverman et al. |
| 10,266,543 B2 | 4/2019 | Bonfanti et al. |
| 2005/0054590 A1 | 3/2005 | Averett |
| 2006/0258682 A1 | 11/2006 | Liao et al. |
| 2007/0225303 A1 | 9/2007 | Ogita et al. |
| 2009/0285782 A1 | 11/2009 | Gao et al. |
| 2010/0143299 A1 | 6/2010 | Gao et al. |
| 2014/0148433 A1 | 5/2014 | Follmann et al. |
| 2015/0274676 A1 | 10/2015 | McGowan et al. |
| 2015/0299221 A1 | 10/2015 | Bonfanti et al. |
| 2015/0336907 A1 | 11/2015 | Gembus et al. |

FOREIGN PATENT DOCUMENTS

| | | |
|---|---|---|
| CN | 101784548 A | 7/2010 |
| EP | 0882727 | 12/1998 |
| EP | 0899263 A3 | 3/1999 |
| EP | 1552842 A1 | 6/2003 |

(Continued)

OTHER PUBLICATIONS

Isobe, et al., "Synthesis and Biological Evaluation of Novel 9-Substituted-8-Hydroxyadenine Derivatives as Potent Inferferon Inducers", J. Med. Chem., vol. 49; pp. 2088-2095 (2006).

(Continued)

*Primary Examiner* — Noble E Jarrell
(74) *Attorney, Agent, or Firm* — Brian C. Trinque; Lathrop GPM LLP

(57) ABSTRACT

This invention relates macrocyclic purine derivatives, processes for their preparation, pharmaceutical compositions, and their use in treating viral infections.

9 Claims, No Drawings

Specification includes a Sequence Listing.

(56) References Cited

FOREIGN PATENT DOCUMENTS

| | | |
|---|---|---|
| EP | 1110951 A1 | 6/2006 |
| EP | 1939198 A1 | 7/2008 |
| EP | 1970373 A1 | 9/2008 |
| EP | 2133353 A1 | 12/2009 |
| EP | 2138497 A1 | 12/2009 |
| JP | 64063582 | 3/1989 |
| JP | 2000053653 | 2/2000 |
| JP | 2000053654 | 2/2000 |
| JP | 2008222557 A | 9/2008 |
| JP | 2009528989 A | 8/2009 |
| JP | 2010522151 A | 7/2010 |
| JP | 2010532353 A | 10/2010 |
| WO | 199801448 A1 | 1/1998 |
| WO | 199808847 A1 | 3/1998 |
| WO | 199814448 A1 | 4/1998 |
| WO | 199850370 A1 | 11/1998 |
| WO | 199928321 A1 | 6/1999 |
| WO | 199932122 A1 | 7/1999 |
| WO | 199940091 A1 | 8/1999 |
| WO | 199941253 A1 | 8/1999 |
| WO | 200006577 A1 | 2/2000 |
| WO | 200061562 A1 | 10/2000 |
| WO | 2002087513 A2 | 11/2002 |
| WO | 2002088080 A2 | 11/2002 |
| WO | 2003055890 A1 | 7/2003 |
| WO | 2005007672 A2 | 1/2005 |
| WO | 2005092892 A1 | 10/2005 |
| WO | 2006015985 A1 | 2/2006 |
| WO | 2006050843 A1 | 5/2006 |
| WO | 2006117670 A1 | 11/2006 |
| WO | 2007034881 A1 | 3/2007 |
| WO | 2007056208 A1 | 5/2007 |
| WO | 2007063934 A1 | 6/2007 |
| WO | 2007084413 A2 | 7/2007 |
| WO | 200793901 A1 | 8/2007 |
| WO | 2008009078 A2 | 1/2008 |
| WO | 2008073785 A2 | 6/2008 |
| WO | 2008075103 A1 | 6/2008 |
| WO | 2008114008 A1 | 9/2008 |
| WO | 2008114817 A1 | 9/2008 |
| WO | 2008114819 A1 | 9/2008 |
| WO | 2008115319 A2 | 9/2008 |
| WO | 2008147697 A1 | 12/2008 |
| WO | 2009005687 A1 | 1/2009 |
| WO | 2009023179 A2 | 2/2009 |
| WO | 2009030998 A1 | 3/2009 |
| WO | 2009067081 A1 | 5/2009 |
| WO | 2009080836 A2 | 7/2009 |
| WO | 2009099650 A2 | 8/2009 |
| WO | 2009032668 A3 | 9/2009 |
| WO | 2009134624 A1 | 11/2009 |
| WO | 2010006025 A1 | 1/2010 |
| WO | 2010007116 A3 | 1/2010 |
| WO | 2010133885 A1 | 11/2010 |
| WO | 2011049825 A1 | 4/2011 |
| WO | 2011049987 | 4/2011 |
| WO | 2011062253 A1 | 5/2011 |
| WO | 2011062372 A3 | 5/2011 |
| WO | 2012066335 A1 | 5/2012 |
| WO | 2012067269 A1 | 5/2012 |
| WO | 2012136834 | 10/2012 |
| WO | 2013068438 A1 | 5/2013 |
| WO | 2013117615 A1 | 8/2013 |
| WO | 2012156498 A1 | 11/2013 |
| WO | 2014053595 A1 | 4/2014 |

OTHER PUBLICATIONS

Jurk, et al., "Human TLR7 or TLR8 Independently Confer Responsiveness to the Antiviral Compound R-848", Nature Immunology, Jun. 2002, pp. 499, vol. 3 (6).
Kurimoto, et al., "Synthesis and Evaluation of 2-Substituted 8-Hydroxyadenines as Potent Interferon Inducers with Improved Oral Bioavailabilities", Bioorganic & Medicinal Chemistry, vol. 12; pp. 1091-1099 (2004).
Lee, et al., "Activation of Anti-Hepatitis C Virus Responses via Toll-Like Receptor 7", PNAS, vol. 3 (6); pp. 1828-1833 (Feb. 7, 2006).
Roethle, et al., "Identification and Optimization of Pteridinone Toll-Like Receptor 7 (TLR7) Agonists for the Oral Treatment of Viral Hepatitis", Journal of Medicinal Chemistry, vol. 56; pp. 7324-73333 (2013).
Bizanek, et al., Isolation and Structure of an Intrastrand Cross-Link Adduct of Mitomycin C nd DNA, Biochemistry, 1992, pp. 3084-3091, vol. 31.
McGowan et al., "Novel Pyrimidine Toll-Like Receptor 7 and 8 Dual Agonists to Treat Hepatitis B Virus", Journal of Medicinal Chemistry, 2016, pp. 7936-7949, vol. 59 No. 17.
Organic Syntheses Collective, "3-Methylcoumarone", Organic Syntheses Collective, 1963, pp. 43-46, vol. 4.
Tomonori, et al., "Ti-Crossed-Claisen Condensation between Carboxylic Ester and Acid Chlorides or Acids: A Highly Selective and General Method for the Preparation of Various-Keto Esters", Journal of the American Chemical Society, vol. 127:pp. 2854-2855 (2005).
Jules A. Hoffmann, "The Immune Response of *Drosophila*", nature, 2003, vol. 426, Issue 6, pp. 33-38.
Christelle Moreau et al., "Synthesis of Cyclic Adenosine 5'-diphosphate Ribose Analogues: a C2' endo/syn "southern" Ribose Conformation Underlies Activity At The Sea Urchin cADPR Receptor", Organic & Biomolecular Chemistry, 2011, vol. 9, No. 1, pp. 278-290.
Kiyoshi Takeda, et al., "Toll-Like Receptors", Annu. Rev. Immunol., 2003, vol. 21, pp. 335-376.
Richard J. Ulevitch, "Therapeutics Targeting The Innate Immune System", Nature Reviews: Immunology, 2004, vol. 4, pp. 512-520.
International Search Report for Corresponding International Application PCT/EP2013/064763 dated Aug. 7, 2013.
Fried et al., Peginterferon-alfa-2a plus ribavirin for chronic hepatitis C virus infection, N Engl J Med 2002; 347: 975-82.
De Clercq, E.: et al., (S)-9-(2,3-Dihydroproply)adenine: An Aliphatic Nucleoside Analog with Broad-Spectrum Antiviral Activity, Science 1978, 200, 563-565.
Grimm, M. et al., Toll-like receptor (TLR) 7 and TLR8 expression on CD133+ cells in colorectal cancer points to a specific role for inflammation induced TLRs in tumourigenesis and tumour progression, Eur. J. Cancer 46, (2010), 2849-57.
Vedantham, S., et al., Mechanism of Interferon Action in Hairy Cell Leukemia: A Model Effective Cancer Biotherapy, Cancer Res. 1992, 52, 1056.
Hood, J.D. et al.,Immunoprofiling toll-like receptor ligands comparison of immunostimulatory and proinflammatory profiles in ex vivo human blood models, Hum. Vaccines 2010, 6,322-335.
Warshakoon, H. et al., Potential adjuvantic properties of innate immune stimuli, Hum. Vaccines 2009, 5, 381-394.
International Search Report for Corresponding Application No. PCT/EP2014/066219, dated Nov. 13, 2014.
Kanzler. Nature Medicine, 2007, 13(5), 552-9.
Wermuth. The Practice of Medicinal Chemistry, 1996, 203-37.
Zhao, et al., "Toll-Like Receptors and Prostate Cancer", Frontiers in Immunology, vol. 5 (Article 352): pp. 1-7 (Jul. 2014).
International Search Report for Corresponding Application No. PCT/EP2013/066673, dated Sep. 6, 2013.
Abdillahi, et al, "Synthesis of a Novel Series of Thieno[3,2-d]pyrimidin-4-(3H)-ones", Synthesis, vol. 9: pp. 1428-1430 (2010).
Banker (Editor), "Prodrugs", Modem Pharmaceutics, Third Edition: pp. 596 (1976).
Baraldi, et al, "New Strategies for the Synthesis of A3 Adenosine Receptor Antagonists", Bioorganic & Medicinal Chemistry, vol. 11: pp. 4161-4169 (2003).
Barker, et al., "A Rapid Conversion of 3-Oxothiolanes into 3-Aminothiophenes", Synthetic Communications, vol. 32(16): pp. 2565-2568 (2002).
Bell, et al., "Chemistry of 5-Pyrimidinecarboxaldehydes", Journal of Heterocyclic Chemistry, vol. 29: pp. 41-44 (Jan.-Feb. 1983).
Bennet, et al. (Editor), "Part XIV Oncology", Cecil Textbook of Medicine.vol. 1, 20th Edition: pp. 1004-1010 (1996).

(56) References Cited

OTHER PUBLICATIONS

Brittain, et al., "Effects of Pharmaceutical Processing on Drug Polymorphs and Solvates", Polymorphism in Pharmaceutical Solids, 1999, pp. 331-360, Chapter 8.
Bruns, et al., "Solubilities of Adenosine Antagonists Determined by Radioreceptor Assay", Journal of Pharmacy and Pharmacology, vol. 41: pp. 590-594 (1989).
Chawla, et al., "Challenges in Polymorphism of Pharmaceuticals", Current Research & Information on Pharmaceutical Sciences, vol. 5(1): pp. 9-12 (Jan.-Mar. 2004).
De Nardo, "Toll-Like Receptors: Activation, Signalling and Transcriptional Modulation", Cytokine, 2015, pp. 181-189, vol. 74.
Dermer. "Another Anniversary for the War on Cancer", Bio/Technology, vol. 12: pp. 320 (Mar. 1994).
Douglas, Jr, Introduction of Viral Diseases•, Cecil Textbook of Medicine, 2Dth Edition, vol. 2: pp. 1973-1942 (1996).
Freshney, et al., Culture of Animal Cells, Manual of Basic Technique, 1983, pp. 1-6, Chapter 1.
Hackam, et al, Translation of Research Evidence From animals to Humans-. JAMA, vol. 296 (14): pp. 1731-1732 (2006).
Horscroft, et al, "Antiviral applications of toll-like receptor agonists", J. Antimicrob. Chemother., pp. 1-13 (Jan. 18, 2016).
Huddleston, et al., "A Convenient Synthesis of 2-Substituted 3-Hydroxy- And 3-Amino-Thiophens From Derivatives of 2-Choroacrylic Acid", Synthetic Communications, vol. 9(8): pp. 731-734 (1979).
Isobe, et al., "Synthesis and Structure-Activity Relationships of 2-Substituted-8-hydroxyadenine Derivatives as Orally Available Interferon Inducers without Emetic Side Effects", bioorganic & Mediciinal Chemistry, Vo. 11:pp. 3641-3647, (2003).
Jiang, et al., "Synthesis of 4-chlorothieno[3,2-d]pyrimidine", Chemical Industry and Engineering Progress, vol. 30: pp. 2532-35, (2011). [With English Abstract].
Jordan, "Tamoxifen: A Most Unlikely Pioneering Medicine", Nature Reviews, vol. 2: pp. 205-213, (Mar. 2003).
Krieger, et al, Enhancement of Hepatitis C Virus RNA Replication by Cell Culture, Journal of Virology, May 1, 2001, 4614-1624, 75-10, DE.
Kurimoto, et al., "Synthesis and Structure-Activity Relationships of 2-Amino-B-hydroxyadenines as Orally Active Interferon Inducing Agents", Bioorganic & Medicinal Chemistry, vol. 11: pp. 5501-5508 (2003).
Liu, et al., "Synthesis and Biological Activity of 3-and 5-Amino Derivatives of Pyridine-2Carboxaldehyde Thiosemicarbazone", J. Med. Chem, Vo. 39: pp. 2586-2593 (1996).
Lohmann et al, Viral and Cellular Determinants of Hepatitis C Virus RNA Replication in Cell Culture, Journal of Virology, Mar. 2003, pp. 3007-3019, vol. 77, No. 5.
Lohmann, et al., Replication of Subgenomic Hepatitis C Virus RNAs in a Hepatoma Cell Line, Science, 1999, pp. 110-113, vol. 285.
Makkouk et al., "The potential use of Toll-Like Receptors (TLR) agonistd and antagonists as prophylactic and/or therapeutic agents", Immunopharmacology and Immunotoxicology, vol. 31(3): pp. 331-338 (2009).
Mesguiche, et al., "4-Alkoxy-2,6-diaminopyrimidine Derivatives: Inhibitors of Cyclin Dependent Kinases 1 and 2", Bioorganic & Medicinal Chemistry Letters, vol. 13: pp. 217-22 (2003).
Musmuca, et al, "Small-Molecule interferon Inducers. Toward the Comprehension of the Molecular Determinants through Ligand-Based Approaches", J. Chem. Inf. Model., vol. 49: pp. 1777-1786 (2009).

Newman, et al., "Solid-State Analysis of the Active Pharmaceutical Ingredient in Drug Products", Drug Discovery Today, Oct. 19, 2003, pp. 898-905, vol. 8(19).
O'Hara, et al., "Regioselective Synthesis of Imidazo[4,5-g]quinazoline Quinone Nucleosides and Quinazoline mino Nucleosides. Studies of their Xanthine Oxidase and Purine Nucleoside Phosphorylase Substrate Activity", J. Org. Chem. vol. 56., pp. 776-785 (1991).
Ohto, et al., "Structure and Function of Toll-Like Receptor 8", Microbes and Infections, vol. 16: pp. 273-282 (2014).
Thomas, et al., "Investigating Toll-Like Receptor Agonists for Potential to Treat Hepatitis C Virus Infection", Antimicrobial Agents and Chemotherapy, vol. 51(8): pp. 2969-2978 (Aug. 2007).
Tran, et al., "Design and optimization of orally active TLR7 agonists for the treatment of hepatitis C virus infection", Bioorganic & Medicinal Chemistry Letters, vol. 21: pp. 2389-2393 (2011).
Ulrich, et al., "Crystallization", Kirk-Othmer Encyclopedia of Chemical Technology, Chapter4: pp. 1-63, (Aug. 16, 2002).
Vippagunta, et al., "Crystalline Solids", Advance Drug Delivery Reviews, vol. 48: pp. 3-26 (2001).
Wolff, et al, Burger's Medicinal Chemistry and Drug Discovery,-, 1994, pp. 975-977, 5th Edition, vol. 1.
Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).
Yu et al, "Toll-Like Receptor 7 Agonists: Chemical Feature Based", PLOS ONE, vol. 8 (3): pp. 1-11 e56514, (Mar. 20, 2013).
Yu, et al., Biochimica et "Dual Character of Toll-Like Receptor Signaling: Pro-Tumorigenic Effects and Anti-Tumor Functions", Biochimica et Biophysica Acta, vol. 1835: pp. 144-154 (2013).
International Search Report for corresponding application No. PCT/WP2012/059234, dated Nov. 18, 2013.
Extended European Search Report for Corresponding Application No. EP11166538.6, dated Nov. 22, 2011.
International Search Report for Corresponding Application No. PCT/EP2012/072090, dated Jan. 4, 2013.
International Search Report for Corresponding Application No. PCT/EP2013/052372, dated Apr. 17, 2013.
International Search Report for Corresponding Application No. PCT/EP2013/064763, dated Aug. 3, 2013.
International Search Report for Corresponding Application No. PCT/EP2013/070990, dated Jan. 17, 2014.
International Search Report for Corresponding Application No. PCT/EP2013/070488, dated Nov. 14, 2011.
International Search Report for Corresponding Application No. PCT/EP2013/073901, dated Dec. 16, 2101.
International Search Report for Corresponding Application No. PCT/EP2014/053273, dated Mar. 18, 2014.
International Search Report for Corresponding Application No. PCT/EP2014/056270, dated Jul. 21, 2014.
International Search Report for Corresponding Application No. PCT/EP2014/060603, dated Jul. 15, 2014.
International Search Report for Corresponding Application No. PCT/EP2014/063467, dated Nov. 13, 2014.
U.S. Appl. No. 14/781,291 / US2016-0304531A1 / U.S. Pat. No. 10,266,543, filed Sep. 29, 2015 / Oct. 20, 2016 / Apr. 23, 2019, Jean-François Bonfanti.
U.S. Appl. No. 16/389,751, filed Apr. 19, 2019, Jean-François Bonfanti.
U.S. Appl. No. 14/408,681 / US2015-0299221A1 / U.S. Pat. No. 10,280,180, filed Dec. 17, 2014 / Oct. 22, 2015 / May 7, 2019, Jean-François Bonfanti.

MACROCYCLIC PURINES FOR THE TREATMENT OF VIRAL INFECTIONS

CROSS-REFERENCE TO RELATED APPLICATIONS

This application is a continuation of U.S. patent application Ser. No. 14/408,681 filed on Dec. 17, 2014, which is a national phase entry of International Application No. PCT/EP2013/064763, filed on Jul. 12, 2013, which claims priority to EP Patent Application No. 12176330.4, filed on Jul. 13, 2012, each of which is incorporated herein in its entirety.

SEQUENCE LISTING

The instant application contains a Sequence Listing which has been submitted electronically in ASCII format and is hereby incorporated by reference in its entirety. This ASCII copy, created on May 2, 2019, is named TIP0269USCNT1_SL.txt and is 586 bytes in size.

This invention relates macrocyclic purine derivatives, processes for their preparation, pharmaceutical compositions, and their use in treating viral infections.

The present invention relates to the use of macrocyclic purine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For detailed reviews on toll-like receptors see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, and an improved safety profile compared to the compounds of the prior art.

In the treatment of certain viral infections, regular injections of interferon (IFN-alfa) can be administered, as is the case for hepatitis C virus (HCV). For more information reference Fried et. al. Peginterferon-alfa plus ribavirin for chronic hepatitis C virus infection, *N Engl J Med* 2002; 347: 975-82. Orally available small molecule IFN inducers offer the potential advantages of reduced immunogenicity and convenience of administration. Thus, novel IFN inducers are potentially effective new class of drugs for treating virus infections. For an example in the literature of a small molecule IFN inducer having antiviral effect see De Clercq, E.; Descamps, J.; De Somer, P. Science 1978, 200, 563-565.

IFN-alfa is also given in combination with other drugs in the treatment of certain types of cancer (refer to Eur. J. Cancer 46, 2849-57, and Cancer Res. 1992, 52, 1056 for examples). TLR 7/8 agonists are also of interest as vaccine adjuvants because of their ability to induce pronounced Th1 response (refer to Hum. Vaccines 2010, 6, 1-14, and Hum. Vaccines 2009, 5, 381-394 for examples).

In accordance with the present invention a compound of formula (I) is provided

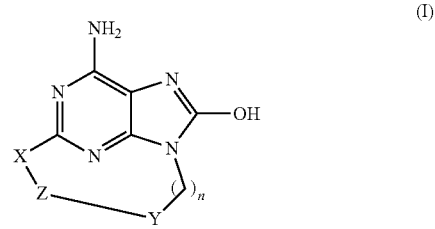

n = 1 to 3 and pharmaceutically accepted salts thereof, wherein
X is oxygen, nitrogen, sulfur or

Y represents an aromatic ring or heterocyclic ring comprising at least a nitrogen, optionally substituted by one or more substituents independently selected from $C_{1-6}$alkyl, $C_{1-4}$alkoxy, trifluoromethyl or halogen, Z represents $C_{1-10}$ saturated or unsaturated alkyl optionally substituted by an alkyl or alkylhydroxyl;

or Z represents $C_{1-6}$alkyl-NH—C(O)— $C_{1-6}$alkyl- or $C_{1-6}$alkyl-NH—C(O)— $C_{1-6}$alkyl-O—;

or Z represents $C_{1-10}$alkyl-O— wherein said alkyl is unsaturated or saturated and can optionally be substituted by an alkyl or alkylhydroxyl, or Z represents $C_{1-6}$alkyl-O—$C_{1-6}$alkyl- wherein said alkyl is unsaturated or saturated and can optionally be substituted by an alkyl or alkylhydroxyl or Z represents $C_{1-6}$alkyl-O—$C_{1-6}$alkyl-O— wherein said alkyl is unsaturated or saturated and can optionally be substituted by an alkyl or alkylhydroxyl.

Part of the invention is also those compounds of formula (I) wherein
X is O, N—$C_{1-4}$alkyl, NH, S or

Y represents an aromatic ring or heterocyclic ring comprising at least a nitrogen, optionally substituted by one or more substituents independently selected from $C_{1-6}$alkyl, $C_{1-4}$alkoxy, trifluoromethyl, halogen, C(O)NH—$C_{1-6}$alkyl, NH(CO)—$C_{1-6}$alkyl, CN, NH—$C_{1-6}$alkyl, N—($C_{1-6}$alkyl)$_2$, C(O)—$C_{1-6}$alkyl or OH, Z represents $C_{1-10}$ saturated or unsaturated alkyl optionally substituted by an alkyl or alkylhydroxyl or OH;

or Z represents $C_{1-6}$alkyl-NH—C(O)—$C_{1-6}$alkyl- or $C_{1-6}$alkyl-NH—C(O)—$C_{1-6}$alkyl-O—;

or Z represents $C_{1-6}$alkyl-NCH$_3$—C(O)—$C_{1-6}$alkyl- or $C_{1-6}$alkyl-NCH$_3$—C(O)—$C_{1-6}$alkyl-O—;

or Z represents $C_{1-6}$alkyl-C(O)—NH—$C_{1-6}$alkyl- or $C_{1-6}$alkyl-C(O)—NH—$C_{1-6}$alkyl-O—;

or Z represents $C_{1-6}$alkyl-C(O)—NCH$_3$—$C_{1-6}$alkyl- or $C_{1-6}$alkyl-C(O)—NCH$_3$—$C_{1-6}$alkyl-O—;

or Z represents $C_{1-10}$alkyl-O— wherein said alkyl is unsaturated or saturated and can optionally be substituted by an alkyl or alkylhydroxyl or OH;

or Z represents $C_{1-10}$alkyl-NH— wherein said alkyl is unsaturated or saturated and can optionally be substituted by an alkyl or alkylhydroxyl or OH;

or Z represents $C_{1-6}$alkyl-O—$C_{1-6}$alkyl- wherein said alkyl is unsaturated or saturated and can optionally be substituted by an alkyl or alkylhydroxyl or OH;

or Z represents $C_{1-6}$alkyl-O—$C_{1-6}$alkyl-O— wherein said alkyl is unsaturated or saturated and can optionally be substituted by an alkyl or alkylhydroxyl or OH.

Preferred compounds having one of the following formula's according to the invention were selected from the group of:

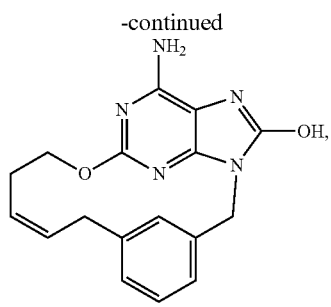

EZ

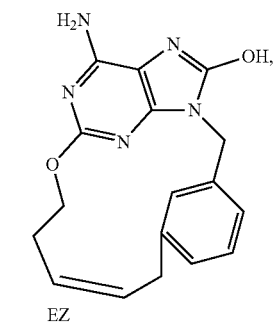

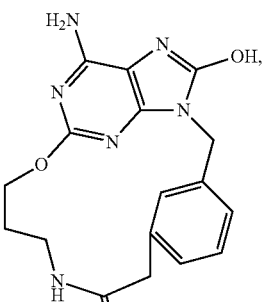

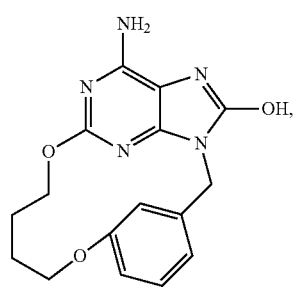

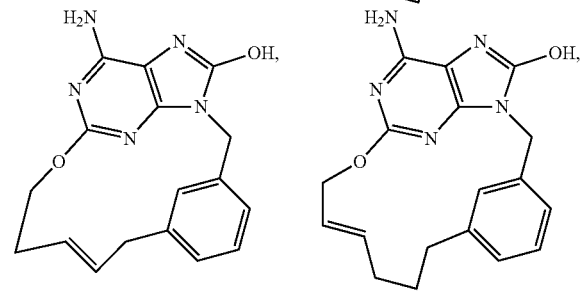

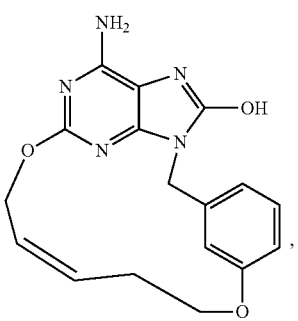

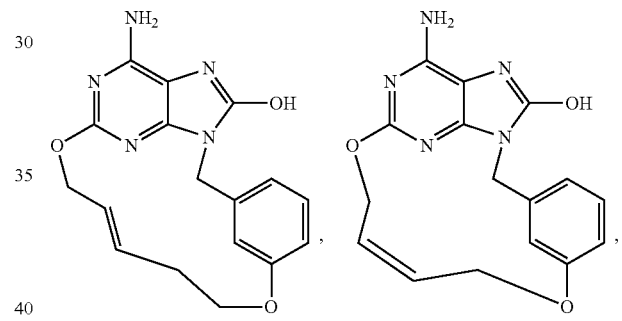

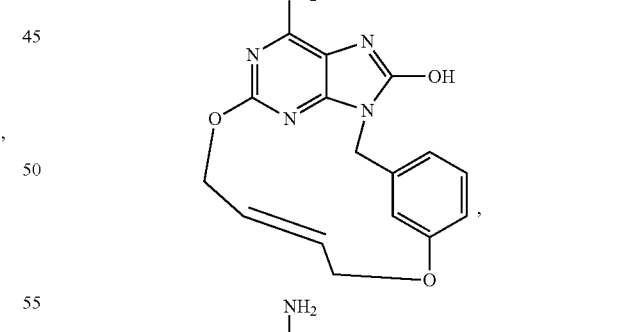

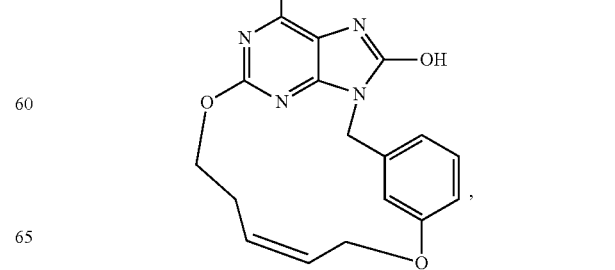

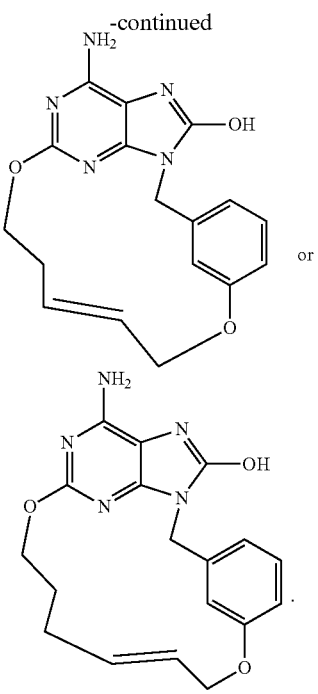

Other preferred compounds according to the invention are compounds having the following numbers (as mentioned in the Tables 1 and 2 respectively): 32, 45, 60, 64, 65, 68, 75, 87, 90, 91 and 92.

Part of the invention is also a pharmaceutical composition comprising a compound of formula (I) or a pharmaceutically acceptable salt, solvate or polymorph thereof together with one or more pharmaceutically acceptable excipients, diluents or carriers.

Furthermore to the invention belongs a compound of formula (I) or a pharmaceutically acceptable salt, solvate or polymorph thereof or a pharmaceutical composition above mentioned for use as a medicament.

The invention also relates to a compound of formula (I) or a pharmaceutically acceptable salt, solvate or polymorph thereof or a pharmaceutical composition above mentioned for use in the treatment of a disorder in which the modulation of TLR7 is involved.

The term "alkyl" refers to a straight-chain or branched-chain mostly saturated (but in specific compounds according to the invention being unsaturated) aliphatic hydrocarbon containing the specified number of carbon atoms.

The term "halogen" refers to fluorine, chlorine, bromine or iodine.

The term "alkoxy" refers to an alkyl (carbon and hydrogen chain) group singular bonded to oxygen like for instance a methoxy group or ethoxy group.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the invention can be present in a so-called "tautomer(s)" formation referring to isomers of organic compounds that readily interconvert by a chemical reaction called tautomerization. This reaction results in the formal migration of a hydrogen atom or proton, accompanied by a switch of a single bond and adjacent double bond.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

OVERALL SCHEME IN THE PREPARATION OF FINAL PRODUCTS: METHOD 1

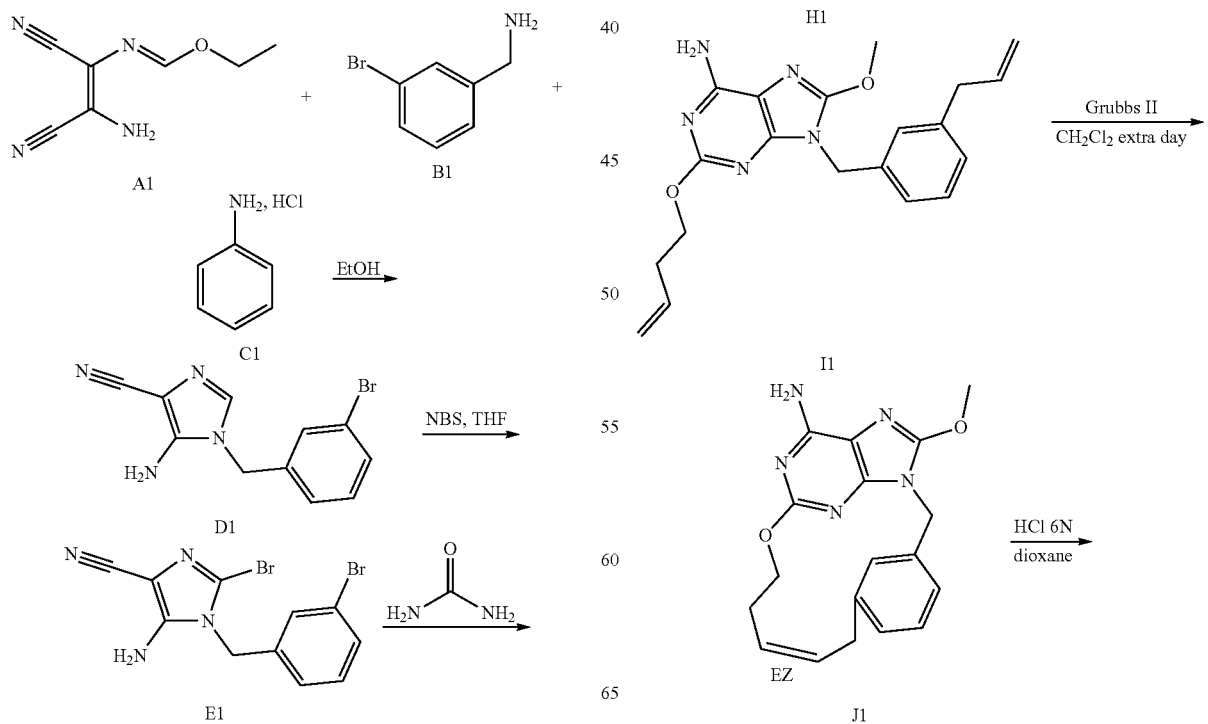

-continued

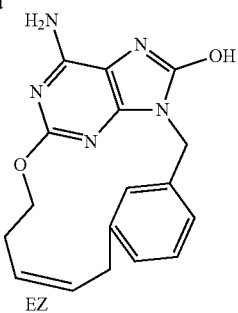

EZ

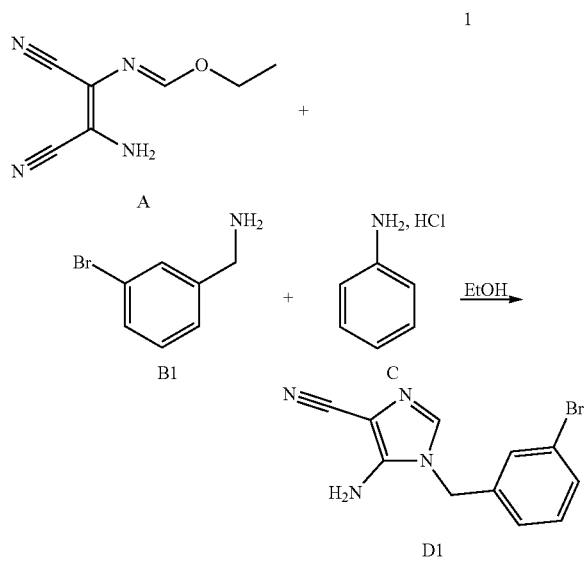

Synthesis of Intermediate D1

At 10° C., 3-bromobenzylamine (11.9 g, 63.96 mmol) was added drop wise to a mixture of A1 (10 g, 60.91 mmol) and C1 (125 mg, 0.97 mmol) in EtOH (100 mL). The mixture was stirred at RT overnight. 120 mL of NaOH 1N was added drop wise and the mixture was stirred at RT for 1 h. The precipitate was filtered off, washed with a minimum of cold EtOH and dried to give 12.74 g (75% yield) of intermediate D1.

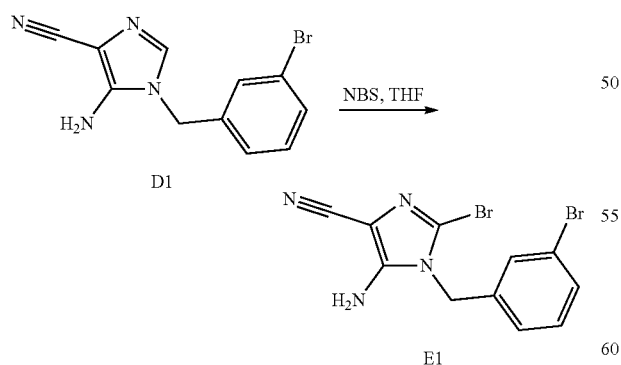

Synthesis of Intermediate E1

N-Bromosuccinimide (7.56 g, 42.47 mmol) was added portion wise to a suspension of D1 (10.7 g, 38.61 mmol) in THF (100 mL) keeping the temperature at 15° C., then the reaction mixture was stirred at 15° C. for 10 minutes. The mixture was poured into an aqueous solution of NaHCO₃ and EtOAc. The layers were decanted and separated. The organic layer was dried over MgSO₄, filtered and solvent was evaporated. The crude compound was taken up in CH₃CN, the precipitate was filtered off and dried to give 7.5 g (55% yield) of a part of intermediate E1. The filtrate was evaporated and was purified by chromatography over silica gel (Irregular SiOH 20-45 µm; mobile phase (99% CH₂Cl₂, 1% CH₃OH). The pure fractions were collected and concentrated under reduced pressure to give 2.8 g (20% yield) of a second batch of intermediate E1.

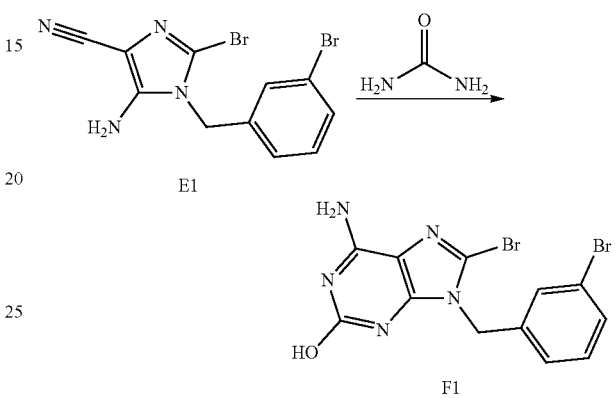

Synthesis of Intermediate F1

A mixture of E1 (8.3 g, 23.31 mmol) in urea (14 g, 233.1 mmol) was heated at 160° C. for 4 h. Urea (14 g, 233.1 mmol) was added again and the mixture was stirred at 160° C. for 2 h. The mixture was cooled to RT and water was added. The precipitate was triturated and filtered off, washed with water and dried under vacuum at 60° C. to give 9.25 g (99% yield) of intermediate F1.

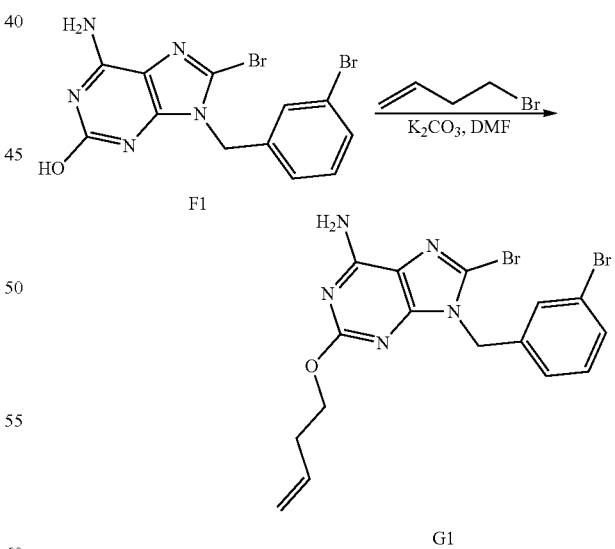

Synthesis of Intermediate G1

A mixture of F1 (3 g, 7.52 mmol), 4-Bromo-1-butene (2.29 mL, 22.55 mmol), K₂CO₃ (3.11 g, 22.55 mmol) in dry DMF (40 mL) was stirred at 50° C. for 12 h. The solvent was evaporated. The residue was taken up in EtOAc. The organic layer was washed with water, dried over MgSO₄, filtered and the solvent was evaporated. The crude was purified by flash chromatography over silica gel (15-40 μm, 50 g, CH$_2$Cl$_2$/CH$_3$OH: 98-2). The pure fractions were collected and evaporated to dryness to give 1.95 g (57% yield) of intermediate G1.

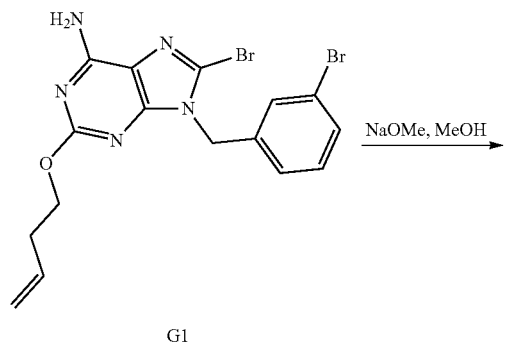

G1

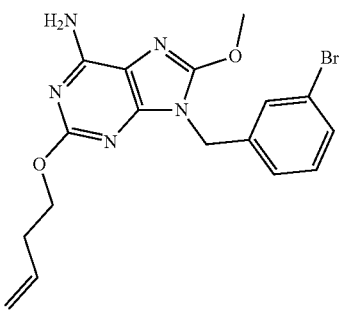

H1

Synthesis of Intermediate H1

At RT, sodium methoxide (30 wt % solution in CH$_3$OH) (8.4 mL, 45.24 mmol) was added drop wise to a mixture of G1 (4.1 g, 9.05 mmol) in CH$_3$OH (100 mL). The mixture was stirred at 60° C. for 6 h. The mixture was poured into water. The aqueous layer was extracted with EtOAc. The organic layer was washed with brine, dried over MgSO$_4$, filtered and the solvent was evaporated to give 3.8 g (100% yield) of intermediate H1. The crude compound was directly used in the next step.

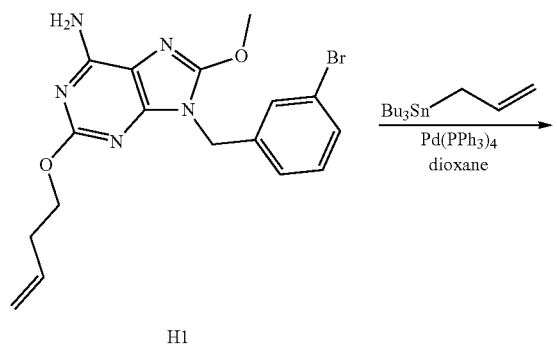

H1

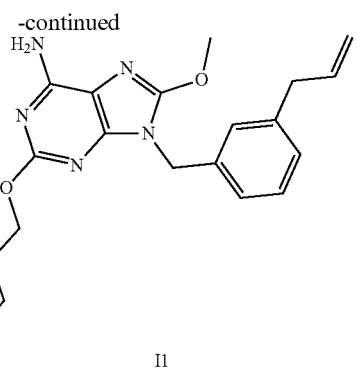

I1

Synthesis of Intermediate I1

The reaction was performed twice in parallel.

A mixture of H1 (2*1.75 g, 8.66 mmol), allyltri-N-butyltin (2*1.32 mL, 8.66 mmol) and tetrakis(triphenylphosphine)palladium(0) (2*500 mg, 0.87 mmol) in dioxane (2*17.5 mL) was stirred at 140° C. for 1 h. The mixture was cooled to RT and was poured into a KF water solution (1 g/100 mL). The mixture was stirred for 10 min at RT. EtOAc was added and the mixture was filtered through a pad of Celite®. The Celite® was washed with EtOAc. The layers were decanted. The organic layer was dried over MgSO$_4$, filtered and the solvent was evaporated. The crude was purified by flash chromatography over silica gel (15-40 μm, 120 g, CH$_2$Cl$_2$/CH$_3$OH/NH$_4$OH: 98.5/1.5/0.1) The pure fractions were collected and concentrated under reduced pressure to give 1.76 g (56% yield) of intermediate I1.

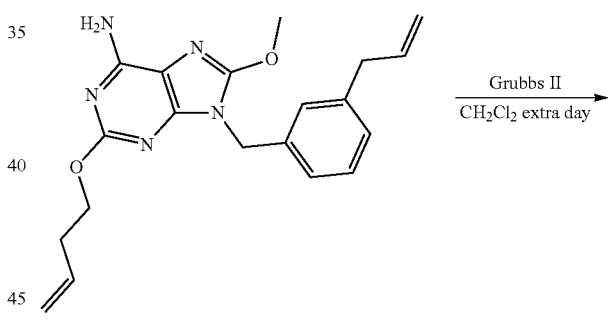

I1

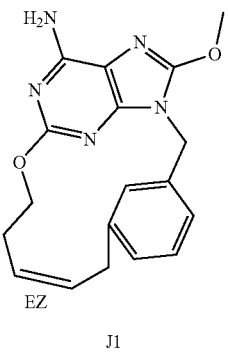

J1

Synthesis of Intermediate J1

I1 (950 mg, 2.6 mmol) was added to CH$_2$Cl$_2$ extra dry (760 mL) and the resulting mixture was degassed by bubbling N$_2$ through the solution for 30 min. Grubbs catalyst 2$^{nd}$ generation (222 mg, 0.26 mmol) was added in one portion and the mixture was stirred under a N$_2$ flow for 24 h. The solvent was evaporated and the crude compound was immediately purified by flash chromatography over silica gel (15-40 μm, 10 g, CH$_2$Cl$_2$/CH$_3$OH/NH$_4$OH: 98.5/1.5/0.1) The pure fractions were collected and concentrated under reduced pressure to give 280 mg of intermediate 11 and 200 mg (23% yield) of intermediate J1 (as a mixture of two isomers E and Z).

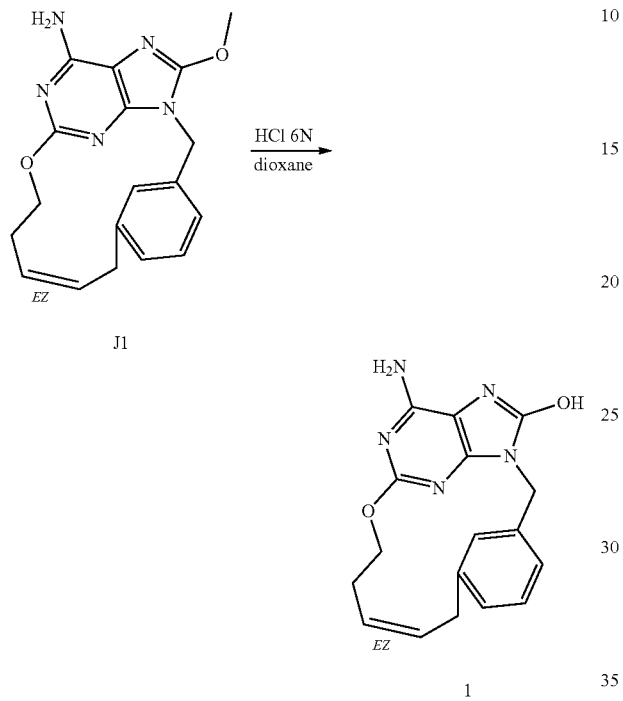

Synthesis of Final Compound 1

A mixture of J1 (200 mg, 0.59 mmol) in HCl 6N (2 mL) and dioxane (5 mL) was stirred at RT for 16 h. The mixture was washed with EtOAc (15 mL) then the mixture was basified at 0° C. with K$_2$CO$_3$ (a precipitate appears) and was extracted many times with EtOAc and CH$_3$OH. The organic layer was dried over MgSO$_4$, filtered and the solvent was evaporated. The residue was recrystallized from CH$_3$CN, the precipitate was filtered off and dried to give 108 mg (56% yield) of compound 1 (mixture of isomers E/Z 55/45).

OVERALL SCHEME IN THE PREPARATION OF FINAL PRODUCTS: METHOD 2

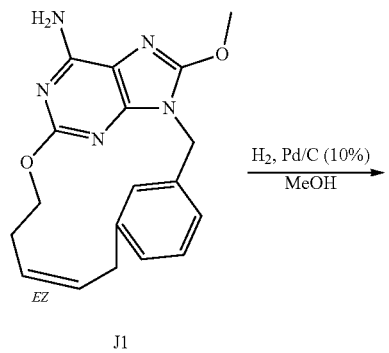

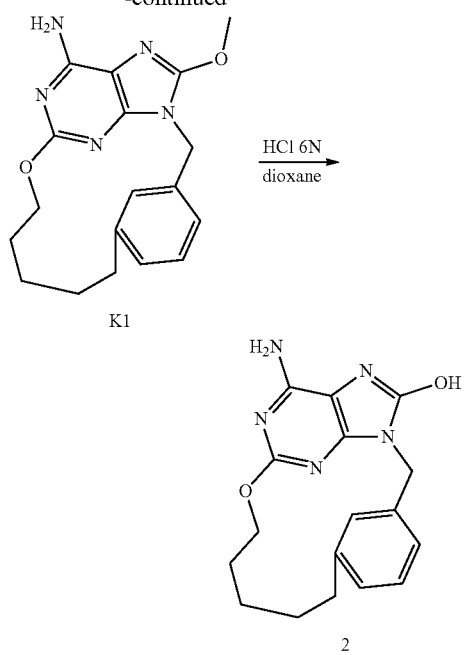

Synthesis of Intermediate K1

A mixture of J1 (130 mg, 0.39 mmol), Pd/C (10%) (20 mg, 0.02 mmol) in CH$_3$OH (30 mL) was hydrogenated under an atmospheric pressure of H$_2$ for 4 h. The catalyst was removed by filtration through Celite®. The Celite® was washed with CH$_3$OH. The filtrate was evaporated to give 126 mg (96% yield) of intermediate K1, used as such in the next step.

Synthesis of Final Compound 2

At RT, a mixture of K1 (110 mg, 0.32 mmol) in HCl 6N (1 mL) and dioxane (2 mL) was stirred for 6 h. The mixture was poured into ice and was neutralized with NaOH 3N. The precipitate was filtered off, washed with water, EtOH, then with diethylether and dried to give 79 mg (75% yield) of compound 2.

OVERALL SCHEME IN THE PREPARATION OF FINAL PRODUCTS: METHOD 3

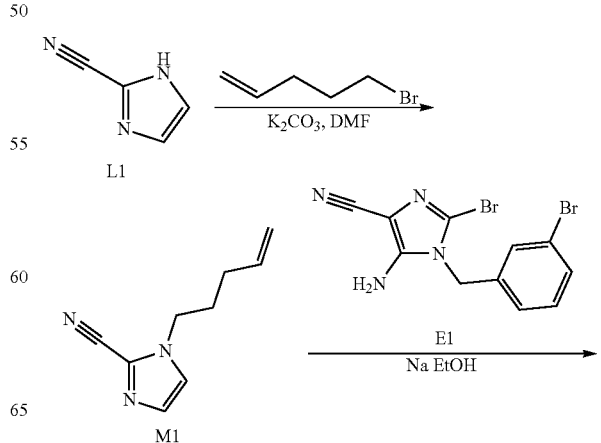

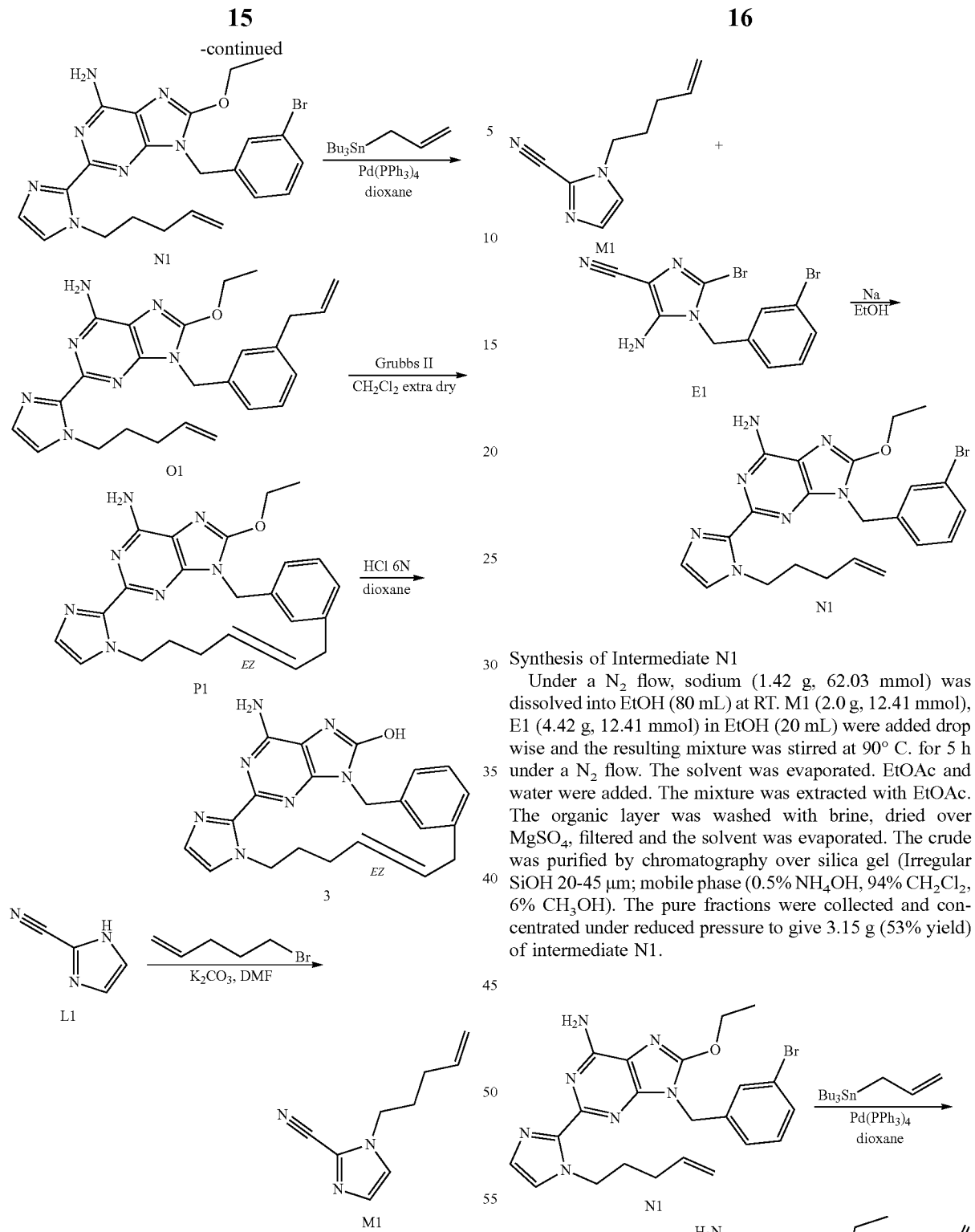

Synthesis of Intermediate N1

Under a N$_2$ flow, sodium (1.42 g, 62.03 mmol) was dissolved into EtOH (80 mL) at RT. M1 (2.0 g, 12.41 mmol), E1 (4.42 g, 12.41 mmol) in EtOH (20 mL) were added drop wise and the resulting mixture was stirred at 90° C. for 5 h under a N$_2$ flow. The solvent was evaporated. EtOAc and water were added. The mixture was extracted with EtOAc. The organic layer was washed with brine, dried over MgSO$_4$, filtered and the solvent was evaporated. The crude was purified by chromatography over silica gel (Irregular SiOH 20-45 µm; mobile phase (0.5% NH$_4$OH, 94% CH$_2$Cl$_2$, 6% CH$_3$OH). The pure fractions were collected and concentrated under reduced pressure to give 3.15 g (53% yield) of intermediate N1.

Synthesis of Intermediate M1

L1 (3.0 g, 32.23 mmol), 5-Bromo-1-pentene (4.8 g, 32.23 mmol) and K$_2$CO$_3$ (5.34 g, 38.67 mmol) in DMF (75 mL) was stirred at 60° C. for 12 h. The mixture was concentrated under reduced pressure. The residue was taken up in EtOAc. The organic layer was washed with water, dried over MgSO$_4$, filtered and the solvent was evaporated to give 4.6 g (89% yield) of intermediate M1 used as such in the next step.

Synthesis of Intermediate O1

A mixture of N1 (0.50 g, 1.04 mmol), allyltri-N-butyltin (0.32 mL, 1.04 mmol) and tetrakis(triphenylphosphine)palladium(0) (120 mg, 0.10 mmol) in dioxane (4 mL) was stirred at 140° C. for 1 h. The mixture was cooled to RT and was poured into a KF water solution (5 g/100 mL). The mixture was stirred for 10 min at RT. EtOAc was added and the layers were decanted. The organic layer was washed with brine, dried over $MgSO_4$, filtered and the solvent was evaporated. The crude was purified by chromatography over silica gel (Irregular SiOH 15-40 μm; mobile phase (0.5% $NH_4OH$, 95% $CH_2Cl_2$, 5% $CH_3OH$). The pure fractions were collected and concentrated under reduced pressure to give 300 mg (65% yield) of intermediate O1.

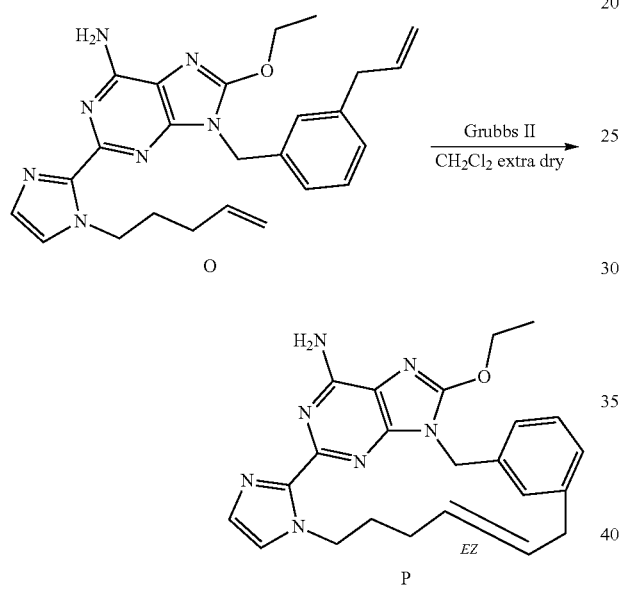

Synthesis of Intermediate P1

O1 (1.80 g, 4.06 mmol) was added to $CH_2Cl_2$ extra dry (1080 mL) and the resulting mixture was degassed by bubbling $N_2$ through the solution for 30 min. Grubbs catalyst $2^{nd}$ generation (346 mg, 0.41 mmol) was added in one portion and the mixture was stirred at RT under a $N_2$ flow for 24 h. The mixture was concentrated under reduced pressure. The crude was purified by flash chromatography over silica gel (15-40 μm, 120 g, $CH_2Cl_2/CH_3OH/NH_4OH$: 96/4/0.5). The pure fractions were collected and concentrated under reduced pressure to give 1.47 g of crude product. The residue was purified by Reverse phase chromatography on (X-Bridge-C18 5 μm 30*150 mm), mobile phase (Gradient from 80% $NH_4HCO_3$ 0.5% pH10 buffer, 20% $CH_3CN$ to 0% $NH_4HCO_3$ 0.5% pH10 buffer, 100% $CH_3CN$). The pure fractions were collected and concentrated under reduced pressure to give 83 mg (5% yield) of intermediate P1 (as a mixture of two isomers E and Z) and 800 mg of intermediate O1.

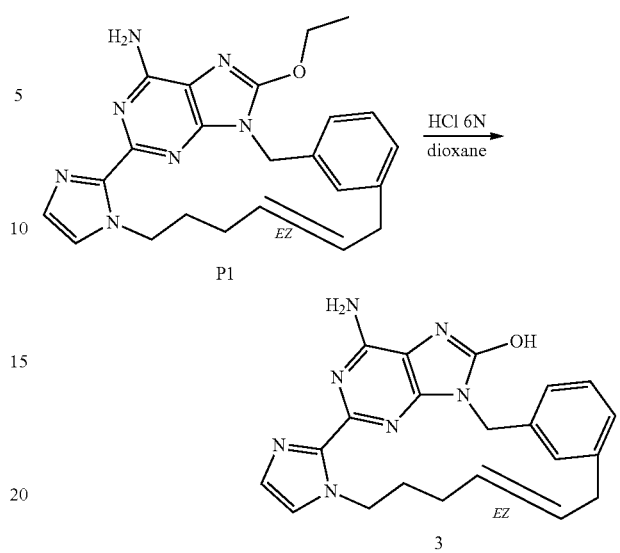

Synthesis of Final Compound 3

P1 (40 mg, 0.10 mmol) in HCl 6N (2 mL) and dioxane (2 mL) was stirred at RT for 18 h. At 0° C., the mixture was basified with $K_2CO_3$ and was extracted with EtOAc and $CH_3OH$. The organic layer was dried over $MgSO_4$, filtered and the solvent was evaporated. The crude was purified by flash chromatography over silica gel (15-40 μm, 12 g, $CH_2Cl_2/CH_3OH/NH_4OH$: 90/10/0.5). The pure fractions were collected and concentrated under reduced pressure to give 23 mg. The compound was taken up in diethylether, the precipitate was filtered off and dried to give 15 mg (40% yield) of compound 3 (as a mixture of two isomers E/Z 70/30).

OVERALL SCHEME IN THE PREPARATION OF FINAL PRODUCTS: METHOD 4

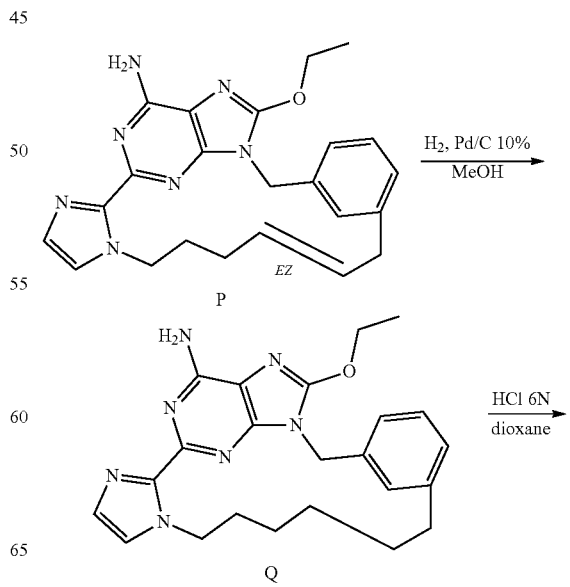

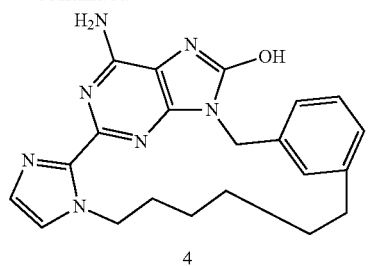

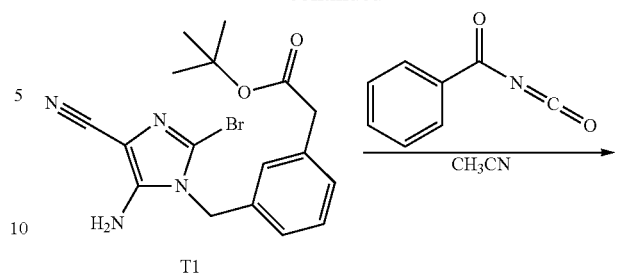

Synthesis of Intermediate Q1

A mixture of P1 (70 mg, 0.17 mmol), Pd/C 10% (18 mg, 0.02 mmol) in CH$_3$OH (5 mL) was hydrogenated under an atmospheric pressure of H$_2$ for 4 h. The catalyst was removed by filtration through a pad of Celite®. The Celite® was washed with CH$_3$OH and the filtrate was evaporated. The crude was purified by flash chromatography over silica gel (15-40 μm, 10 g, CH$_2$Cl$_2$/CH$_3$OH/NH$_4$OH: 96/4/0.5). The pure fractions were collected and concentrated under reduced pressure to give 50 mg (71% yield) of intermediate Q1.

Synthesis of Final Compound 4

Q1 (50 mg, 0.12 mmol) in HCl 6N (1 mL) and dioxane (1 mL) was stirred at RT for 18 h. The precipitate was filtered off, washed with dioxane and dried to give 38 mg (71% yield) of compound 4 (1HCl, 1H$_2$O).

OVERALL SCHEME IN THE PREPARATION OF FINAL PRODUCTS: METHOD 5

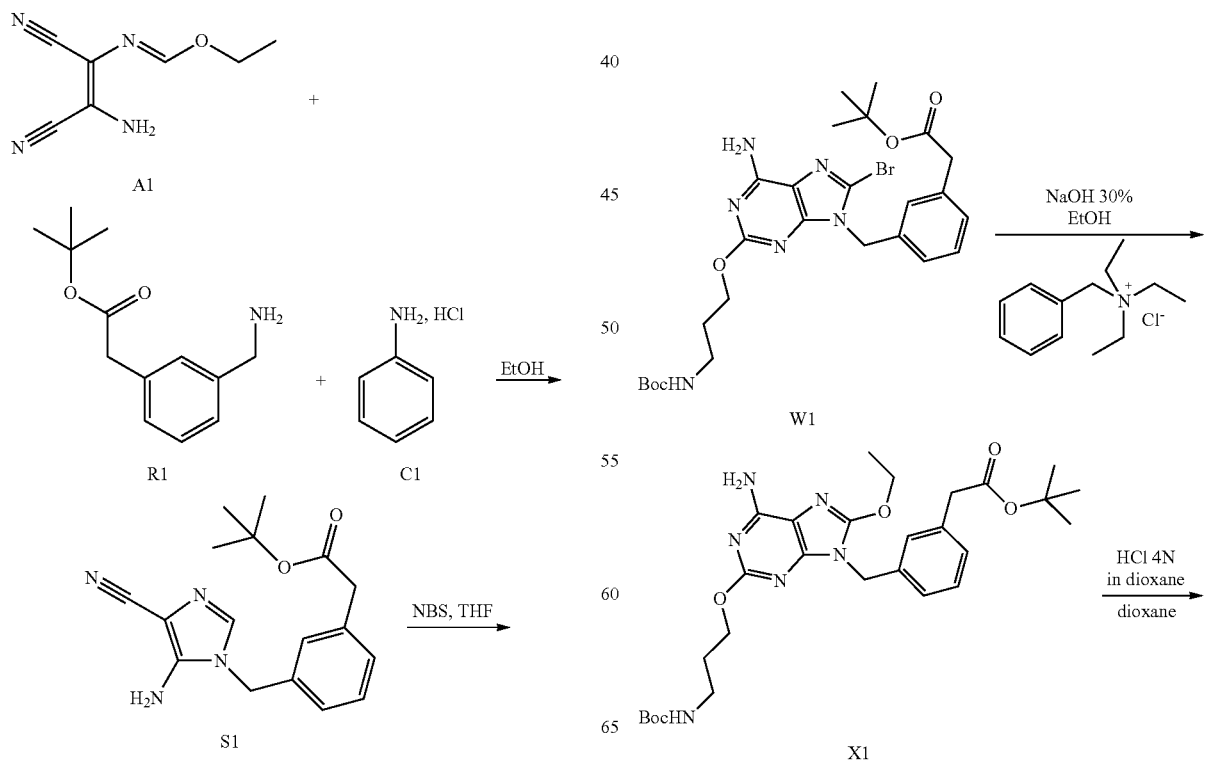

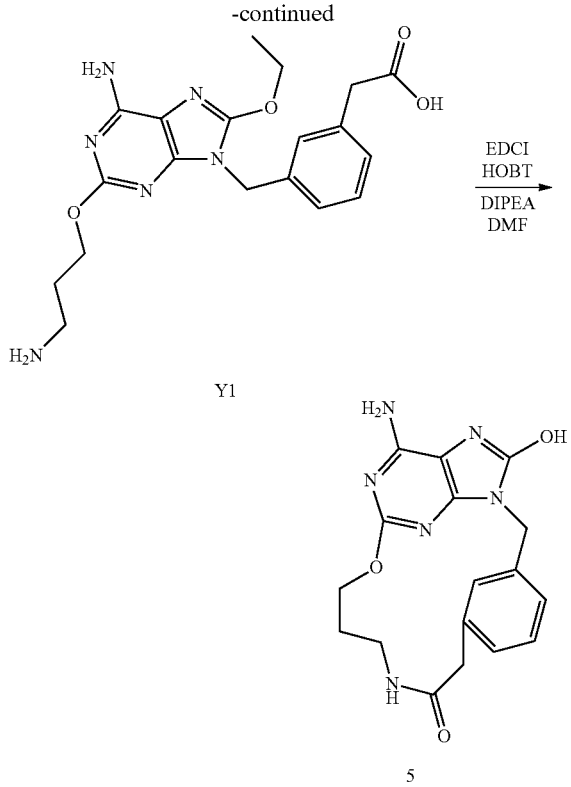

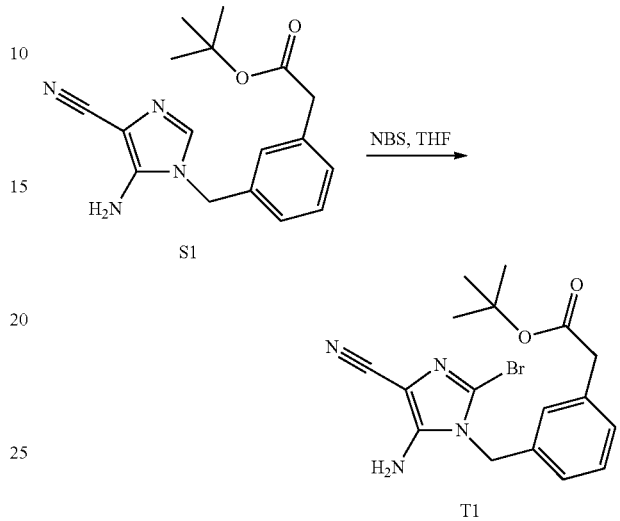

and the solvent was evaporated. The crude was purified by chromatography over silica gel (Irregular SiOH 20-45 μm; mobile phase (0.1% NH₄OH, 98% CH₂Cl₂, 2% CH₃OH). The pure fractions were collected and concentrated under reduced pressure to give 5.1 g (49% yield) of intermediate S.

Synthesis of Intermediate T1

At 10° C., under a N₂ flow, N-bromosuccinimide (2.90 g, 16.33 mmol) was added portion wise to a mixture of S1 (5.1 g, 16.33 mmol) in THF (100 mL). The mixture was stirred for 10 min at 10° C. The mixture was poured into a solution of NaHCO₃ 10% in water and EtOAc. The layers were decanted. The organic layer was dried over MgSO₄, filtered and solvent was evaporated. The crude was purified by flash chromatography over silica gel (15-40 μm, 80 g, CH₂Cl₂/CH₃OH 99-1). The pure fractions were collected and concentrated under reduced pressure to give 3.75 g (59% yield) of intermediate T1.

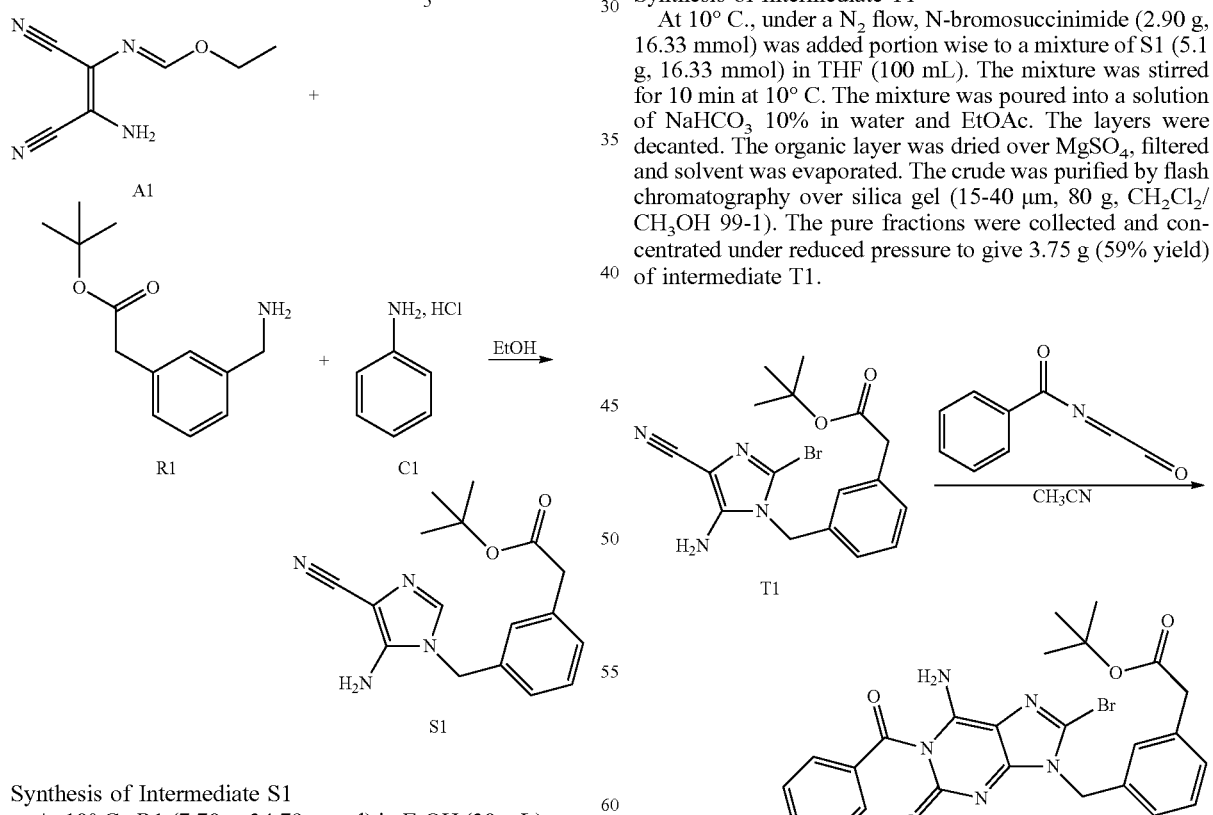

Synthesis of Intermediate S1

At 10° C., R1 (7.70 g, 34.79 mmol) in EtOH (30 mL) was added drop wise to a mixture of A1 (5.44 g, 33.14 mmol), C1 (68 mg, 0.53 mmol) in EtOH (25 mL). The mixture was stirred at RT overnight. 60 mL of NaOH 1N was added drop wise and the mixture was stirred at RT for 1 h. The mixture was extracted with CH₂Cl₂ (3 times). The combined organic layers were washed with brine, dried over MgSO₄, filtered Synthesis of Intermediate U1

Benzoyl isocyanate (7.05 g, 47.92 mmol) was added to a mixture of T1 (3.75 g, 9.58 mmol) in CH₃CN (80 mL) under stirring at RT. The mixture was stirred at RT overnight. The solvent was evaporated, the residue was dissolved in 2-propanol/25% aqueous NH₃ 1:1 (200 mL) and the resulting solution was stirred at RT for 72 h. The solvent was evaporated and the resulting mixture was poured into water, neutralized with diluted HCl and extracted with EtOAc. The layers were filtered through a pad of Celite®, the Celite® was washed with EtOAc. The filtrate was decanted. The organic layer was dried over MgSO₄, filtered and the solvent was evaporated. The crude compound was purified by flash chromatography over silica gel (15-40 μm, 80 g, CH₂Cl₂/CH₃OH/NH₄OH: 98/2/0.1). The pure fractions were collected and concentrated under reduced pressure to give 1.70 g (33% yield) of intermediate U1.

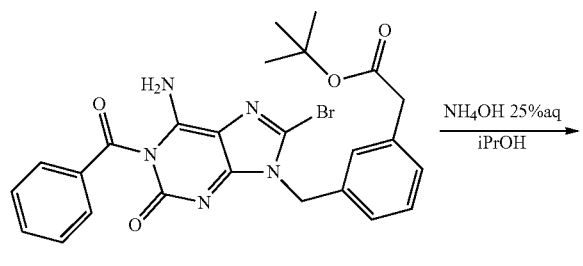

Synthesis of Intermediate V1

A mixture of U1 (1.6 g, 2.97 mmol) in NH₄OH 25% (160 mL) and iPrOH (160 mL) was stirred at RT for 72 h. iPrOH was evaporated and water was added. The mixture was extracted with EtOAc. A precipitate appeared between the 2 phases. The precipitate was filtered off and dried to give 880 mg (68% yield) of intermediate V1. The organic layer was dried over MgSO₄, filtered and the solvent was evaporated to give 680 mg of intermediate U1.

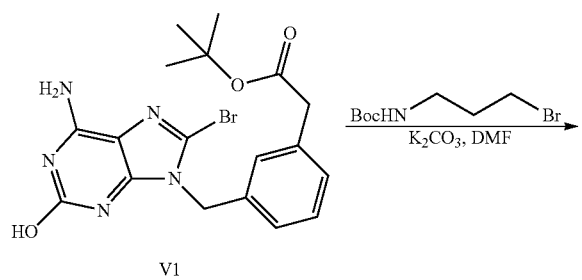

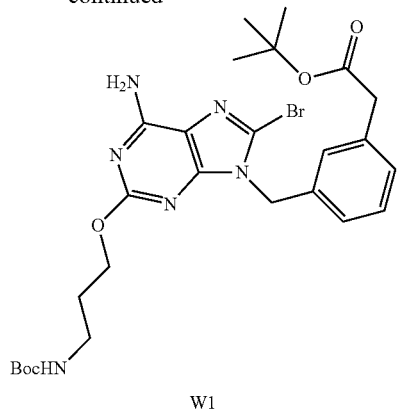

Synthesis of Intermediate W1

A mixture of V1 (520 mg, 1.20 mmol), tert-butyl N-(3-bromopropyl)carbamate (570 mg, 2.40 mmol) and K₂CO₃ (496 mg, 3.59 mmol) in DMF (20 mL) was stirred at 80° C. for 5 h. After cooling down to RT, the mixture was poured into water and was extracted with EtOAc. The organic layer was washed with water, brine, dried over MgSO₄, filtered and the solvent was evaporated to give 800 mg (>100% yield) of intermediate W1. The crude compound was used directly in the next step.

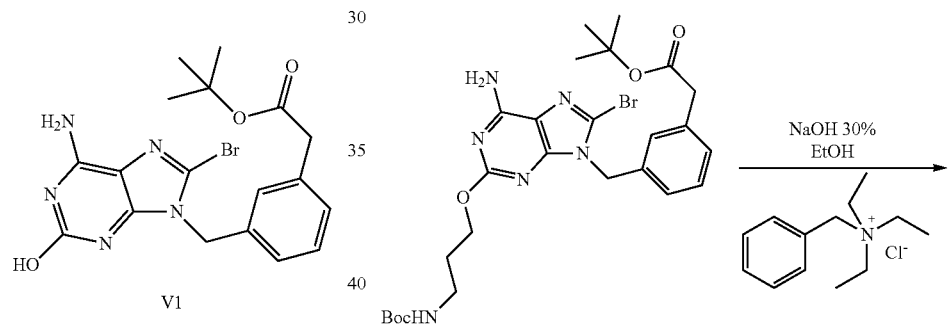

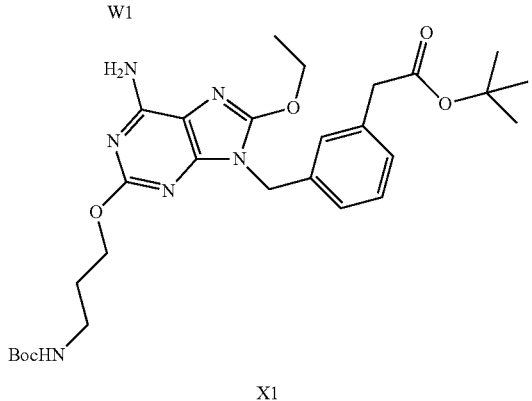

Synthesis of Intermediate X1

A mixture of W1 (0.60 g, 1.01 mmol), benzyltriethylammonium chloride (11.5 mg, 0.05 mmol) in NaOH 30% (15 mL) and EtOH (15 mL) was stirred at 60° C. for 4 h. The mixture was half-concentrated. The pH was adjusted to 5 with HCl 3N. The mixture was extracted with EtOAc (twice). The combined organic layers were dried over MgSO₄, filtered and the solvent was evaporated to give 500 mg (98% yield) of intermediate X1.

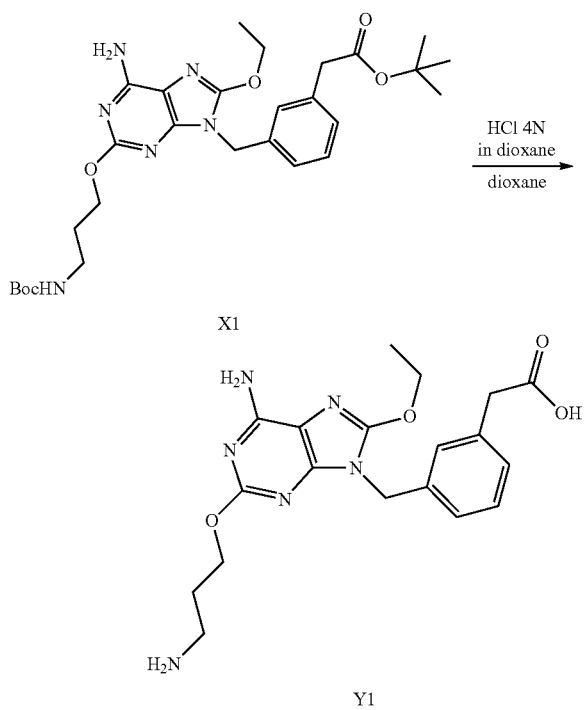

Synthesis of Intermediate Y1

At 0° C., HCl 4N in dioxane (1.25 mL, 4.99 mmol) was added drop wise to a mixture of X1 (0.50 g, 1 mmol) in dioxane (2.5 mL). The mixture was stirred at RT for 12 h. The mixture was evaporated until dryness to give 450 mg (>100% yield) of intermediate Y1. The crude compound was used without any further purification in the next step.

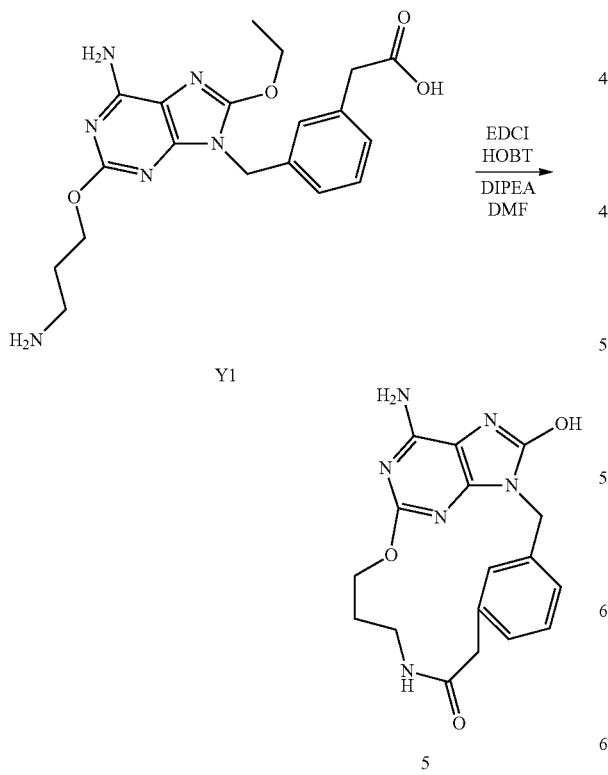

Synthesis of Final Compound 5

1-(3-Dimethylaminopropyl)-3-ethylcarbodiimide hydrochloride (520 mg, 2.72 mmol) and 1-hydroxybenzotriazole (367 mg, 2.72 mmol) were slowly added to a mixture of Y1 (370 mg, 0.91 mmol), diisopropylethylamine (0.78 mL, 4.53 mmol) in DMF (270 mL). The mixture was stirred at RT for 24 h. The solvent was evaporated until dryness. The residue was taken up in $CH_2Cl_2$—$CH_3OH$ (90-10) and was washed with water. A precipitate appeared in the decantation funnel. The precipitate was filtered off to give 103 mg. This precipitate was taken up in hot EtOH, stirred at reflux for 1 h, cooled to RT and filtered off. The crude was purified by reverse phase on (X-Bridge-C18 5 μm 30*150 mm), mobile phase (gradient from 75% $NH_4HCO_3$ 0.5% pH10 buffer, 25% $CH_3OH$ to 0% $NH_4HCO_3$ 0.5% pH10 buffer, 100% $CH_3OH$). The pure fractions were collected and concentrated under reduced pressure to give 8 mg (pure) and 50 mg (crude). The crude was purified by reverse phase on (X-Bridge-C18 5 μm 30*150 mm), mobile phase (gradient from 90% trifluoroacetic acid 0.05%, 10% $CH_3OH$ to 0% trifluoroacetic acid 0.05%, 100% $CH_3OH$). The pure fractions were collected and concentrated under reduced pressure to give 20 mg. The 2 fractions (8 mg and 20 mg) were combined, taken up in dioxane and $CH_3CN$ and 0.50 mL of HCl 4N in dioxane was added. The mixture was stirred at RT for 2 h. The precipitate was filtered off and dried to give 28 mg (7% yield) of compound 5 (HCl salt).

OVERALL SCHEME IN THE PREPARATION OF FINAL PRODUCTS: METHOD 6

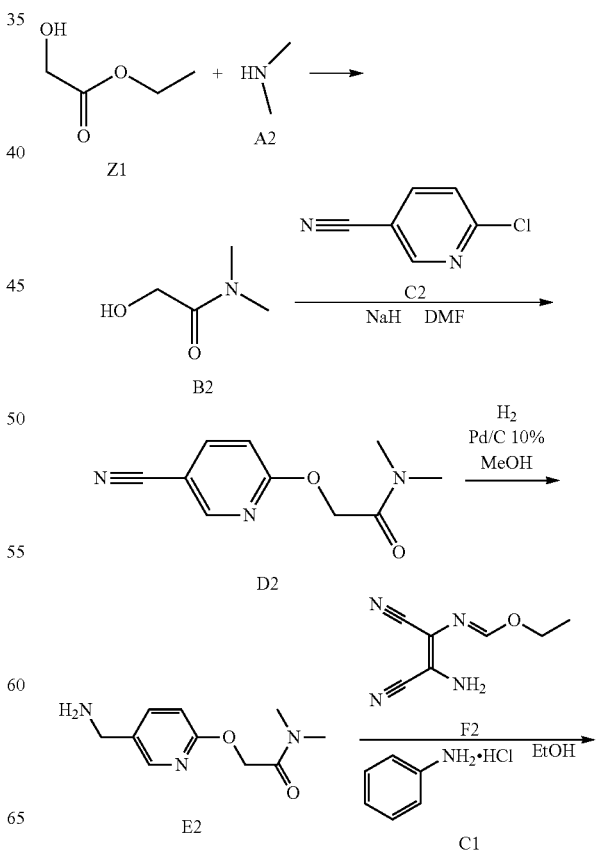

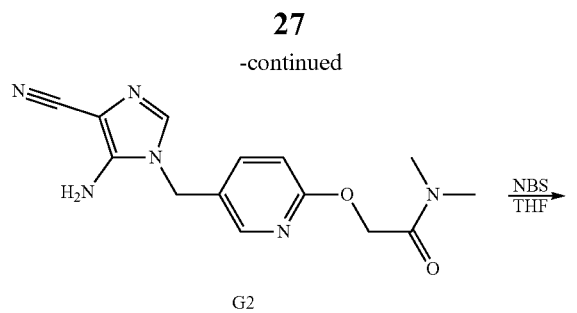

G2

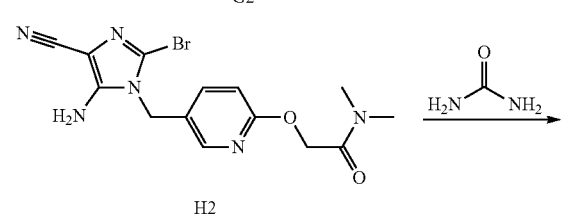

H2

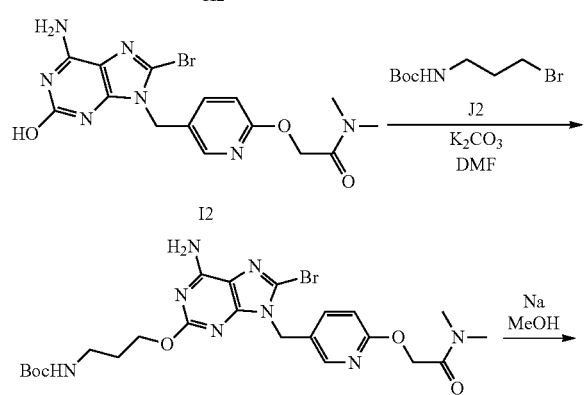

I2

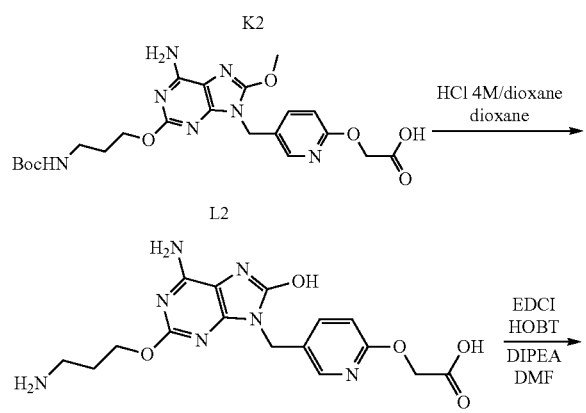

K2

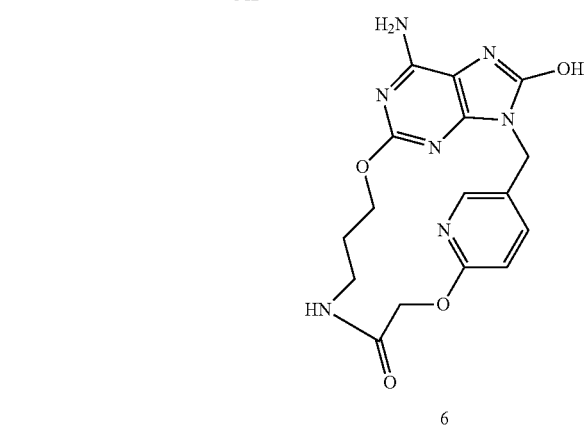

L2

M2

6

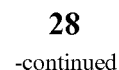

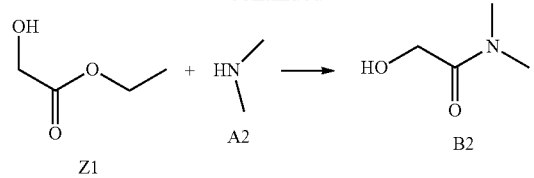

Synthesis of Intermediate B2

A solution of ethyl glycolate (10.0 g, 96.06 mmol) in dimethylamine (40% solution in water) (100 mL) was stirred at RT for 16 h and concentrated under vacuum. The residue was taken up in EtOH and concentrated again. The cycle was performed 3 times to give 9.75 g (98% yield) of intermediate B2.

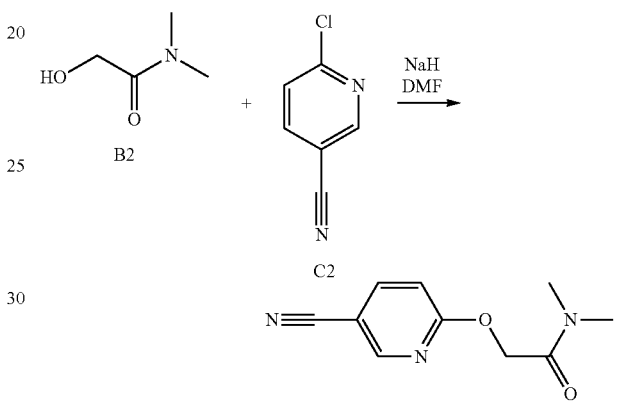

Synthesis of Intermediate D2

At 0° C. under a $N_2$ flow, NaH (2.16 g, 54.13 mmol) was added to a solution of B2 (4.09 g, 39.69 mmol) in DMF (36 mL) at RT. The mixture was stirred at RT for 30 min and 6-chloroniconitrile C2 (5.0 g, 36.09 mmol) was added (exothermic) and the mixture was stirred at RT for 16 h. A 10% aqueous solution of $NaHCO_3$ (150 mL) was added, then brine solution was added. The aqueous layer was extracted with EtOAc (twice). The organic layer was dried over $MgSO_4$, filtered and the solvent was evaporated to give 7.0 g (95% yield) of intermediate D2.

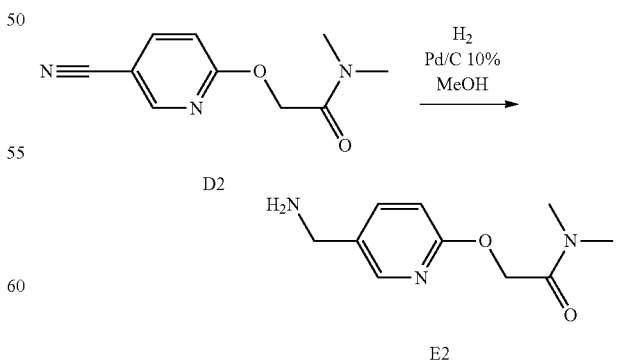

Synthesis of Intermediate E2

Pd/C 10% (2.0 g) was added to a solution of D2 (7.0 g, 34.11 mmol) in MeOH (140 mL). The reaction mixture was stirred for 16 h at RT under H₂ atmosphere (1 atm). Pd/C 10% (1.5 g, 0.04 mmol) was added and the reaction mixture was stirred with the same conditions for 4 h. The catalyst was filtered over a pad of Celite®. The Celite® was washed with CH₃OH and the filtrate was concentrated under vacuum. This fraction was combined with another batch before purification.

The residue was purified by flash chromatography over silica gel (15-40 μm, 120 g, CH₂Cl₂/CH₃OH/NH₄OH: 92/8/0.5) The pure fractions were collected and concentrated under reduced pressure to give 2.2 g (27% yield) of intermediate E2.

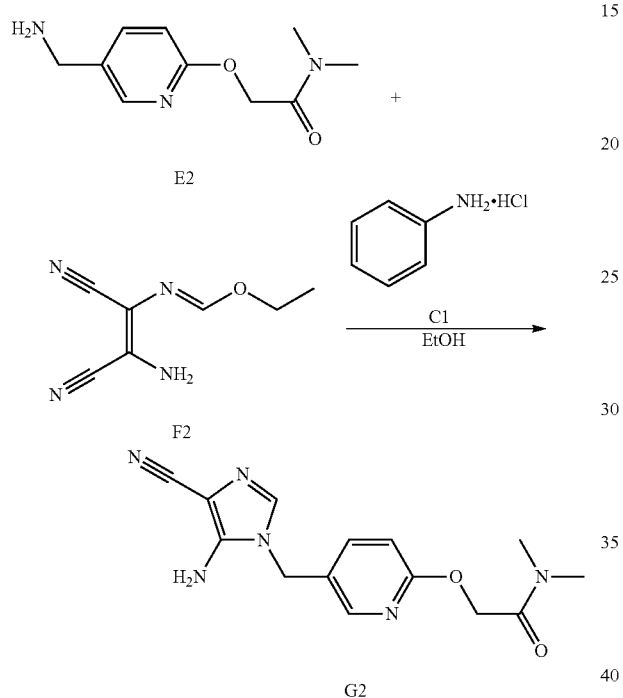

Synthesis of Intermediate G2

E2 (2.2 g, 10.51 mmol) in EtOH (10 mL) was added drop wise to a solution of F2 (1.64 g, 10.01 mmol) and aniline hydrochloride (20 mg, 0.16 mmol) in EtOH (10 mL) at 10° C. The reaction mixture was stirred at RT for 20 h. An aqueous solution of NaOH 1M (25 mL) was added drop wise to the solution at 10° C. and the resulting mixture was stirred at RT for 1 h. The precipitate was filtered off, washed with a minimum of cold EtOH and dried under vacuum to give 2.25 g (75% yield) of intermediate G2. G2 was directly used in the next step without further purification.

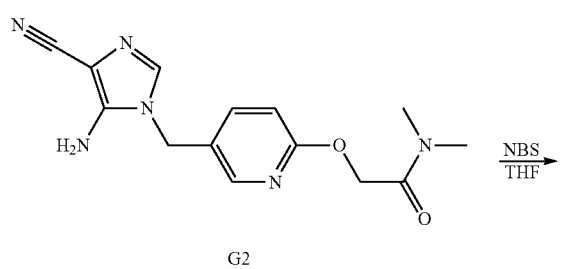

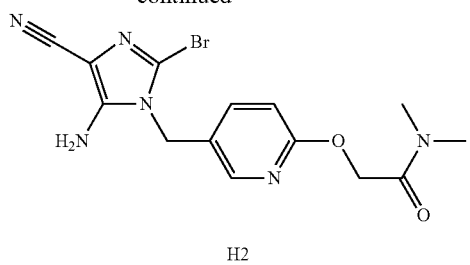

Synthesis of Intermediate H2

A solution of N-bromosuccinimide (1.47 g, 8.24 mmol) in THF (50 mL) was added drop wise over 25 min to a solution of G2 (2.25 g, 7.49 mmol) in THF (80 mL) at 0° C. The mixture was stirred at 0° C. for 30 min and then at RT for 45 min. The mixture was taken up in CH₂Cl₂, washed with a saturated aqueous solution of NaHCO₃, then with brine, dried over MgSO₄, filtered and concentrated. The crude compound was crystallized from CH₃CN, the precipitate was filtered off and dried to give 0.79 g (27% yield) of intermediate H2. The filtrate was evaporated and the residue was purified by flash chromatography over silica gel (15-40 μm, 50 g, CH₂Cl₂/CH₃OH/NH₄OH: 97/3/0.1). The pure fractions were collected and concentrated to give 0.71 g (25% yield) of intermediate H2.

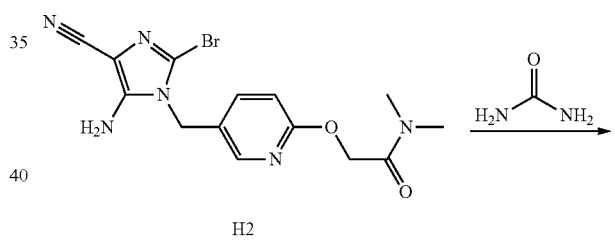

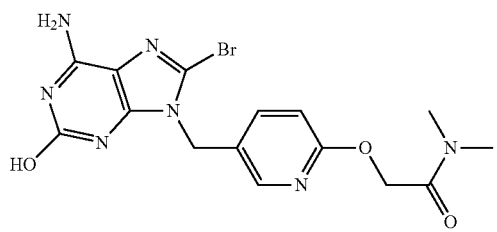

Synthesis of Intermediate 12

A mixture of H2 (1.4 g, 3.69 mmol) in urea (13.3 g, 221.51 mmol) was heated at 160° C. for 6 h. The mixture was cooled to RT and water was added. The precipitate was triturated and filtered off, washed with water and dried under vacuum at 60° C. to give 1.05 g (67% yield) of intermediate 12.

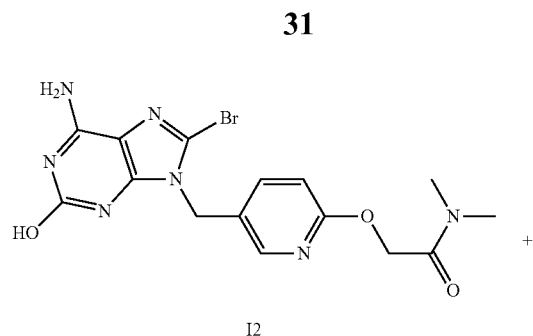

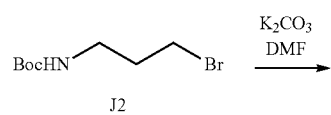

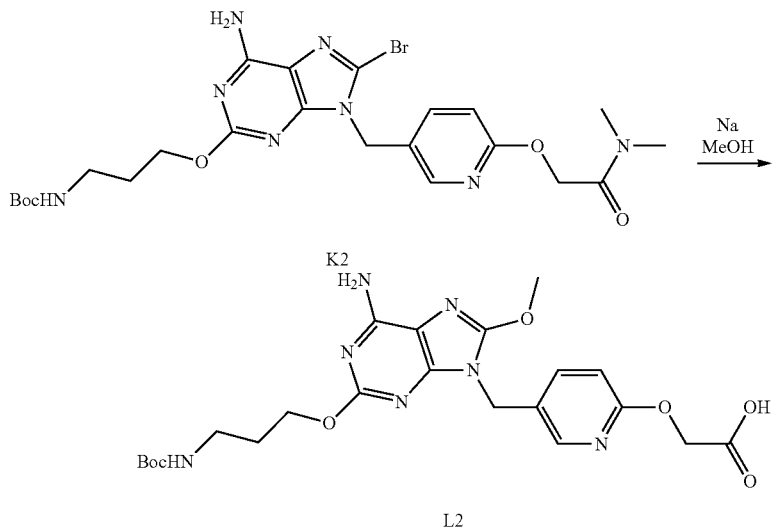

Synthesis of Intermediate K2

A mixture of I2 (1.23 g, 2.91 mmol), tert-butyl-N-(3-bromopropyl)carbamate J2 (1.04 g, 4.37 mmol), K₂CO₃ (604 mg, 4.37 mmol) in DMF (20 mL) was stirred at 50° C. for 12 h. The solvent was evaporated. The residue was taken up in EtOAc. The organic layer was washed with water, dried over MgSO₄, filtered and the solvent was evaporated. The residue was purified by flash chromatography over silica gel (15-40 µm, 80 g, CH₂Cl₂/CH₃OH/NH₄OH: 95/5/0.5). The pure fractions were collected and concentrated to give 0.97 g (57% yield) of intermediate K2.

Synthesis of Intermediate L2

At RT, sodium (446 mg, 19.42 mmol) was added to MeOH (30 mL). The mixture was stirred until sodium was in solution (exothermic). K2 (750 mg, 1.29 mmol) was added and the mixture was stirred at 50° C. for 16 h under a N₂ flow. Water was added and the pH was adjusted to 5-6. The aqueous layer was extracted with EtOAc. The organic layer was dried over MgSO₄, filtered and the solvent was evaporated to give 0.54 g (83% yield) of intermediate L2.

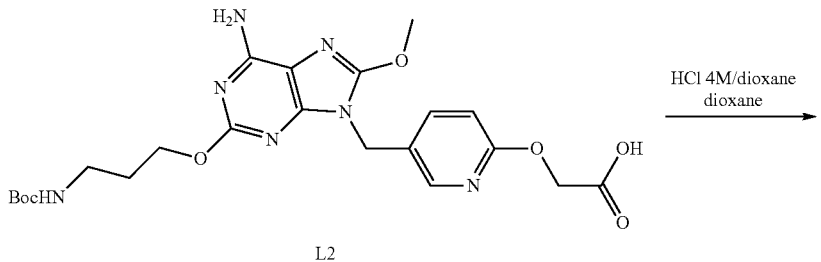

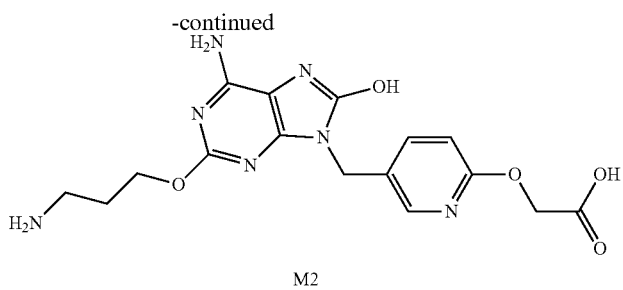

M2

Synthesis of Intermediate M2

At 0° C., HCl 4M in dioxane (2.68 mL, 10.73 mmol) was added drop wise to a mixture of L2 (0.54 g, 1.07 mmol) in dioxane (20 mL). The mixture was stirred at RT for 12 h. The mixture was evaporated until dryness to give 0.74 g (>100% yield). The crude compound was used without any further purification in the next step.

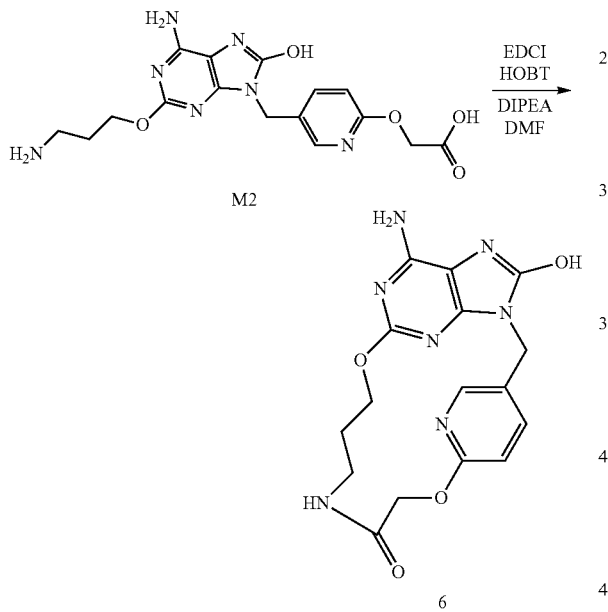

Synthesis of Final Compound 6

1-(3-Dimethylaminopropyl)-3-ethylcarbodiimide hydrochloride (675 mg, 3.52 mmol) and hydroxybenzotriazole (476 mg, 3.52 mmol) were slowly added to a mixture of M2 (500 mg, 1.17 mmol), diisopropylethylamine (1.01 mL, 5.87 mmol) in DMF (360 mL). The mixture was stirred at RT for 24 h. The solvent was evaporated until dryness. The residue was taken up in water. The precipitate was filtered off, washed with water and dried. The residue was purified by reverse phase chromatography on (X-Bridge-C18 5 m 30*150 mm), mobile phase (gradient from 90% trifluoroacetic acid 0.05%, 10% MeOH to 0% trifluoroacetic acid 0.05%, 100% MeOH). The pure fractions were collected and concentrated to give 75 mg of compound 6 and 100 mg (crude precipitate). The pure fraction (75 mg) was taken up in dioxane and CH₃CN and 1 mL of HCl 4N in dioxane was added. The mixture was stirred at RT for 2 h. The precipitate was filtered off and dried to give 57 mg (12% yield) of compound 6 (HCl salt).

OVERALL SCHEME IN THE PREPARATION OF FINAL PRODUCTS: METHOD 7

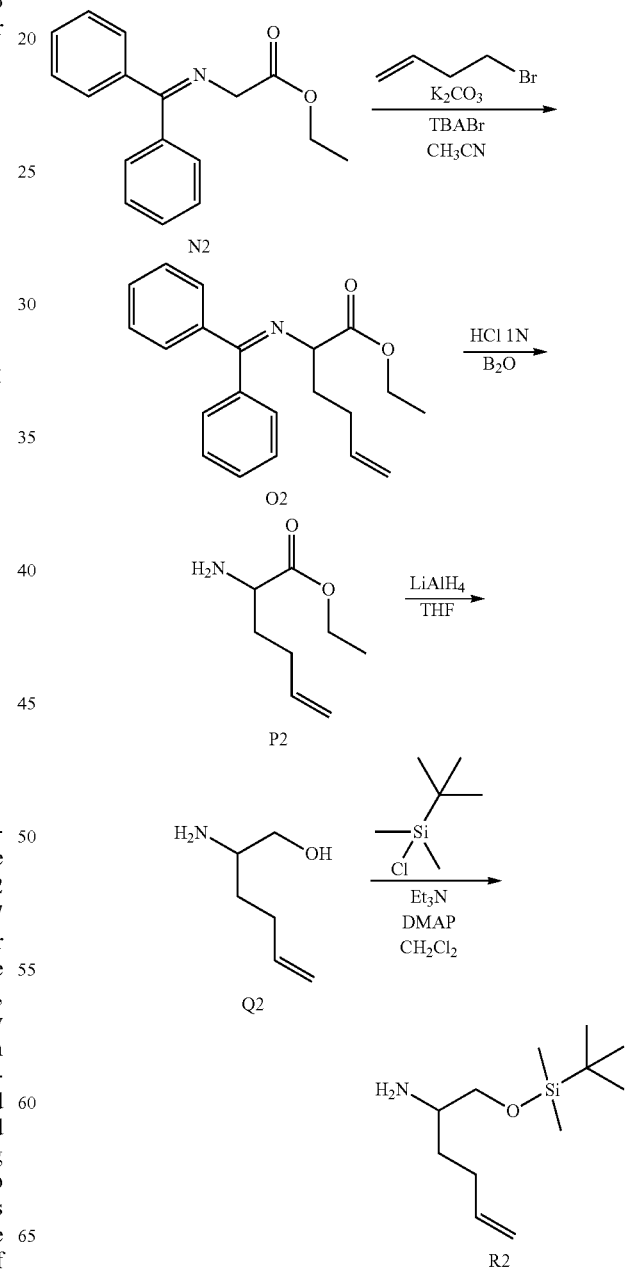

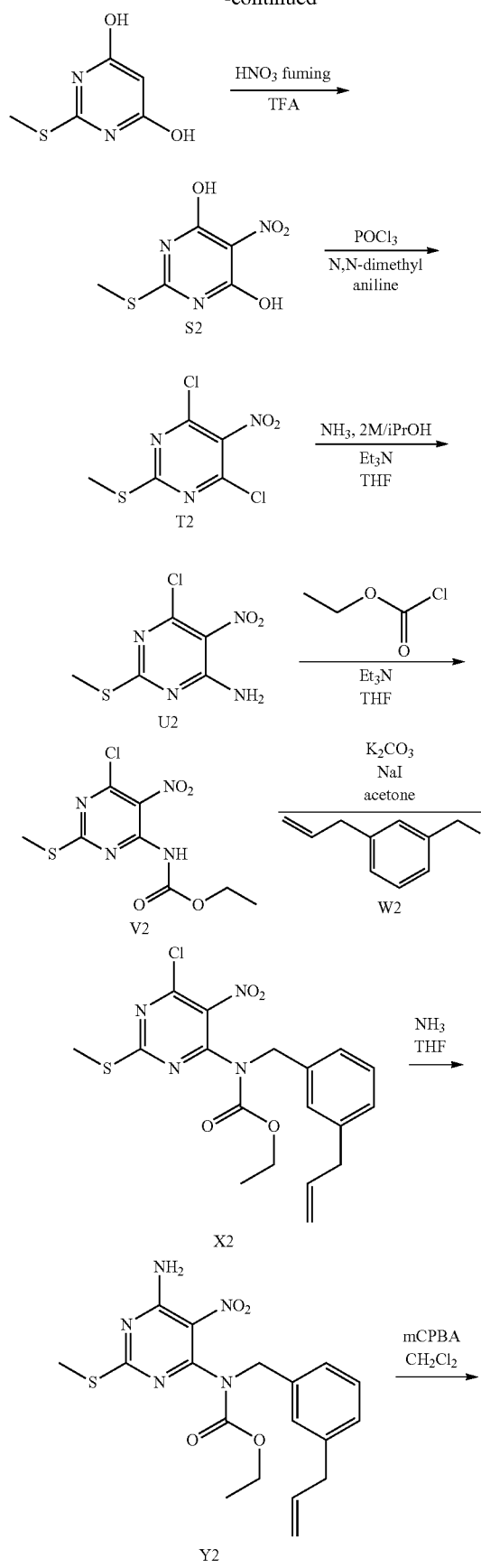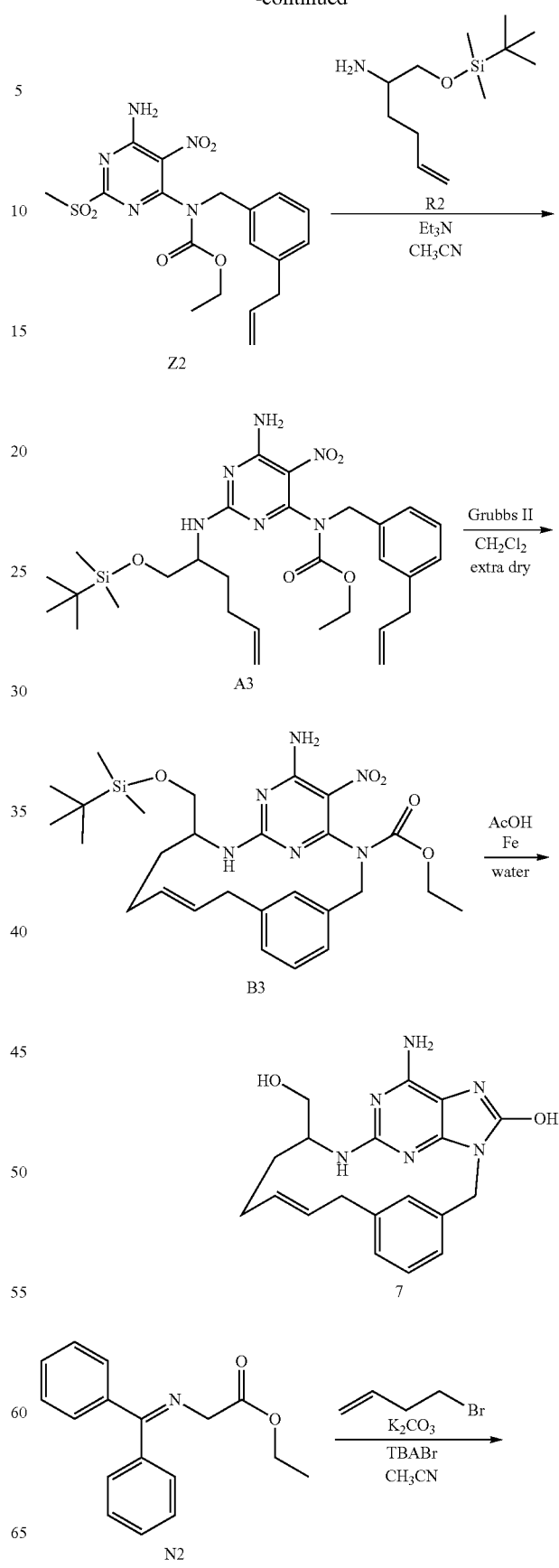

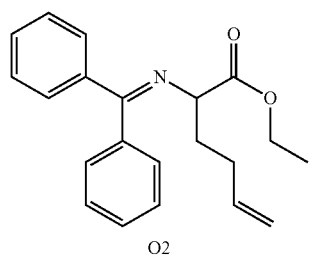

O2

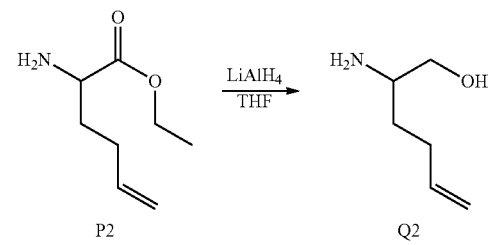

Synthesis of Intermediate O2

4-Bromo-1-butene (8.6 mL, 84.17 mmol) was added to a mixture of N2 (15 g, 56.11 mmol), K₂CO₃ (23.3 g, 168.33 mmol), tetrabutylammonium bromide (1.81 g, 5.61 mmol) in CH₃CN (75 mL). The resulting mixture was stirred at reflux for 18 h. The mixture was cooled to RT. The solvent was evaporated. Water and EtOAc were added. The layers were decanted. The organic layer was dried over MgSO₄, filtered and the solvent was evaporated. The residue was purified by flash chromatography over silica gel (15-40 µm, 120 g, Heptane/EtOAc: 93-7). The pure fractions were collected and concentrated to give 14.8 g (82% yield) of intermediate O2.

Synthesis of Intermediate Q2

Under a N₂ flow, LiAlH₄ (4.4 g, 114.50 mmol) was suspended into THF (150 mL) at 10° C. P2 (9 g, 57.25 mmol) in THF (150 mL) was added drop wise. The reaction was allowed to warm to RT and was stirred at RT for 30 min. The reaction was cooled to −10° C. and was quenched by the addition of water (5 mL), NaOH 3N (5 mL) and again water (14 mL). The suspension was filtered through a pad of Celite®. The Celite® was washed with THF and the filtrate was concentrated under vacuum. The residue was taken up in EtOAc, dried over MgSO₄, filtered and the solvent was evaporated to give 5.3 g (80% yield) of intermediate Q2.

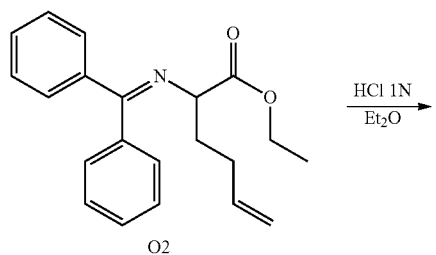

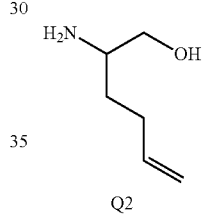

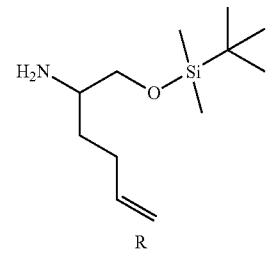

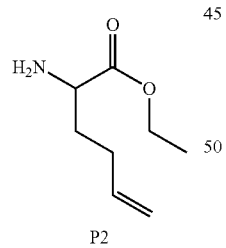

P2

Synthesis of Intermediate P2

At 0° C., HCl 1N (120 mL, 119.47 mmol) was added drop wise to a mixture of O2 (19.2 g, 59.74 mmol) in Et₂O (250 mL). The mixture was stirred at 0° C. for 30 min then stirred vigorously at RT for 12 h. The resulting layers were decanted. The aqueous layer was basified until pH 8 with K₂CO₃ (powder) then extracted with Et₂O (3 times). The aqueous layer was saturated with K₂CO₃ then extracted again with CH₂Cl₂ (2 times). The organic layers were combined, dried over MgSO₄, filtered and the solvent was evaporated to give 7.9 g (84% yield) of intermediate P2.

Synthesis of Intermediate R2

At 0° C., tert-butyldimethylsilyl chloride (1.31 g, 8.68 mmol) was added to a mixture of Q2 (1.0 g, 8.68 mmol), Et₃N (1.33 mL, 9.55 mmol), 4-dimethylaminopyridine (106 mg, 0.87 mmol) in CH₂Cl₂ (30 mL). The mixture was stirred at RT for 24 h. Water was added and the layers were decanted. The organic layer was dried over MgSO₄, filtered and the solvent was evaporated to give 1.70 g (85% yield) of intermediate R2.

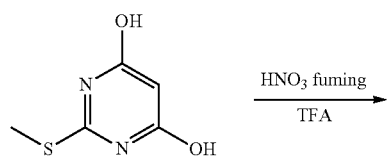

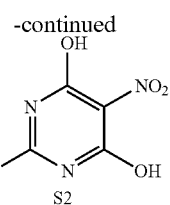

Synthesis of Intermediate S2

A solution of 4,6-dihydroxy-2-methylthiopyrimidine (50 g, 316.09 mmol) in trifluoroacetic acid (210 mL) was stirred at RT for 30 min. The mixture was cooled to 5° C. then $HNO_3$ fuming (19.5 mL, 426.73 mmol) was added drop wise at 5° C. The temperature was maintained at 10-15° C. during the addition. The ice bath was removed and when the temperature reached 20° C., a violent exothermic event occurred (from 20° C. to 45° C. in 5 seconds). The mixture was stirred at RT for 16 h. The mixture was poured into a mixture of water and ice. The precipitate was filtered off and washed with water. The precipitate was dried under vacuum at 50° C. to give 42 g (65% yield) of intermediate S2. This intermediate was directly used in the next step without any further purification.

Synthesis of Intermediate U2

A solution of $NH_3$ 2M in iPrOH (115 mL, 229.31 mmol) was added drop wise to a solution of T2 (36.7 g, 152.87 mmol) and $Et_3N$ (23.4 mL, 168.16 mmol) in THF (360 mL) (the temperature was maintained at RT with an ice-water bath during the addition). The reaction mixture was stirred at RT for 5 h. The mixture was evaporated to dryness. Water and EtOAc were added to the residue. The layers were separated and the aqueous layer was extracted with EtOAc (twice). The combined organic layers were dried over $MgSO_4$, filtered, and the solvent was removed under reduced pressure to give 34.5 g (100% yield) of intermediate U2.

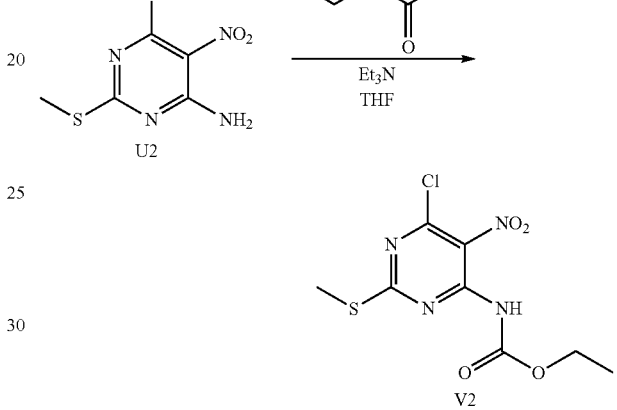

Synthesis of Intermediate V2

Ethyl chloroformate (13.5 mL, 138.90 mmol) was added to a solution of U2 (39.8 g, 126.27 mmol) and $Et_3N$ (26.5 mL, 189.40 mmol) in THF (1300 mL). The mixture was stirred at RT for 6 h and the solvent was partially evaporated under reduced pressure. The residue was taken up in $CH_2Cl_2$ and water. The layers were separated; the aqueous layer was extracted with $CH_2Cl_2$ (twice). The combined organic layers were dried over $MgSO_4$, filtered and the solvent was removed under reduced pressure. The residue was purified by preparative LC on (Irregular SiOH 20-45 µm 1000 g DAVISIL), mobile phase (gradient from 85% heptane, 15% AcOEt to 80% heptane, 20% AcOEt). The pure fractions were collected and concentrated to give 35 g (95% yield) of intermediate V2.

Synthesis of Intermediate T2

N,N-dimethylaniline (76.7 mL, 0.61 mol) was added drop wise to $POCl_3$ (93.7 mL, 1.01 mol) at 0° C. S2 (41 g, 201.79 mmol) was added portion wise at 0° C. then the mixture was warmed to 100° C. for 2 h. The solution was concentrated under vacuum and the residual $POCl_3$ was removed by azeotropic evaporation with toluene (3 times). The resulting oil was taken up in a solution of $CH_2Cl_2$-Heptane (70-30) and was filtered through a glass filter of $SiO_2$. The filtrate was concentrated and the residue was purified by preparative LC on (Irregular SiOH 20-45 µm 1000 g DAVISIL), mobile phase (80% Heptane, 20% $CH_2Cl_2$). The pure fractions were collected and concentrated to give 37.8 g (78% yield) of intermediate T2.

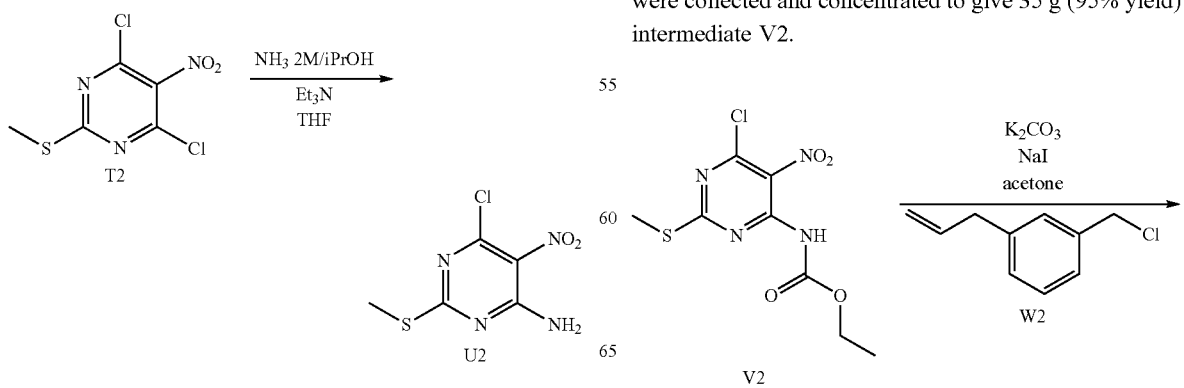

-continued

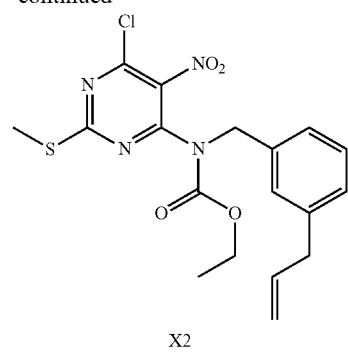

X2

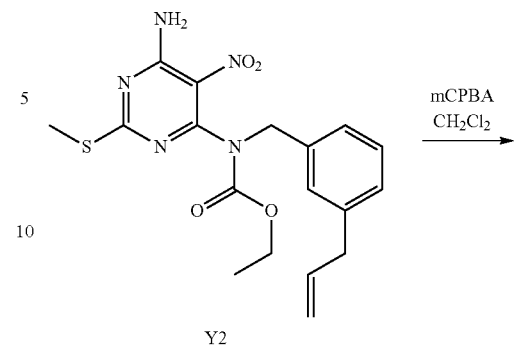

Y2

Synthesis of Intermediate X2

A mixture of V2 (5.0 g, 17.08 mmol), W2 (2.85 g, 17.08 mmol), K$_2$CO$_3$ (3.54 g, 25.6 mmol) and NaI (2.56 g, 17.08 mmol) in acetone (200 mL) were stirred at RT for 48 h. The mixture was filtered off and the filtrate was evaporated to dryness. The residue was purified by flash chromatography over silica gel (15-40 µm, 220 g, CH$_2$Cl$_2$/heptane 50-50). The pure fractions were collected and concentrated to give 7.4 g (100% yield) of intermediate X2.

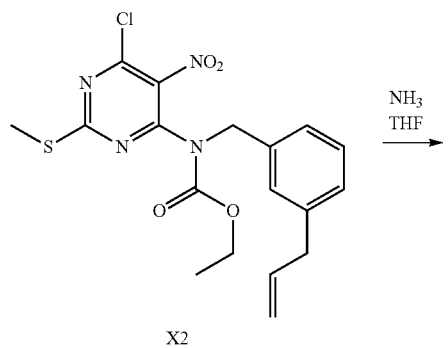

X2

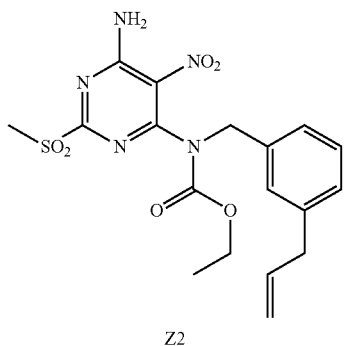

Z2

Synthesis of Intermediate Z2

3-chloroperoxybenzoic acid (2.44 g, 9.91 mmol) in CH$_2$Cl$_2$ (20 mL) was added drop wise to a solution of Y2 (2.0 g, 4.96 mmol) in CH$_2$Cl$_2$ (100 mL) at RT. The mixture was stirred at RT for 20 h. An aqueous solution of Na$_2$S$_2$O$_3$ (5 eq) was added to the mixture. The layers were separated and the aqueous layer was extracted with CH$_2$Cl$_2$ (twice). The combined organic layers were washed with a saturated aqueous solution of NaHCO$_3$, dried over MgSO$_4$, filtered and the solvent was removed under reduced pressure to give 2.70 g (>100% yield) of intermediate Z2. This intermediate was directly used in the next step without further purification.

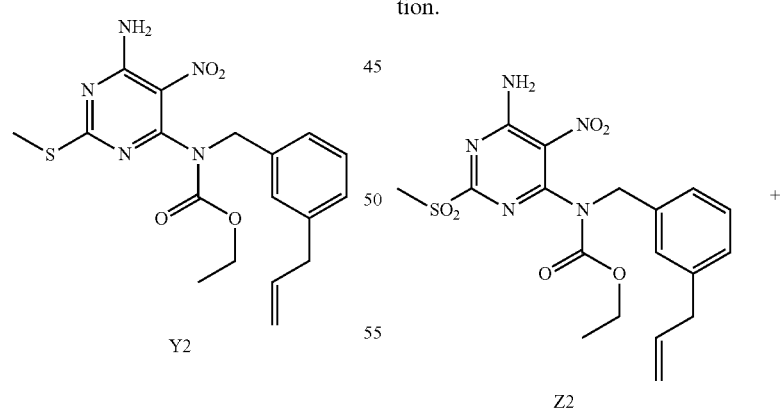

Y2

Z2

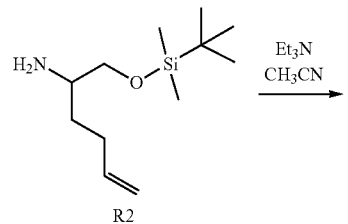

R2

Synthesis of Intermediate Y2

A solution of X2 (7.20 g, 17.03 mmol) and NH$_3$ 30% in water (100 mL) in THF (100 mL) was stirred at RT for 2 h. Solvent was removed under reduced pressure. The residue was suspended in water and extracted with CH$_2$Cl$_2$. The organic layer was washed with water and dried over MgSO$_4$, filtered and the solvent was evaporated under vacuum to give 7.1 g (100% yield) of intermediate Y2 (a yellow oil). This intermediate was directly used in the next step.

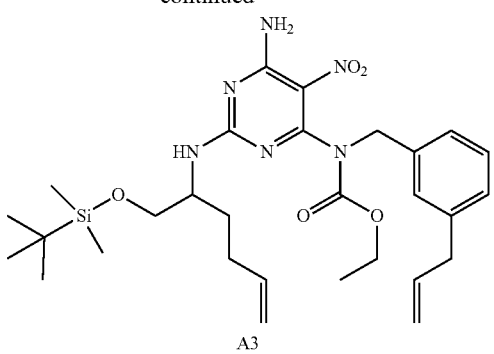

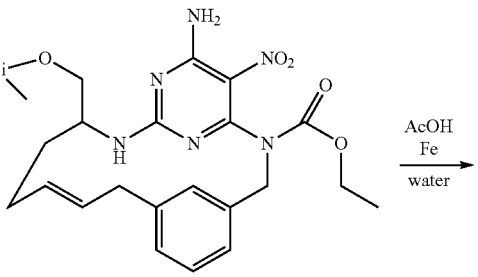

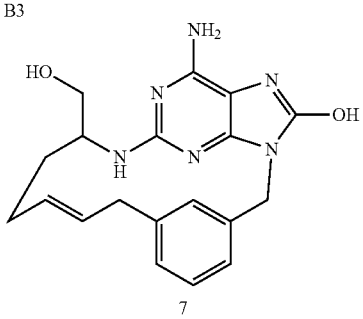

Synthesis of Intermediate A3

A mixture of Z2 (2.16 g, 4.96 mmol), R2 (1.70 g, 7.44 mmol) and Et₃N (1.04 mL, 7.44 mmol) in CH₃CN (70 mL) was stirred at RT for 2 h. Water was added and the mixture was extracted with EtOAc (twice). The organic layer was washed with brine, dried over MgSO₄, filtered and the solvent was evaporated. The residue was purified by flash chromatography over silica gel (15-40 µm, 90 g, CH₂Cl₂/CH₃OH/99.5-0.5). The pure fractions were collected and concentrated to give 1.10 g (38% yield) of intermediate A3.

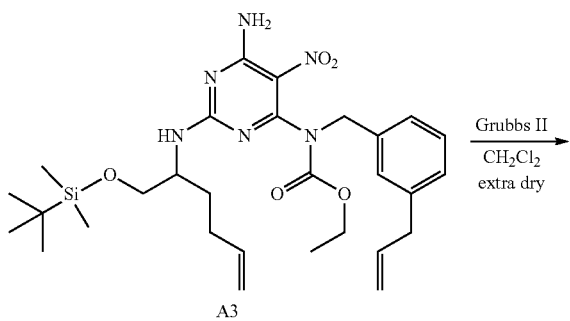

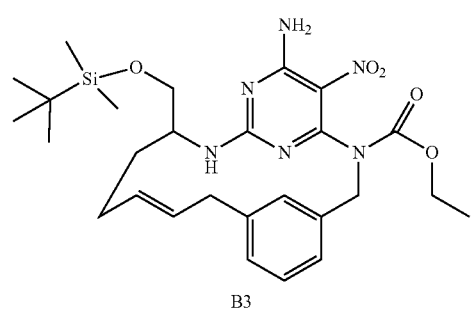

Synthesis of Intermediate B3

A3 (1.05 g, 1.80 mmol) was added to CH₂Cl₂ extra dry (230 mL) and the resulting mixture was degassed by bubbling N₂ through the solution for 30 min. Grubbs catalyst 2$^{nd}$ generation (153 mg, 0.18 mmol) was added in one portion and the mixture was stirred at RT under N₂ flow for 24 h. The mixture was concentrated. The residue was purified by preparative LC on (irregular SiOH 15-40 µm 300 g MERCK), mobile phase (80% heptane, 20% AcOEt). The pure fractions were collected and concentrated to give 0.70 g (70% yield) of intermediate B3.

Synthesis of Final Compound 7

Fe (385 mg, 6.90 mmol) was added to a mixture of B3 (640 mg, 1.15 mmol) in AcOH (6.8 mL) and water (1.36 mL). The mixture was heated at 100° C. using one single mode microwave (Biotage Initiator) with a power output ranging from 0 to 400 W for 40 min. The mixture was filtered on a pad of Celite® and rinsed with AcOH. The filtrate was concentrated under vacuum and co-evaporated with toluene (twice) to dryness. The residue was taken up in CH₂Cl₂/MeOH/NH₄OH 90-10-0.5. A precipitate was filtered (the precipitate (1.0 g) contained expected compound) and the filtrate was evaporated to be purified by chromatography;

The residue (of filtrate) was purified by flash chromatography over silica gel (15-40 µm, 80 g, CH₂Cl₂/CH₃H/NH₄H: 90-10-0.5). The pure fractions were collected and evaporated to give 52 mg of fraction 1.

The precipitate previously obtained was purified by chromatography (the compound and SiO₂ were mixed before elution). The residue was purified by flash chromatography over silica gel (15-40 µm, 25 g, CH₂Cl₂/CH₃H/NH₄H: 90-10-0.5). The pure fractions were collected and concentrated to give 80 mg of fraction 2.

Fraction 1 and fraction 2 were combined, and then solidified from CH₃CN to afford 95 mg (23% yield) of compound 7 (E isomer with 3.5% of Z isomer).

OVERALL SCHEME IN THE PREPARATION OF FINAL PRODUCTS: METHOD 8

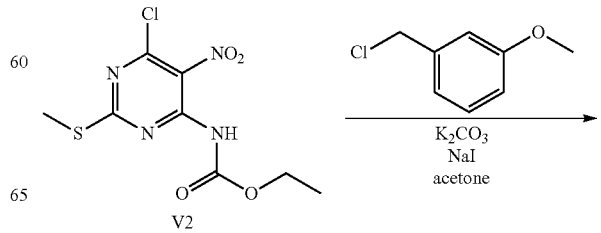

-continued

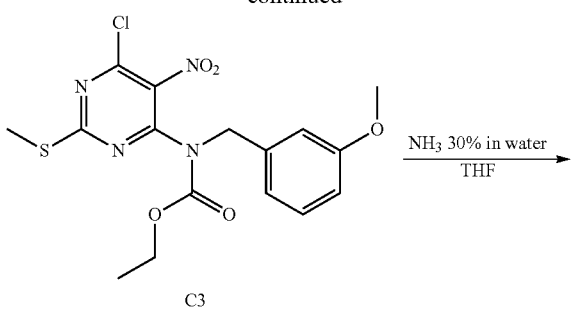

C3

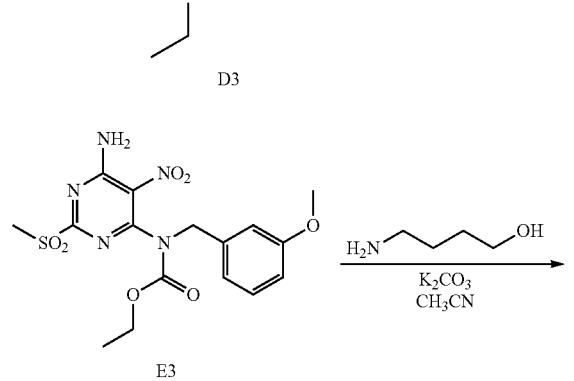

D3

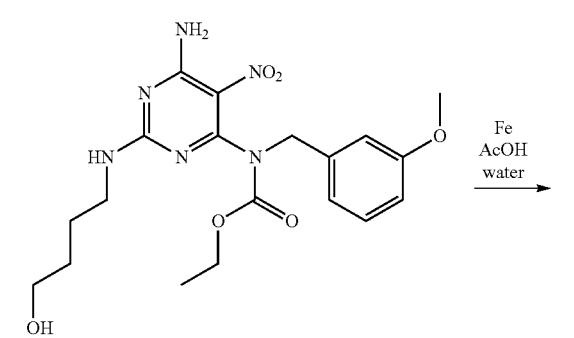

E3

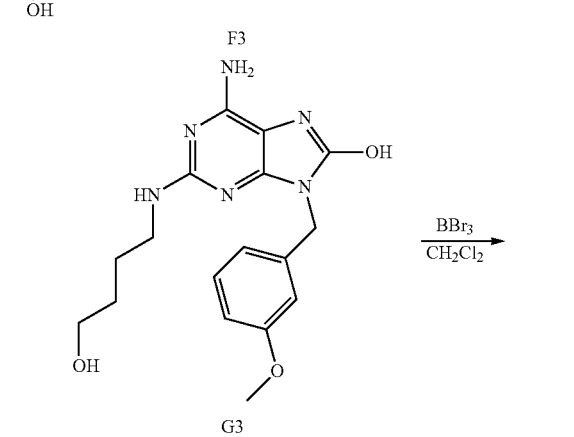

F3

G3

-continued

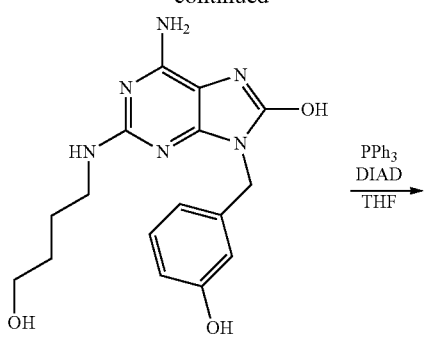

H3

8

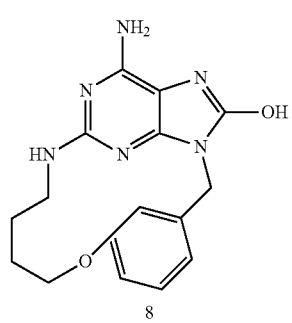

V2

C3

Synthesis of Intermediate C3

V2 (1.7 g, 5.8 mmol), 3-methoxybenzyl chloride (0.93 mL, 6.4 mmol), K₂CO₃ (2 g, 14.5 mmol) and sodium iodide (0.87 g, 5.8 mmol) in acetone (60 mL) were stirred at RT for 16 h. The solution was filtered off and the filtrate was evaporated under reduced pressure. The crude product was purified by preparative LC (irregular SiOH 15-40 μm, 80 g Merck, mobile phase heptane/CH₂Cl₂ 70/30). The pure fractions were collected and concentrated to give 1.4 g (58% yield) of intermediate C3.

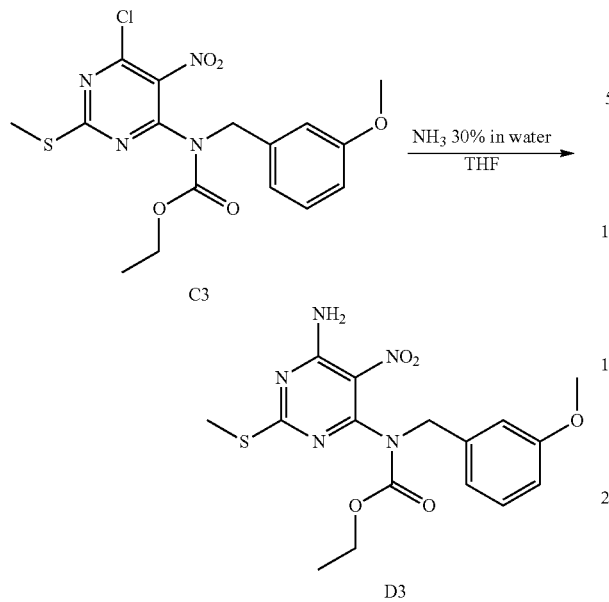

C3

D3

Synthesis of Intermediate D3

C3 (1.4 g, 3.4 mmol) was stirred in NH$_3$ 30% in water (30 mL) and THF (30 mL) at RT for 16 h. The mixture was concentrated and the residue was dried by azeotropic evaporation with EtOH (twice) to give 1.3 g (97% yield). The crude product was used without further purification in the next step.

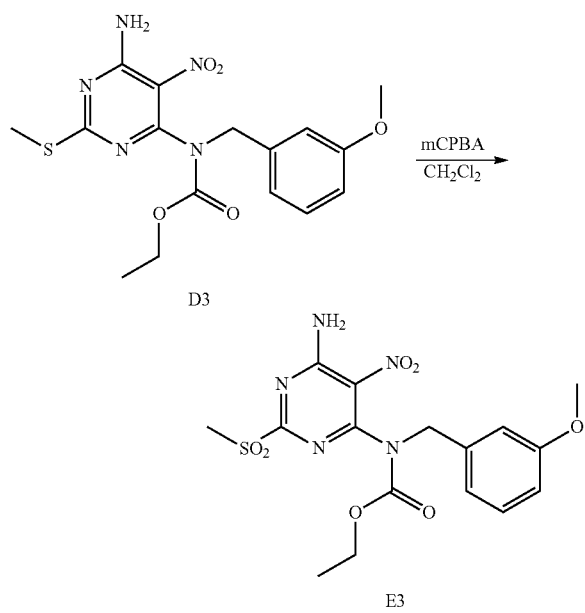

D3

E3

Synthesis of Intermediate E3

3-chloroperoxybenzoic acid (2.04 g, 8.3 mmol) was added to a solution of D3 (1.3 g, 3.3 mmol) in CH$_2$Cl$_2$ (80 mL) at RT. The mixture was stirred at RT for 20 h. An aqueous solution of Na$_2$S$_2$O$_3$ (2.61 g, 16.52 mmol) was added to the mixture. The layers were separated and the aqueous layer was extracted with CH$_2$Cl$_2$ (twice). The combined organic layers were washed with a saturated aqueous solution of NaHCO$_3$, dried over MgSO$_4$, filtered and the solvent was evaporated to give 1.4 g (100% yield) of intermediate E3.

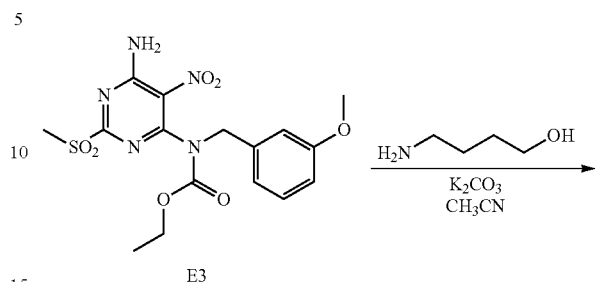

E3

F3

Synthesis of Intermediate F3

A mixture of E3 (1.4 g, 3.3 mmol), 4-amino-1-butanol (0.45 mL, 3 mmol) and K$_2$CO$_3$ (414 mg, 4.9 mmol) in CH$_3$CN (65 mL) was stirred at 80° C. for 1 h30. The salts were filtered and water was added to the filtrate. The mixture was extracted with CH$_2$Cl$_2$ (twice). The organic layer was dried over MgSO$_4$, filtered and the solvent was evaporated. The crude was purified by preparative LC (irregular SiOH 15-40 μm, 80 g Merck, mobile phase CH$_2$Cl$_2$/MeOH/NH$_4$OH 98/2/0.1). The pure fractions were collected and concentrated to give 1.2 g (84% yield) of intermediate F3.

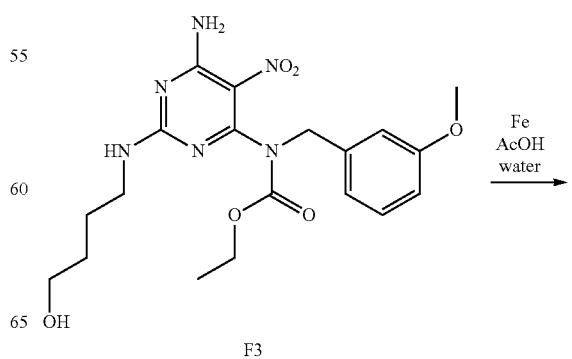

F3

-continued

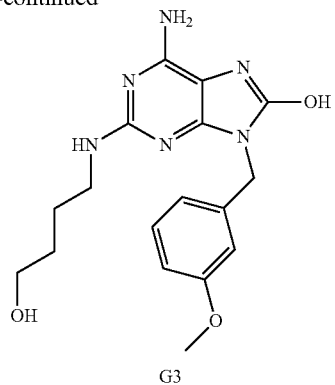

G3

Synthesis of Intermediate G3

Fe (1.54 g, 27.6 mmol) was added to a mixture of F3 (1.2 g, 2.76 mmol) in AcOH (24 mL) and water (8.6 mL). The mixture was stirred vigorously at RT for 24 h. The reaction mixture was concentrated under vacuum and the residue was diluted with EtOAc and water. The mixture was filtered on a pad of Celite® and rinsed with EtOAc. The layers were separated and the organic layer was washed with a saturated aqueous solution of NaHCO₃ (twice), then brine, dried over MgSO₄, filtered and concentrated under vacuum. The residue was purified by chromatography over silica gel column (15-40 µm, 40 g) in CH₂Cl₂/MeOH/NH₄OH (90/10/0.5). The pure fractions were collected and concentrated. This fraction was solidified from CH₃CN/diisopropylether to give 0.70 g (71% yield) of intermediate G3.

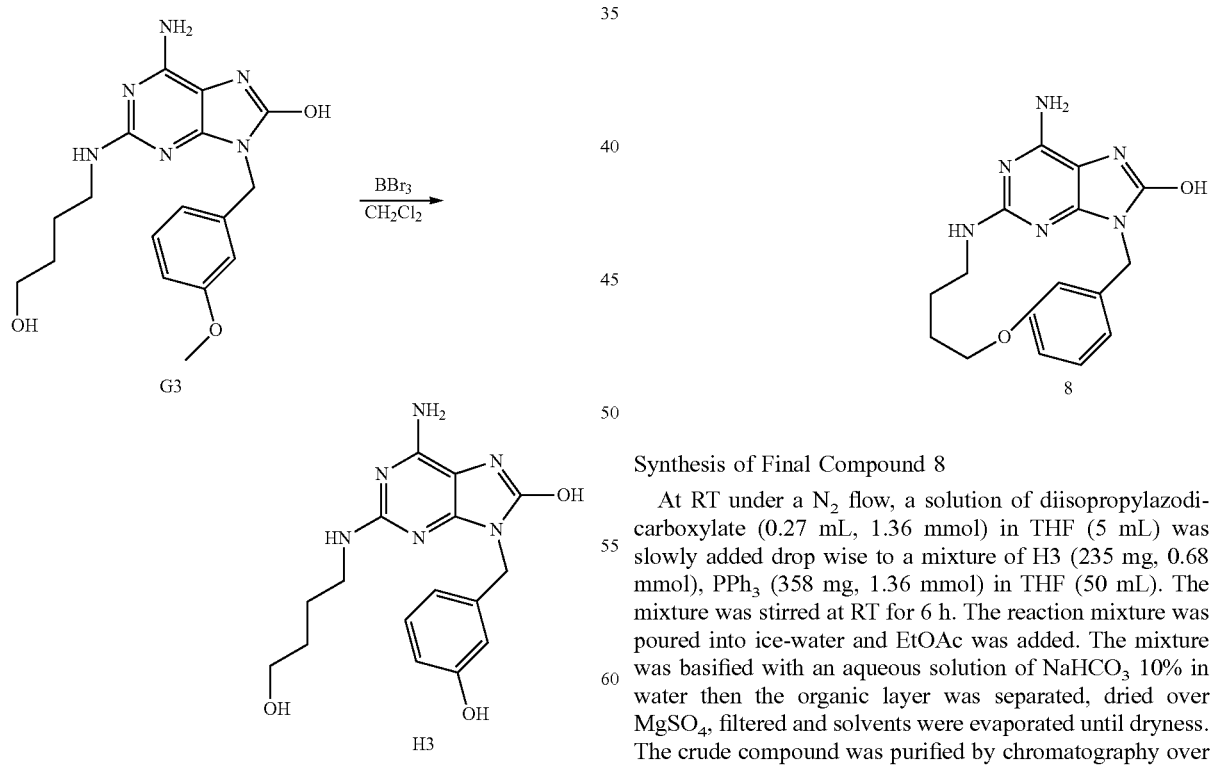

Synthesis of Intermediate H3

At −60° C., under a N₂ flow, BBr₃ (5.6 mL, 5.6 mmol) was added drop wise to a mixture of G3 (400 mg, 1.1 mmol) in CH₂Cl₂ (40 mL). The mixture was stirred at −60° C. for 1 h, and then at RT for 12 h, under a N₂ flow. 1 mL of CH₃OH was added drop wise at 0° C. The mixture was then poured into a saturated solution of K₂CO₃ in water. The mixture was extracted with a solution of CH₂Cl₂/MeOH. The organic layer was dried over MgSO₄, filtered and the solvent was evaporated. The crude compound was purified by chromatography over silica gel column (15-40 µm, 40 g) in CH₂Cl₂/MeOH/NH₄OH (90/10/0.5). The pure fractions were collected and concentrated. The residue was solidified from CH₃CN/diisopropylether to give 265 mg (69% yield) of intermediate H3.

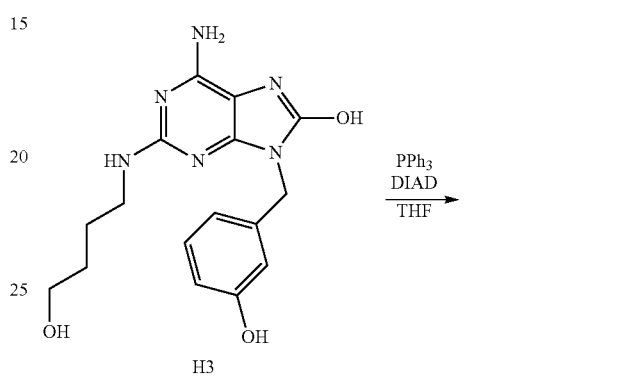

Synthesis of Final Compound 8

At RT under a N₂ flow, a solution of diisopropylazodicarboxylate (0.27 mL, 1.36 mmol) in THF (5 mL) was slowly added drop wise to a mixture of H3 (235 mg, 0.68 mmol), PPh₃ (358 mg, 1.36 mmol) in THF (50 mL). The mixture was stirred at RT for 6 h. The reaction mixture was poured into ice-water and EtOAc was added. The mixture was basified with an aqueous solution of NaHCO₃ 10% in water then the organic layer was separated, dried over MgSO₄, filtered and solvents were evaporated until dryness. The crude compound was purified by chromatography over silica gel column (15-40 µm, 40 g) in CH₂Cl₂/MeOH/NH₄OH (95/5/0.1). The pure fractions were collected and evaporated. The residue was solidified from CH₃CN/diisopropylether to give 75 mg (34% yield) of compound 8.

OVERALL SCHEME IN THE PREPARATION OF FINAL PRODUCTS: METHOD 9

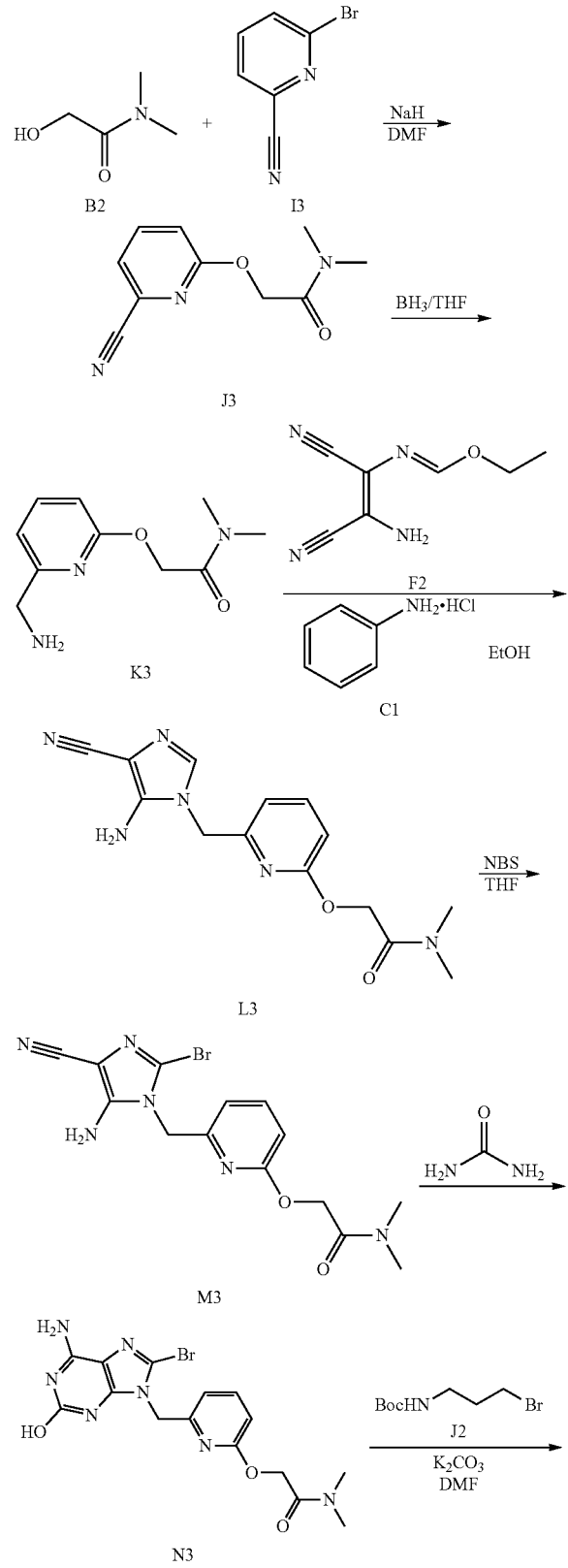

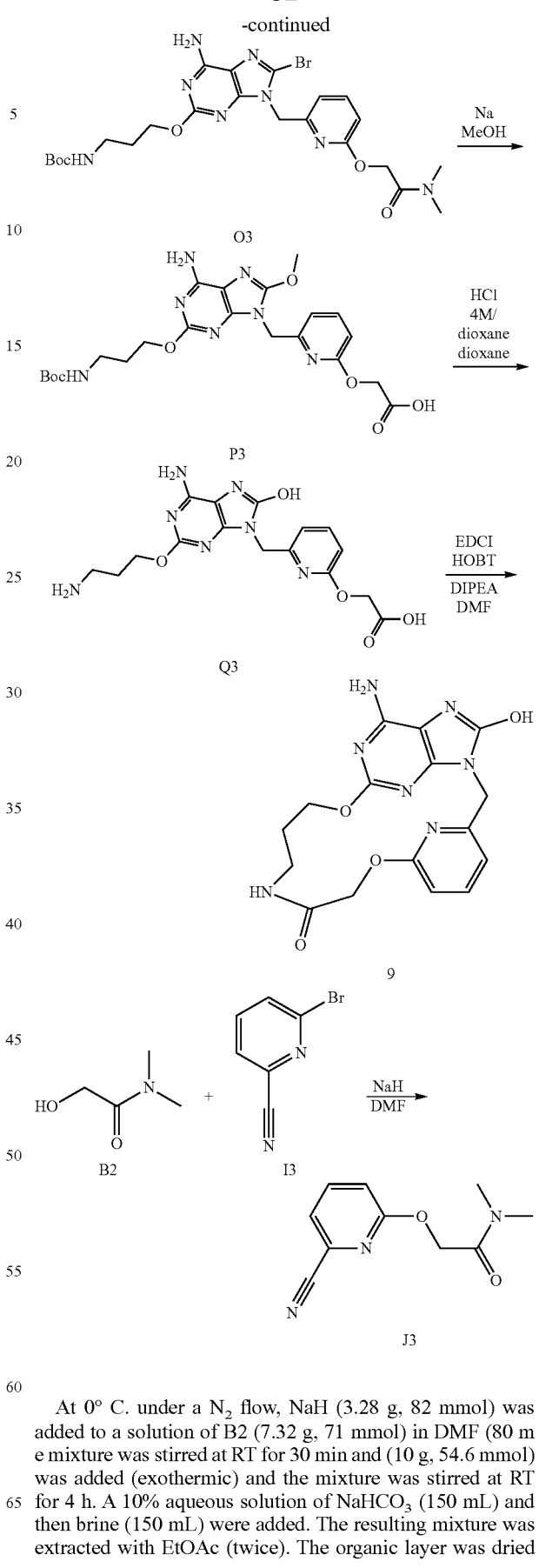

At 0° C. under a N$_2$ flow, NaH (3.28 g, 82 mmol) was added to a solution of B2 (7.32 g, 71 mmol) in DMF (80 m e mixture was stirred at RT for 30 min and (10 g, 54.6 mmol) was added (exothermic) and the mixture was stirred at RT for 4 h. A 10% aqueous solution of NaHCO$_3$ (150 mL) and then brine (150 mL) were added. The resulting mixture was extracted with EtOAc (twice). The organic layer was dried over MgSO₄, filtered and the solvent was evaporated. The residue was taken up in the minimum of AcOEt, the precipitate was filtered off and dried to give intermediate J3 (9.04 g, 81% yield).

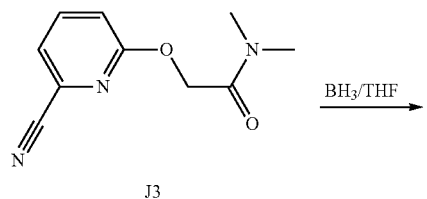

Synthesis of Intermediate K3

At 0° C., under a N₂ flow, BH₃/THF (110 mL, 39 mmol) was added drop wise to a solution of J3 (9.0 g, 43.9 mmol) in THF (60 mL). The mixture was stirred at RT for 2 h then quenched with HCl 2M and stirred at RT for 12 h. The reaction mixture was evaporated until dryness. The residue was taken up in CH₂Cl₂—CH₃OH—NH₄OH 90-10-1. The precipitate was filtered off (minerals) and the filtrate was concentrated. Purification was carried out by flash chromatography over silica gel (15-40 μm, 330 g, CH₂Cl₂/CH₃OH/NH₄OH: 96/4/0.5 to 90/10/0.5). The pure fractions were collected and evaporated to dryness to give intermediate K3 (6.2 g, 73% yield).

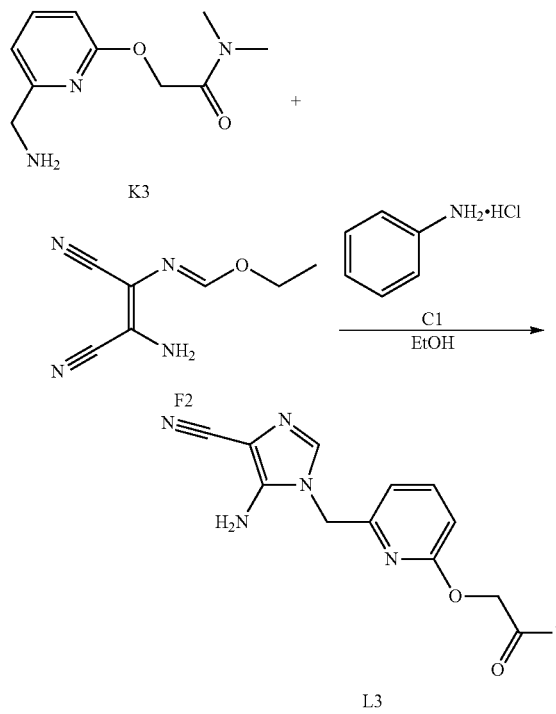

Synthesis of Intermediate L3

K3 (6.2 g, 29.5 mmol) in EtOH (30 mL) was added drop wise to a solution of F2 (4.6 g, 28 mmol) and aniline hydrochloride (56 mg, 0.43 mmol) in EtOH (25 mL) at 10° C. The reaction mixture was stirred at RT for 20 h. An aqueous solution of NaOH 1M (25 mL) was added drop wise to the solution at 10° C. and the resulting mixture was stirred at RT for 1 h. The precipitate was filtered off, washed with a minimum of cold EtOH and dried under vacuum. Mother layers were concentrated, a second precipitate was obtained in CH₂Cl₂, filtered and dried under vacuum. The two batches were combined to give intermediate L3 (2.44 g, 29% yield).

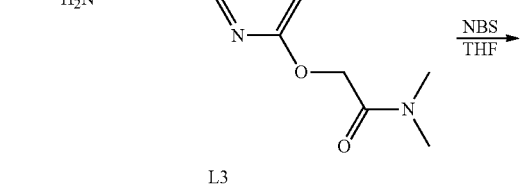

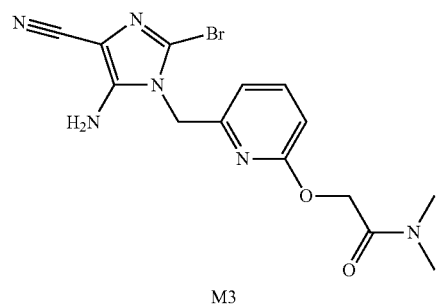

Synthesis of Intermediate M3

A solution of NBS (0.326 g, 1.83 mmol) in THF (15 mL) was added drop wise over 25 min to a solution of L3 (0.5 g, 1.67 mmol) in THF (15 mL) at 0° C. The mixture was stirred at 0° C. for 30 min and then at RT for 45 min. The mixture was taken up in CH₂Cl₂, washed with a saturated aqueous solution of NaHCO₃, dried over MgSO₄, filtered and evaporated under vacuum. This crude compound was solidified from CH₃CN. The precipitate was filtered off and dried to give intermediate M3 (216 mg, 34% yield).

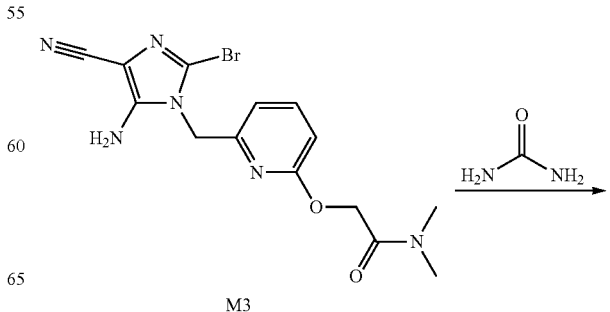

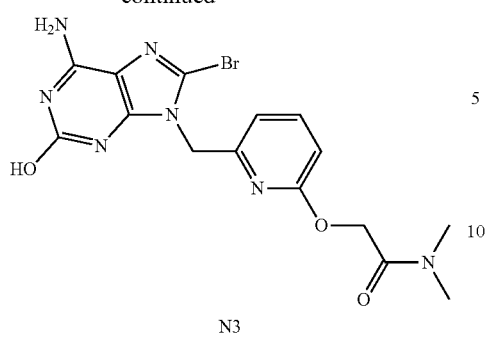

N3

Synthesis of Intermediate N3

A mixture of M3 (1.04 g, 2.74 mmol) in urea (4.9 g, 82.28 mmol) was heated at 160° C. for 4 h. Urea (3 g, 2.64 mmol) was added again and the mixture was stirred at 160° C. for 12 h. The mixture was cooled to RT and water was added. The precipitate was triturated and filtered off, washed with water and dried under vacuum at 60° C. to give intermediate N3. The crude compound was used directly in the next step.

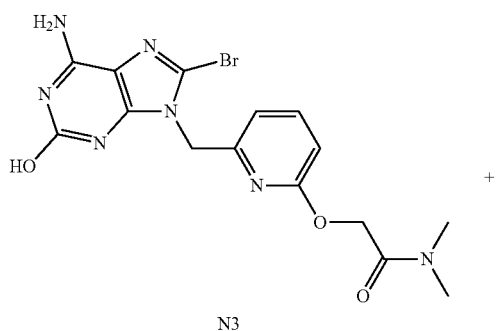

O3

Synthesis of Intermediate O3

A mixture of N3 (crude), J2 (1.557 g, 6.54 mmol), $K_2CO_3$ (904 mg, 6.54 mmol) in DMF (30 mL) was stirred at 50° C. for 12 h. The solvent was evaporated. The residue was taken up in EtOAc. The organic layer was washed with water, dried over $MgSO_4$, filtered and the solvent was evaporated. The crude compound was purified by preparative LC on (irregular SiOH 15-40 μm 300 g Merck), mobile phase: 0.3% $NH_4OH$, 97% $CH_2Cl_2$, 3% MeOH to give intermediate O3 (280 mg, 11% yield).

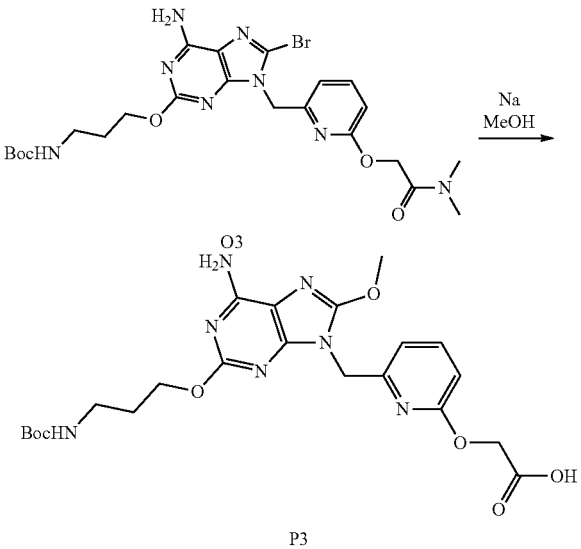

P3

Synthesis of Intermediate P3

At RT, Na (167 mg, 7.25 mmol) was added to MeOH (11 mL). The mixture was stirred until Na was in solution (exothermic). O3 (280 mg, 0.48 mmol) was added and the mixture was stirred at 50° C. for 16 h under a $N_2$ flow. Water was added and the pH was adjusted (with HCl 1N) to 5-6. The aqueous layer was extracted with EtOAc. The aqueous phase was saturated with $K_2CO_3$ powder and extracted with AcOEt. The combined organic phases were dried over $MgSO_4$, filtered and solvent was evaporated to give intermediate P3 (140 mg, 58% yield).

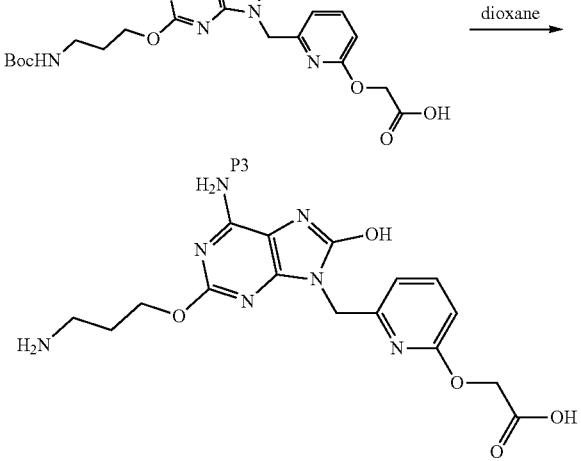

Q3

Synthesis of Intermediate Q3

At 0° C., HCl (4M in dioxane) (0.7 mL, 2.78 mmol) was added drop wise to a mixture of P3 (140 mg, 2.78 mmol) in dioxane (5 mL). The mixture was stirred at RT for 12 h. The solvent was evaporated until dryness to give intermediate Q3. The crude compound was used in the next step without any further purification.

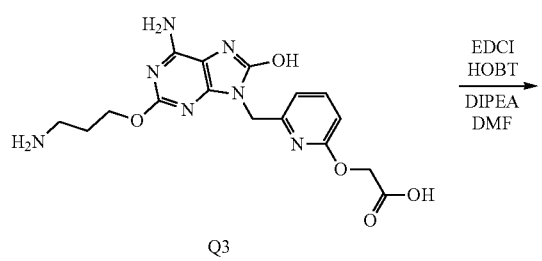

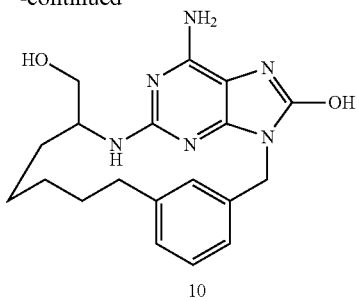

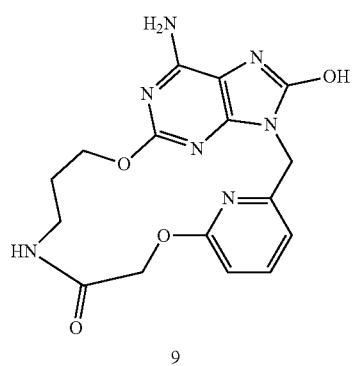

Synthesis of Final Compound 9

1-(3-Dimethylaminopropyl)-3-ethylcarbodiimide hydrochloride (318 mg, 1.66 mmol) and hydroxybenzotriazole (224 mg, 1.66 mmol) were slowly added to a mixture of Q3 (crude), diisopropylethylamine (0.476 mL, 2.76 mmol) in DMF (170 mL). The mixture was stirred at RT for 24 h. The solvent was evaporated until dryness. The residue was taken up in water. The precipitate was filtered off, washed with water and dried. The crude compound was purified by reverse phase on (X-Bridge-C18 5 μm 30*150 mm), mobile phase (Gradient from 90% NH$_4$HCO$_3$ 0.5%, 10% CH$_3$CN to 0% NH$_4$HCO$_3$ 0.5%, 100% CH$_3$CN) to give final compound 9 (37 mg, 18% yield).

OVERALL SCHEME IN THE PREPARATION OF FINAL PRODUCTS: METHOD 10

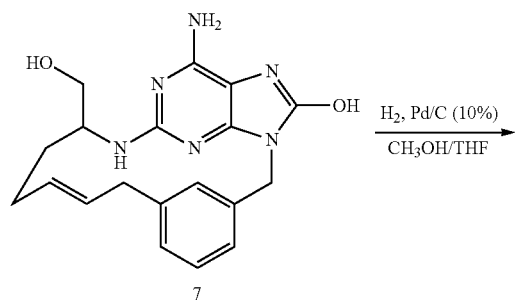

Synthesis of Final Compound 10:

A mixture of compound 7 (100 mg, 0.27 mmol), Pd/C (10%) (14.5 mg, 0.014 mmol) in CH$_3$OH/THF 50/50 (10 mL) was hydrogenated under an atmospheric pressure of H$_2$ for 4 h. The catalyst was removed by filtration through a filter (chromafil Xtra 0.45 m). The filtrate was concentrated. This fraction was solidified from CH$_3$CN, the precipitate was filtered off and dried to give final compound 10 (81 mg, 81% yield).

OVERALL SCHEME IN THE PREPARATION OF FINAL PRODUCTS: METHOD 11

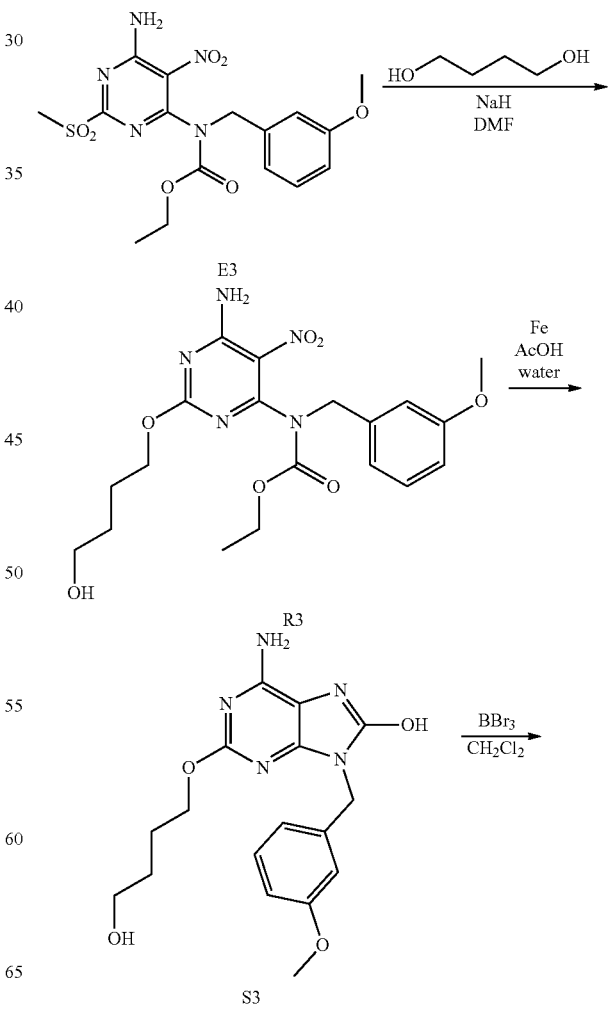

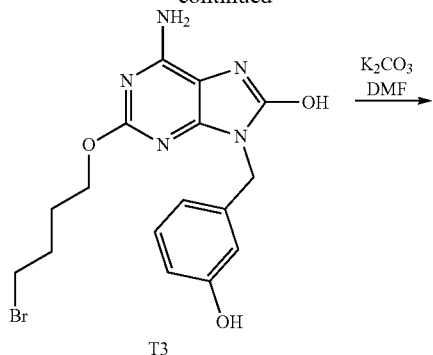

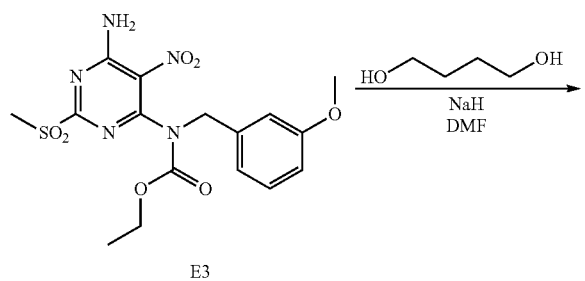

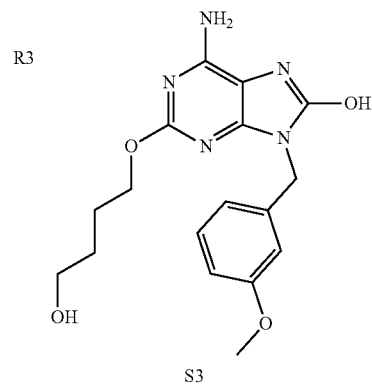

Synthesis of Intermediate S3

Iron powder (2.27 g, 40.65 mmol) was added to a mixture of R3 (1.77 g, 4.07 mmol) in AcOH (35 mL) and water (11 mL). The mixture was stirred at 50° C. for 8 h. The reaction mixture was diluted with water and was basified with $K_2CO_3$ 10% in water. EtOAc and $CH_3OH$ were added and the resulting mixture was filtered through a pad of Celite®. The Celite® was washed with $CH_2Cl_2/CH_3OH$ (80/20). The filtrate was decanted. The organic layer was dried over $MgSO_4$, filtered and the solvent was evaporated. The fraction was taken up in $CH_3CN$, the precipitate was filtered off and dried to give intermediate S3 (1.2 g, 82% yield).

Synthesis of Intermediate R3

At 0° C. under a $N_2$ flow, NaH (705 mg, 17.6 mmol) was added to a solution of 1,4-butanediol (3.2 g, 35.26 mmol) in DMF (30 mL). The mixture was stirred for 30 min at RT, then E3 (2.5 g, 5.87 mmol) was added. The mixture was stirred at RT for 1 h. Ice was added and the mixture was extracted with EtOAc. The organic layer was dried over $MgSO_4$, filtered and the solvent was evaporated. Purification was carried out by flash chromatography over silica gel (15-40 μm, 80 g, $CH_2Cl_2/CH_3OH/NH_4OH$: 97/3/0.1). The pure fractions were collected and evaporated to dryness to give intermediate R3 (1.78 g, 70% yield).

Synthesis of Intermediate T3

At −60° C. under a N$_2$ flow, BBr$_3$ (13.6 mL, 13.6 mmol) was added drop wise to a mixture of S3 (980 mg, 2.727 mmol) in CH$_2$Cl$_2$ (40 mL). The mixture was stirred at −60° C. for 1 h under a N$_2$ flow. The mixture was stirred 5 h at 0° C. 5 mL of CH$_3$OH was added drop wise at −60° C. The mixture was then poured into a saturated solution of K$_2$CO$_3$. The mixture was extracted with CH$_2$Cl$_2$/CH$_3$OH. The organic layer was dried over MgSO$_4$, filtered and the solvent was evaporated to give intermediate T3 (0.55 g, 49% yield), which was directly used in the next step without further purification.

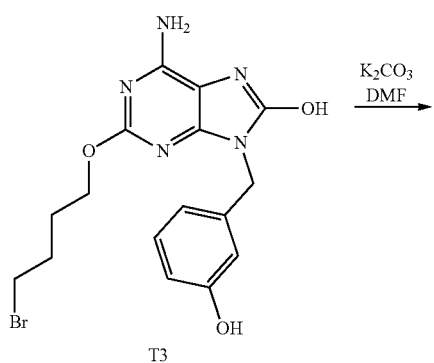

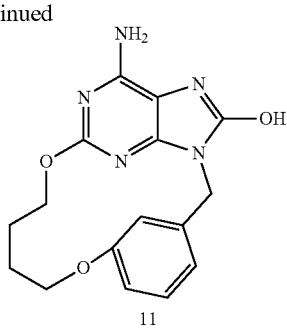

Synthesis of Final Compound 11

A mixture of T3 (537 mg, 1.32 mmol), K$_2$CO$_3$ (182 mg, 1.32 mmol) in DMF (71 mL) was stirred at 80° C. for 12 h. The crude mixture was filtered off and the filtrate was concentrated under reduced pressure. The residue was taken up in the minimum of DMF and 5 g of SiO$_2$ 35-70 μm was added. The resulting suspension was evaporated until dryness and put on the top of a 50 g chromatography column and eluted with a gradient of CH$_2$Cl$_2$—CH$_3$OH—NH$_4$OH 95-5-0.5 to 90-10-0.5. The fractions containing the expected compounds were combined and concentrated under reduced pressure. The solid was crystallized from CH$_3$CN, the precipitate was filtered off and dried to give final compound 11 (33 mg, 8% yield).

OVERALL SCHEME IN THE PREPARATION OF FINAL PRODUCTS: METHOD 12

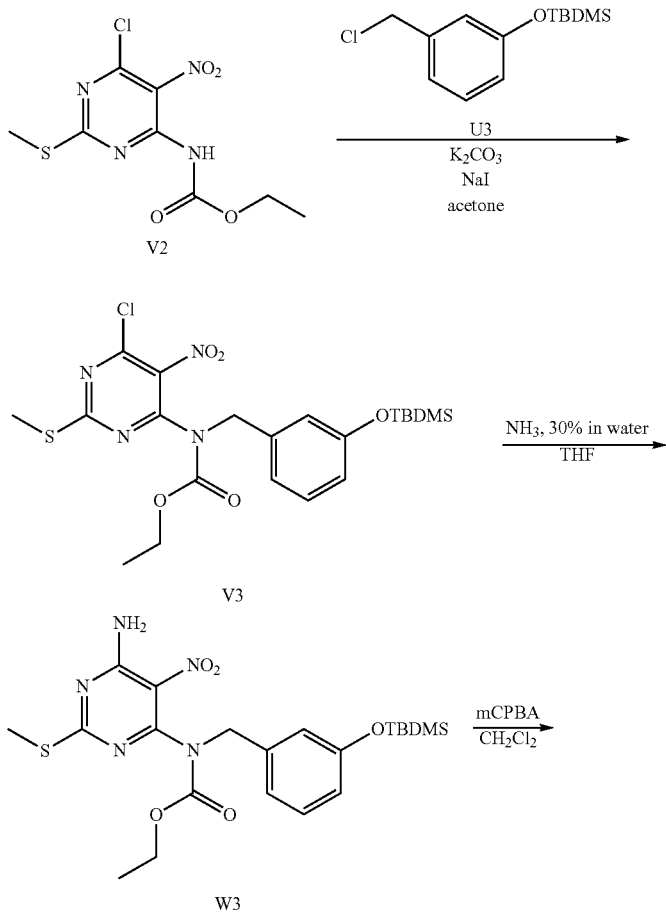

-continued
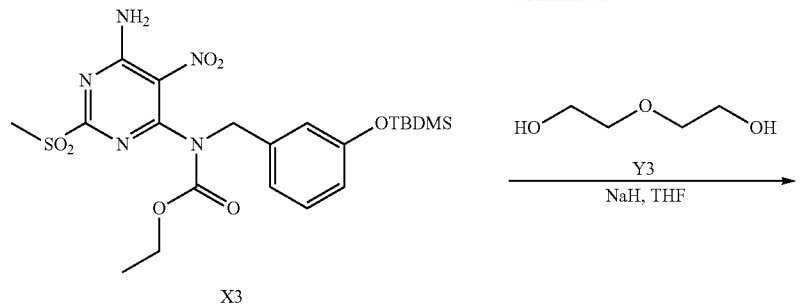
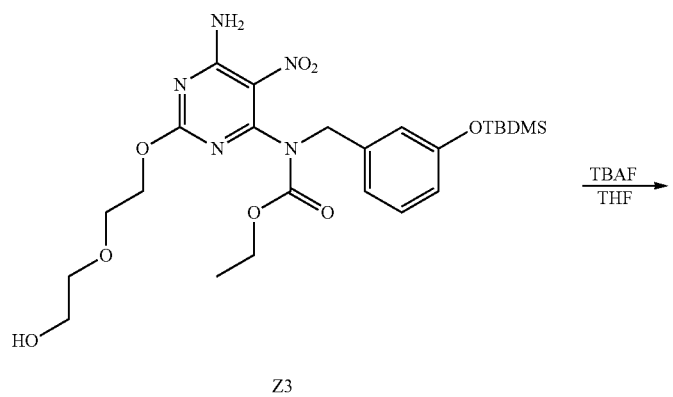
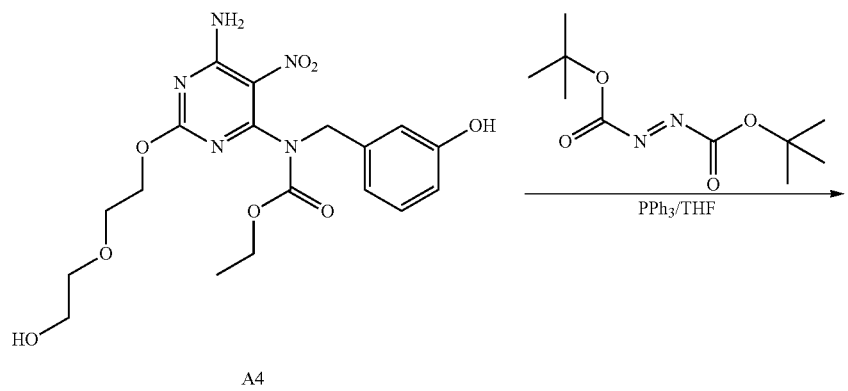
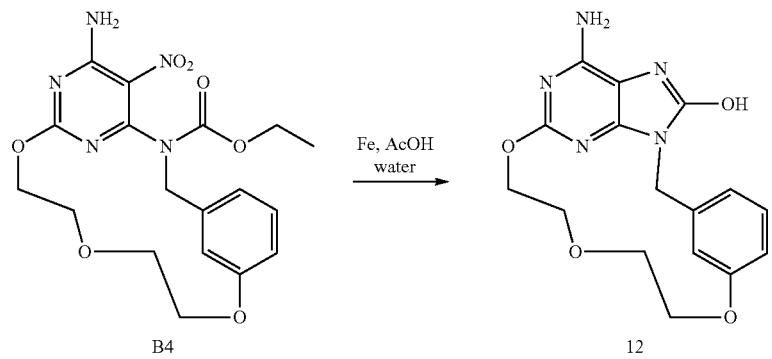

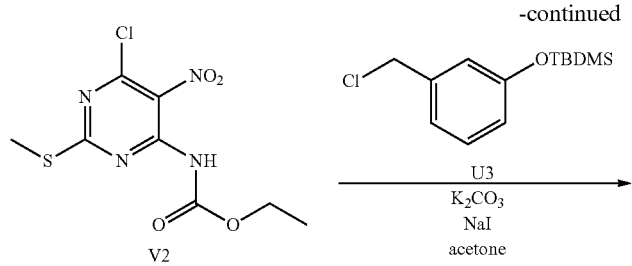
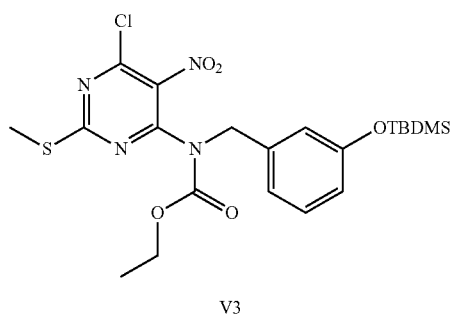

Synthesis of Intermediate V3

V2 (1.4 g, 4.8 mmol), U3 (1.44 g, 4.8 mmol), $K_2CO_3$ (1.65 g, 12 mmol) and NaI (0.72 g, 4.8 mmol) in acetone (60 mL) were stirred at RT for 16 h. The solution was filtered off and the filtrate was evaporated under reduced pressure. The crude product was purified by preparative LC (irregular SiOH 15-40 μm, 80 g Merck, mobile phase heptane/$CH_2Cl_2$ 85/15) to give intermediate V3 (2.3 g, 94% yield).

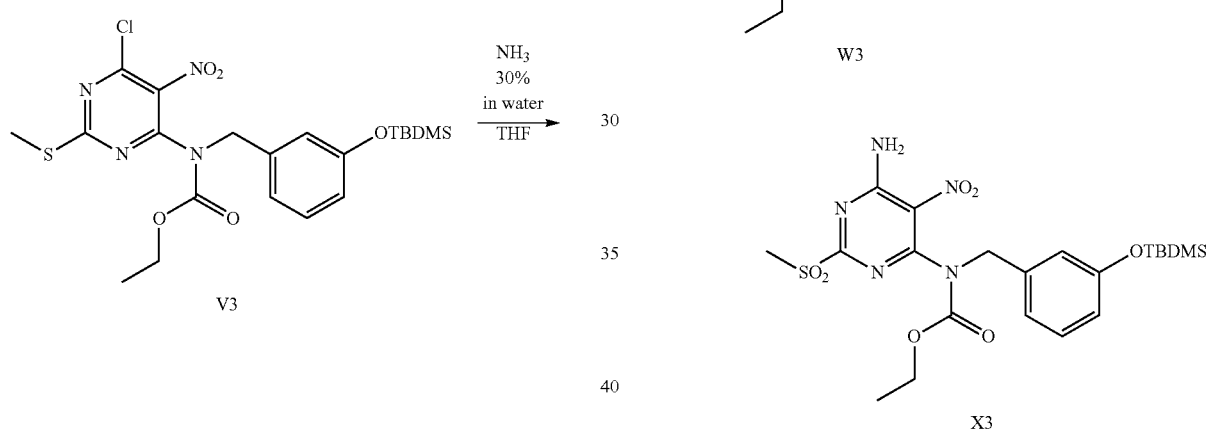

Synthesis of Intermediate W3

V3 (2.3 g, 4.5 mmol) was stirred in $NH_3$ (30% in water) (40 mL) and THF (40 mL) at RT for 16 h. The mixture was concentrated under vacuum and the residue was dried by azeotropic evaporation of EtOH (twice). The crude product was purified by preparative LC (irregular SiOH 15-40 μm, 40 g Merck, mobile phase heptane/AcOEt 85/15) to give intermediate W3 (1.25 g, 56% yield).

Synthesis of Intermediate X3

3-chloroperoxybenzoic acid (2.04 g, 8.2 mmol) was added to a solution of W3 (1.3 g, 3.3 mmol) in $CH_2Cl_2$ (70 mL) at RT. The mixture was stirred at RT for 20 h. An aqueous solution of $Na_2S_2O_3$ (5 eq) was added to the mixture. The two layers were separated and the aqueous layer was extracted with $CH_2Cl_2$ (twice). The combined organic layers were washed with a saturated aqueous solution of $NaHCO_3$, dried over $MgSO_4$, filtered and the solvent was removed under reduced pressure. The crude product was used directly in the next step without any further purification.

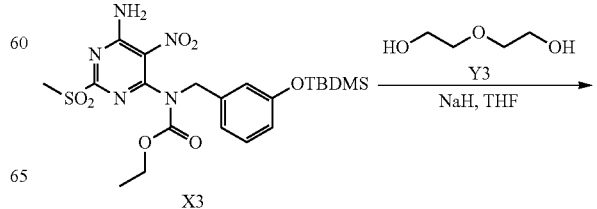

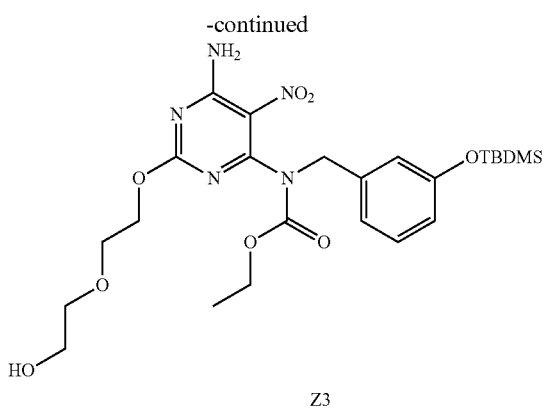

Z3

Synthesis of Intermediate Z3

At 0° C. under a $N_2$ flow, NaH (457 mg, 11.4 mmol) was added to a solution of Y3 (2.1 ml, 22.8 mmol) in THF (100 mL). The mixture was stirred for 30 min at RT, then X3 (2 g, 3.8 mmol) in solution into 20 ml of THF was added at 0° C. The mixture was stirred at 5° C. for 15 min. Ice was added and the mixture was extracted with EtOAc. The crude compound was purified by chromatography over silicagel (15-40 μm, 80 g) in $CH_2Cl_2$/MeOH/$NH_4OH$ (98/2/0.1) to give intermediate Z3 (1 g, 48% yield).

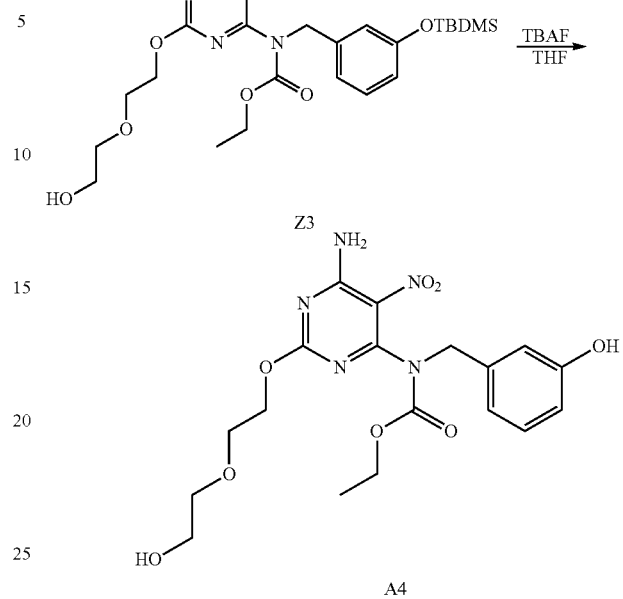

A4

Synthesis of Intermediate A4

Tetrabutylammonium fluoride (0.653 mL, 0.65 mmol) was added drop wise to a solution of Z3 (0.3 g, 0.544 mmol) in THF (10 mL) at RT. The reaction was stirred at RT for 3 h. The mixture was diluted with EtOAc and poured into water. The organic layer was separated, washed with brine, dried over $MgSO_4$, filtered and the solvent was evaporated to give intermediate A4 (220 mg, 92% yield).

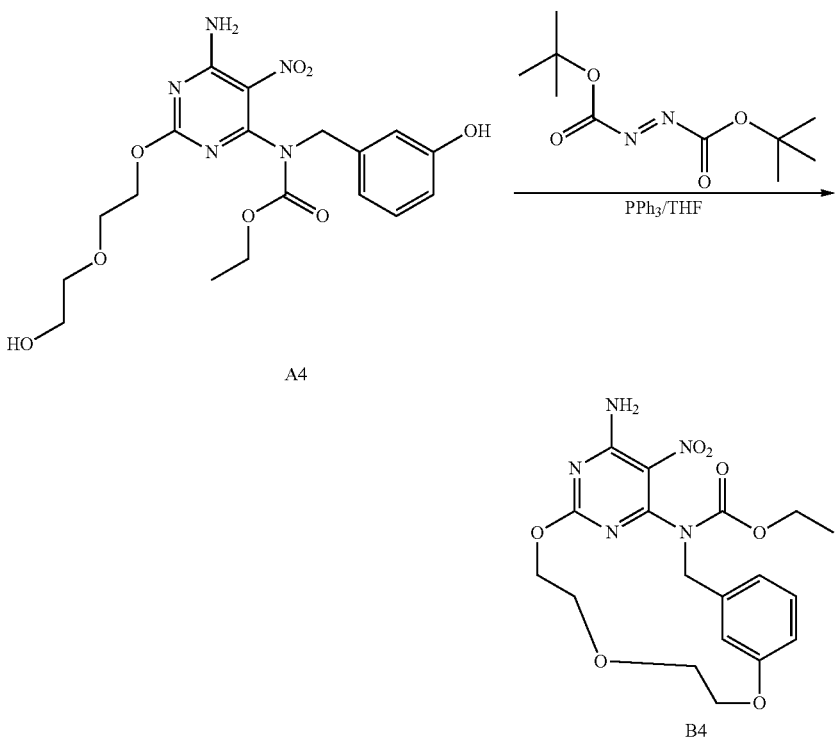

Synthesis of Intermediate B4

At RT under a N$_2$ flow, a solution of di-tert-butyl azodicarboxylate (0.72 ml, 3.2 mmol) in THF (10 mL) was slowly added drop wise to a mixture of A4 (0.7 g, 1.6 mmol) and PPh$_3$ (0.84 g, 3.2 mmol) in THF (120 mL). The mixture was stirred at RT for 12 h. The reaction mixture was poured into ice-water and EtOAc was added. The mixture was basified with an aqueous 10% solution of NaHCO$_3$, then the organic layer was separated, dried over MgSO$_4$, filtered and solvents were evaporated until dryness to give intermediate B4 (60 mg, 9% yield).

Synthesis of Final Compound 12

Iron powder (80 mg, 1.43 mmol) was added to a mixture of B4 (60 mg, 0.143 mmol) in AcOH (1.3 mL) and water (0.5 mL). The mixture was stirred vigorously at RT for 6 h. The reaction mixture was concentrated under vacuum and the residue was diluted with CH$_2$Cl$_2$/MeOH 90/10 and water. The aqueous layer was saturated with K$_2$CO$_3$ and extracted with CH$_2$Cl$_2$/MeOH 90/10. The organic layers were dried over MgSO$_4$, filtered and concentrated under vacuum. The crude compound was purified by chromatography over silicagel (15-40 μm, 40 g) in CH$_2$Cl$_2$/MeOH/NH$_4$OH (90/10/0.5). Crystallization from CH$_3$CN/Diisopropylether gave final compound 12 (14 mg, 29% yield).

OVERALL SCHEME IN THE PREPARATION OF FINAL PRODUCTS: METHOD 13

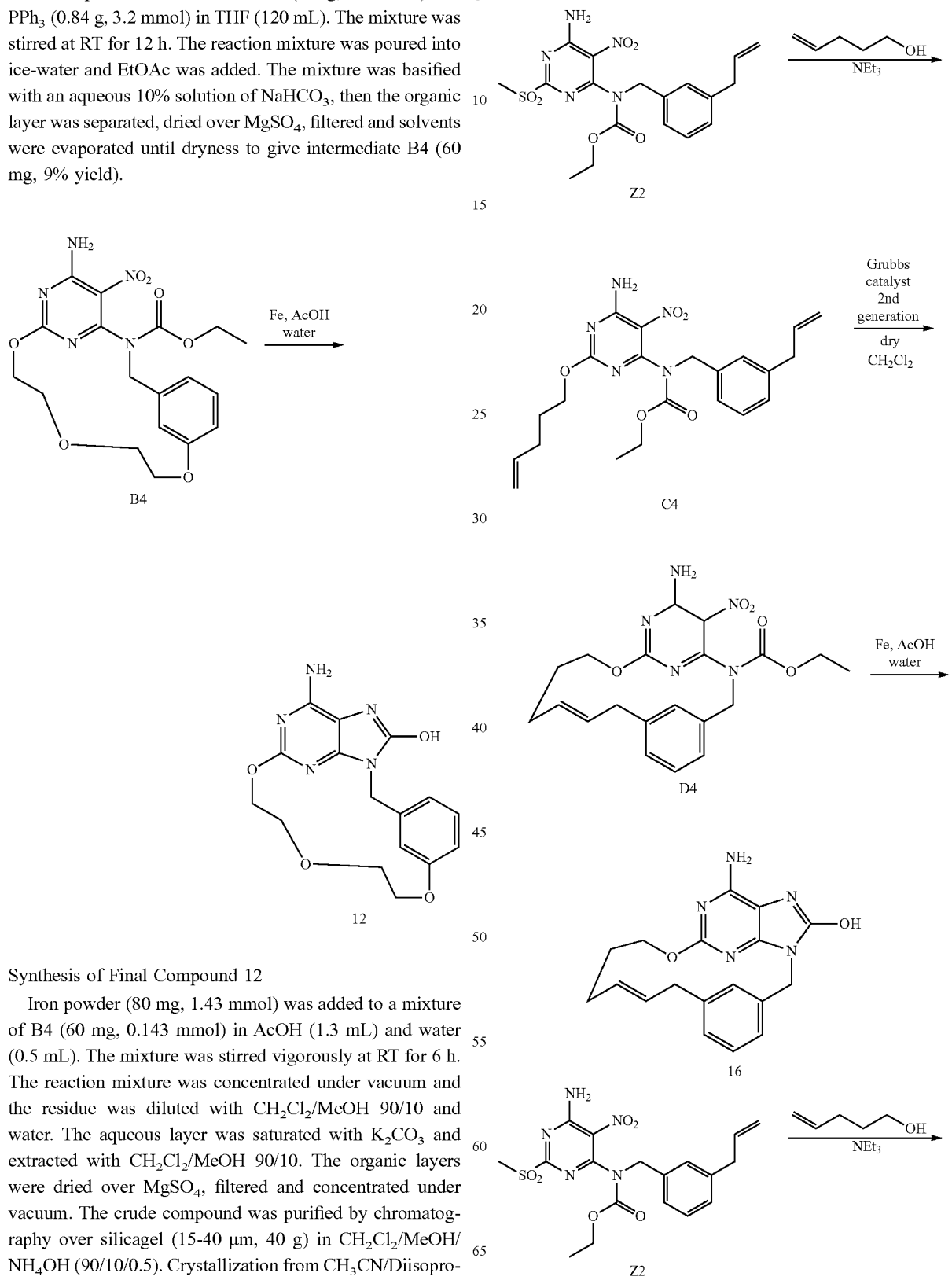

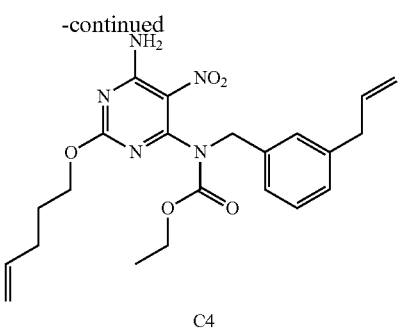

C4

Synthesis of Intermediate C4

A solution of Z2 (2.12 g, 4.87 mmol) and NEt₃ (677 µL, 4.87 mmol) in 4-penten-1-ol (75 mL) was stirred at RT for 48 h. The solvent was removed under vacuum. The crude compound was purified by preparative LC (irregular SiOH 15-40 µm, 90 g Merck, mobile phase gradient: heptane/ CH₂Cl₂ 50/50 to 0/100) to give intermediate C4 (1.6 g, 66% yield) as a yellow oil.

Synthesis of Intermediate D4

Grubbs catalyst 2$^{nd}$ generation (41 mg, 48.47 mmol) was added to a degassed solution of C4 (208 mg, 0.47 mmol) in CH₂Cl₂ (150 mL) at RT. The solution was stirred at RT for 2 h. SiliaBond® DMT (Ru scavenger from Silicycle®) (298 mg, 0.388 mmol) was added and the mixture was stirred at RT for 6 h and the solution was filtered off over Celite®. The filtrate was concentrated under vacuum. The crude compound was purified by preparative LC (irregular SiOH 15-40 µm, 90 g Merck, mobile phase gradient: from heptane/ AcOEt 100/0 to 70/30). The fractions containing the expected product were collected and partially evaporated and the precipitate was filtered off to give 736 mg of intermediate D4 (73% yield, containing 6% of Z isomer). 297 mg of this batch was purified by preparative LC (Stability Silica 5 µm 150×30.0 mm, mobile phase gradient: from Heptane/AcOEt 85/15 to 0/100) to give 195 mg of intermediate D4 as a white solid (pure isomer E). Purity of isomer E was checked by analytical reversed phase chromatography (Column Nucleodur Sphinx 150×4.6 mm, mobile phase: Gradient from 70% MeOH, 30% HCOOH 0.1% to 100% MeOH). This batch of pure E isomer was used in the next step.

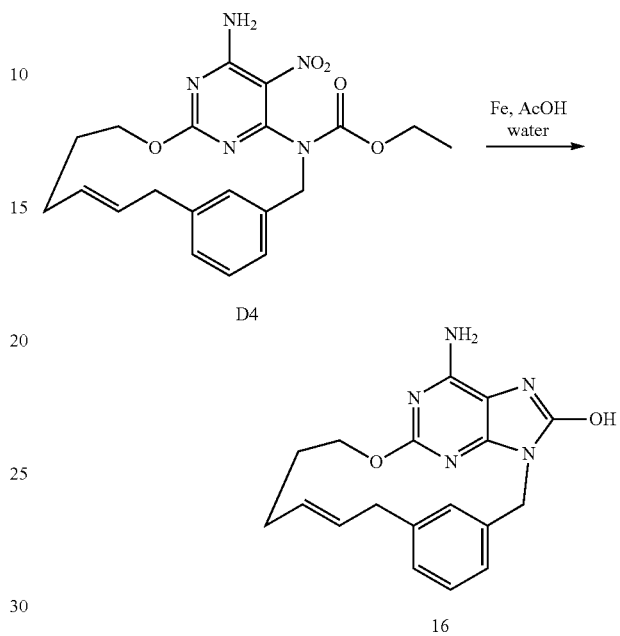

16

Synthesis of Final Compound 16

Iron powder (158 mg, 2.83 mmol) was added to a solution of D4 (195 mg, 0.47 mmol) in AcOH (8 mL) and water (741 µL). The mixture was heated at 100° C. using one single mode microwave (Biotage Initiator EXP 60) with a power output ranging from 0 to 400 W for 1 h. The mixture was filtered on a pad of Celite® and rinsed with DMF (250 mL). The filtrate was concentrated under vacuum and the residue was triturated in CH₂Cl₂/MeOH (80:20). The precipitate was filtered off, rinsed with CH₂Cl₂/MeOH (80:20). The resulting yellow solid was solubilized in DMF and filtered on a pad of Celite®. The filtrate was concentrated under vacuum and the residue was triturated in CH₂Cl₂/MeOH (90:10). The precipitate was filtered off to give final compound 16 as a white solid (17 mg, 10% yield).

OVERALL SCHEME IN THE PREPARATION OF FINAL PRODUCTS: METHOD 14

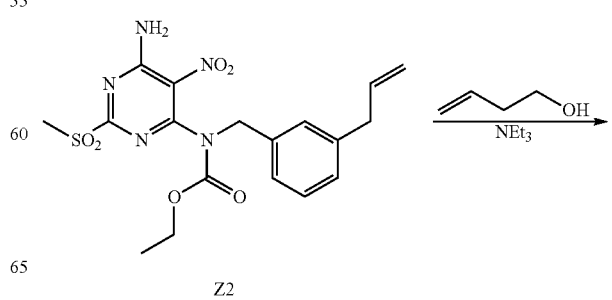

Z2

73

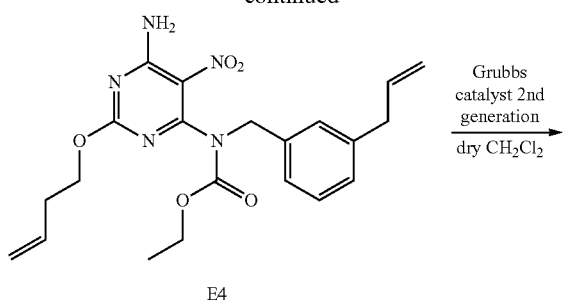

E4

74

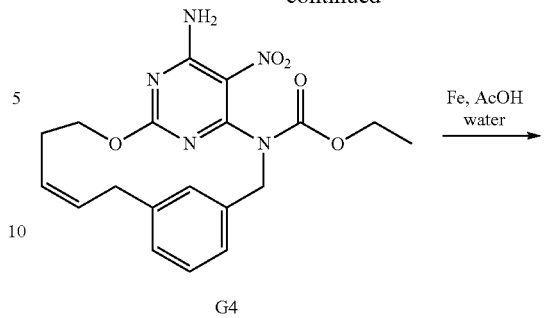

G4

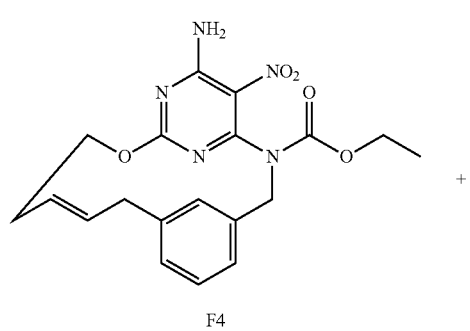

F4

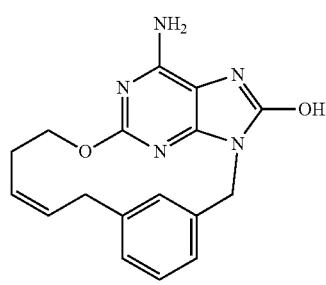

17

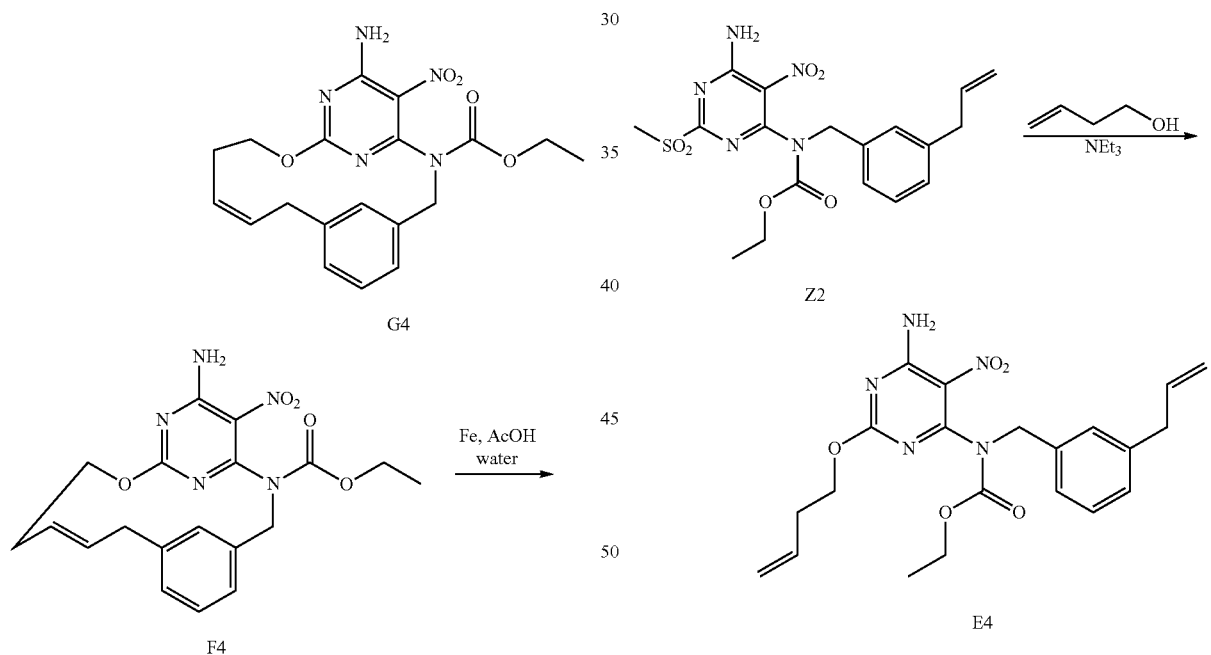

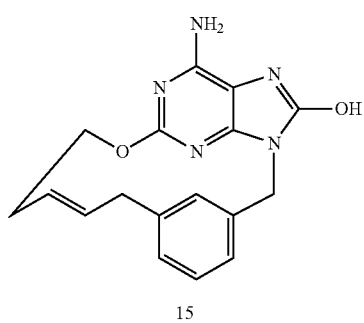

15

Synthesis of Intermediate E4

A solution of Z2 (3.8 g, 5.06 mmol) and NEt₃ (844 ptL, 6.07 mmol) in 3-buten-1-ol (68 mL) was stirred at RT for 20 h, then stirred at 30° C. for 1 h. The solvent was removed under vacuum to give 5 g of yellow oil. The crude was purified by preparative LC (Irregular SiOH 15-40 µm, 120 g Grace, mobile phase gradient: Heptane/CH₂Cl₂ from 50/50 to 10/90). The fractions containing the expected product were combined and the solvent was removed under vacuum to give 2.2 g of intermediate E4 as a yellow oil.

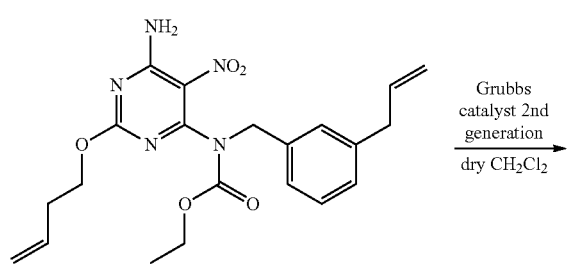

E4

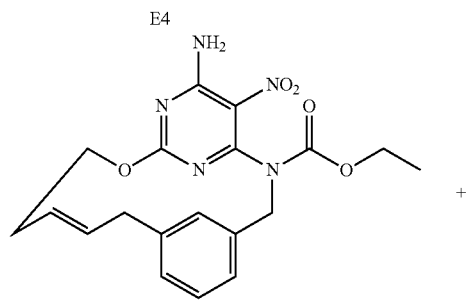

F4

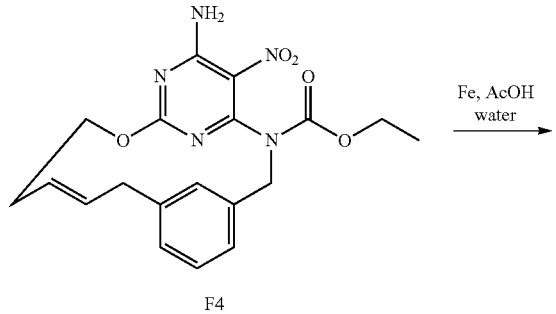

F4

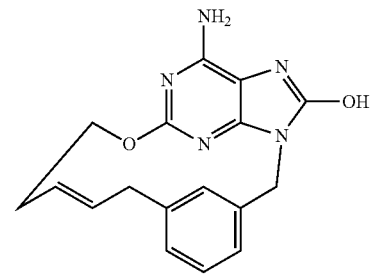

15

LC (Stability Silica 5 m 150×30.0 mm, mobile phase gradient: from CH$_2$Cl$_2$/MeOH 100/0 to 98/2) to give 175 mg of F4 (14% yield, isomer E) as a yellow solid and 130 mg of G4 (10% yield, isomer Z) as a white solid.

In total, 447 mg of intermediate F4 (E isomer) and 130 mg of intermediate G4 (Z isomer) were obtained.

Synthesis of Intermediates F4 and G4:

E4 (1.34 g, 3.14 mmol) was added to dry CH$_2$Cl$_2$ (1 L) and the resulting mixture was degassed by N$_2$ bubbling through the solution for 30 min. Grubbs catalyst 2$^{nd}$ generation (134 mg, 0.157 mmol) was added in one portion and the mixture was stirred at RT under N$_2$ atmosphere for 16 h. SiliaBond® DMT (0.965 g, 1.25 mmol) was added and the mixture was stirred at RT for 16 h and the solution was filtered over Celite®. The filtrate was evaporated under vacuum to give 1.89 g of brown solid. The crude was purified by preparative LC (Irregular SiOH 15-40 μm, 50 g Merck, mobile phase gradient: Heptane/AcOEt from 100/0 to 80/20). The fractions containing the expected product were partially evaporated (AcOEt), the product was precipitated and filtered off to give 162 mg of intermediate F4 (13% yield, E isomer) as a yellow solid. The other fractions containing the expected products were combined and the solvent was removed under vacuum to give 244 mg of white solid (mixture of F4 (E isomer) and G4 (Z isomer)).

The same reaction was carried out in parallel starting from 895 mg of E4. From this reaction, a batch of 110 mg of F4 was isolated (13% yield, isomer E). A second batch of 184 mg was obtained (mixture of F4 (E isomer) and G4 (Z isomer)).

The two batches containing a mixture of E and Z isomers were combined (428 mg) and were purified by preparative Synthesis of Final Compound 15:

Iron (93 mg, 1.67 mmol) was added to a solution of F4 (111 mg, 0.278 mmol) in acetic acid (5 mL) and distilled water (330 μL). The mixture was heated at 100° C. using one single mode microwave (Biotage Initiator EXP 60) with a power output ranging from 0 to 400 W for 1 h. The mixture was concentrated under vacuum and triturated in AcOH/H$_2$O (50:50). The precipitate was filtered off to give a grey solid, which was solubilized in DMF and filtered on a pad of Celite®. The filtrate was concentrated under reduced pressure to give a white-brown solid. This solid was triturated in AcOH/H$_2$O (50:50); the precipitate was filtered off to give 40 mg of final compound 15 (45% yield) as a white solid.

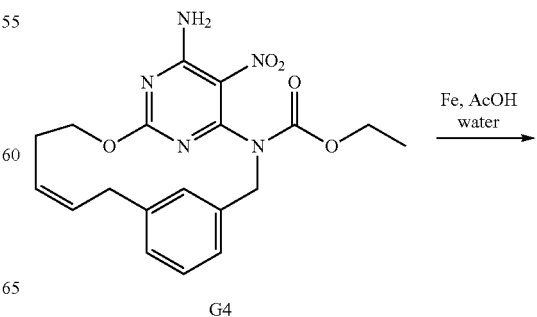

G4

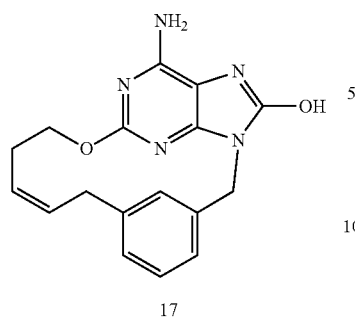

17

Synthesis of Final Compound 17:

Iron (109 mg, 1.95 mmol) was added to a solution of G4 (130 mg, 0.325 mmol) in acetic acid (6 mL) and distilled water (390 μL). The mixture was heated at 100° C. using one single mode microwave (Biotage Initiator EXP 60) with a power output ranging from 0 to 400 W for 1 h 30. The mixture was concentrated under vacuum and triturated in a solution of AcOH/$H_2O$ (50:50). The precipitate was filtered off to give a grey solid, which was triturated in AcOH/$H_2O$ (50:50); the precipitate was filtered off and solubilized in DMF. The mixture was filtered on a pad of Celite® and the filtrate was concentrated under vacuum to give a white solid. This solid was triturated in a cold solution of AcOH/$H_2O$ (50:50); the precipitate was filtered off to give 18 mg of final compound 17 (17% yield) as a white solid.

OVERALL SCHEME IN THE PREPARATION OF FINAL PRODUCTS: METHOD 15

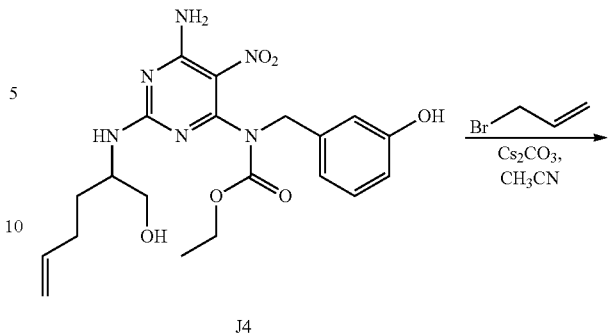

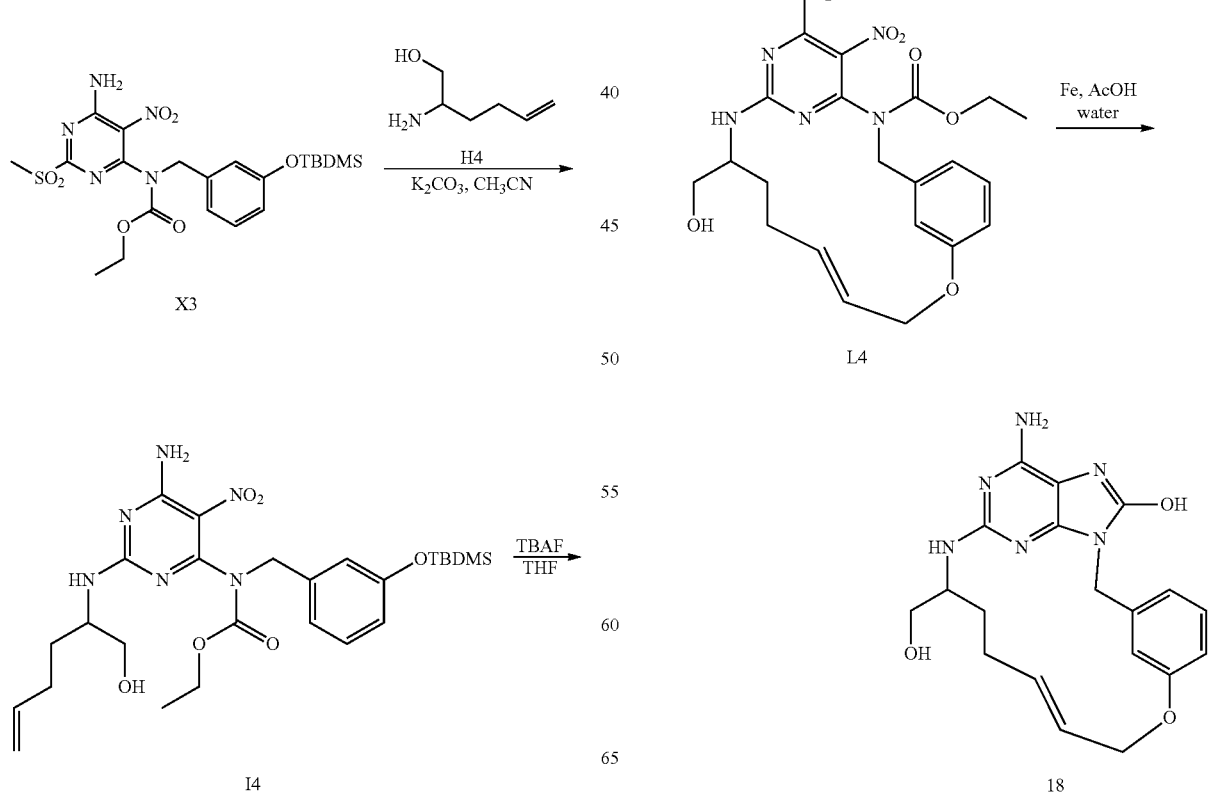

-continued

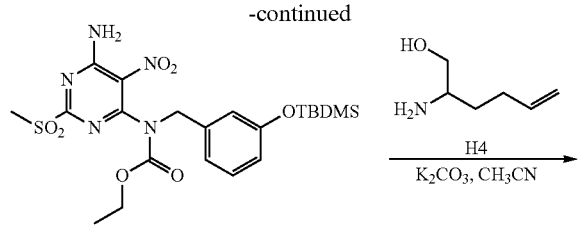

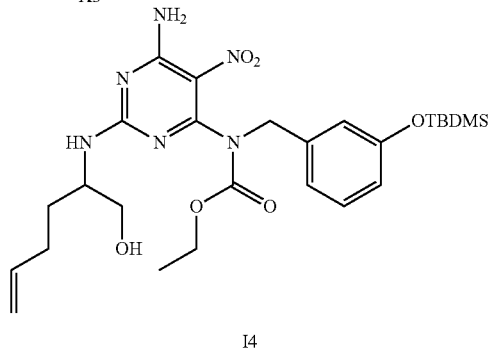

I4

Synthesis of Intermediate 14:

A mixture of X3 (4 g, 7.61 mmol), H4 (1.1 g, 9.13 mmol) and K₂CO₃ (1.3 g, 9.13 mmol) in CH₃CN (120 mL) was stirred at 80° C. for 1.5 h. Water was added and the mixture was extracted with EtOAc (twice). The organic layer was dried over MgSO₄, filtered and the solvent was evaporated under reduced pressure. The crude was purified by chromatography over silica gel (15-40 μm; 120 g) in CH₂Cl₂/MeOH/NH₄OH 98/2/0.1 to give 2.7 g (63% yield) of intermediate 14.

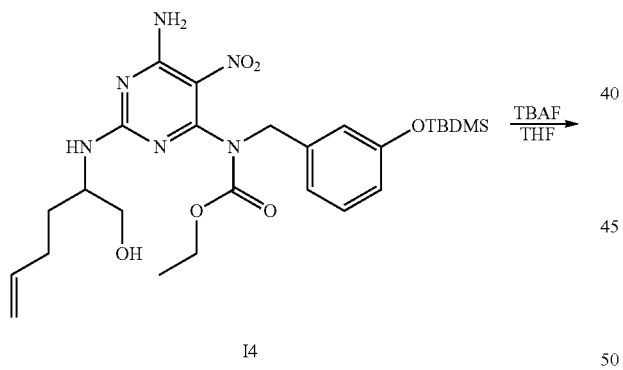

I4

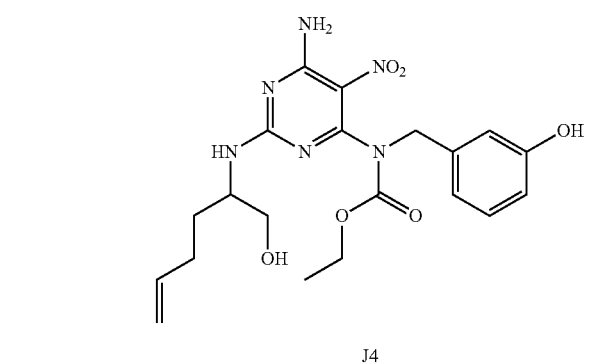

J4

Synthesis of Intermediate J4:

Tetrabutylammonium fluoride (5.6 mL, 5.56 mmol) was added drop wise to a solution of 14 (2.6 g, 4.64 mmol) in THF (125 mL) at room temperature. The reaction was stirred at room temperature for 3 hours. The mixture was diluted with EtOAc and poured into water. The organic layer was washed with brine, dried over MgSO₄, filtered and the solvent was evaporated under reduced pressure. The crude was purified by preparative LC (irregular SiOH 15-40 μm, 80 g Grace, mobile phase: CH₂Cl₂/MeOH/NH₄OH 96/4/0.1) to give 1.82 g of intermediate J4. The crude compound was used in the next step.

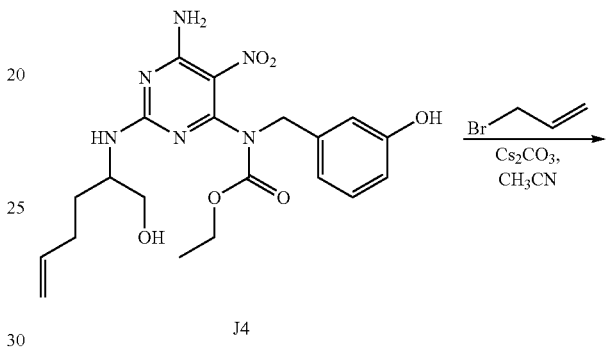

J4

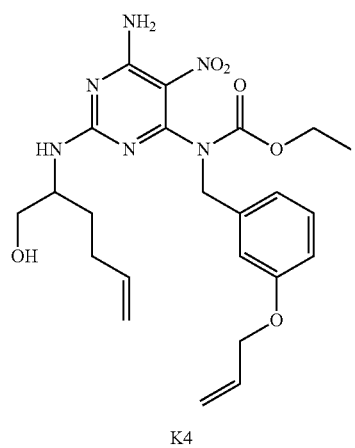

K4

Synthesis of Intermediate K4:

A mixture of J4 (1.82 g, 4.08 mmol), Cs₂CO₃ (1.47 g, 4.49 mmol), allyl bromide (0.39 mL, 4.49 mmol) in CH₃CN (60 ml) was stirred at RT for 5 h and then at 50° C. for 1 h. The reaction mixture was poured into ice-water and EtOAc was added. The mixture was basified with an aqueous solution of NaHCO₃ 10% in water. The organic layer was separated, dried over MgSO₄, filtered and the solvents were evaporated until dryness to give 1.94 g of intermediate K4. The crude compound was used directly in the next step.

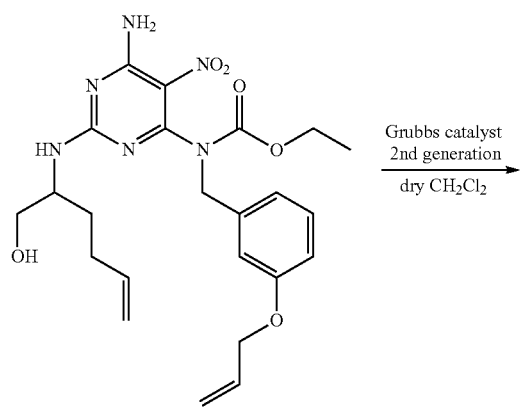

K4

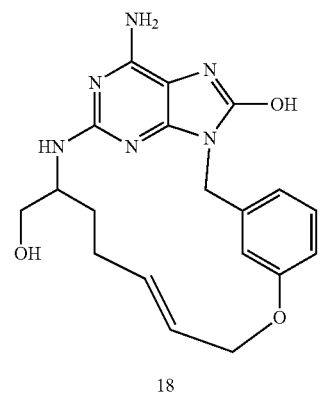

18

Synthesis of Final Compound 18:

Iron (200 mg, 3.58 mmol) was added to a mixture of L4 (182 mg, 0.40 mmol) in acetic acid (4.3 mL) and distilled water (0.85 mL). The mixture was stirred at RT for 12 h. 6.5 mL of acetic acid were added and the mixture was stirred at 50° C. for 3 h, and then at 80° C. for 2 h.

The crude was purified by Reverse phase on (X-Bridge-C18 5 μm 30*150 mm), mobile phase (Gradient from 90% formic acid 0.1%, 10% $CH_3CN$ to 0% formic acid 0.1%, 100% $CH_3CN$) to give 44 mg (29% yield) of final compound 18.

OVERALL SCHEME IN THE PREPARATION OF FINAL PRODUCTS: METHOD 16

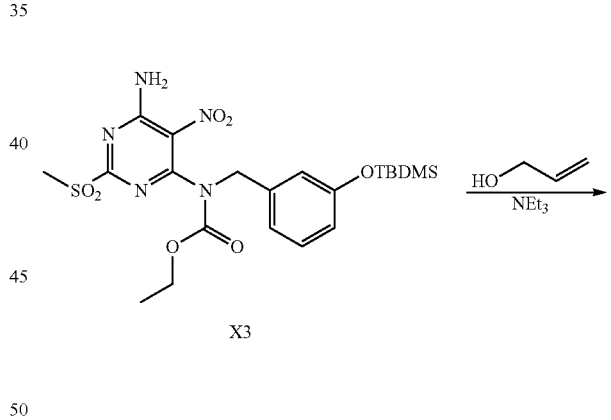

X3

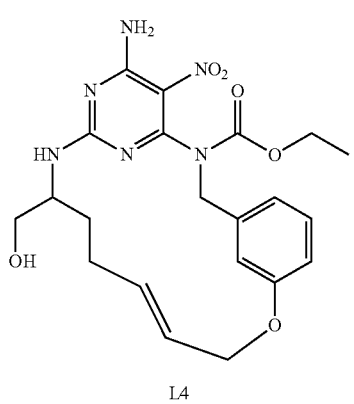

L4

Synthesis of Intermediate L4:

Grubbs catalyst $2^{nd}$ generation (100 mg, 0.117 mmol) was added to a degassed solution of K4 (570 mg, 1.17 mmol) in $CH_2Cl_2$ (225 mL) at RT. The solution was stirred at RT for 36 h.

SiliaBond® DMT (1.8 g) was added to the reaction mixture, which was stirred at RT 18 hours. The mixture was filtered through a pad of Celite®. The Celite® was washed with $CH_2Cl_2$. The filtrate was evaporated under reduced pressure. Purification was carried out by flash chromatography over silica gel (15-40 μm, 40 g, $CH_2Cl_2/CH_3OH/NH_4OH$ 97.5/2.5/0.1). The pure fractions were collected and evaporated to dryness. The dry solid was purified again by achiral SFC on (AMINO 6 m 150×21.2 mm), mobile phase (80% $CO_2$, 20% MeOH) to give 182 mg (34% yield) of intermediate L4 (E isomer).

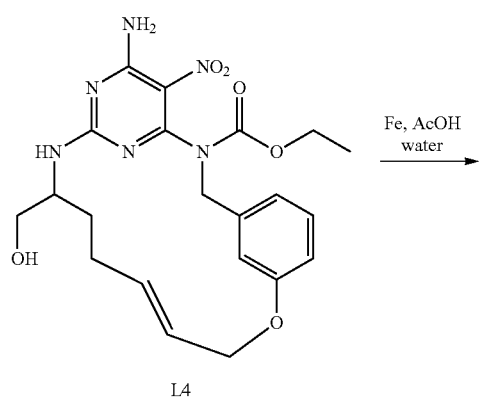

L4

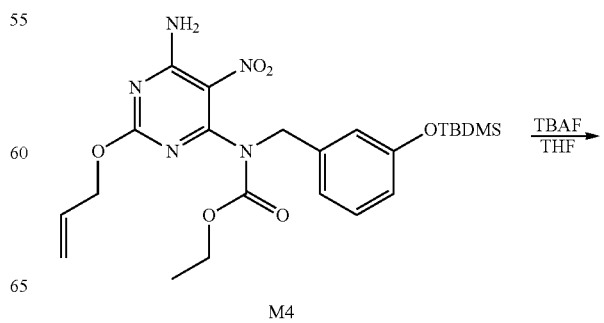

M4

83
-continued
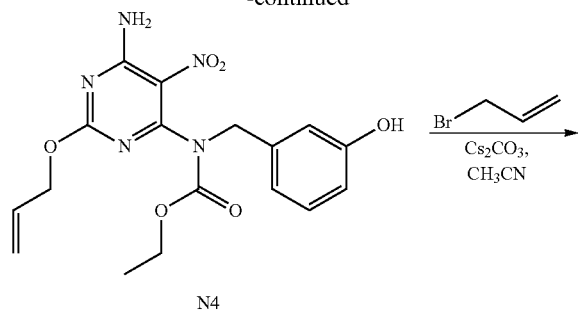
N4
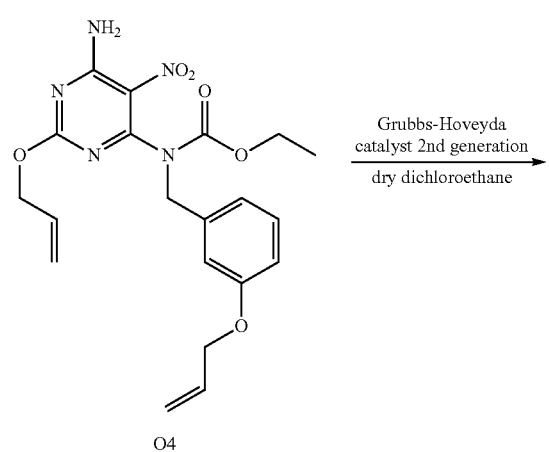
O4
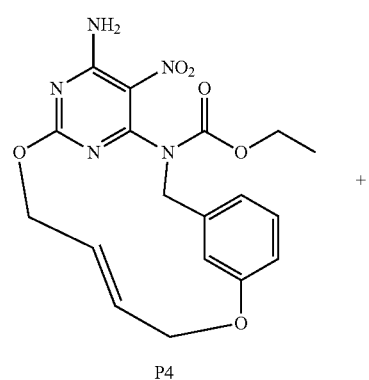
P4
+
84
-continued
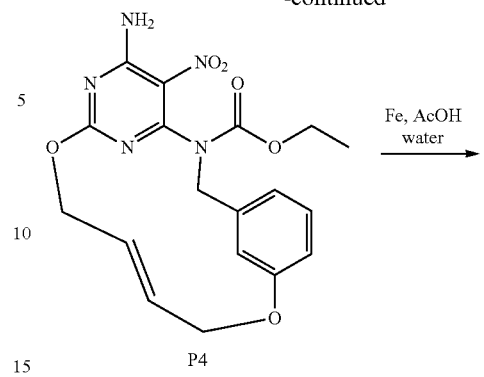
P4
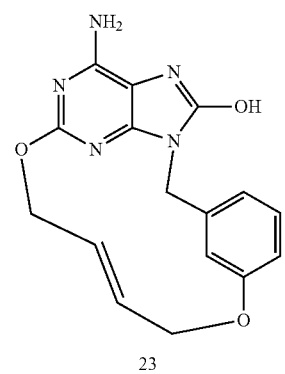
23
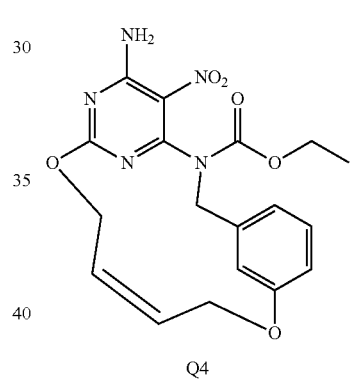
Q4
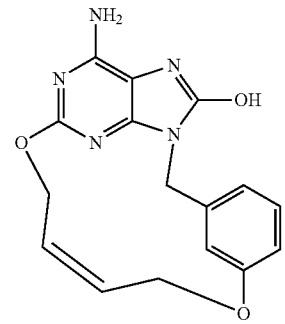
22
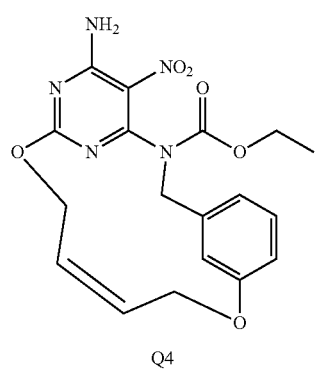
Q4
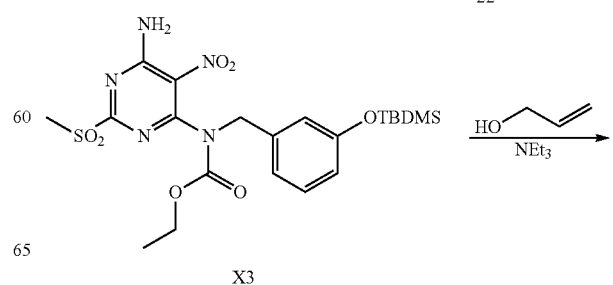
X3

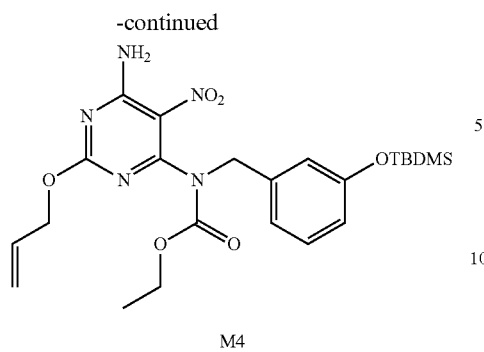

M4

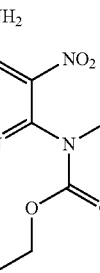

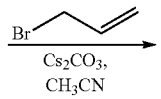

N4

Synthesis of Intermediate M4:

A solution of X3 (1.4 g, 2.66 mmol) and NEt₃ (0.44 mL, 0.46 mmol) in allylic alcohol (14 mL) was stirred at 80° C. for 1 h. CH₂Cl₂ and H₂O were added and the mixture was decanted. The organic layer was dried over MgSO₄ and concentrated under reduced pressure. The crude product was purified by preparative LC (irregular SiOH 15-40 μm, 80 g Merck, mobile phase heptane/AcOEt 85/15) to give 500 mg (37% yield) of intermediate M4.

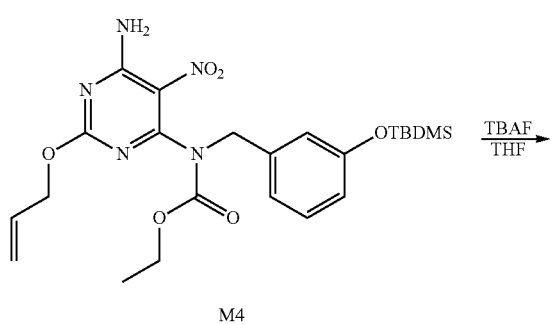

M4

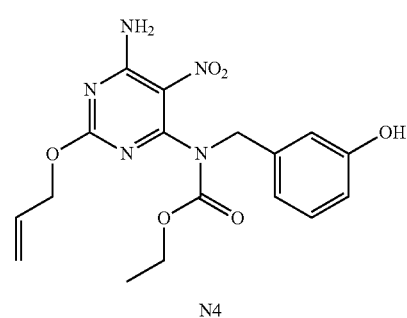

N4

Synthesis of Intermediate N4:

Tetrabutylammonium fluoride (4.5 mL, 4.5 mmol) was added drop wise to a solution of M4 (1.9 g, 3.77 mmol) in THF (90 mL) at room temperature. The reaction was stirred at room temperature for 3 hours. The reaction mixture was diluted with EtOAc and poured into water. The organic layer was washed with brine and dried over MgSO₄, filtered and the solvent was evaporated under reduced pressure. The crude product was purified by preparative LC (irregular SiOH 15-40 μm, 40 g Merck, mobile phase heptane/AcOEt 70/30) to give 900 mg (61% yield) of intermediate N4.

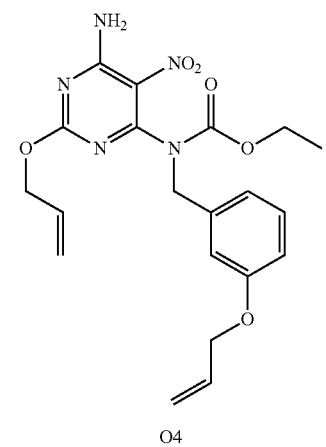

O4

Synthesis of Intermediate O4:

A mixture of N4 (2.5 g, 6.42 mmol), Cs₂CO₃ (3.14 g, 9.63 mmol), allyl bromide (0.83 mL, 9.63 mmol) in CH₃CN (100 mL) was stirred at 70° C. for 1 h. The reaction mixture was poured into ice-water and EtOAc was added. The mixture was basified with an aqueous saturated solution of NaHCO₃. The organic layer was then separated, dried over MgSO₄, filtered and the solvents were evaporated until dryness. The crude compound was purified by chromatography over silicagel (15-40 μm, 80 g) in heptane/AcOEt 80/20 to give 1.47 g (53% yield) of intermediate O4.

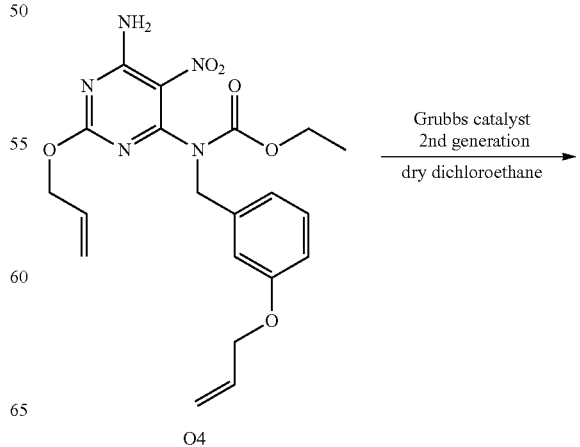

O4

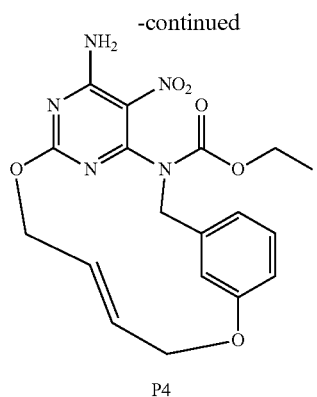

P4

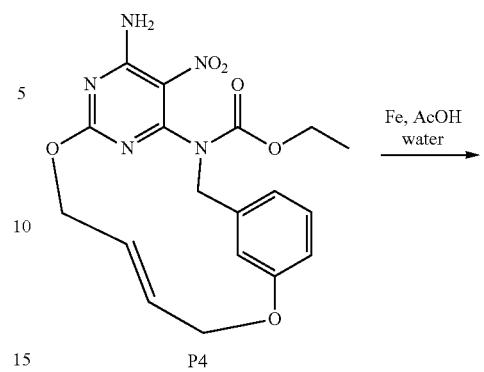

P4

Fe, AcOH
water
→

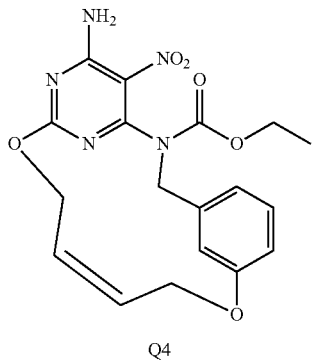

Q4

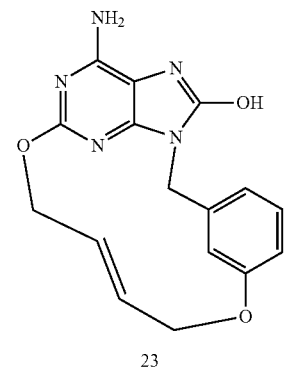

23

Synthesis of Intermediates P4 and Q4:

A solution of 04 (400 mg, 0.93 mol) and cholorocyclohexylborane 1 M solution in hexane (186 μL, 0.19 mmol) in dry dichloroethane (220 mL) was stirred at 80° C. and under $N_2$ atmosphere for 1 h. 0.033 eq of Grubbs-Hoveyda catalyst $2^{nd}$ generation (20 mg, 0.031 mmol) was added and the mixture was stirred in a sealed tube at 120° C. for 1 h. The tube was then opened, 0.033 eq of Grubbs-Hoveyda catalyst $2^{nd}$ generation (20 mg, 0.031 mmol) was added and the mixture was stirred in the sealed tube at 120° C. for 1 h. The tube was then opened, 0.033 eq of Grubbs-Hoveyda catalyst $2^{nd}$ generation (20 mg, 0.031 mmol) was added and the mixture was stirred in the sealed tube at 120° C. for 2 h. SiliaBond® DMT (1.43 g, 0.745 mmol) was added to the mixture, which was stirred at RT for 12 h. The mixture was filtered through a pad of Celite® and concentrated under reduced pressure. The crude product was purified first by preparative LC (irregular SiOH 15-40 μm, 40 g Merck, mobile phase heptane/AcOEt 80/20) and then by achiral SFC on (Amino 6 m 150×21.2 mm), mobile phase (83% $CO_2$, 17% MeOH) to give 55 mg (15%) of intermediate P4 (isomer E) and 80 mg (21% yield) of intermediate Q4 (isomer Z).

Synthesis of Final Compound 23:

Iron (264 mg, 4.73 mmol) was added to a mixture of P4 (190 mg, 0.47 mmol) in acetic acid (10 mL) and distilled water (2 mL). The mixture was stirred vigorously at 50° C. for 5 h. The reaction mixture was concentrated under vacuum and the residue was diluted with $CH_2Cl_2$/MeOH 90/10 and water. The mixture was saturated with $K_2CO_3$, extracted with $CH_2Cl_2$/MeOH 90/10. The organic layers were dried over $MgSO_4$, filtered and concentrated under vacuum. The crude compound was purified by chromatography over silicagel (15-40 μm, 40 g) in $CH_2Cl_2$/MeOH/$NH_4OH$ (90/10/0.5) to give 40 mg (26% yield) of final compound 23.

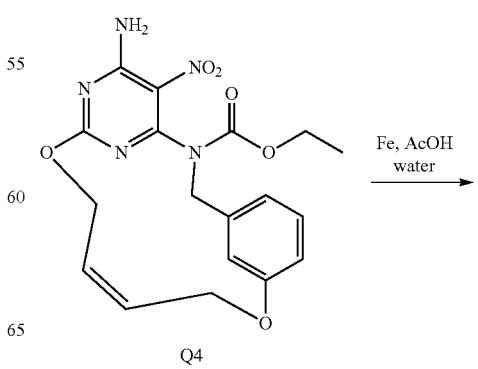

Q4

Fe, AcOH
water
→

-continued

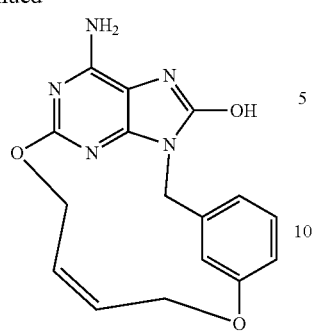

22

Synthesis of Final Compound 22:

Iron (334 mg, 5.98 mmol) was added to a mixture of Q4 (240 mg, 0.6 mmol) in acetic acid (12 mL) and water (2.5 mL). The mixture was stirred vigorously at 50° C. for 5 h. The reaction mixture was concentrated under vacuum and the residue was diluted with CH$_2$Cl$_2$/MeOH 90/10 and water. The mixture was saturated with K$_2$CO$_3$, extracted with CH$_2$Cl$_2$/MeOH 90/10. The organics layer were dried over MgSO$_4$, filtered and concentrated under vacuum. The crude compound was purified by chromatography over silicagel (15-40 μm, 40 g) in CH$_2$Cl$_2$/MeOH/NH$_4$OH (90/10/0.5) to give 70 mg (36% yield) of final compound 22.

OVERALL SCHEME IN THE PREPARATION OF FINAL PRODUCTS: METHOD 17

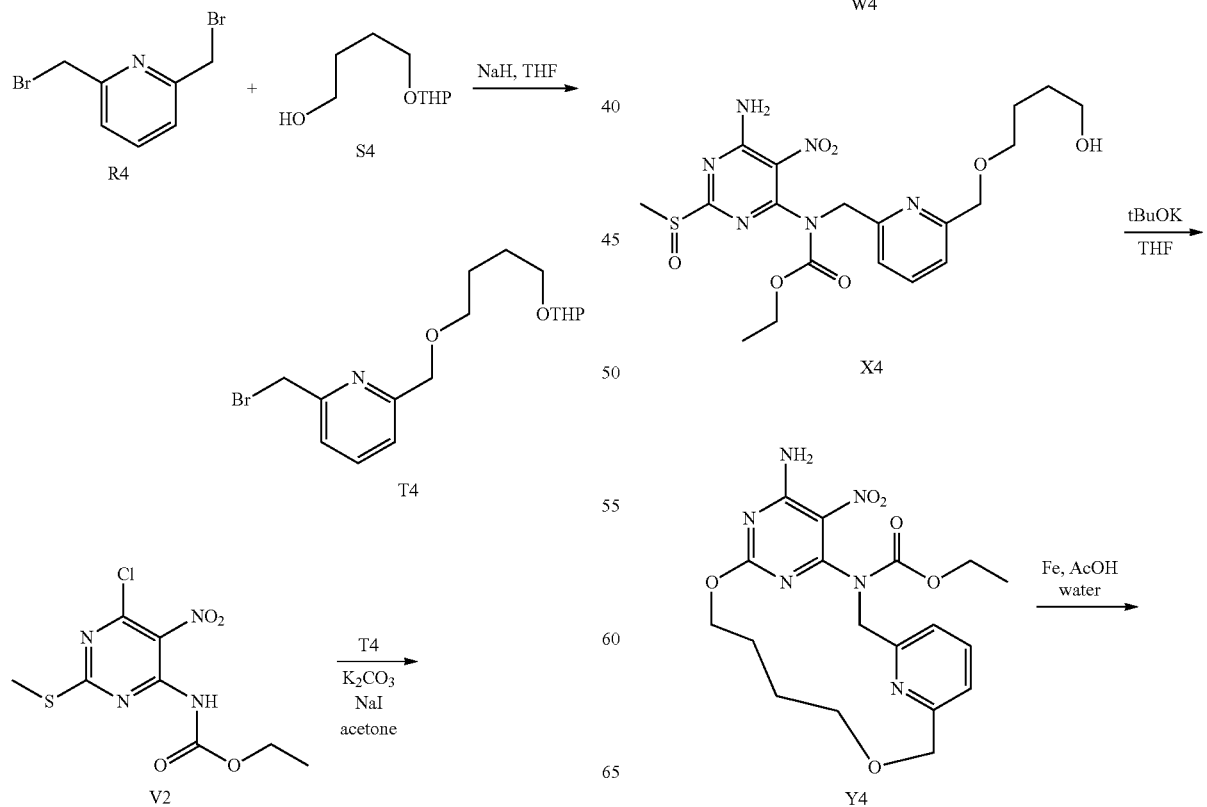

-continued

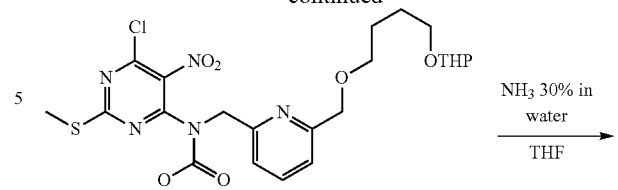
U4

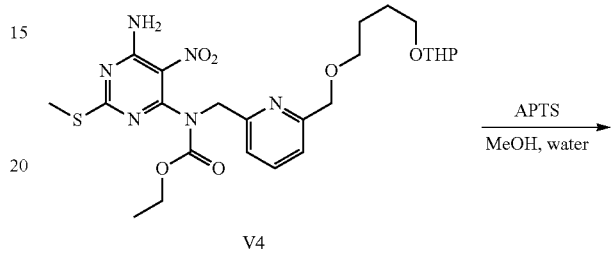
V4

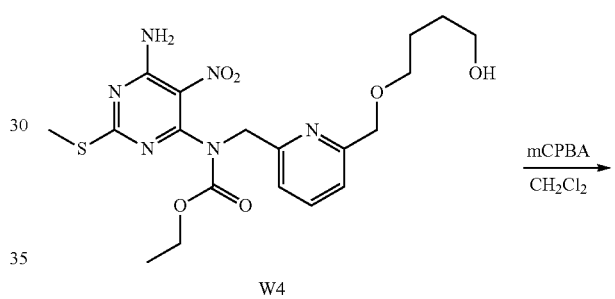
W4

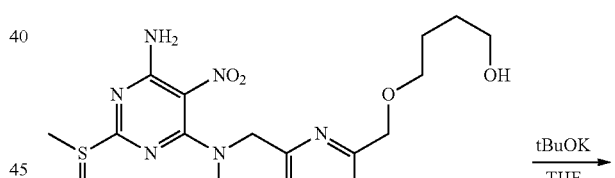
X4

Y4

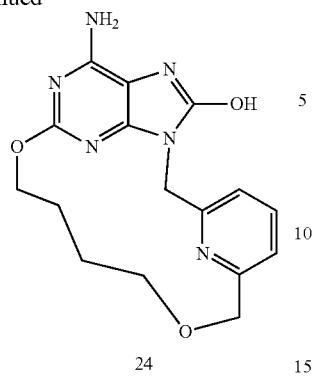

24

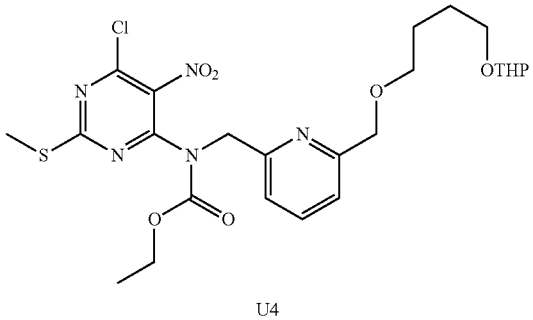

U4

Synthesis of Intermediate U4:

A mixture of V2 (1 g, 3.42 mmol), T4 (1.35 g, 3.76 mmol), K₂CO₃ (1.18 g, 8.54 mmol) and NaI (512 mg, 3.42 mmol) in acetone (25 mL) was stirred at RT overnight. The precipitate was filtered off, washed with acetone and the filtrate was concentrated under reduced pressure. The crude product was purified by chromatography over silica gel column (15-41 µm; 40 g) in heptane/AcOEt 80/20 to give 1.4 g (72% yield) of intermediate U4.

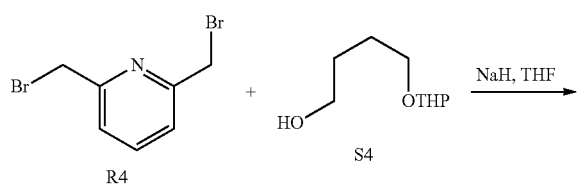

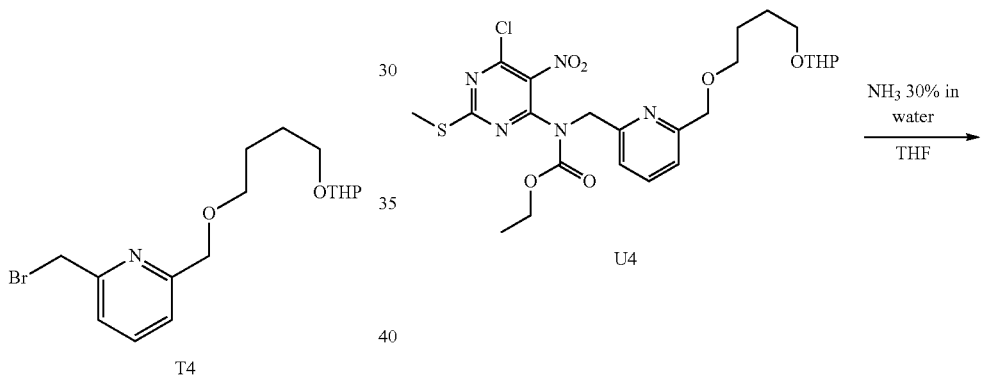

Synthesis of Intermediate T4:

At 0° C., NaH (695 mg, 17.36 mmol) was added portion wise to S4 (1.52 g, 8.68 mmol) in THF (70 mL). The mixture was stirred at 0° C. for 30 min and then added drop wise at 0° C. to R4 (4.6 g, 17.36 mmol) in THF (45 mL). The reaction was stirred at RT overnight. A very little quantity of ice was added and expected compound was extracted with AcOEt. The solvent was evaporated under reduced pressure. The crude product was purified by chromatography over silica gel (15-40 µm; 220 g) in heptane/AcOEt 80/20 to 60/40 to give 1.44 g (23% yield) of intermediate T4.

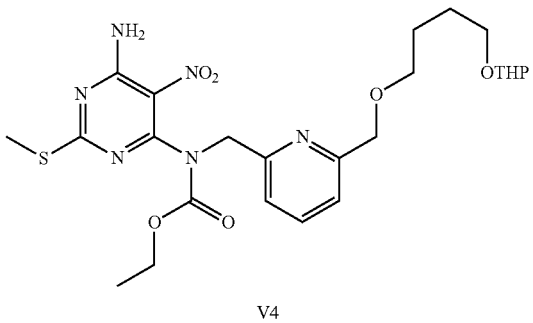

V4

Synthesis of Intermediate V4:

U4 (1.5 g, 2.63 mmol) was stirred in NH₃ 30% in water (30 mL) and THF (30 mL) at RT for 2 h. The mixture was concentrated under vacuum and the residue was dried by azeotropic distillation with EtOH (twice). The crude product (1.3 g, 89% yield) was used without further purification in the next step.

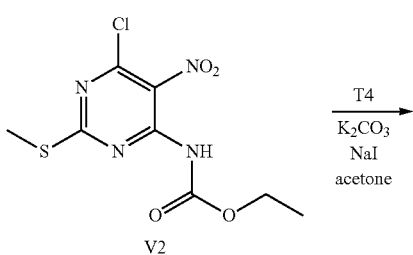

Synthesis of Intermediate W4:

At RT, para-toluene sulfonic acid monohydrate (81 mg, 0.47 mmol) was added to a mixture of V4 (2.60 g, 4.72 mmol) in MeOH (26 mL) and water (2.60 mL). The mixture was stirred at RT overnight and then at 60° C. for 12 h. The reaction mixture was diluted with EtOAc and was basified with $K_2CO_3$ 10% in water. The organic layer was separated, dried over $MgSO_4$, filtered and the solvent was evaporated under reduced pressure to give 2 g (90% yield) of intermediate W4.

Synthesis of Intermediate X4:

Meta-chloroperoxybenzoic acid (951 mg, 3.86 mmol) in $CH_2Cl_2$ (40 mL) was added drop wise to a solution of W4 (1.80 g, 3.86 mmol) in $CH_2Cl_2$ (10 mL) at RT. The mixture was stirred at RT for 6 h. An aqueous solution of $Na_2S_2O_3$ (2 eq) was added to the mixture. The two layers were separated and the aqueous layer was extracted with $CH_2Cl_2$ (twice). The combined organic layers were dried over $MgSO_4$, filtered and the solvent was removed under reduced pressure. Purification was carried out by flash chromatography over silica gel (15-40 μm, 80 g, $CH_2Cl_2/CH_3OH$: 95/5). The pure fractions were collected and evaporated to dryness to give 1.4 g (75% yield) of intermediate X4.

Synthesis of Intermediate Y4:

At 0° C., under a $N_2$ flow, tBuOK (577 mg, 5.14 mmol) was added to a mixture of X4 (1.24 g, 2.57 mmol) in THF (418 mL). The mixture was stirred at 80° C. overnight. Water was added and the mixture was extracted with EtOAc. The organic layer was dried over $MgSO_4$, filtered and the solvent was evaporated. Purification was carried out by flash chromatography over silica gel (15-40 μm, 50 g, $CH_2Cl_2/CH_3OH$ 98/2). The pure fractions were collected and evaporated to dryness to give 85 mg (7% yield) of intermediate Y4.

-continued

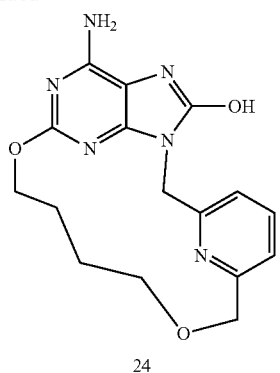

24

Synthesis of Final Compound 24:

Iron (68 mg, 1.22 mmol) was added to a mixture of Y4 (85 mg, 0.21 mmol) in acetic acid (2.2 mL) and water (0.24 mL). The mixture was stirred at 50° C. for 3 h. The mixture was filtered, washed with AcOH and the filtrate was concentrated under reduced pressure. The crude compound was taken up in DMF and 2 g of SiO$_2$ 63-200 µm was added. The resulting suspension was evaporated until dryness and put on a top on a 25 g purification cartridge.

Purification was carried out by flash chromatography over silica gel (15-40 µm, 25 g, CH$_2$Cl$_2$/CH$_3$OH/NH$_4$OH: 95/5/0.5). The pure fractions were collected and evaporated to dryness to give 31 mg. The compound was solidified from CH$_3$CN, the precipitate was filtered off and dried to give 22 mg (32% yield) of final compound 24.

OVERALL SCHEME IN THE PREPARATION OF FINAL PRODUCTS: METHOD 18

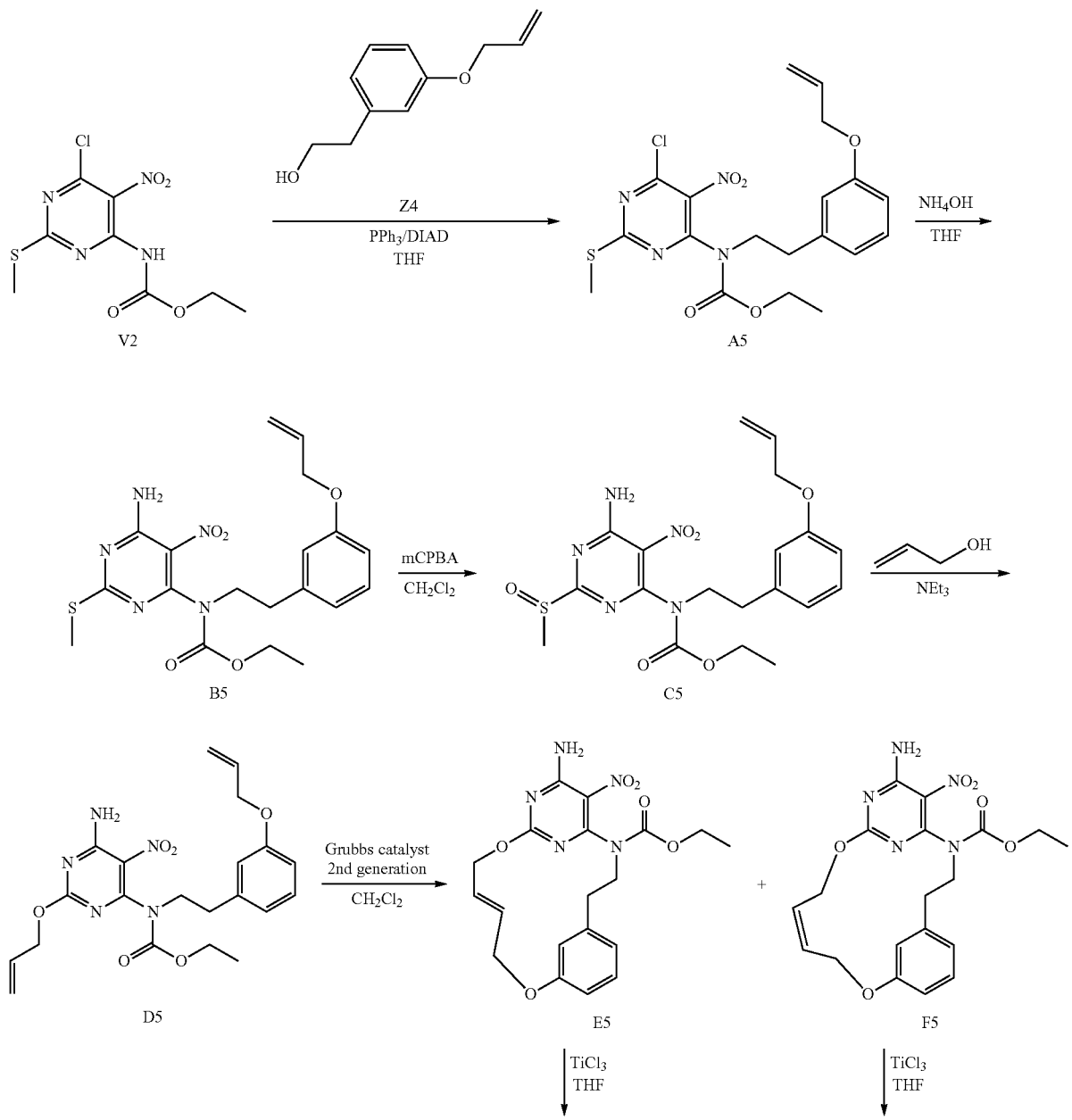

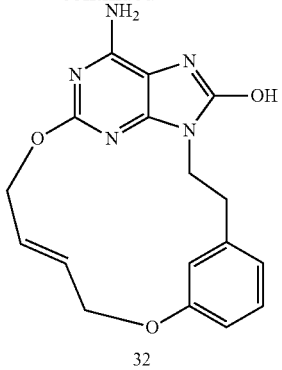

32

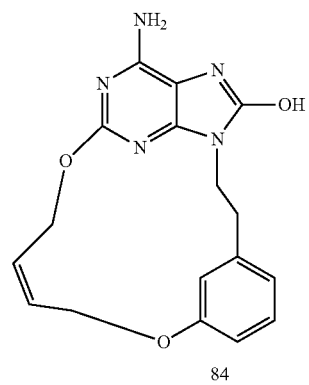

84

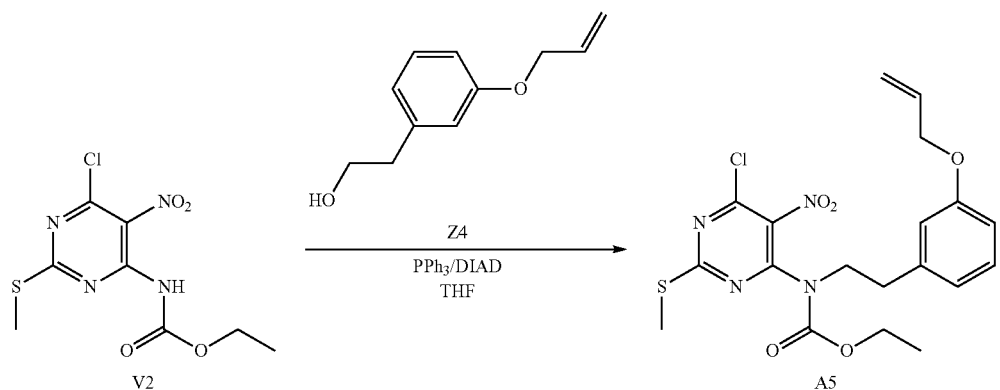

Synthesis of Intermediate A5:

At 0° C., diisopropylazodicarboxylate (20.4 mL; 102.5 mmol) was added drop wise to a mixture of V2 (20 g; 68.33 mmol), Z4 (12.2 g; 68.33 mmol) and PPh₃ (27 g; 102.5 mmol) in THF (500 mL). The mixture was stirred at RT for 12 h. EtOAc and water were added. The layers were decanted. The organic layer was washed with water, dried over MgSO₄, filtered and the solvent was evaporated. The crude compound was purified by flash chromatography over silica gel (15-40 μm, 330 g, CH₂Cl₂/Heptane 70/30). The pure fractions were collected and evaporated to dryness to give 12 g (39% yield) of intermediate A5.

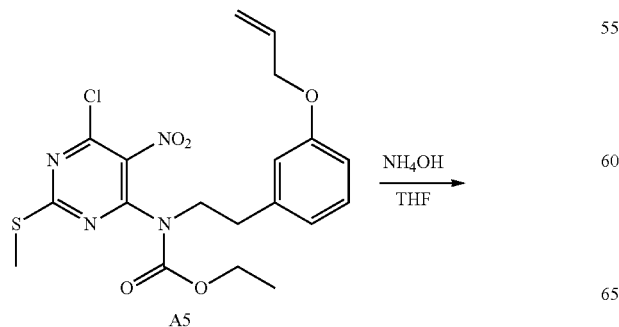

-continued

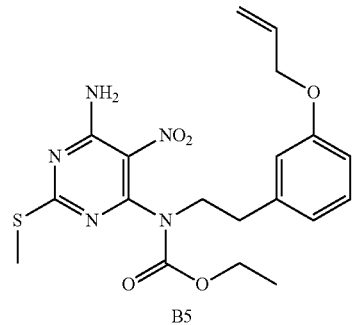

B5

Synthesis of Intermediate B5:

A mixture of A5 (5.4 g; 11.92 mmol) in NH3 30% in water (100 mL) and THF (100 mL) was stirred at RT for 1.3 h. The mixture was concentrated. The residue was taken up with toluene and concentrated (the process was repeated twice) to give 5.15 g of intermediate B5.

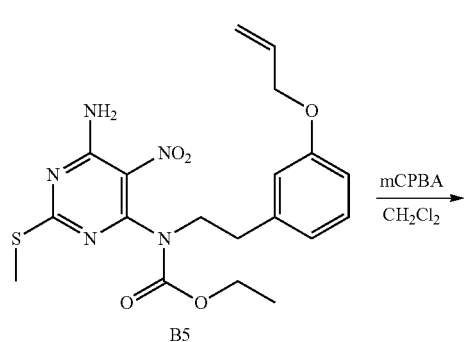

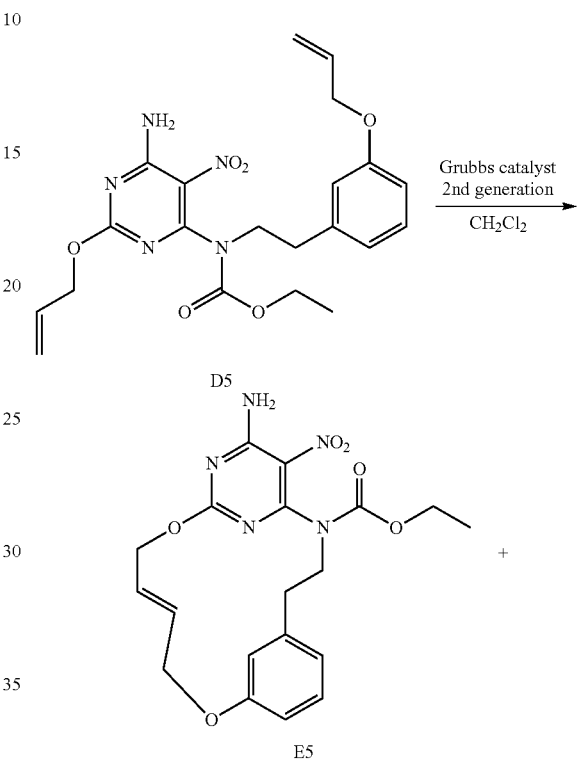

Synthesis of Intermediate D5:

A mixture of C5 (5.6 g; 12.46 mmol), NEt$_3$ (2.6 mL; 18.69 mmol) in allyl alcohol (47.6 mL) was stirred at 100° C. for 30 min. The mixture was concentrated and the crude compound was purified by flash chromatography over silica gel (15-40 µm, 330 g, Heptane/AcOEt 80/20). The pure fractions were collected and evaporated to dryness to give 3.45 g of intermediate D5 (62% yield).

Synthesis of Intermediate C5:

At 0° C., 3-chloroperbenzoic acid (2.93 g; 11.86 mmol) in CH$_2$Cl$_2$ (20 mL) was added to a mixture of B5 (5.14 g; 11.86 mmol) in CH$_2$Cl$_2$ (100 mL). The mixture was stirred at RT for 3 h. An aqueous solution of Na$_2$S$_2$O$_3$ (2 eq) was added to the mixture. 2 layers were separated and the aqueous layer was extracted with CH$_2$Cl$_2$ (twice). The combined organic layers were washed with a saturated aqueous solution of NaHCO$_3$, dried over MgSO$_4$, filtered and the solvent was removed under reduced pressure to give 6.7 g of intermediate C5 (containing sulfone analog) which was directly used in the next step.

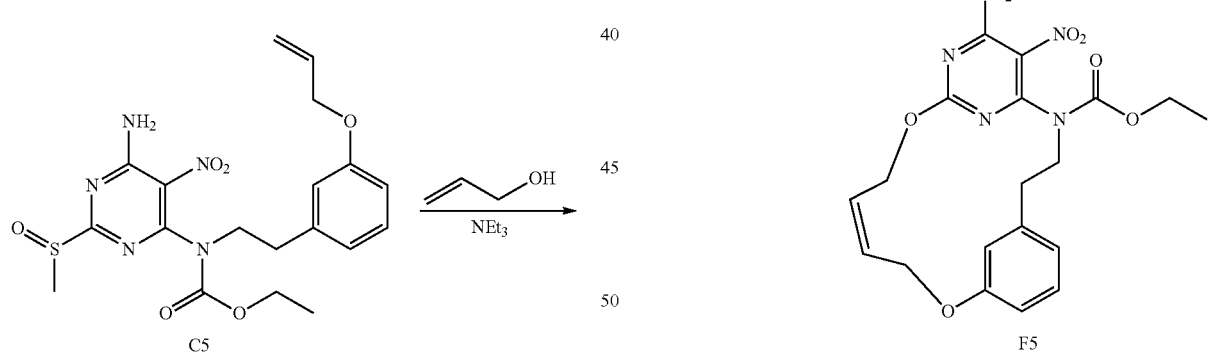

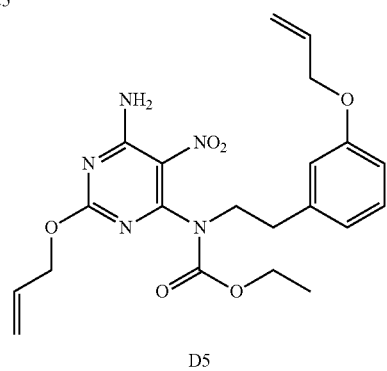

Synthesis of Intermediates E5 and F5:

Experiment was performed in 4 batches of 2 g of D5.

Grubbs catalyst 2$^{nd}$ generation (1.54 g; 1.80 mmol) was added in 3 times (3*514 mg) (at t=0, t=12 h, t=24 h) to a mixture of D5 (8 g; 18.04 mmol) in CH$_2$Cl$_2$ extra dry (3470 mL). The mixture was stirred at RT for 36 h. SiliaBon® DMT (24 g; 14.43 mmol) was added then the mixture was stirred 24 h at RT. The solid was filtered off and the solvent was evaporated to give 8.2 g. Purification was carried out by flash chromatography over silica gel (15-40 µm, 330 g, CH$_2$Cl$_2$/MeOH 99.5/0.5) The pure fractions were collected and evaporated to dryness to give 4.55 g of a mixture of E5 and F5 after filtration and drying of a solid in CH$_2$Cl$_2$/Diisopropylether. The two isomers were separated by achiral SFC (Stationary phase: Chiralpak IA 5 μm 250*20 mm), Mobile phase: 70% CO$_2$, 30% MeOH) to give 4.07 g of intermediate E5 (isomer E, 54% yield) and 187 mg of intermediate F5 (isomer Z, 2.5% yield).

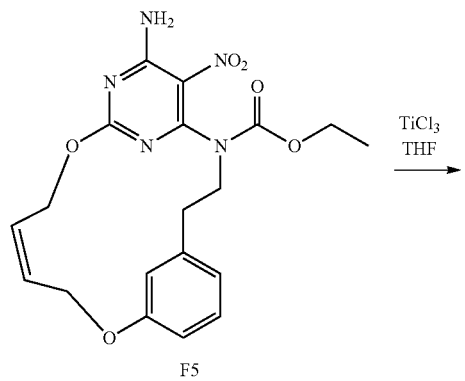

F5

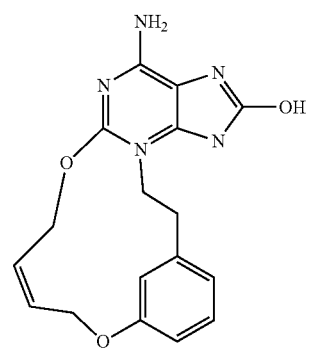

84

Synthesis of Final Compound 84:

At RT, TiCl$_3$ (5.5 mL; 6.45 mmol) was added drop wise to a mixture of F5 (134 mg; 0.32 mmol) in THF (20 mL). The mixture was stirred at RT overnight. At 0° C., the mixture was basified with K$_2$CO$_3$ powder. The resulting muddy mixture was filtered through a pad of Celite® and the Celite® was washed with a solution of AcOEt/CH$_3$OH 8/2. The filtrate was dried over MgSO$_4$, filtered and the solvent was evaporated to give 182 mg of a crude compound. MeOH was added, a solid appeared, it was filtered and dried under vacuum at 90° C. to 66 mg of final compound 84 (60% yield).

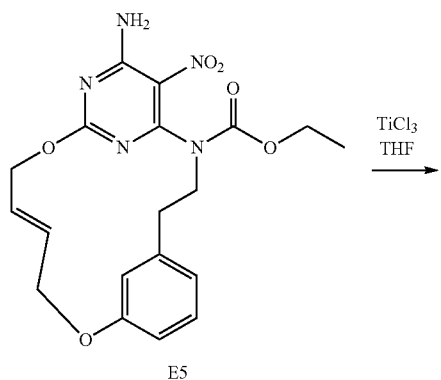

E5

-continued

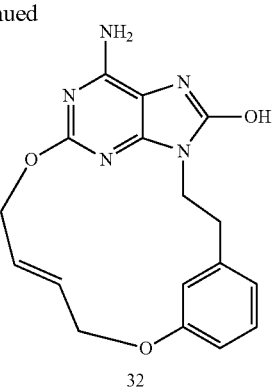

32

Synthesis of Final Compound 32:

At RT, TiCl$_3$ (60 mL; 69.811 mmol) was added drop wise to a mixture of E5 (1.45 g; 3.49 mmol) in THF (130 mL). The mixture was stirred at RT overnight. At 0° C., the mixture was basified with K$_2$CO$_3$ powder. The resulting muddy mixture was filtered through a pad of Celite® and the Celite® was washed with a solution of AcOEt/CH$_3$OH 8/2. The filtrate was partially evaporated to give 1.1 g of crude compound after filtration of a white solid and drying under vacuum. The crude compound was purified by preparative LC (Stationary phase: dry loading 220 g+10 g 15-40 μm Grace), Mobile phase: 0.5% NH$_4$OH, 97% CH$_2$Cl$_2$, 3% MeOH to 0.5% NH$_4$OH, 90% CH$_2$Cl$_2$, 10% MeOH) to give 730 mg of final compound 32 after evaporation of solvent and drying under vacuum (62% yield).

OVERALL SCHEME IN THE PREPARATION OF FINAL PRODUCTS: METHOD 19

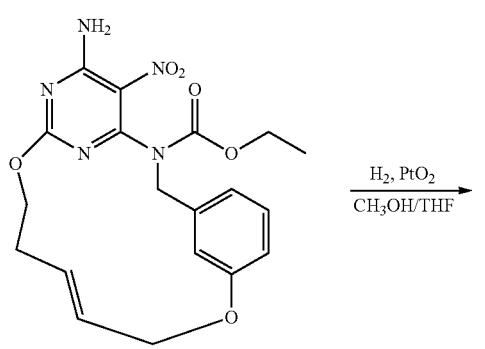

G5

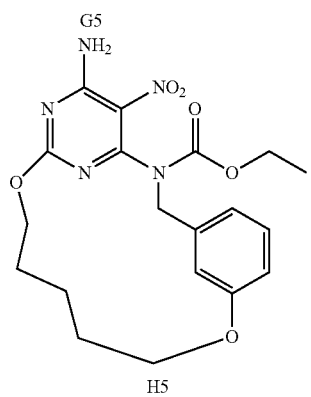

H5

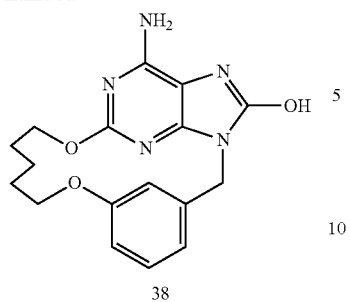

38

Synthesis of Intermediate H5:

Intermediate G5 was synthesized using the procedure described for intermediate P4.

A mixture of G5 (250 mg, 0.60 mmol), $PtO_2$ (25 mg) in $CH_3OH$/THF (50/50) (20 mL) was hydrogenated under an atmospheric pressure of $H_2$ for 30 mn. The catalyst was removed by filtration. The filtrate was concentrated under reduced pressure. The crude compound was purified by preparative LC on (irregular 15-40 μm 30 g Merck), mobile phase (80% Heptane, 20% AcOEt). >The resulting compound was further purified by achiral SFC on (2-Ethylpyridine 6 μm 150×30 mm), mobile phase (70% $CO_2$, 30% $CH_3OH$) to give 113 mg of intermediate H5 (45% yield).

Synthesis of Final Compound 38:

Iron (147 mg; 2.63 mmol) was added to a mixture of H5 (110 mg; 0.26 mmol) in acetic acid (7 mL) and water (1.5 mL). The mixture was stirred vigorously at RT for 6 h at 50° C. The reaction mixture was concentrated in vacuo and the residue was taken up by a mixture of DMF/THF, filtered through a pad of Celite® and evaporated. The crude product was diluted with acetic acid/water, a precipitate was filtered off, washed with $CH_3OH$ and dried to give 55 mg of final compound 38 (61% yield).

OVERALL SCHEME IN THE PREPARATION OF FINAL PRODUCTS: METHOD 20

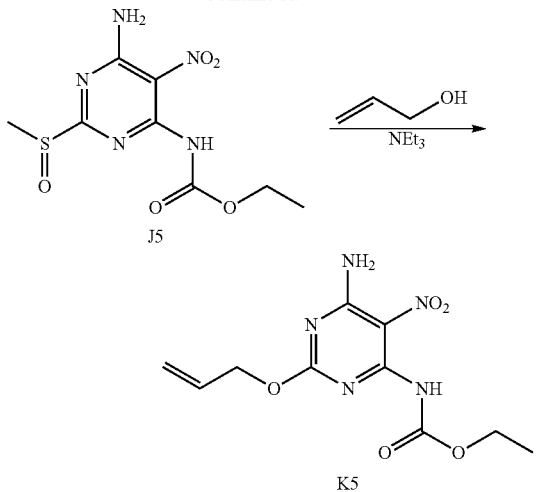

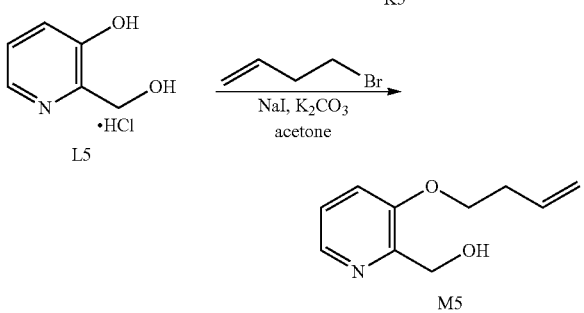

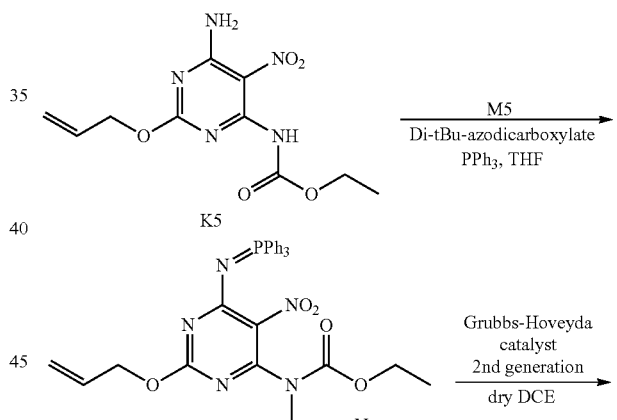

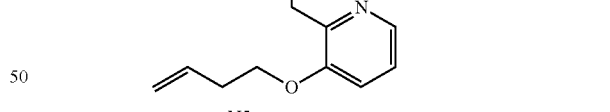

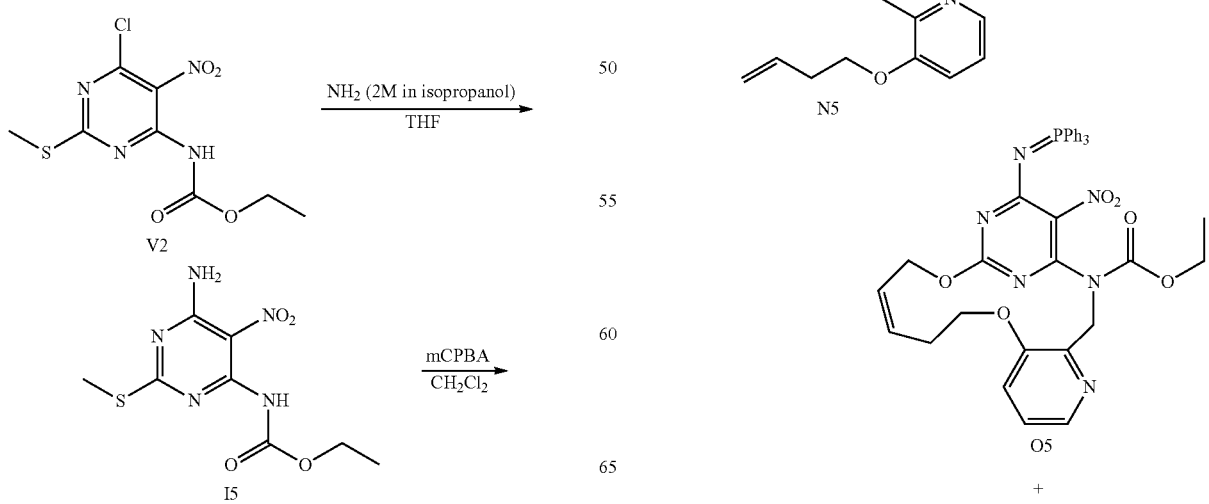

+

-continued

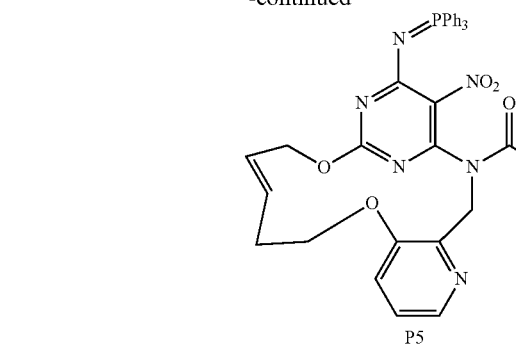
P5

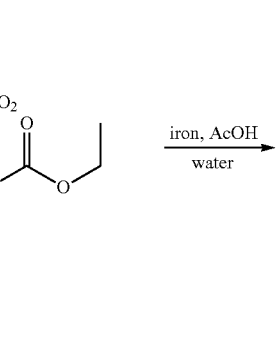
O5

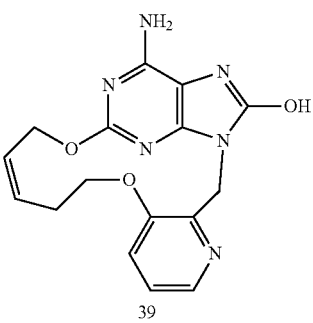
39

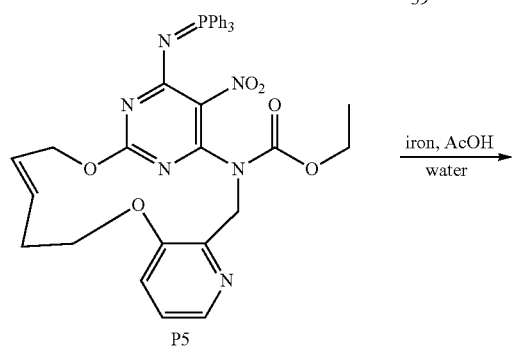
P5

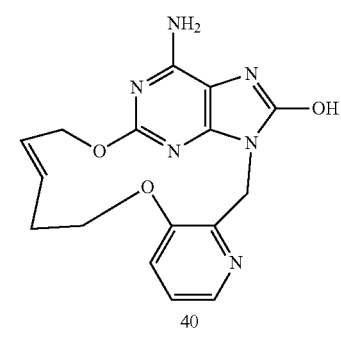
40

-continued

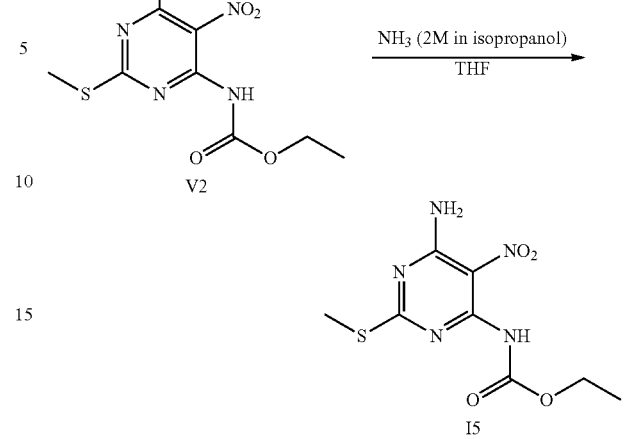
V2

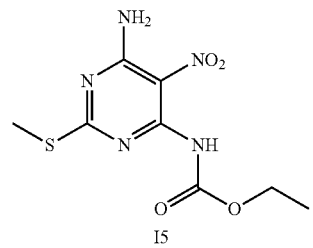
I5

Synthesis of Intermediate 15:

The reaction was done in 2 batches of 15 g of V2.

Here is the protocol for one batch of 15 g:

NH$_3$ (2M in isopropanol) (51 mL; 102 mmol) was added to a solution of V2 (15 g; 51.2 mmol) in THF (250 mL) at RT for 2 h. The two batches were mixed. The suspension was concentrated to dryness. The solid was dissolved in CH$_2$Cl$_2$. The organic layer was washed with water (once), dried over MgSO$_4$, filtered and the solvent was removed under reduced pressure to give 28.5 g of intermediate 15 (100% yield) as a white solid.

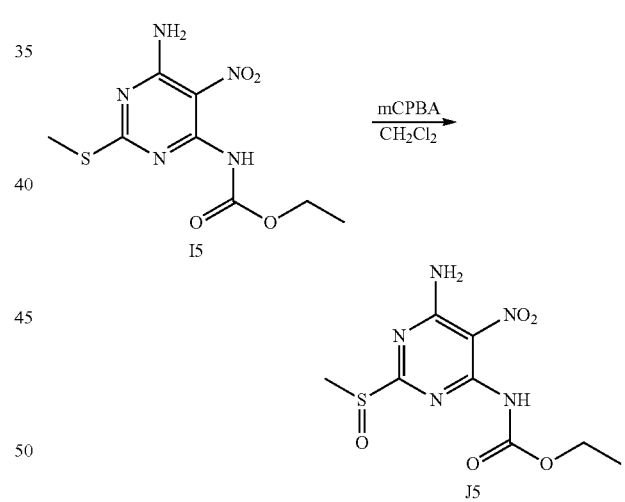
I5

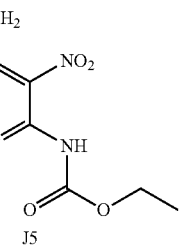
J5

Synthesis of Intermediate J5:

The reaction was done in 2 batches of 14 g of 15.

Here is the protocol for one batch of 14 g:

A solution of meta-chloroperbenzoic acid (9.58 g; 40.0 mmol) in CH$_2$Cl$_2$ (500 mL) was added drop wise to a solution of 15 (14 g; 33.3 mmol) in CH$_2$Cl$_2$ (2 L) at RT. The mixture was stirred at RT for 16 h. The solution was filtered to give 18 g of fraction 1.

A 10% aqueous solution of Na$_2$S$_2$O$_3$ and a saturated aqueous solution of NaHCO$_3$ were added to the filtrate. The layers were separated and the organic layer was dried over MgSO$_4$, filtered and the solvent was removed in vacuo to give 14 g of intermediate J5 as a yellow solid. The crude compound was used directly in the next reaction step.

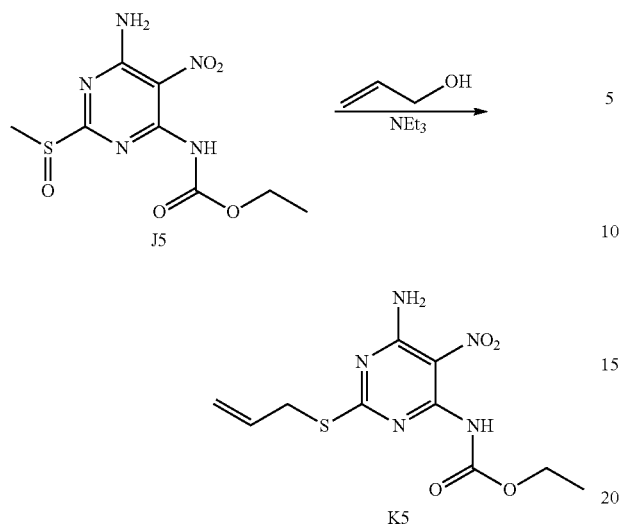
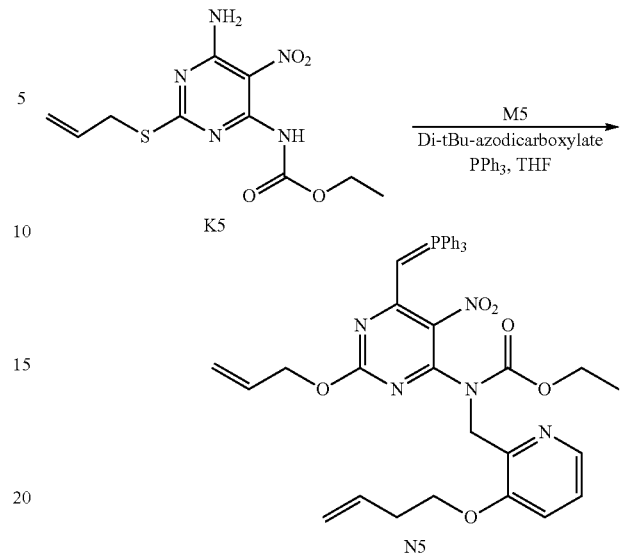

Synthesis of Intermediate K5:

A solution of J5 (6 g; 20.7 mmol) and NEt$_3$ (3.2 mL; 22.8 mmol) in allyl alcohol (120 mL) was stirred at RT for 16 h. The solvent was removed in vacuo to give a yellow solid. The crude compound was purified by preparative LC (Irregular SiOH 15-40 µm, 120 g Grace, mobile phase gradient: from CH$_2$Cl$_2$/EtOAc, 100/0 to 85/15) to give 4 g of intermediate K5 as a pale yellow solid (68% yield).

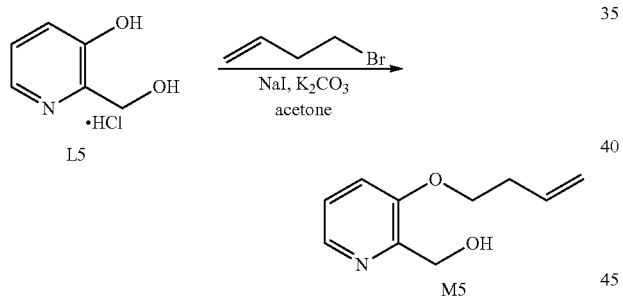

Synthesis of Intermediate M5:

To a suspension of L5 (5.2 g; 32.2 mmol) and K$_2$CO$_3$ (11.1 g; 80.5 mmol) in acetone (250 mL) was added 4-bromo-1-butene (4.1 mL; 40.2 mmol), and the mixture was heated at 60° C. during 16 h. 4-bromo-1-butene (4.1 mL; 40.2 mmol) and NaI (0.965 g; 6.43 mmol) were added, and the mixture was heated at 60° C. during 5 days, during which successive additions of 4-bromo-1-butene (2×4.1 mL; 80.4 mmol), K$_2$CO$_3$ (2×2.22 g; 32.2 mmol), and NaI (3.86 g; 25.7 mmol) were performed in order to achieve complete conversion, as observed by TLC. The mixture was filtered and the filtrate was concentrated in vacuo to give a brown oil. The crude compound was purified by preparative LC on (Irregular SiOH 20-45 m, 450 g Matrex), mobile phase (0.7% NH$_4$OH, 85% Heptane, 15% iPrOH) to afford 3.6 g of intermediate M5 as an orange oil (62% yield).

Synthesis of Intermediate N5:

The reaction was performed in 3 batches.

Typical Procedure for One Batch:

Under nitrogen, a solution of K5 (667 mg; 2.35 mmol), M5 (633 mg; 3.53 mmol), PPh$_3$ (926 mg; 3.53 mmol) and di-tert-butylazodicarboxylate (813 mg; 3.53 mmol) in dry THF (20 mL) was heated at 130° C. using one single mode microwave (Biotage Initiator EXP 60) with a power output ranging from 0 to 400 W for 1 h.

The 3 batches were combined and evaporated under vacuum to give 9.8 g of a brown oil. The crude compound was purified by preparative LC on (Irregular SiOH 20-45 µm 450 g Matrex), mobile phase (Gradient from 60% Heptane, 40% AcOEt to 50% Heptane, 50% AcOEt) to afford 1.1 g of intermediate N5 (22% yield) as a yellow solid.

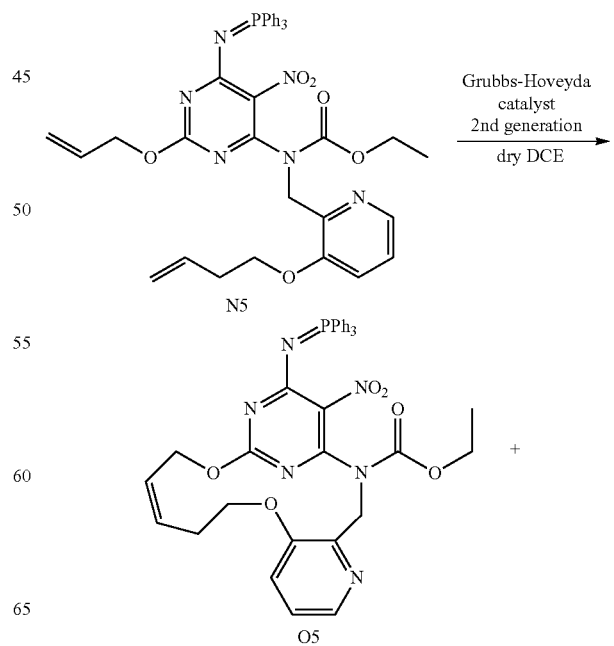

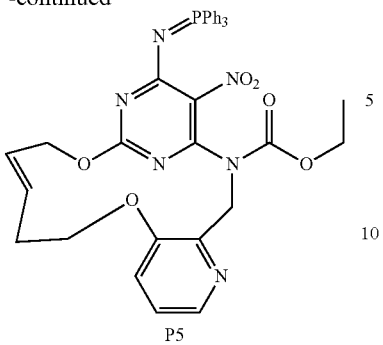

Synthesis of Intermediates O5 and P5:

A solution of N5 (950 mg; 1.35 mmol) and chlorodicyclohexylborane (1 M in hexane) (270 µL; 270 µmol) in dry dichloroethane (452 mL) was stirred at 80° C. for 1 h. Grubbs-Hoveyda catalyst $2^{nd}$ generation (35 mg; 56.2 µmol) was added and the mixture was stirred at 120° C. for 1 h then more catalyst (35 mg; 56.2 µmol) was added. The mixture was stirred at 120° C. for 24 h. Grubbs-Hoveyda catalyst $2^{nd}$ generation (57 mg; 90.9 mmol) was added again and the mixture was stirred at 120° C. for 6 h. SiliaBond® DMT (3.11 g; 1.62 mmol) was added and the mixture was stirred at RT for 24 h, then the dark solid was filtered off and the filtrate was evaporated in vacuo. The crude compound was purified by preparative LC (irregular SiOH 15-40 µm, Merck 90 g; mobile phase gradient: from heptane/iPrOH 90/10 to 65/35) to give 0.12 g of intermediate O5 (13% yield), 0.47 g of a mixture of intermediates O5 and P5 (52% yield) and 28 mg of intermediate P5 (3% yield).

The mixture of intermediates O5 and P5 was further purified by preparative LC (Stability silica 5 µm 150×30.0 mm, mobile phase gradient: from heptane/AcOEt 85/15 to 0/100) to give 120 mg of intermediate O5 and 224 mg of intermediate P5.

global yield: 54% (E-isomer O5: 28%, Z-isomer P5: 26%).

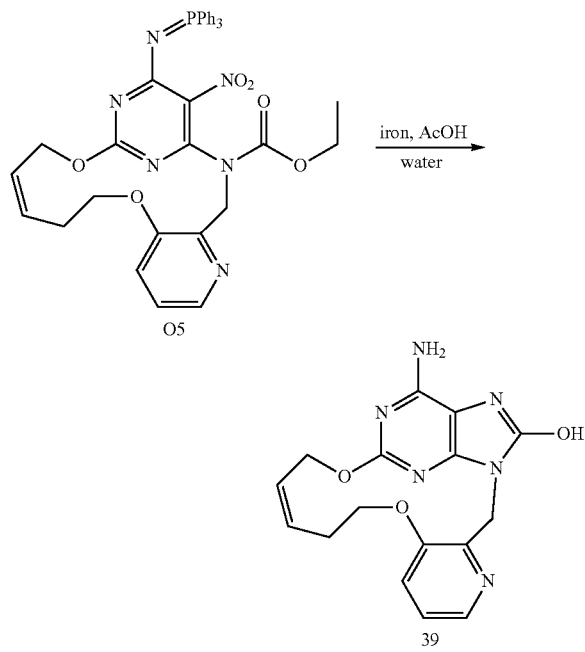

Synthesis of Final Compound 39:

A mixture of O5 (240 mg; 0.355 mmol) and iron (119 mg; 2.13 mmol) in acetic acid (4.3 mL) and water (0.4 mL) were heated at 100° C. using one single mode microwave (Biotage Initiator EXP 60) with a power output ranging from 0 to 400 W for 1 h. The solvent was removed in vacuo and the residue was taken up with DMF. The mixture was filtered over Celite® and the filtrate was evaporated in vacuo to give fraction 1. SiliaBond® imidazole (Fe scavenger from Silicycle®) (3.67 g; 4.25 mmol) was added to fraction 1 in DMF (50 mL). The mixture was stirred at RT for 16 h and filtered over Celite® and the filtrate was evaporated in vacuo to give 100 mg of fraction 2. Fraction 2 was purified by preparative LC (irregular SiOH 15-40 µm, 25 g Merck, dry loading, mobile phase gradient: from $CH_2Cl_2$/MeOH/$NH_3$ aq 95/5/0.5 to 85/15/1.5) to give 9 mg of final compound 39 as a white solid (7% yield).

OVERALL SCHEME IN THE PREPARATION OF FINAL PRODUCTS: METHOD 21

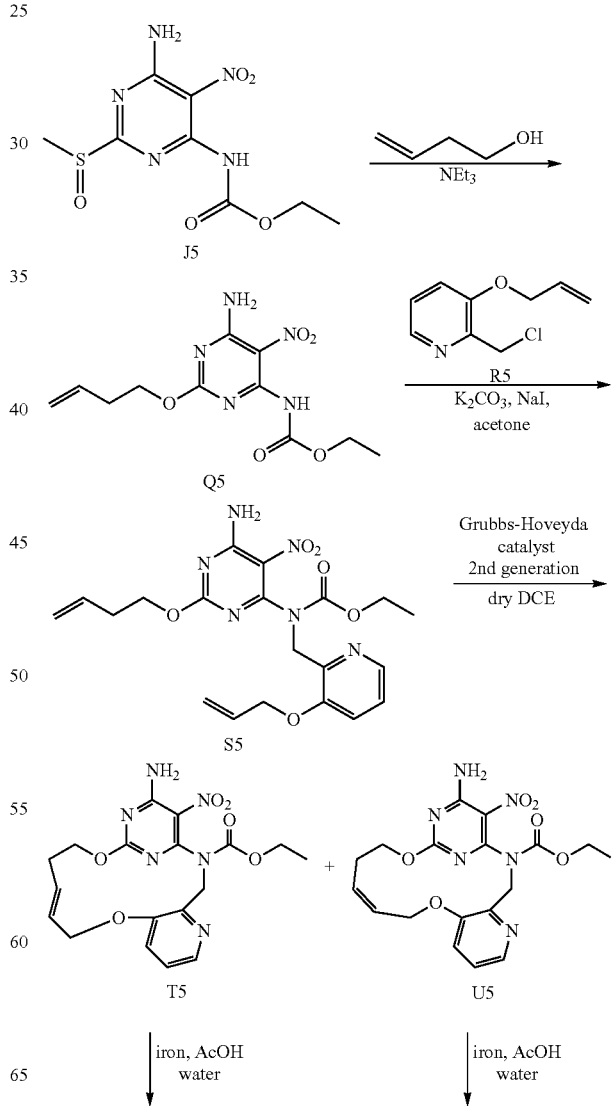

111

-continued

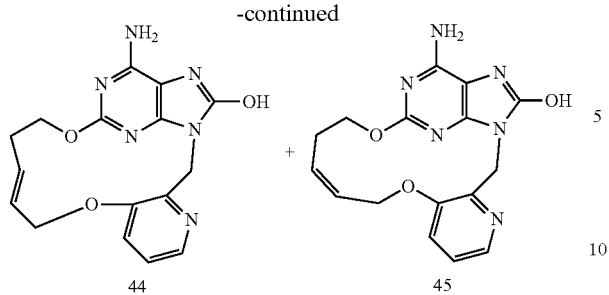

112

-continued

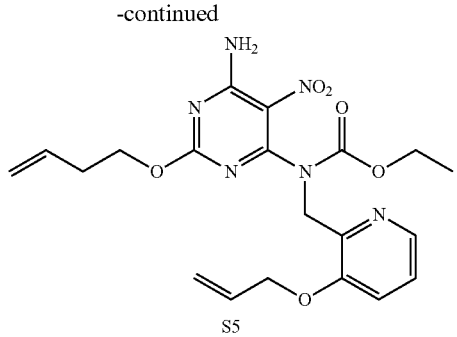

Synthesis of Intermediate S5:

Q5 (12.8 g; 43.2 mmol), R5 (16.1 g; 77.8 mmol), $K_2CO_3$ (14.9 g; 108 mmol) and NaI (6.48 g; 43.2 mmol) in acetone (690 mL) were stirred at RT for 1 h and then the mixture was heated at 75° C. for 16 h. The mixture was cooled to RT and was filtered through a pad of Celite®. The filtrate was evaporated in vacuo to give fraction 1. Fraction 1 was combined with another batch (reaction with 67.46 mmol of Q5) to be purified by preparative LC (2 serial chromatography, irregular SiOH, 15-40 µm, 220 g Grace, liquid injection, mobile phase gradient: from $CH_2Cl_2$/EtOAc 100/0 to 50/50) to give 1.97 g of fraction 2 as a brown solid and 10.7 g of fraction 3 as a brown solid.

The two fractions were taken up and diluted with $CH_2Cl_2$. Heptane was added and the mixture was partially evaporated in vacuo to give a pale brown precipitate which was filtered off to give 11.26 g of intermediate S5 as an off-white solid (59% yield).

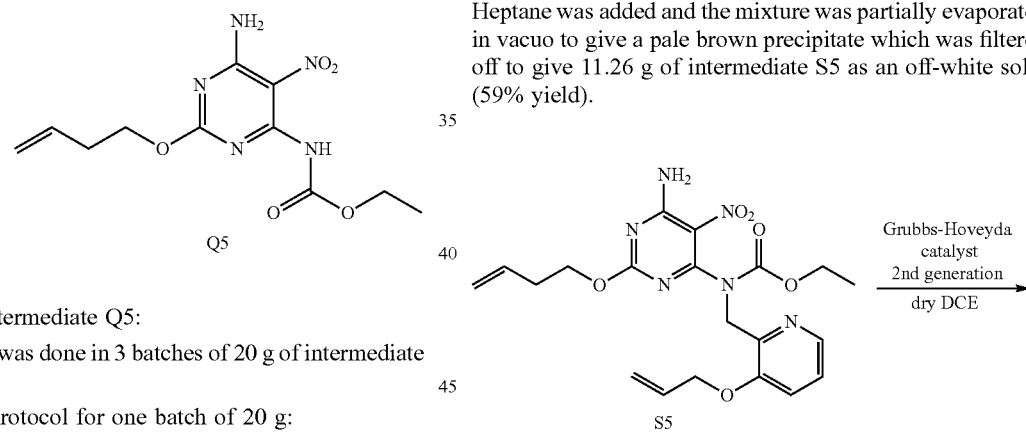

Synthesis of Intermediate Q5:

The reaction was done in 3 batches of 20 g of intermediate J5.

Here is the protocol for one batch of 20 g:

A solution of J5 (20 g; 69.1 mmol) and $NEt_3$ (11.5 mL; 83.0 mmol) in 3-buten-1-ol (500 mL) was stirred at RT for 16 h. The solvent was removed in vacuo to give a yellow solid. The combined 3 reactions were purified by preparative LC (Irregular SiOH 15-40 µm, 750 g Grace, mobile phase gradient: $CH_2Cl_2$/EtOAc from 100/0 to 80/20). The fractions containing product were combined and the solvent was removed in vacuo to give 39 g of intermediate Q5 (63% yield).

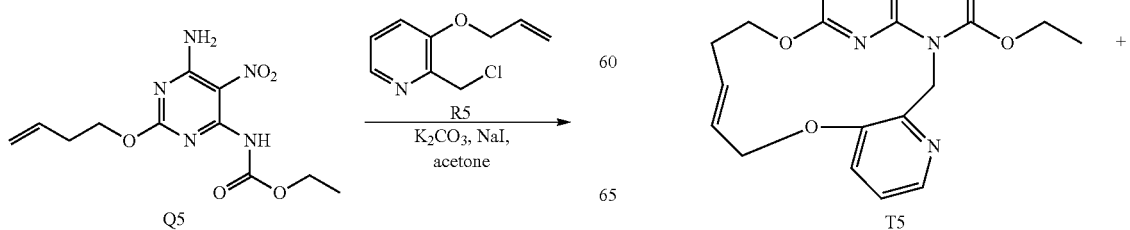

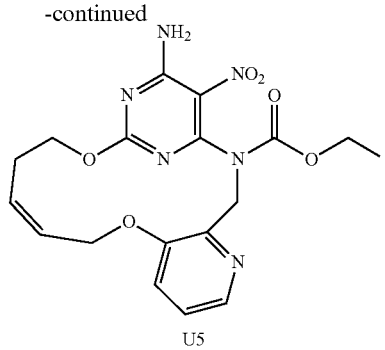

U5

Synthesis of Intermediates T5 and U5:

This reaction was performed in 2 batches using respectively 2.75 g and 1.51 g of intermediate S5.

Typical procedure for 1 batch:

A solution of S5 (1.51 g; 3.40 mmol) and chlorodicyclohexylborane (1M in hexane) (0.679 mL; 0.679 mmol) in dry dichloroethane (908 mL) degassed by $N_2$ bubbling for 15 min was stirred at 80° C. under $N_2$ atmosphere for 1 h. Grubbs-Hoveyda catalyst $2^{nd}$ generation (213 mg; 0.340 mmol) was added and the mixture was stirred at 80° C. for 1 h. SiliaBond® DMT (4.45 g; 2.72 mmol) was added and the resulting mixture was stirred at RT for 20 h. The 2 batches were combined and filtered through a pad of Celite®. The filtrate was evaporated in vacuo to give 4.2 g of a brown solid. The solid was purified by preparative LC (regular SiOH, 30 µm, 200 g Interchim, mobile phase gradient: from $CH_2Cl_2$/AcOEt 100/0 to 25/75) to give 2.5 g of fraction 1 and 1.3 g of of intermediate T5 (32%, E isomer). Fraction 1 was taken-up with $CH_2Cl_2$ then heptane was added. $CH_2Cl_2$ was partially evaporated in vacuo and the resulting precipitate was filtered and dried under vacuum to give 1.52 g of intermediate U5 (38% yield, Z isomer).

Synthesis of Final Compound 45:

This reaction was performed in 5 batches using respectively 0.5 g, 3 times 1 g, and two times 1.45 g of intermediate U5.

Here is the procedure for 2 batches of 1.45 g:

Under $N_2$ atmosphere, U5 (1.45 g; 3.48 mmol) was added portion wise to a solution of acetic acid (193 mL) and water (19 mL) heated at 70° C. After complete dissolution, iron (1.17 g; 20.9 mmol) was added in one portion and the mixture was stirred at 70° C. for 4 h. The 2 batches were combined and filtered hot through a pad of Celite® and the Celite® was rinsed with hot acetic acid. The resulting filtrate was concentrated to give a brown residue which was taken up with MeOH, sonicated and heated to give a yellow precipitate which was filtered off to give fraction 1 as a yellow solid. Fraction 1 was taken up with acetic acid (30 mL) and sonicated until partial dissolution. Water was added (700 mL) and the resulting mixture was sonicated for 1 h, cooled to 0° C. (ice bath) to give a precipitate which was filtered off (glass frit n° 5) to give an off-white solid. The solid was taken up with MeOH, mixed with 3 other batches (obtained with 0.5 g and 2 times 1 g of U5). The resulting mixture was sonicated, heated and cooled to 0° C. (ice bath) and the resulting solid was filtered off (glass frit n° 4) to give 3.5 g of fraction 2 as an off-white solid. Fraction 2 was mixed with the last batch (obtained with 1 g of U5), DMSO (280 mL) was added and the mixture was heated at 100° C. until complete dissolution. The resulting solution was filtered off and the filtrate was added to water (1.7 L). The resulting precipitate was stirred at RT for 16 h. The precipitate was filtered off to give 4.1 g of fraction 3 as an off-white solid.

Fraction 3 was taken up with EtOH and was sonicated at 45° C. for 2 h. The resulting mixture was directly filtered off (glass frit n° 4) to give 3.63 g of fraction 4 as an off-white solid. Fraction 4 was taken up with MeOH (180 mL) and the mixture was stirred at 60° C. for 1 h. The mixture was filtered hot to give 3.47 g of final compound 45 as an off-white solid (54% yield).

OVERALL SCHEME IN THE PREPARATION OF FINAL PRODUCTS: METHOD 22

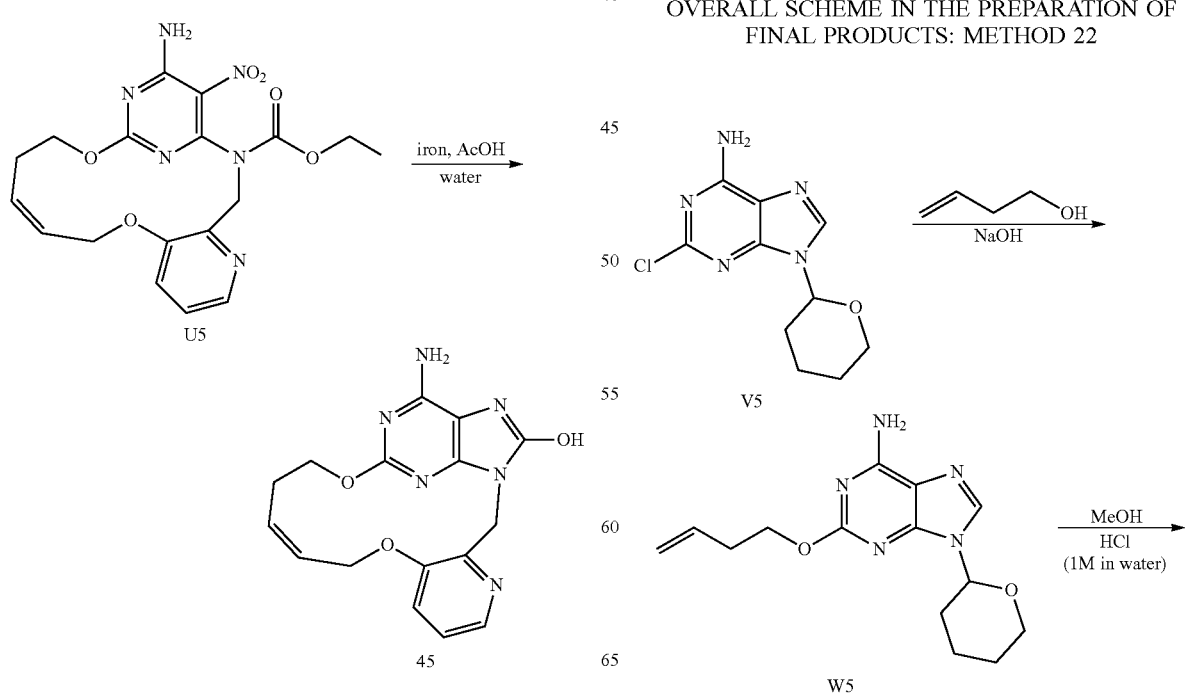

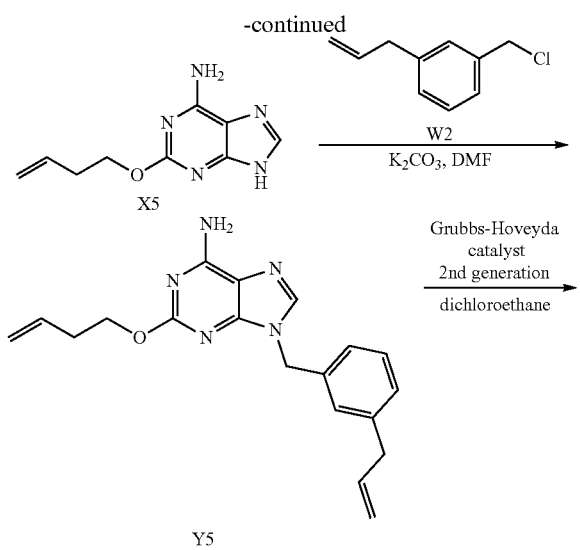

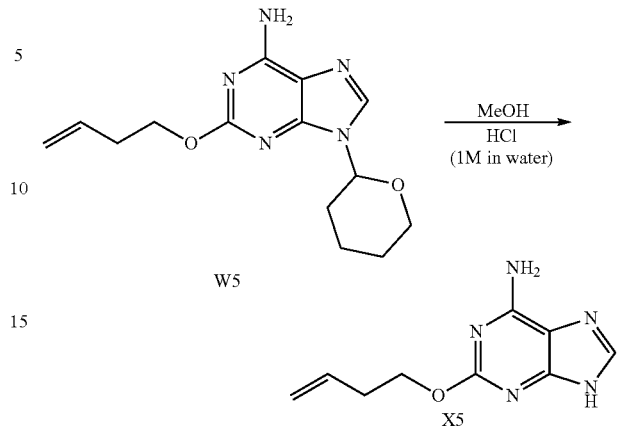

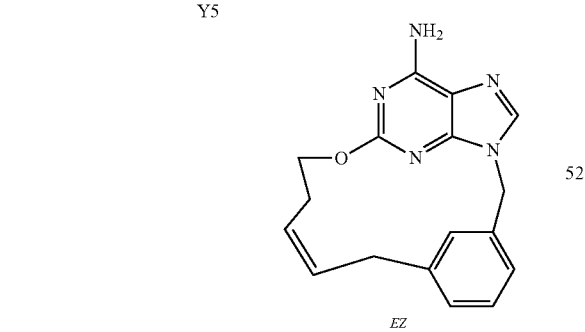

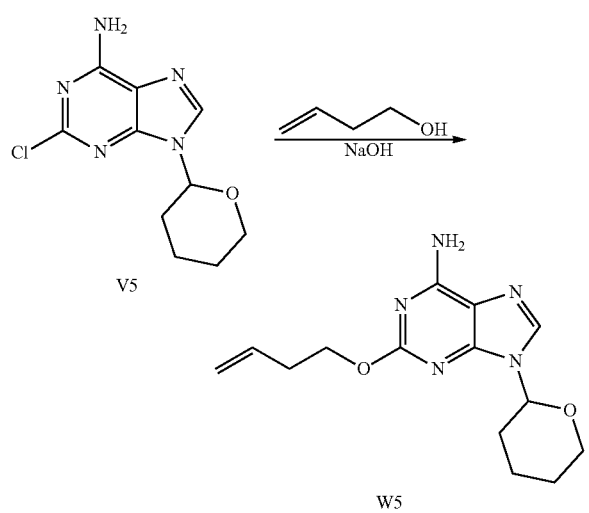

Synthesis of Intermediate W5:

This reaction was performed in 3 batches using respectively 0.2 g, 1.5 g, and 4 g of intermediate V5.

Here is the procedure for the 4 g batch:

V5 (4 g; 15.8 mmol), NaOH (2.52 g; 63.1 mmol) and 3-buten-1-ol (100 mL) were stirred at 90° C. for 24 h. The solvent was removed under reduced pressure to give fraction 1 as a brown oil. Fraction 1 was combined with the two other batches to give fraction 2. Fraction 2 was purified by preparative LC (Irregular SiOH 15-40 µm, 80 g Grace, dry loading, mobile phase gradient: $CH_2Cl_2$/MeOH/$NH_3$ aq from 97/3/0.03 to 80/20/2) to give 3.88 g of intermediate W5 as an orange solid (60% yield).

Synthesis of Intermediate X5:

HCl (1 M in water) (2 mL) was added to a stirred solution of W5 (3.88 g; 13.4 mmol) in MeOH (160 mL) at RT. The resulting mixture was stirred at 60° C. for 4 h. Then HCl (3 M in water) (2 mL) was added and the mixture was stirred at 60° C. for 64 h. The reaction mixture was concentrated in vacuo, the resulting residue was taken up with $CH_2Cl_2$, filtered off and dried under reduced pressure to give 2.72 g of intermediate X5 as a pale brown solid (84% yield). The compound was used directly in the next reaction step.

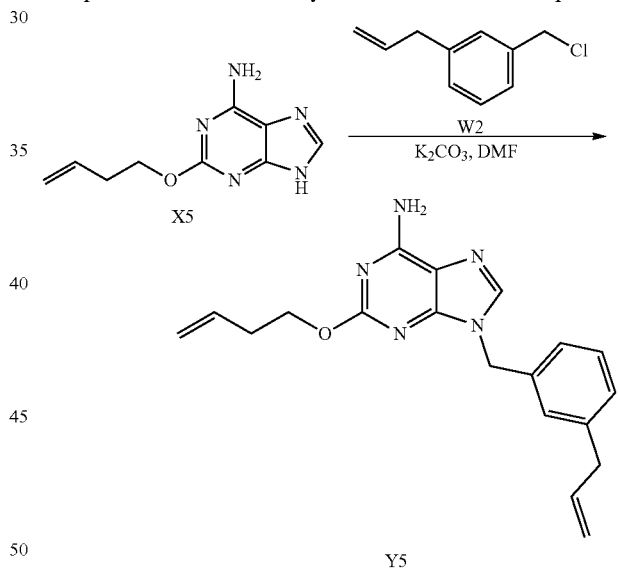

Synthesis of Intermediate Y5:

W2 (2.34 g; 14.0 mmol) was added to a stirred solution of X5 (2.62 g; 12.8 mmol) and $K_2CO_3$ (3.9 g; 28.1 mmol) in DMF (40 mL). The mixture was stirred at RT for 1 h and then at 70° C. for 3 h. The reaction mixture was cooled to RT, diluted with MeOH and filtered on a pad of Celite®. The resulting filtrate was concentrated in vacuo to give fraction 1. Fraction 1 was purified by preparative LC (Irregular SiOH 15-40 µm, 80 g Grace, dry loading, mobile phase gradient: $CH_2Cl_2$/MeOH/$NH_3$ aq from 100/0/0 to 80/20/2) to give 4.6 g of an orange solid. The solid was purified by preparative LC (Irregular SiOH 15-40 µm, 80 g Grace, dry loading, mobile phase gradient: Heptane/$CH_2Cl_2$/MeOH from 100/0/0 to 0/90/10) to give 3 g of intermediate Y5 a pale orange solid. The compound was used as such in the next reaction step.

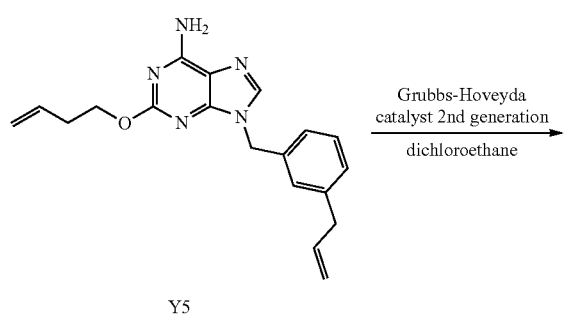

Synthesis of Final Compound 52:

The reaction was performed in 2 batches of 250 mg of intermediate Y5.

Herein is reported the procedure for one batch of 250 mg:

In a schlenk flask, Y5 (250 mg; 0.745 mmol) was dissolved in dry dichloroethane (250 mL) and the solution was degassed by $N_2$ bubbling through the solution for 20 min. Chlorodicyclohexylborane (1 M in hexane) (150 µL; 150 µmol) was added and the resulting solution was stirred at 70° C. for 1 h. Grubbs-Hoveyda catalyst $2^{nd}$ generation (23 mg; 37.3 µmol) was added and the mixture was stirred at 120° C. for 16 h. Catalyst (23 mg; 37.3 µmol) was added again and the mixture was stirred at 120° C. for 4 h. Catalyst (9 mg; 14.9 µmol) was added again and the mixture was stirred at 120° C. for 3 h. SiliaBond® DMT (1.19 g; 0.716 mmol) was added and the mixture was stirred at RT for 16 h. The two batches were mixed and filtered through a pad of Celite®. The resulting filtrate was concentrated to give a brown residue. The residue was purified by preparative LC (Irregular SiOH 15-40 µm, 40 g Merck, dry loading, mobile phase gradient: $CH_2Cl_2$/MeOH/$NH_3$ aq from 100/0/0 to 80/20/0.2) to give 155 mg of final compound 52 as an off-white solid (E/Z mixture, 34% yield).

OVERALL SCHEME IN THE PREPARATION OF FINAL PRODUCTS: METHOD 23

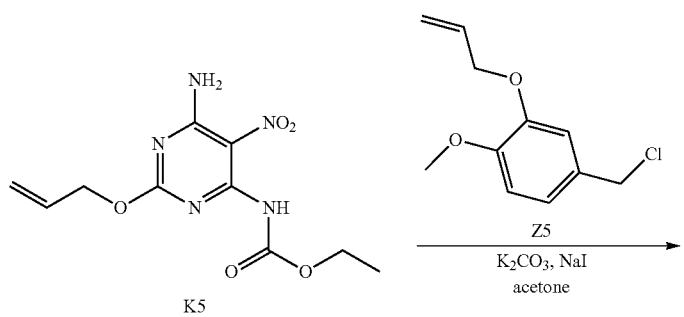

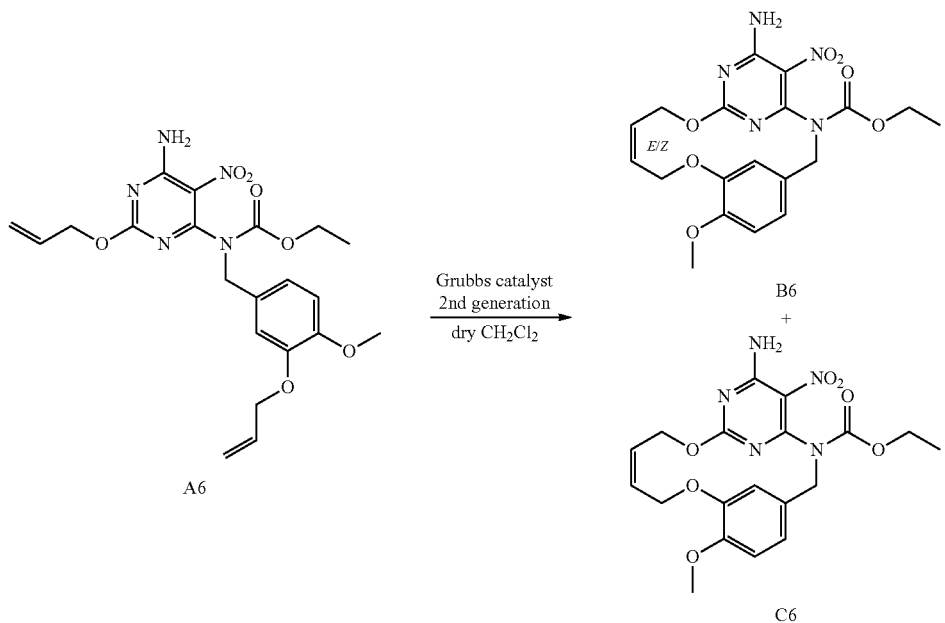

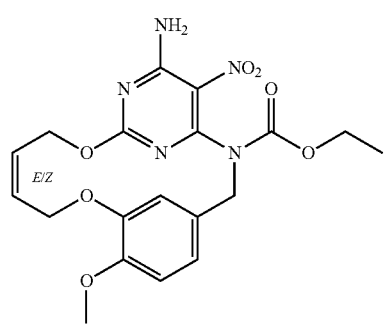
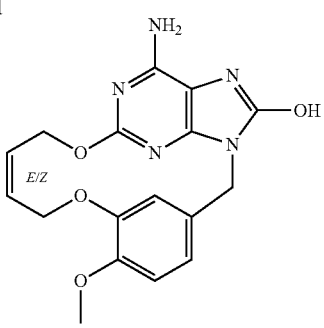
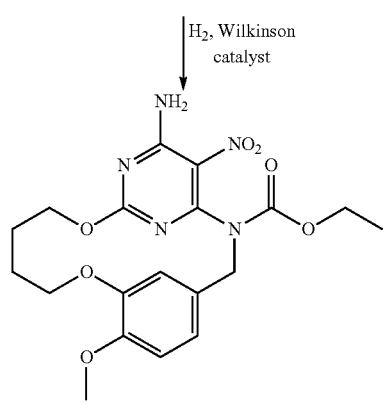
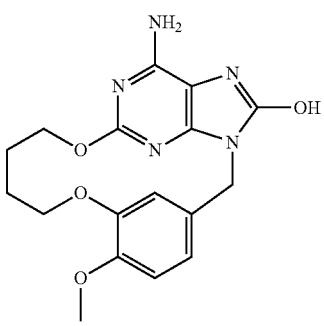
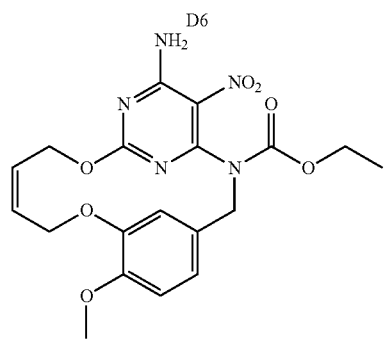
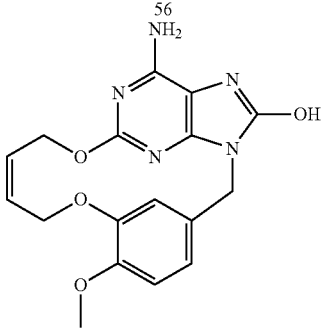
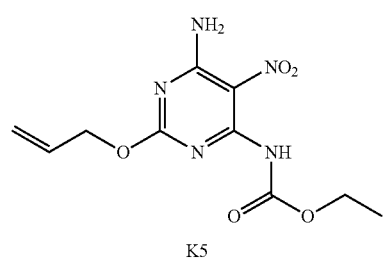
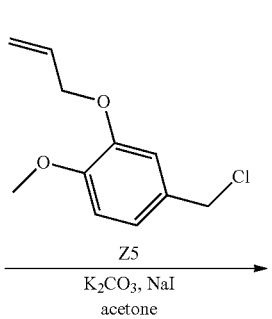
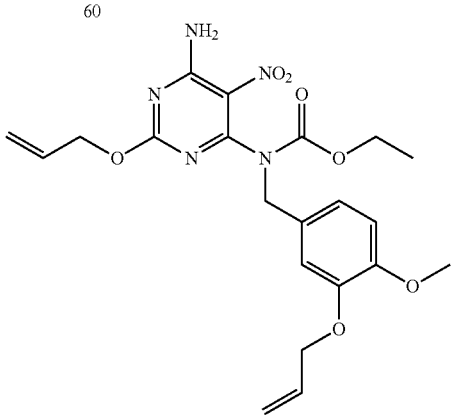
Synthesis of Intermediate A6:
K5 (3.0 g; 10.6 mmol), Z5 (2.5 g; 11.7 mmol), K$_2$CO$_3$ (2.93 g; 21.2 mmol) and NaI (1.6 g; 10.6 mmol) in acetone (150 mL) were stirred at 75° C. for 16 h. The solution was filtered and the filtrate was evaporated under reduced pressure to give fraction 1. Fraction 1 was purified by preparative LC (Irregular SiOH 15-40 µm, 90 g Merck, mobile phase gradient: from Heptane/CH$_2$Cl$_2$/EtOAc 100/0/0 to 0/90/10). The fractions containing product were combined and the solvent was removed in vacuo to give 4.4 g of intermediate A6 (90% yield) as a yellow solid.

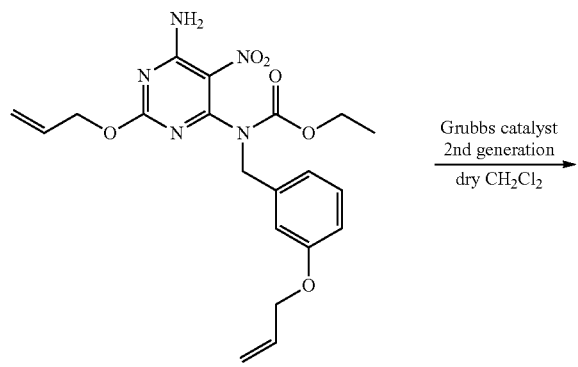

Synthesis of Intermediates B6 and C6:

The reaction was performed in 2 batches of 1.5 g and one batch of 1.2 g of intermediate A6.

Herein is reported the procedure for one batch of 1.5 g:

A6 (1.5 g; 3.27 mmol) was added to dry CH$_2$Cl$_2$ (900 mL) and the resulting mixture was degassed by N$_2$ bubbling through the solution for 30 min. Grubbs catalyst $2^{nd}$ generation (92 mg; 108 µmol) was added in one portion and the mixture was stirred at RT under N$_2$ atmosphere for 2 h. Catalyst (92 mg; 108 µmol) was added again in one portion and the mixture was stirred at RT under N$_2$ atmosphere for 16 h. Catalyst (92 mg; 108 µmol) was added again in one portion and the mixture was stirred at RT under N$_2$ atmosphere for 48 h.

The 3 batches were mixed, SiliaBond® DMT (12 g; 7.31 mmol) was added and the mixture was stirred at RT for 16 h. The reaction mixture was filtered through a pad of Celite® and the filtrate was evaporated in vacuo to give fraction 1 as a brown solid. Fraction 1 was purified by preparative LC (Irregular SiOH 15-40 µm, 70 g Merck, mobile phase gradient: CH$_2$Cl$_2$/EtOAc from 100/0 to 80/20). The fractions containing product were combined and the solvent was removed in vacuo to give fraction 2 and fraction 3. Fraction 2 was solubilized in hot EtOH/Acetone. The mixture was left to cool down to RT. Then the precipitate was filtered off, washed (3 times) with 20 mL of EtOH and dried in vacuo to give 800 mg of intermediate B6 (E/Z mixture) as a yellow solid.

Fraction 3 was solubilized in hot EtOH/Acetone. The mixture was allowed to cool down to RT. Then the precipitate was filtered off, washed (3 times) with 15 mL of EtOH and dried in vacuo to give 300 mg of intermediate B6 (E/Z mixture) as a yellow solid.

Part of intermediate B6 (100 mg) was purified by achiral SFC (Stationary phase: AMINO 6 m 150×21.2 mm, Mobile phase: CO$_2$/MeOH; 75/25) to give 78 mg of intermediate C6 (E isomer) as a yellow solid.

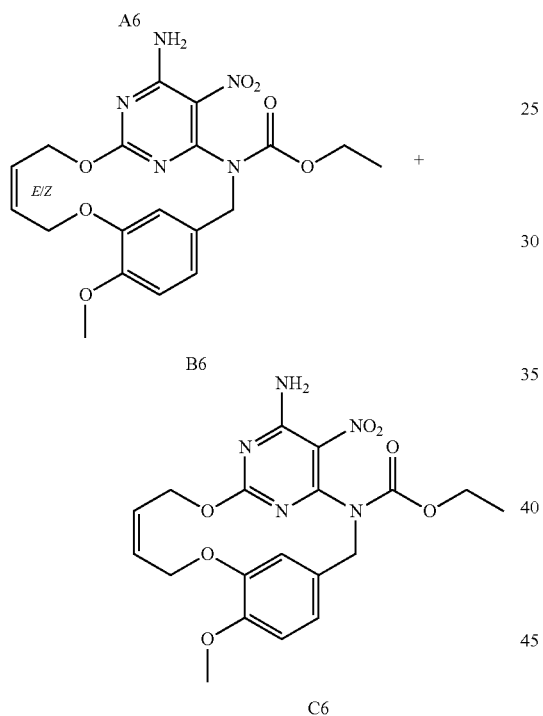

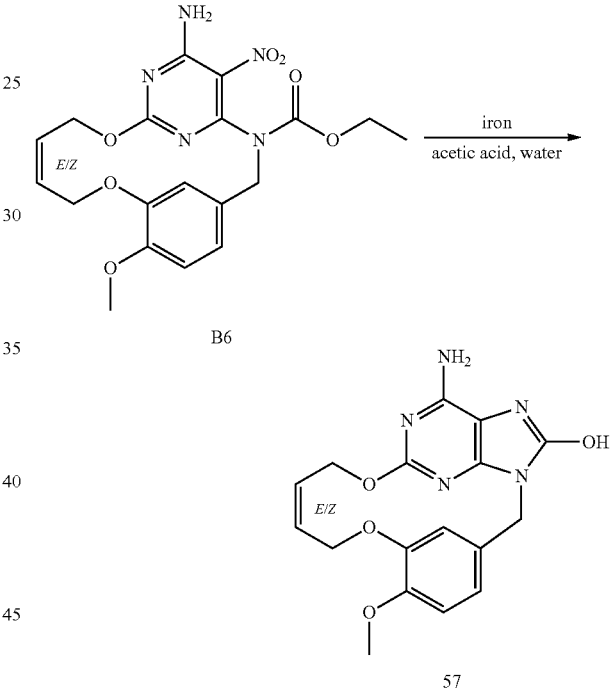

Synthesis of Final Compound 57:

A mixture of B6 (150 mg; 348 µmol) and iron (117 mg; 2.09 mmol) in acetic acid (10 mL) and water (1 mL) was stirred at 80° C. for 2 h. The mixture was filtered through a pad of Celite® and the filtrate was evaporated in vacuo to give fraction 1. Fraction 1 was taken up with DMF. SiliaBond® imidazole (3.6 g; 4.17 mmol) was added and the reaction was stirred at RT for 16 h. The solution was filtered through a pad of Celite®. The filtrate was evaporated in vacuo. The residue was taken up with acetic acid and water (30:70). The precipitate was filtered and dried under vacuum to give fraction 2. Fraction 2 was taken up with MeOH. The precipitate was filtered and dried under vacuum to give fraction 3. Fraction 3 was filtered through a pad of silica gel (mobile phase: DMF), the fractions containing product were combined and the solvent was removed in vacuo to give fraction 4. Fraction 4 was taken up with DMF. SiliaBond® imidazole (3.6 g; 4.17 mmol) was added and stirred at RT for 16 h. The solution was filtered through a pad of Celite®. The filtrate was evaporated in vacuo to give fraction 5. Fraction 5 was taken up with acetic acid and water (70:30). The precipitate was filtered and dried under vacuum to give fraction 6. Fraction 6 was purified by preparative LC (Irregular SiOH 15-40 μm, 10 g Merck, mobile phase gradient: $CH_2Cl_2$/MeOH/$NH_3$ aq from 97/3/0.1 to 80/20/3). The fractions containing product were combined and the solvent was removed in vacuo to give 35 mg of fraction 7 as a white solid. Fraction 7 was taken up with water. The precipitate was filtered, washed (twice) with EtOH and $Et_2O$, dried under vacuum to give 26 mg of final compound 57 as a white solid (21% yield).

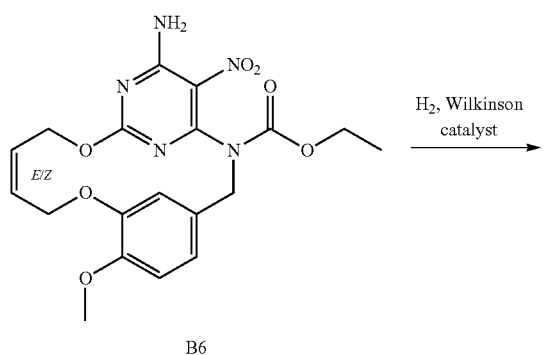

Synthesis of Intermediate D6:

A mixture of B6 (300 mg; 695 μmol), Wilkinson's catalyst (64 mg; 69.5 μmol) in THF/MeOH (50/50) (60 mL) was hydrogenated under 7 bars pressure at RT for 20 h. The mixture was filtered through a pad of Celite® and the filtrate was evaporated in vacuo to give a brown solid. The crude compound was purified by preparative LC (Irregular SiOH 15-40 μm, 25 g Merck, mobile phase gradient: $CH_2Cl_2$/EtOAc from 100/0 to 80/20). The fractions containing product were combined and the solvent was removed in vacuo to give 305 mg of intermediate D (quantitative yield) as a yellow solid.

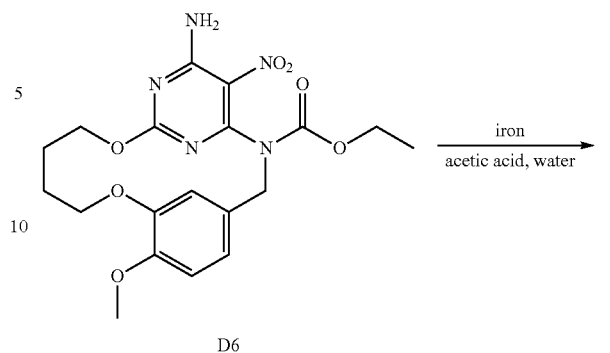

Synthesis of Final Compound 56:

A mixture of D6 (250 mg; 577 μmol) and iron (193 mg; 3.46 mmol) in acetic acid (30 mL) and water (3 mL) was stirred at 120° C. for 6 h, then 2 h at 140° C. The mixture was evaporated in vacuo to give fraction 1. Fraction 1 was taken up with DMF and filtered through a pad of Celite® and the filtrate was evaporated in vacuo to give Fraction 2. Fraction 2 was taken up with AcOH and water (30:70). The solution was extracted with $CH_2Cl_2$/MeOH (9:1) (twice). The organic layer was dried over $MgSO_4$, filtered and the solvent was removed under reduced pressure to give fraction 3. Fraction 3 was purified by preparative LC (Irregular SiOH 15-40 μm, 12 g Grace, mobile phase gradient: $CH_2Cl_2$/MeOH/$NH_3$ aq from 97/3/0.1 to 80/20/3). The fractions containing product were combined and the solvent was removed in vacuo to give 90 mg of final compound 56 (44% yield) as a white solid.

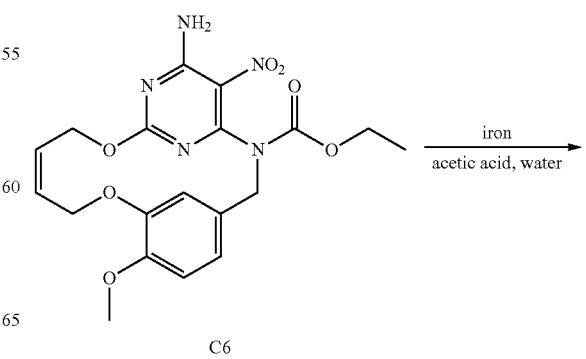

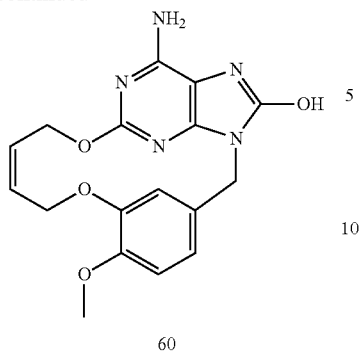

60

Synthesis of Final Compound 60:

A mixture of C6 (70 mg; 162 µmol) and iron (54 mg; 974 µmol) in acetic acid (10 mL) and water (1 mL) was stirred at 120° C. for 5 h. The mixture was evaporated in vacuo to give fraction 1. Fraction 1 was taken up with DMF and filtered through a pad of Celite® and the filtrate was evaporated in vacuo to give fraction 2. Fraction 2 was taken up with AcOH and water (30:70). The precipitate was filtered, washed (twice) with EtOH then Et$_2$O and dried under vacuum to give 46 mg of final compound 60 (80% yield) as a white solid.

OVERALL SCHEME IN THE PREPARATION OF FINAL PRODUCTS: METHOD 24

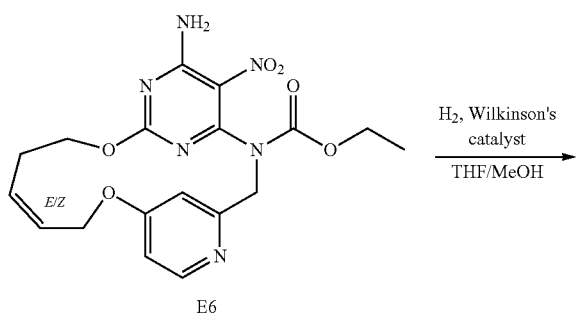

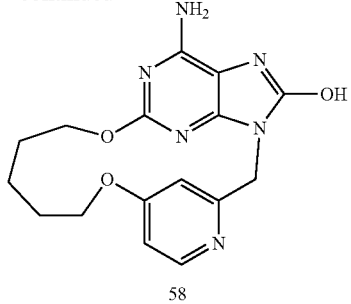

58

Synthesis of Intermediate E6:

Intermediate E6 (mixture of E and Z isomers, 90 mg, 17% yield) was synthesized using the procedure described for intermediates T5 and U5.

Synthesis of Intermediate F6:

A solution of E6 (90 mg; 216 µmol) and Wilkinson's catalyst (20 mg; 21.6 µmol) in THF (7 mL) and MeOH (7 mL) was degassed by N$_2$ bubbling for 10 min. The mixture was hydrogenated under 5 bars pressure at RT for 16 h. The mixture was degassed by N$_2$ bubbling for 10 min and Wilkinson's catalyst (40 mg; 43.2 µmol) was added. The mixture was hydrogenated under 10 bars pressure at RT for 16 h. The mixture was degassed by N$_2$ bubbling for 10 min and Wilkinson's catalyst (20 mg; 21.6 µmol) was added. The mixture was hydrogenated under 10 bars pressure at RT for 16 h. The mixture was filtered over Celite® and the filtrate was concentrated in vacuo to give 140 mg of a green oil. The crude compound was purified by preparative LC (Irregular SiOH 15-40 µm, 4 g Grace, mobile phase gradient: from CH$_2$Cl$_2$/EtOAc 100/0 to 80/20). The fractions containing product were combined and the solvent was removed in vacuo to give 60 mg of intermediate F6 (66% yield) as a yellow oil.

Synthesis of Final Compound 58:

A mixture of F6 (76 mg; 0.182 mmol) and iron (81 mg; 1.45 mmol) in acetic acid (4.2 mL) and water (0.21 mL) was stirred at 80° C. for 6 h, then 100° C. for 16 h. The mixture was filtered through Celite® and the filtrate was evaporated in vacuo. The crude compound was purified by preparative LC (irregular SiOH 15-40 µm, 25 g Merck, dry loading, mobile phase gradient: from CH$_2$Cl$_2$/MeOH/NH$_3$ aq 97/3/0.3 to 85/15/1.5) to give 21 mg of final compound 58 (34% yield).

OVERALL SCHEME IN THE PREPARATION OF FINAL PRODUCTS: METHOD 25

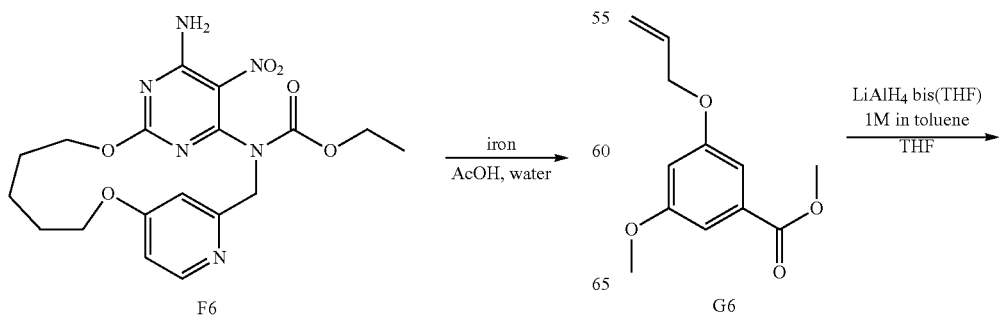

127
-continued
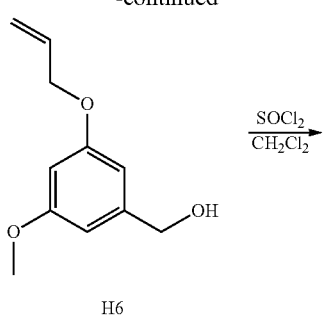
H6
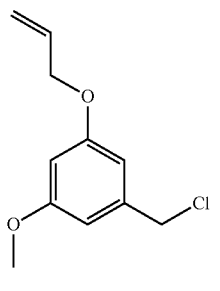
I6
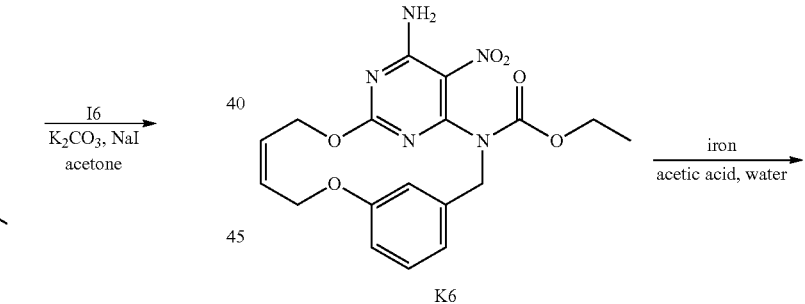
K5 → K6
128
-continued
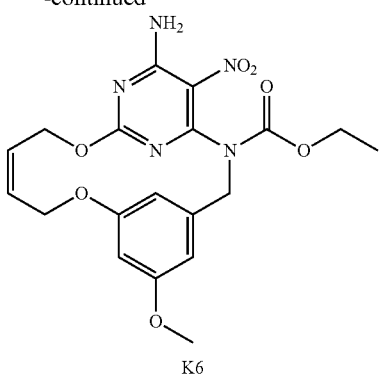
K6
+
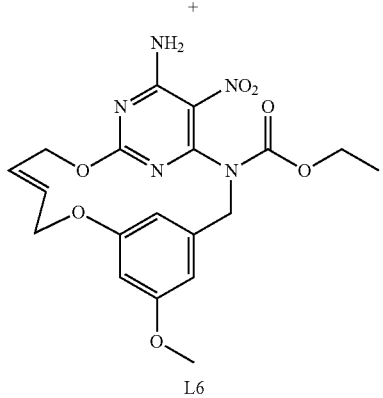
L6
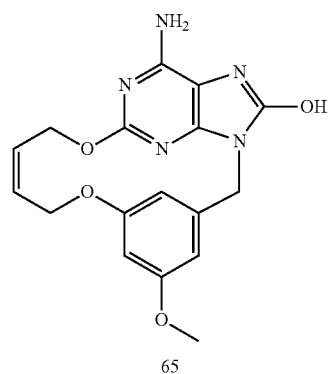

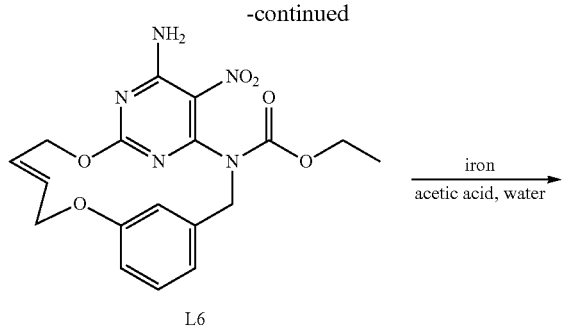

L6

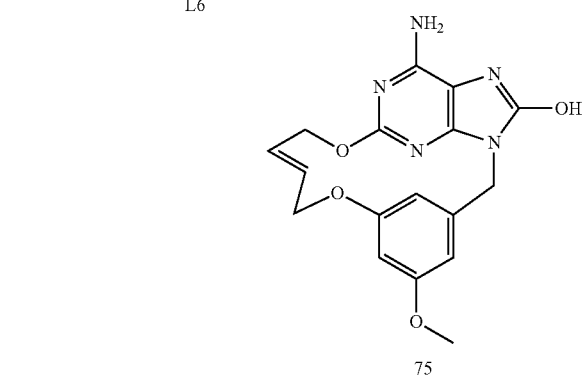

75

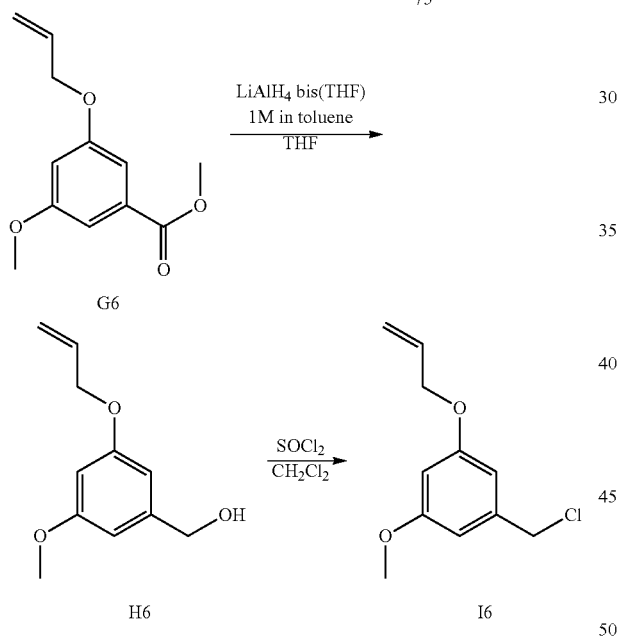

Synthesis of Intermediate 16:

To a solution of G6 (21.11 g; 95.0 mmol) in THF (500 mL) at 0° C. was added drop wise lithium aluminium hydride bis(THF) (1M in toluene) (190 mmol; 190 mL). The solution was stirred for 1 h 30 at 0° C., and then at RT for 1 h 30. The mixture was cooled to 0° C. and was quenched by cautious drop wise addition of 7.5 mL of water, then 7.5 mL of aqueous NaOH (5%) and finally 15 mL of water. After 30 minute of further stirring, the mixture was filtered through a pad of Celite®. The Celite® was washed with EtOAc, the filtrate was evaporated under vacuum to afford 19.64 g (99% yield) of intermediate H6 as a clear yellow oil.

SOCl$_2$ (73 mL; 1.01 mol) was added drop wise to a mixture of H6 (19.6 g; 101 mmol) in CH$_2$Cl$_2$ (450 mL) at 0° C. The mixture was stirred at RT for 3 h. The solvent was evaporated and the residue was dried by azeotropic distillation with toluene (twice) to give 23.6 g of a brown oil. The brown oil was dissolved in CH$_2$Cl$_2$, washed with 2×100 mL of aqueous NaOH 5%, dried over MgSO$_4$, filtered, and evaporated under vacuum to afford 20.5 g of a brown oil. The crude was purified by preparative LC (Stationary phase: Irregular SiOH 20-45 µm 450 g Matrex), Mobile phase: Gradient from 50% Heptane, 50% CH$_2$Cl$_2$ to 0% Heptane, 100% CH$_2$Cl$_2$) to afford intermediate 16 (4.77 g; 22% yield) as a yellow oil.

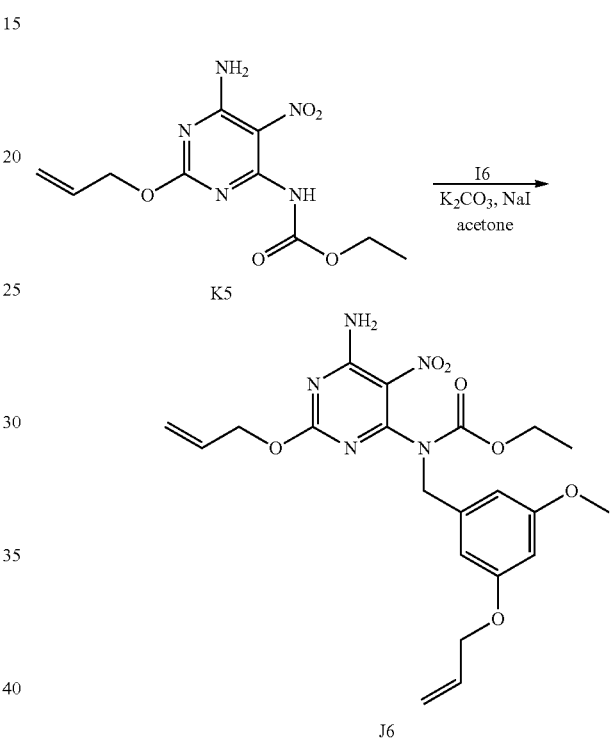

Synthesis of Intermediate J6:

I6 (2.7 g; 12.7 mmol) was added to a solution of K5 (3 g; 10.6 mmol), K$_2$CO$_3$ (2.93 g; 21.2 mmol) and NaI (1.59 g; 10.6 mmol) in acetone (180 mL) was stirred at 70° C. for 16 h. The reaction was combined with another batch (from 200 mg of K5). The mixture was filtered and the filtrate was concentrated in vacuo to give a yellow solid. The solid was taken up in CH$_2$Cl$_2$. The precipitate was filtered and the filtrate was concentrated in vacuo to give 4.14 g of a yellow oil. The crude was purified by preparative LC (Irregular SiOH 15-40 µm, 120 g Grace, mobile phase gradient: from Heptane/EtOAc 100/0 to 50/50). The fractions containing product were combined and the solvent was removed in vacuo to give 3.83 g of a yellow oil, which was re-purified by preparative LC (Irregular SiOH 15-40 µm, 80 g Grace, mobile phase gradient: from CH$_2$Cl$_2$/EtOAc 100/0 to 95/5). The fractions containing product were combined and the solvent was removed in vacuo to give 2.3 g (44% yield) of intermediate J6 as a yellow oil.

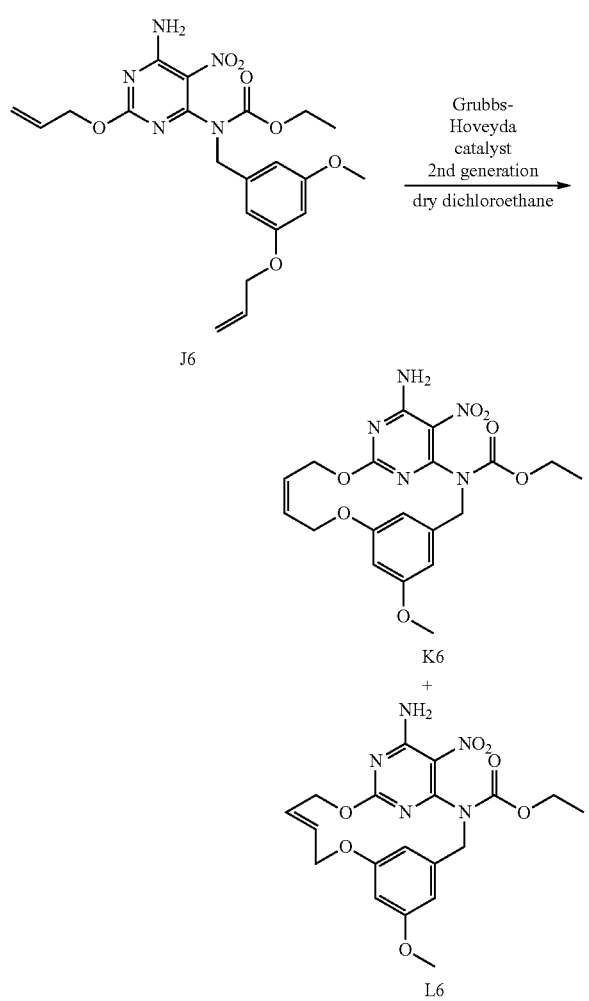

Synthesis of Intermediates K6 and L6:

The reaction was performed in 2 batches.

Typical procedure for one batch:

A solution of J6 (940 mg; 2.05 mmol) and chlorodicyclohexylborane (1M in hexane) (409 μL; 409 μmol) in dry dichloroethane (564 mL) was stirred at 80° C. and under $N_2$ atmosphere for 1 h. Grubbs-Hoveyda catalyst $2^{nd}$ generation (85 mg; 136 μmol) was added and the mixture was stirred at 120° C. for 1 h. More catalyst (85 mg; 136 μmol) was added and the mixture was stirred at 120° C. for 1 h. More catalyst (85 mg; 136 μmol) was added again and the mixture was stirred at 120° C. for 16 h. The 2 batches were combined, SiliaBond® diamine (Ru scavenger from Silicycle®) (2.48 g; 3.97 mmol) was added and the mixture was stirred at RT for 16 h. The mixture was filtered and the filtrate was concentrated in vacuo to give 1.75 g of a black oil. This batch was combined with another one (0.48 mmol scale) to give 2.03 g of a black oil. The black oil was purified by preparative LC (Irregular SiOH 15-40 μm, 50 g Merck, mobile phase gradient: from $CH_2Cl_2$/EtOAc 100/0 to 98/2). The fractions containing product were combined and the solvent was removed in vacuo to give 70 mg of fraction 1 (intermediate K6, Z isomer), 160 mg of fraction 2 (mixture of intermediates K6 and L6 (75/25)) and 116 mg of fraction 3 (mixture of intermediates K6 and L6 (94/6)). Fraction 2 was purified by achiral SFC (Stationary phase: AMINO 6 μm 150×21.2 mm, mobile phase: 85% $CO_2$, 15% MeOH) to give 45 mg of intermediate L6 (4% yield, E isomer) as a yellow oil and 176 mg of intermediate K6 (16% yield, Z isomer) as a white solid (Global Yield: 27%).

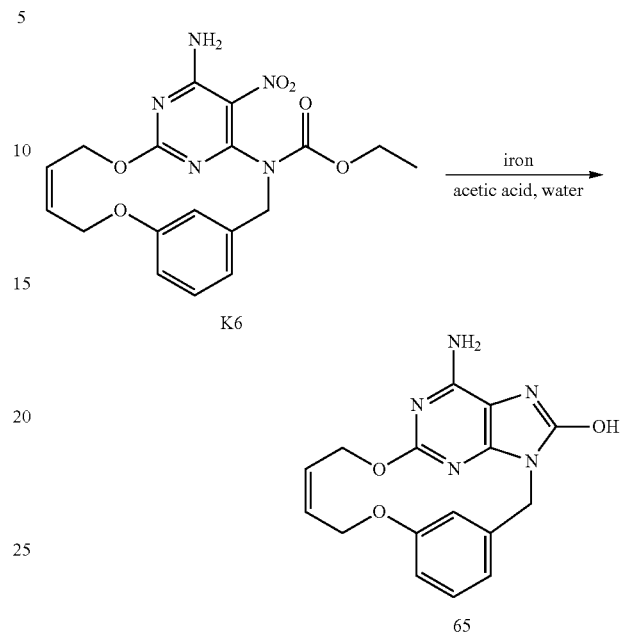

Synthesis of Final Compound 65:

Iron (182 mg; 3.26 mmol) was added to a solution of K6 (176 mg; 0.408 mmol) in acetic acid (10 mL) and water (480 μL). The mixture was stirred at 70° C. for 1 h and was then concentrated in vacuo until dryness. DMF was added, the mixture was heated and filtered hot through Celite® and the Celite® was rinsed with DMF. SiliaBond® imidazole (5.63 g; 26.6 mmol) was added to the filtrate and the mixture was stirred at RT for 16 h. The mixture was filtered through Celite®, the Celite® was rinsed with DMF and the filtrate was concentrated in vacuo. The residue was taken up with acetic acid (1 mL) then water was added and the mixture was cooled to 0° C., leading to precipitation. The precipitate was filtered to give an off-white solid. The solid was taken up in EtOH and heated at 80° C. The mixture was allowed to cool down to RT and the precipitate was filtered to give 50 mg of a white solid. The solid was dried in vacuo overnight and then solubilized in hot DMF and SiliaBond® imidazole (2 g; 2.32 mmol) was added. The mixture was stirred at RT for 16 h. The mixture was filtered through Celite®, the Celite® was rinsed with DMF and the filtrate was concentrated in vacuo to give 44 mg of final compound 65 (30% yield) as a white solid.

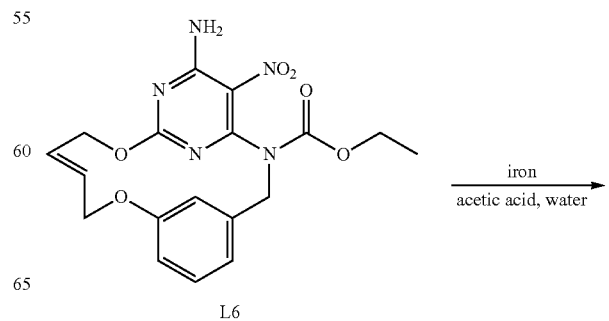

133
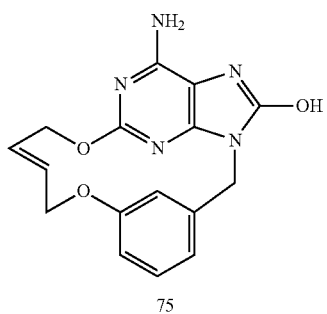
75
Synthesis of Final Compound 75:
Final compound 75 (11 mg, 30% yield) was obtained using the procedure described for final compound 65, starting from 45 mg of intermediate L6.
OVERALL SCHEME IN THE PREPARATION OF FINAL PRODUCTS: METHOD 26
134
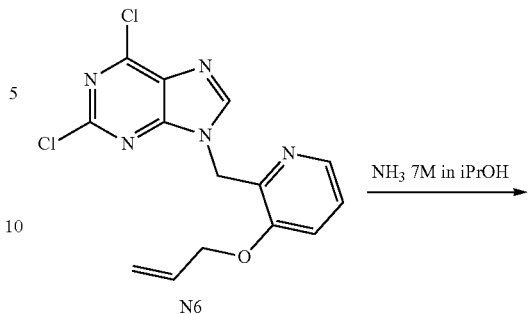
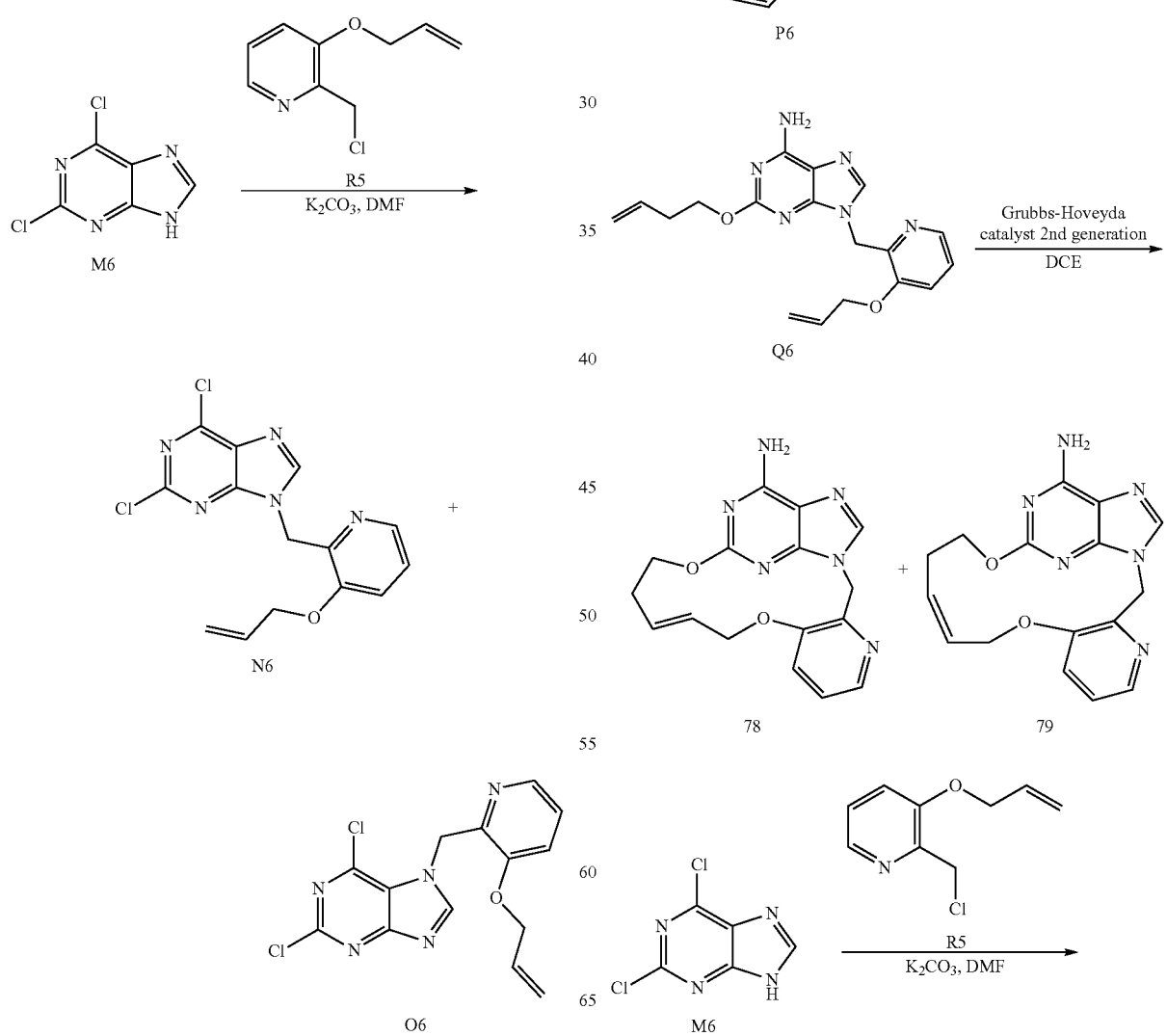

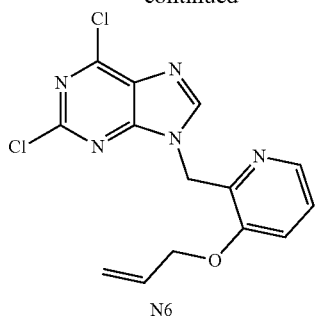

N6

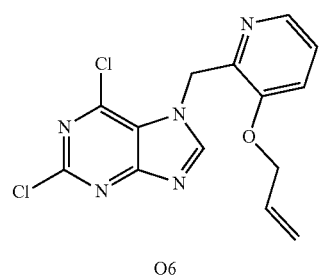

O6

Synthesis of Intermediates N6 and O6:

R5 (8.7 g; 47.6 mmol) in DMF (50 mL) was added drop wise over 1 h to a mixture of M6 (5 g; 26.5 mmol) and K$_2$CO$_3$ (14.6 g; 106 mmol) in DMF (50 mL) at RT and under N$_2$ atmosphere. The mixture was stirred at RT for 72 h. The mixture was evaporated and water/EtOAc were added. The layers were separated and the aqueous layer was extracted with EtOAc (twice). The combined organic layers were washed with water (twice), dried over MgSO$_4$, filtered and dried in vacuo to give a brown solid. The solid was purified together with another batch (1 mmole scale) by preparative LC (Irregular SiOH 15-40 μm, 150 g Merck, mobile phase gradient: from CH$_2$Cl$_2$/EtOAC 100/0 to 90/10). The fractions containing product were combined and the solvent was removed in vacuo to give 2.11 g of intermediate N6 (24% yield) as an orange solid and 2.64 g of a second fraction (mixture of N6 and O6 (83/17).

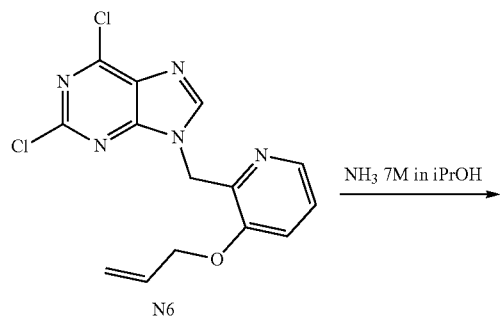

N6

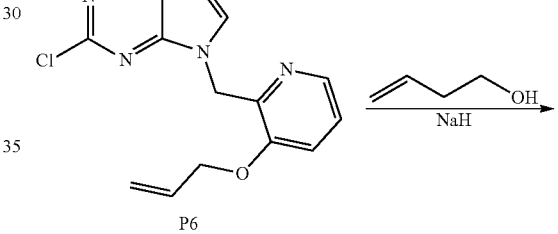

P6

Synthesis of Intermediate P6:

The reaction was performed in Autoclave.

A solution of N6 (1.9 g; 5.65 mmol) in NH$_3$ (7M in isopropanol) (40 mL) was stirred at 120° C. for 16 h. The mixture was cooled down to RT and the precipitate was filtered off. The precipitate was washed with Et$_2$O and dried in vacuo to give 1.42 g of intermediate P6 (79% yield) as a brown solid.

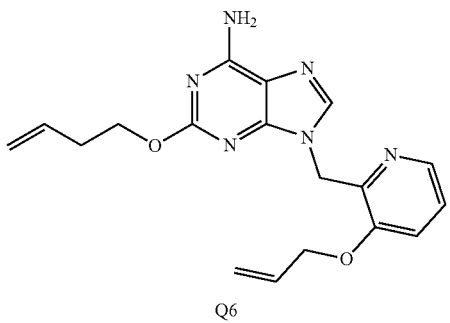

P6

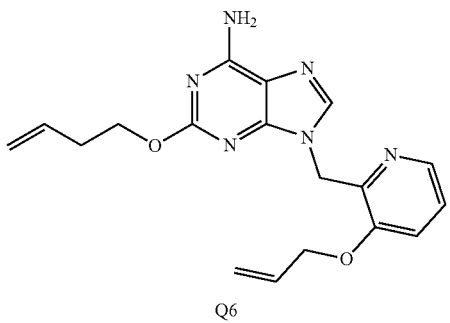

Q6

Synthesis of Intermediate Q6:

A solution of P6 (1.42 g; 4.48 mmol) and NaH (60% in oil) (412 mg; 10.3 mmol) in 3-buten-1-ol (29 mL) was stirred at 90° C. for 16 h. The solvent was removed in vacuo to give a brown solid. The solid was purified by preparative LC (Irregular SiOH 15-40 m, 50 g Merck, mobile phase: CH$_2$Cl$_2$/MeOH 95/5). The fractions containing product were combined and the solvent was removed in vacuo to give 1.26 g of a brown solid. The solid was taken up in Et$_2$O leading to precipitation, the precipitate was filtered and dried in vacuo to give 920 mg of intermediate Q6 (58% yield) as a white solid.

OVERALL SCHEME IN THE PREPARATION OF
FINAL PRODUCTS: METHOD 27

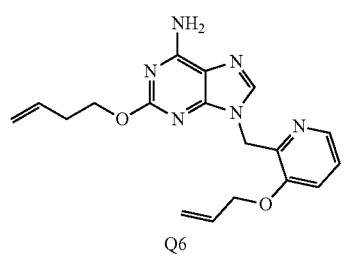

Q6

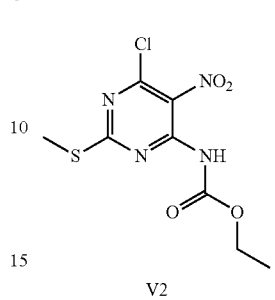

V2

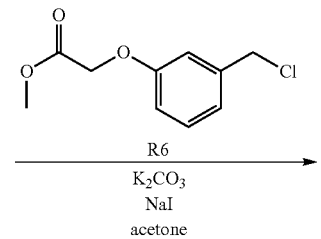

R6

K$_2$CO$_3$
NaI
acetone

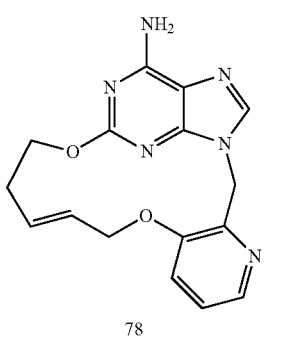

78

+

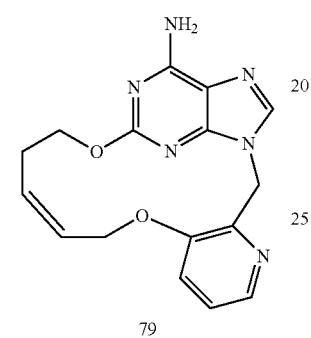

79

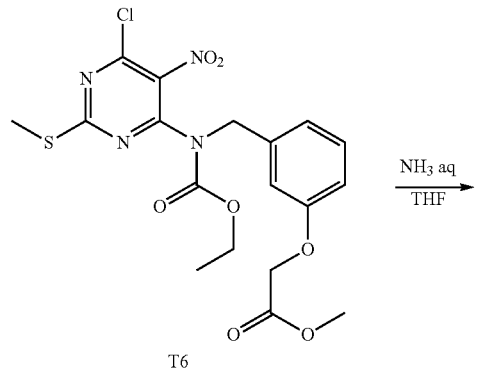

T6

NH$_3$ aq
THF

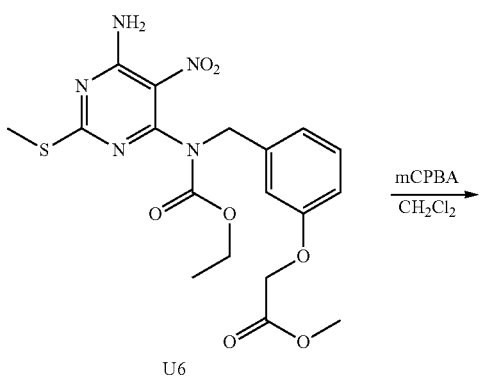

U6 mCPBA
CH$_2$Cl$_2$

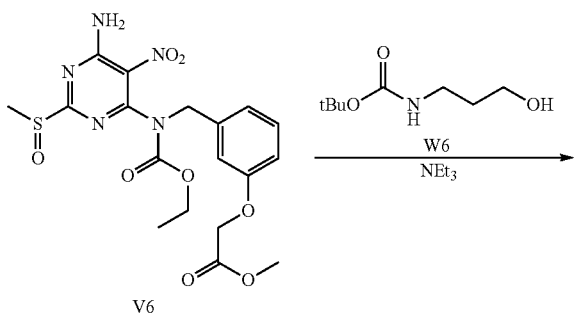

V6

W6
NEt$_3$

Synthesis of Final Compounds 78 and 79:

A solution of Q6 (460 mg; 1.31 mmol) and chlorodicyclohexylborane (1M in hexane) (261 μL; 261 μmol) in dichloroethane (430 mL) was stirred at 80° C. under N$_2$ atmosphere for 1 h. Grubbs-Hoveyda catalyst 2$^{nd}$ generation (82 mg; 131 μmol) was added and the mixture was stirred in sealed tube at 120° C. for 8 h. chlorodicyclohexylborane (1M in hexane) (261 μL; 261 μmol) was added and the mixture was stirred at 80° C. under N$_2$ atmosphere for 1 h. Grubbs-Hoveyda catalyst 2$^{nd}$ generation (82 mg; 131 μmol) was added and the mixture was stirred at 120° C. for 2 h. SiliaBond® DMT (3.48 g; 2.08 mmol) was added and the mixture was stirred at RT for 16 h. The mixture was filtered through Celite® and the filtrate was evaporated in vacuo to give 640 mg of a black solid. The solid was purified together with another batch (1.3 mmole scale) by preparative LC (Irregular SiOH 15-40 μm, 40 g Grace, mobile phase gradient: from CH$_2$Cl$_2$/MeOH 100/0 to 90/10). The fractions containing product were combined and the solvent was removed in vacuo to give 463 mg of a brown solid. The solid was purified by achiral SFC (Stationary phase: AMINO 6 μm 150×21.2 mm, mobile phase: 82% CO$_2$, 18% MeOH (0.3% iPrNH$_2$)) to give 36 mg of final compound 78 (E isomer, 4% yield) as a white solid and a precipitate. This precipitate was purified by preparative LC (Stationary phase: Spherical bare silica 5 μm 150×30.0 mm, mobile phase gradient: from Heptane/EtOAc/MeOH (10% NH$_3$) 71/28/1 to 0/80/20) to give 10 mg of final compound 79 (Z isomer, 1% yield) as a white solid.

-continued

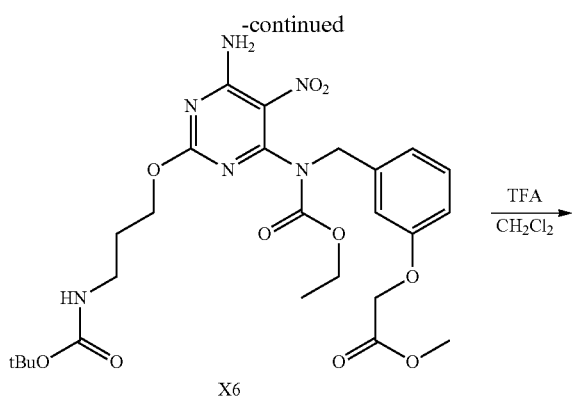

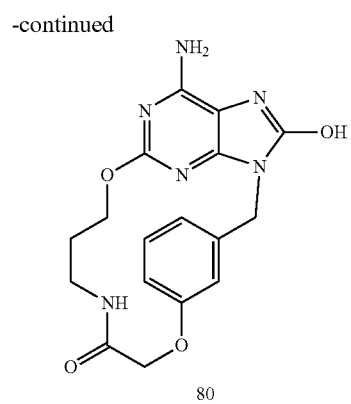

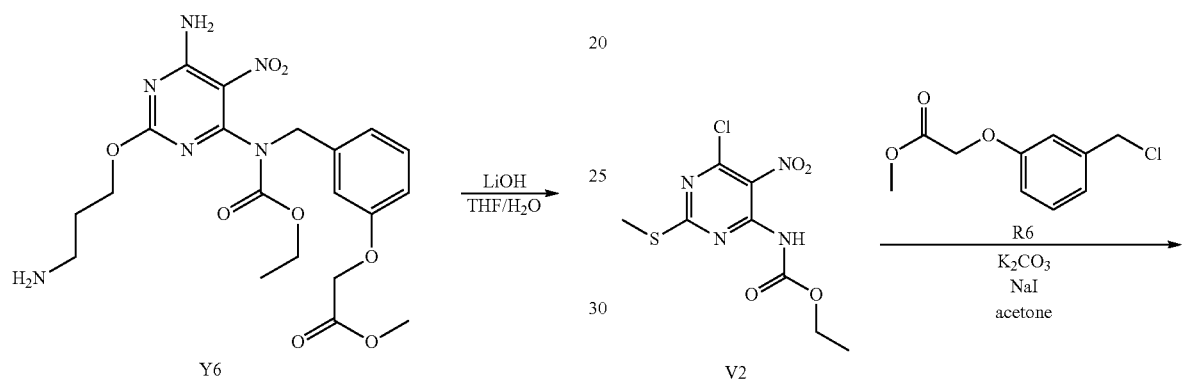

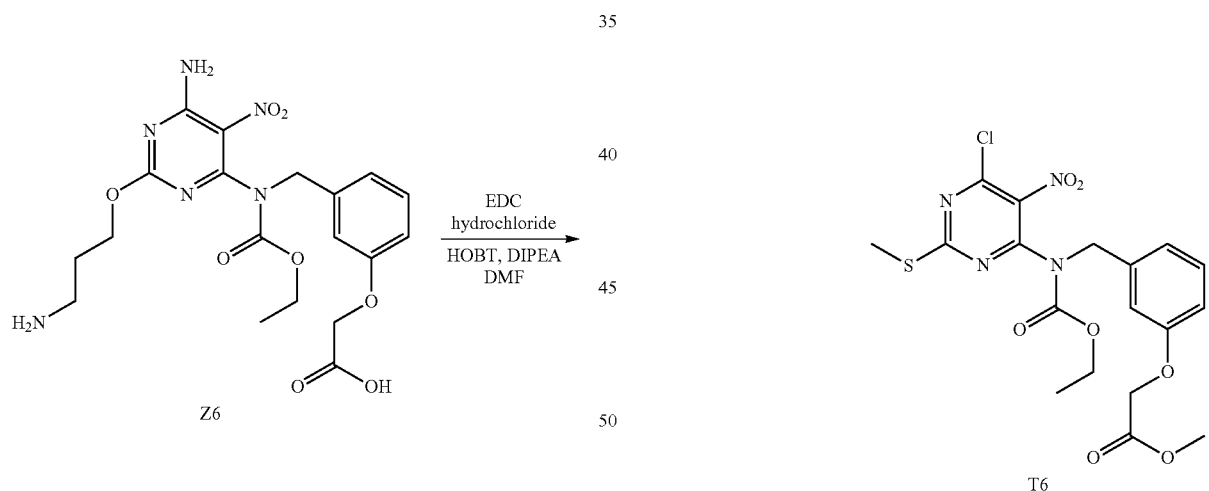

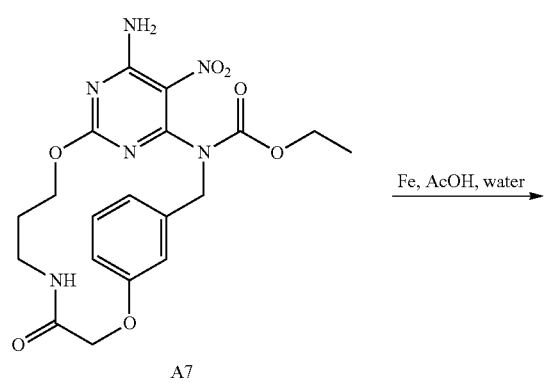

Synthesis of Intermediate T6:

A mixture of V2 (7.04 g; 24.04 mmol), R6 (5.16 g; 24.04 mmol), $K_2CO_3$ (4.98 g; 36.06 mmol) and NaI (3.6 g; 24.04 mmol) in acetone (240 mL) were stirred at RT for 24 h. The precipitate was filtered off, rinsed with acetone. The filtrate was evaporated to give 18.7 g. The crude compound was dissolved into $CH_2Cl_2$. The precipitate was eliminated by filtration and the filtrate was concentrated in vacuo. The crude compound was purified by preparative LC (Stationary phase: Irregular SiOH 20-45 μm 450 g Matrex), mobile phase: 75% heptane, 25% AcOEt) to yield 7.4 g of intermediate T6 (65% yield).

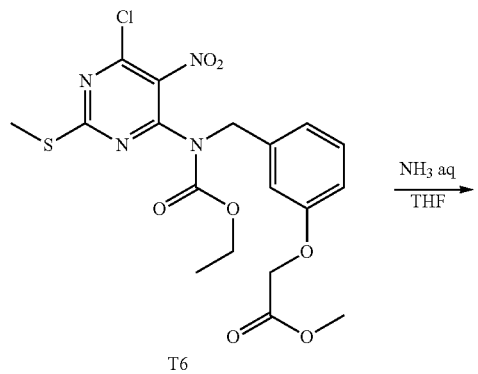
T6

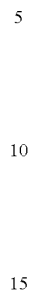
NH₃ aq / THF

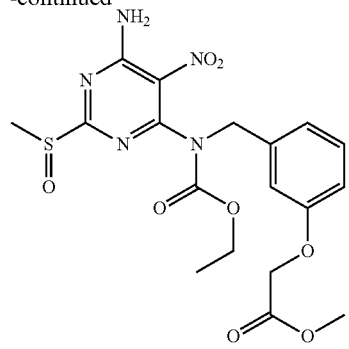
V6

Synthesis of Intermediate V6:

At 0° C., meta-chloroperoxybenzoic acid (1.36 g, 5.54 mmol) in CH₂Cl₂ (25 mL) was added to a mixture of U6 (2.5 g, 5.54 mmol) in CH₂Cl₂ (25 mL). The mixture was stirred at RT for 3 h. An aqueous solution of Na₂S₂O₃ (2 eq) was added to the mixture. 2 layers were separated and the aqueous layer was extracted with CH₂Cl₂ (twice). The combined organic layers were washed with a saturated aqueous solution of NaHCO₃, dried over MgSO₄, filtered and the solvent was removed under reduced pressure to afford 4.0 g of intermediate V6 as a yellow oil which was directly used in the next step.

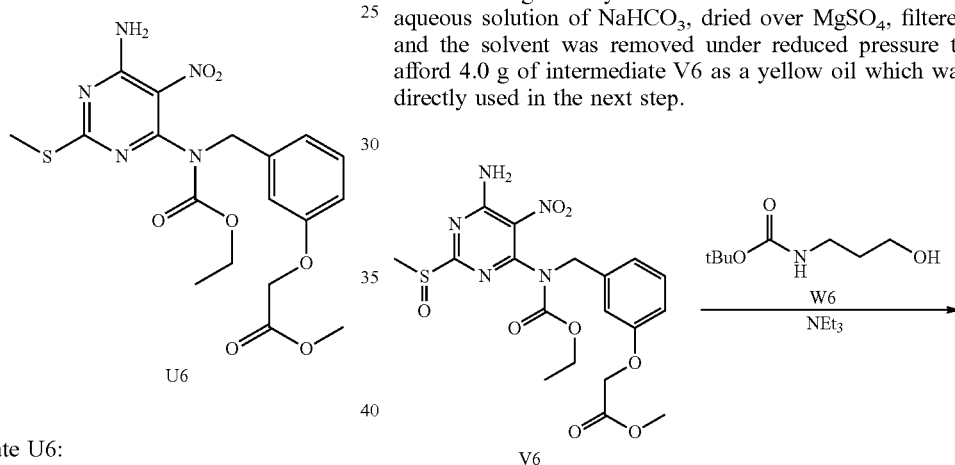

Synthesis of Intermediate U6:

A mixture of T6 (7.25 g, 15.396 mmol) in aqueous solution of NH₃ (30%) (110 mL) and THF (110 mL) was stirred at RT for 1 h. The mixture was concentrated. The residue was taken up with toluene and concentrated (the process was repeated twice). The residue was taken up with CH₂Cl₂, dried over MgSO₄, filtered and the solvent was evaporated to give 7.5 g of intermediate U6. The crude compound was used directly in the next reaction step.

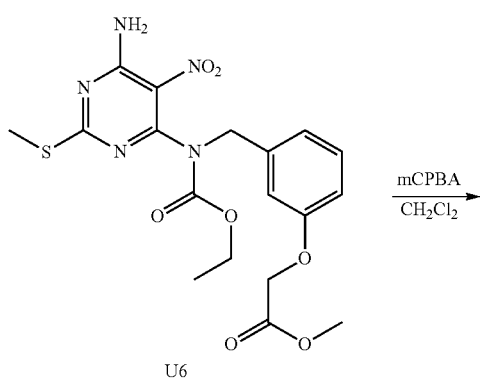
U6

mCPBA / CH₂Cl₂

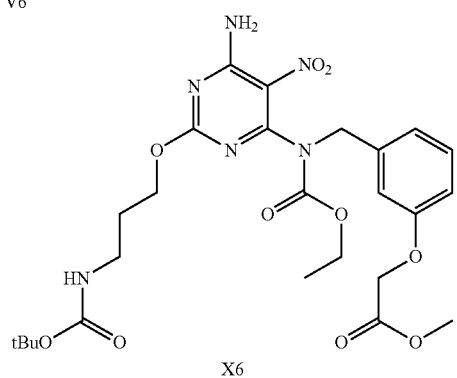
X6

Synthesis of Intermediate X6:

A mixture of V6 (2.58 g, 5.52 mmol) and NEt₃ (1.53 mL, 11.04 mmol) in W6 (28 mL) was stirred at 100° C. for 2.5 h. Water was added and the mixture was extracted with CH₂Cl₂. The organic layer was washed with HCl 0.5N (6 times), dried over MgSO₄, filtered and the solvent was evaporated. The crude was purified by preparative LC (Stationary phase: Irregular SiOH 20-45 μm 450 g Matrex), mobile phase: 98% CH₂Cl₂, 2% iPrOH) to yield 1.3 g of intermediate X6 (41% yield).

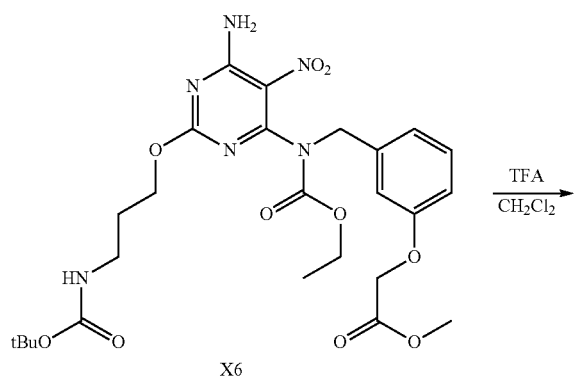

X6

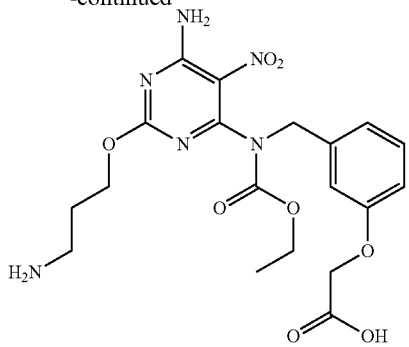

Z6

Synthesis of Intermediate Z6:

At 0° C., LiOH monohydrate (289 mg, 6.89 mmol) was added to a mixture of Y6 (1.1 g, 2.3 mmol) in THF/water (50/50) (10 mL). The mixture was stirred at RT for 12 h. At 0° C., water was added and the mixture was acidified with HCl 3N until pH 2-3. The mixture was extracted with EtOAc. The organic layer was dried over MgSO$_4$, filtered and the solvent was evaporated to yield 0.85 g of intermediate Z6 (80% yield).

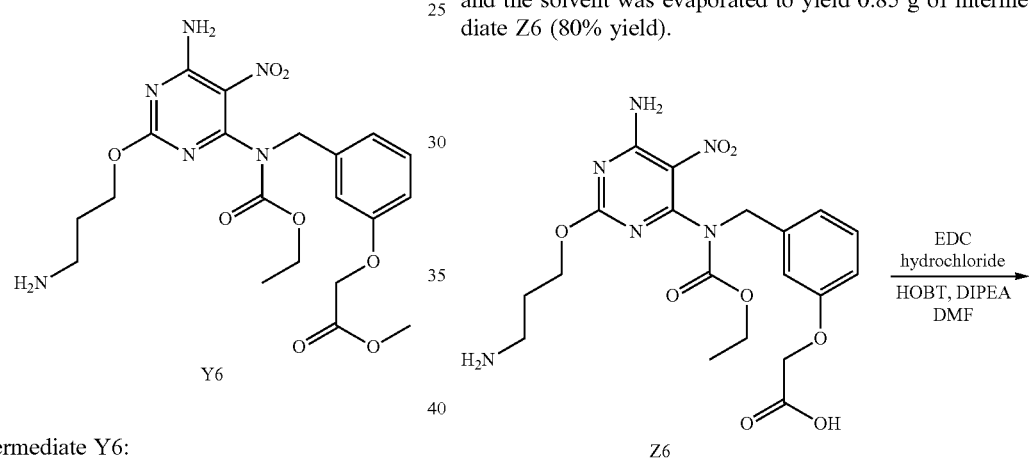

Synthesis of Intermediate Y6:

At 0° C., TFA (1.72 mL, 22.47 mmol) was added drop wise to a mixture of X6 (1.30 g, 2.25 mmol) in CH$_2$Cl$_2$ (25 mL). The mixture was stirred at RT for 12 h. At 0° C., water was added. The mixture was basified with K$_2$CO$_3$ 10% in water and was extracted with CH$_2$Cl$_2$. The organic layer was dried over MgSO$_4$, filtered and the solvent was evaporated to give 1.1 g of intermediate Y6, which was directly used in the next step.

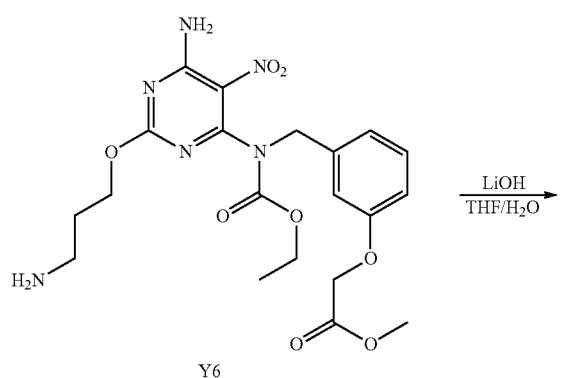

Y6

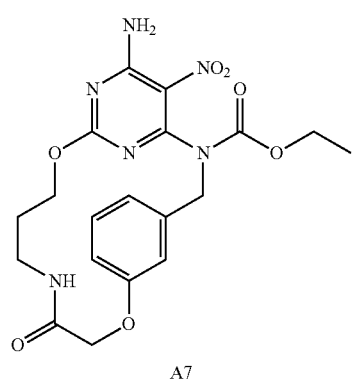

A7

Synthesis of Intermediate A7:

1-Ethyl-3-[3-dimethylaminopropyl]carbodiimide hydrochloride (941 mg, 4.91 mmol) and hydroxybenzotriazole (663 mg, 4.91 mmol) were slowly added to a mixture of Z6 (760 mg, 1.64 mmol), diisopropylethylamine (1.41 mL, 8.18 mmol) in DMF (380 mL). The mixture was stirred at RT for 24 h. The solvent was evaporated until dryness. The residue was taken up with CH$_2$Cl$_2$ and was washed with water, then with brine. The organic layer was dried over MgSO$_4$, filtered and the solvent was evaporated. Purification was carried out by flash chromatography over silica gel (15-40 µm, 40 g, CH$_2$Cl$_2$/CH$_3$OH/NH$_4$OH: 99/1/0.1). The pure fractions were collected and evaporated to dryness to yield 0.61 g of intermediate A7 (84% yield).

OVERALL SCHEME IN THE PREPARATION OF FINAL PRODUCTS: METHOD 28

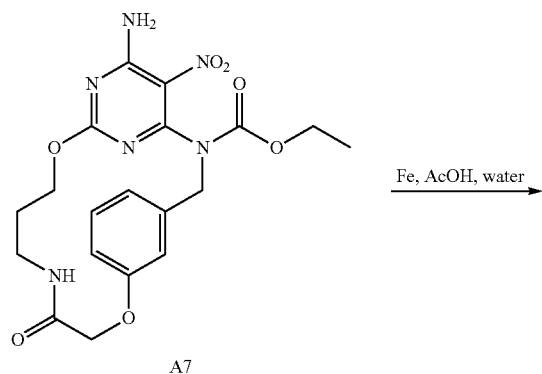

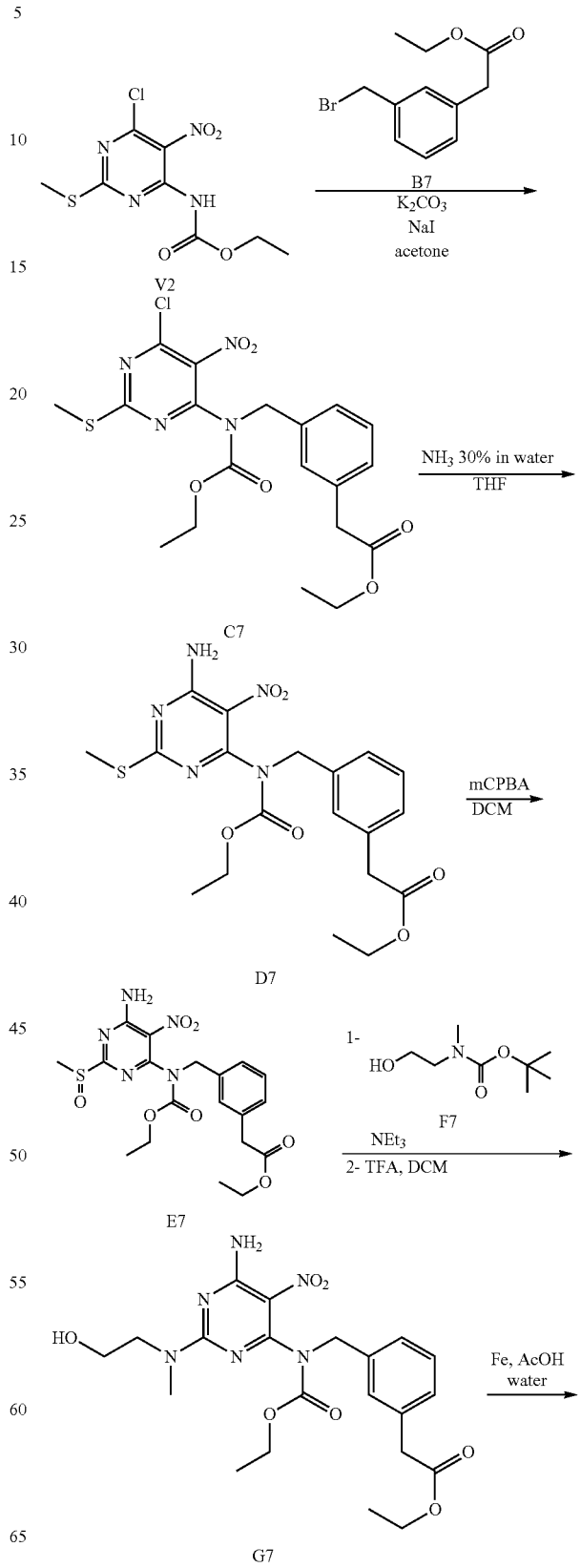

Synthesis of Final Compound 80:

Iron (1.4 g; 25.09 mmol) was added to a mixture of A7 (560 mg; 1.25 mmol) in acetic acid (14.4 mL) and water (1.47 mL). The mixture was stirred at 50° C. for 6 h. The mixture was filtered through Celite®, washed with acetic acid then the filtrate was concentrated under reduced pressure. The crude compound was dissolved into DMF with 4 g of SiO$_2$ 60-200 µm and the resulting suspension was evaporated until dryness and put on the top of a 25 g column chromatography. Purification was carried out by flash chromatography over silica gel (15-40 µm, 25 g, CH$_2$Cl$_2$/CH$_3$OH/NH$_4$OH: 95/5/0.5). The pure fractions were collected and evaporated to dryness and then taken up with CH$_3$OH. The resulting precipitate was filtered off and dried to give 152 mg final compound 80 as the free base (33% yield). The hydrochloride salt was prepared with 10 eq of HCl 4N in dioxane, which was added to the suspension of the compound in CH$_3$OH. The precipitate was stirred for 1 h, filtered then dried under vacuum to yield 109 mg final compound 80 as an HCl salt.

147
-continued

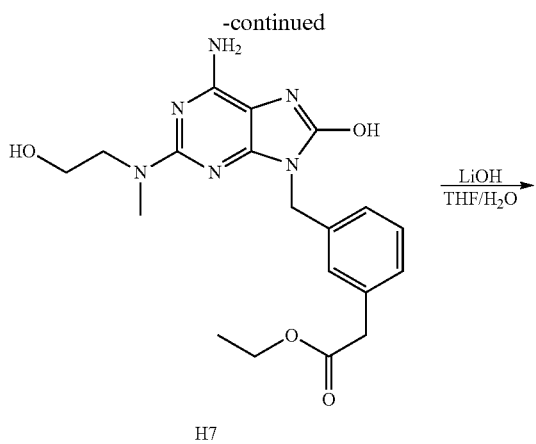

H7

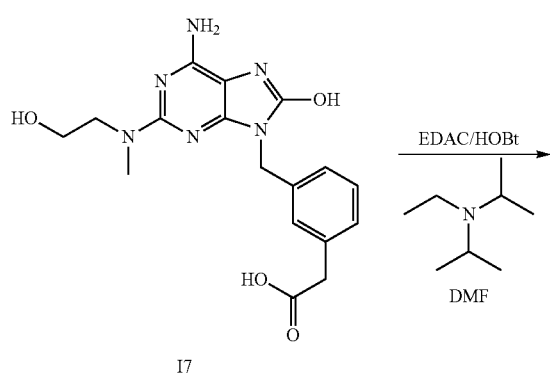

I7

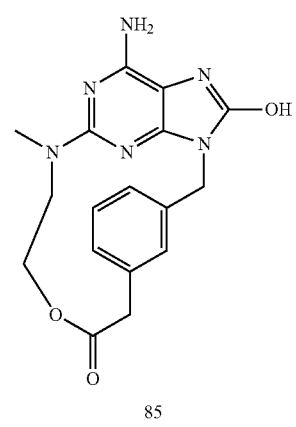

85

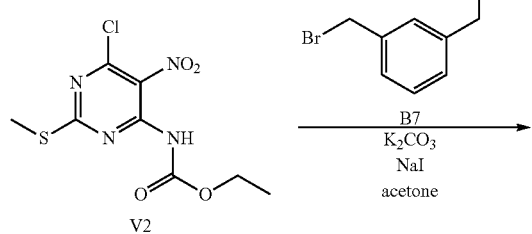

148
-continued

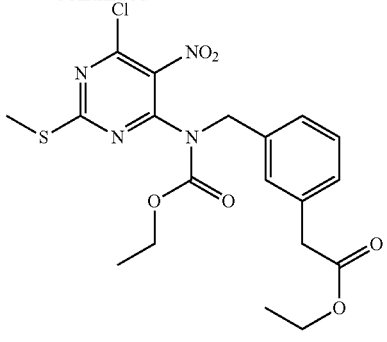

C7

Synthesis of Intermediate C7:

A mixture of V2 (7.5 g; 25.6 mmol), B7 (7.25 g; 28.2 mmol), $K_2CO_3$ (8.85 g; 64 mmol) and NaI (3.85 g; 25.6 mmol) in acetone (220 mL) was stirred at RT for 16 h. The mixture was filtered through a pad of Celite® and the filtrate was evaporated in vacuo to give a yellow oil. The crude was purified by preparative LC (Irregular SiOH 15-40 µm, 120 g Merck, mobile phase gradient: $CH_2Cl_2$/Heptane 70/30). The fractions containing product were combined and the solvent was removed in vacuo. The product was crystallized from diisopropylether to give 11.4 g of intermediate C7 (95% yield).

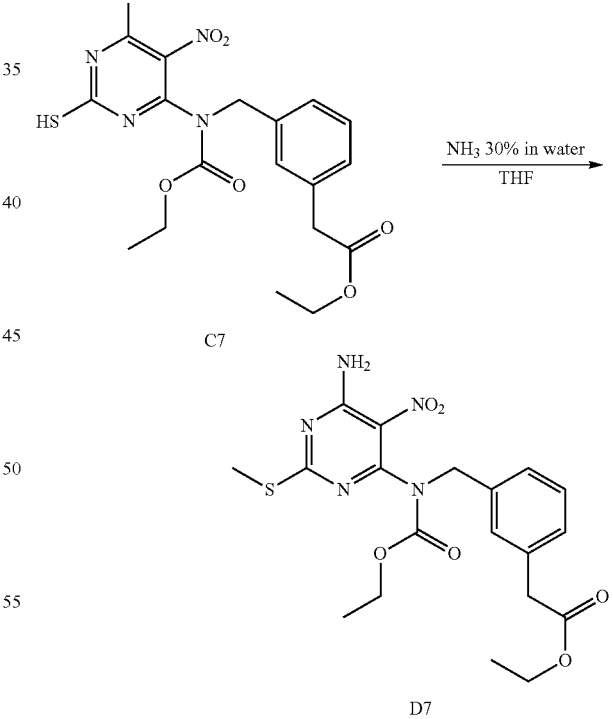

Synthesis of Intermediate D7:

A solution of C7 (11.3 g; 24.1 mmol) and $NH_3$ (30% in $H_2O$) (170 mL) in THF (170 mL) was stirred at RT overnight. The mixture of solvents was removed in vacuo and the residue was taken up by $CH_2Cl_2$, decanted, dried over $MgSO_4$ and concentrated under reduced pressure. The residue was taken up with diisopropylether and the precipitate was filtered off and air-dried to give 10.5 g of intermediate D7 (97% yield).

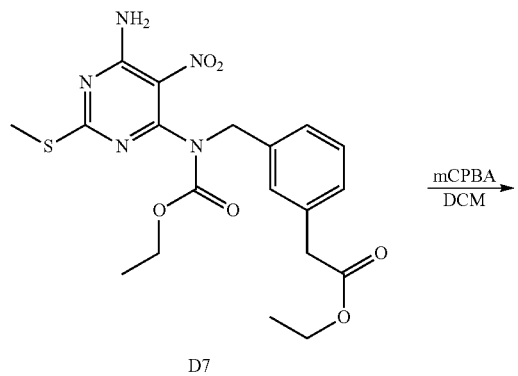

D7

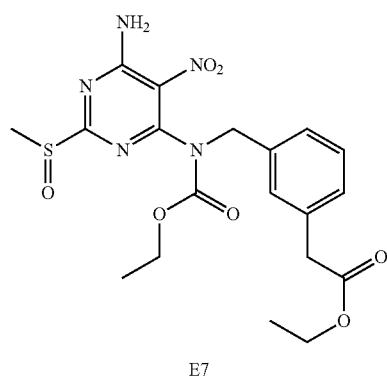

E7

Synthesis of Intermediate E7:

Metachloroperbenzoic acid (6.33 g; 26 mmol) was added portion wise to a solution of D7 (10.5 g; 23.3 mmol) in $CH_2Cl_2$ (300 mL) at RT. The mixture was stirred at RT for 16 h. A 10% aqueous solution of $Na_2S_2O_3$ (4 eq) and an aqueous solution of $NaHCO_3$ were added. The layers were separated and the aqueous layer was extracted with $CH_2Cl_2$ (twice). The combined organic layers were dried over $MgSO_4$, filtered and the solvent was removed under vacuum to give 10.8 g of intermediate E7 (99% yield).

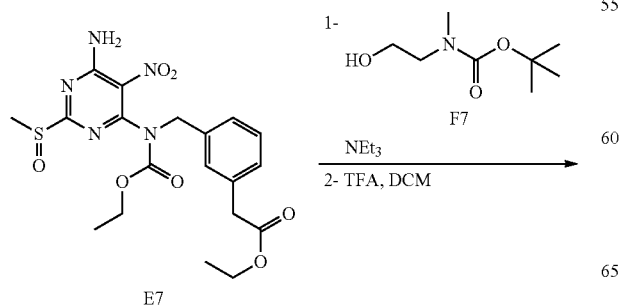

E7

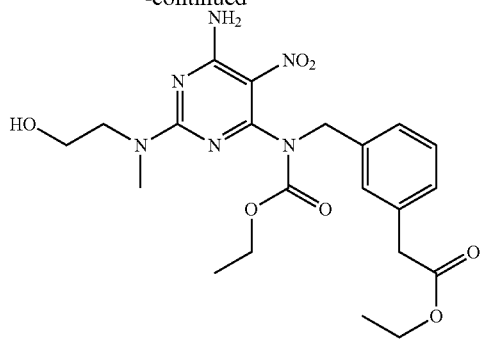

G7

Synthesis of Intermediate G7:

E7 (3.5 g; 7.54 mmol) was added portion wise to a solution of $NEt_3$ (1.15 mL; 8.3 mmol) and F7 (13.2 g; 75.3 mmol) and the resulting mixture was stirred at RT for 16 h. Water and $CH_2Cl_2$ were added, the organic layer was decanted, dried over $MgSO_4$ and concentrated. The crude product was purified by preparative LC (irregular SiOH 15-40 μm, 40 g merck, (MeOH/$CH_2Cl_2$, 0.5/99.5) to afford intermediate G7a (3.6 g).

To a solution of G7a (3.6 g; 6.2 mmol) in $CH_2Cl_2$ (120 mL) was added trifluoroacetic acid (9.5 mL; 41.6 mmol) at RT. The reaction mixture was stirred at RT for 12 h. The reaction mixture was diluted with $CH_2Cl_2$ and was treated with a saturated aqueous solution of $NaHCO_3$. The layers were separated and the organic layer was dried over $MgSO_4$, filtered and the solvent was removed under reduced pressure. The crude product was purified by preparative LC (irregular SiOH 15-40 μm, 40 g Grace, dry loading, mobile phase gradient: from $CH_2Cl_2$/MeOH/$NH_4OH$ 98/2/0.1) to give 1.7 g of intermediate G7 (57% yield).

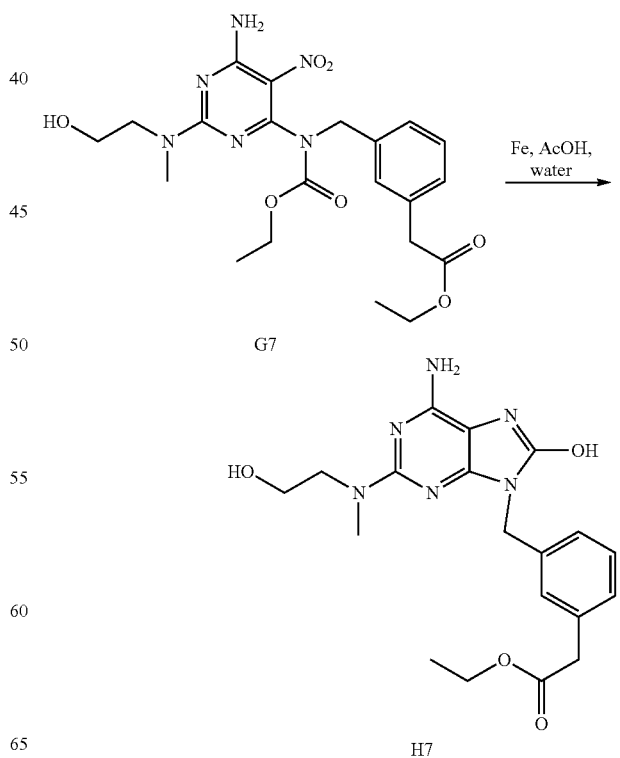

Synthesis of Intermediate H7:

Iron (2.8 g; 50.3 mmol) was added to a mixture of G7 (4 g; 8.4 mmol) in acetic acid (12 mL) and water (3 mL). The mixture was stirred vigorously at 50° C. for 5 h. The reaction mixture was diluted with CH$_2$Cl$_2$, filtered through a pad of Celite® and the filtrate was concentrated under vacuum. The crude compound was taken up with a mixture of CH$_2$Cl$_2$/MeOH (90/10) and a precipitate was filtered of. The filtrate was purified by preparative LC (irregular SiOH 15-40 μm, 80 g Grace, mobile phase CH$_2$Cl$_2$/MeOH 98/2). The product was crystallized from diisopropylether to give 2.1 g of intermediate H7 (62.5% yield).

Synthesis of Intermediate I7:

At 0° C., LiOH monohydrate (157 mg, 3.75 mmol) was added to a mixture of H7 (0.5 g, 1.25 mmol) in THF/H$_2$O (50/50) (10 mL). The mixture was stirred at RT for 12 h. At 0° C., water was added and the mixture was acidified with HCl 3N until pH 2-3. The mixture was extracted with EtOAc. The organic layer was dried over MgSO$_4$, filtered and the solvent was evaporated to give 460 mg of intermediate I7 (99% yield). The crude compound was used directly in the next reaction step.

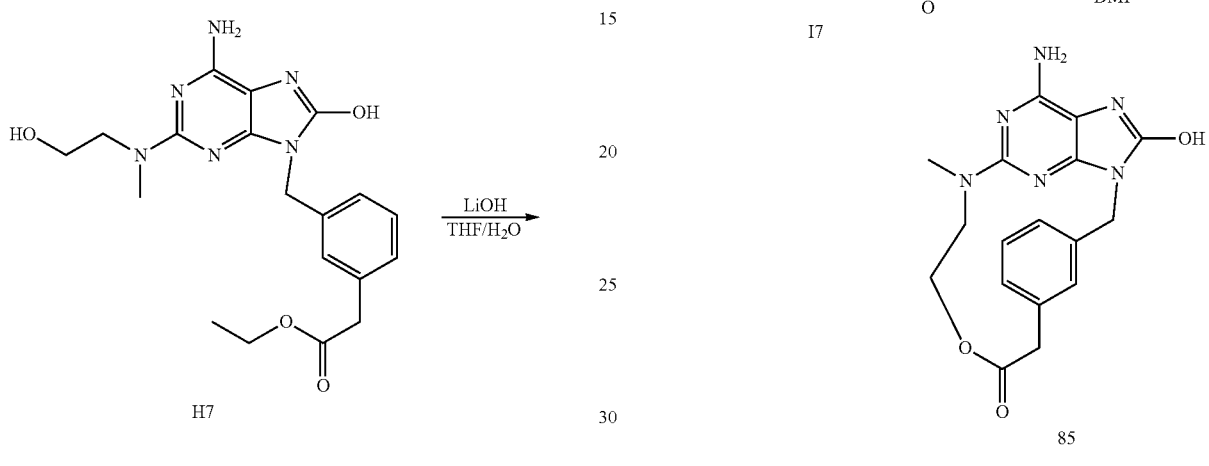

Synthesis of Final Compound 85:

3-Dimethylaminopropyl)-3-ethylcarbodiimide (1 g, 1.5.3 mmol) and 1-hydroxybenzotriazole (720 mg, 5.3 mmol) were slowly added to a mixture of 17 (660 mg, 1.77 mmol), diisopropylethylamine (1.5 mL, 8.86 mmol) in DMF (400 mL). The mixture was stirred at RT for 24 h. The solvent was evaporated until dryness. The residue was taken up with CH$_2$Cl$_2$ and was washed with water, then with brine. The organic layer was dried over MgSO$_4$, filtered and the solvent was evaporated. Purification was carried out by flash chromatography over silica gel (15-40 μm, 80 g, CH$_2$Cl$_2$/CH$_3$OH/NH$_4$OH: 95/5/0.5). The pure fractions were collected and evaporated to dryness to give 47 mg of final compound 85 (7.5% yield).

OVERALL SCHEME IN THE PREPARATION OF FINAL PRODUCTS: METHOD 29

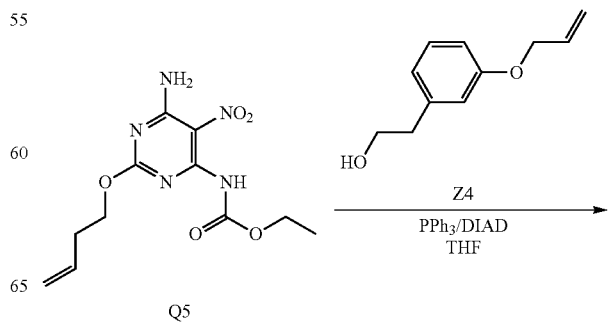

-continued

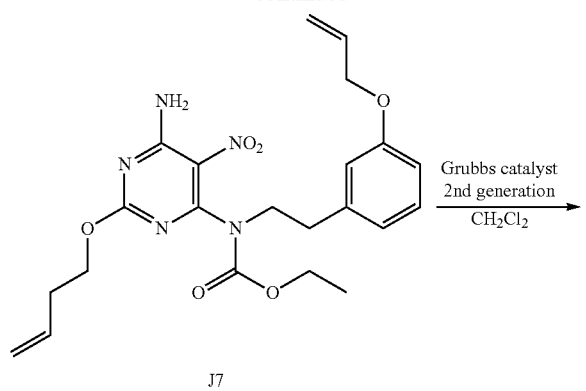

J7

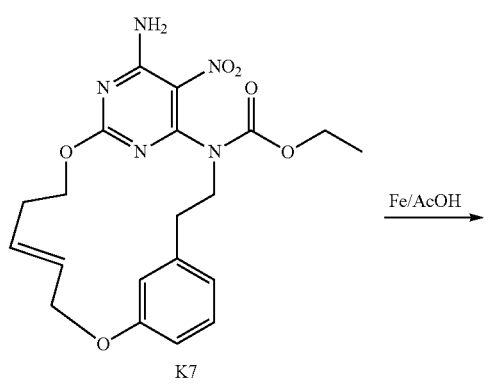

K7

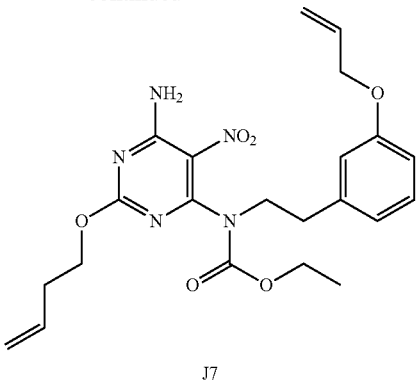 [SMILES: C=CCCOc1nc(N)c([N+](=O)[O-])c(N(CCc2cccc(OCC=C)c2)C(=O)OCC)n1]

J7

Synthesis of Intermediate J7:

At 0° C., diisopropylazodicarboxylate (0.9 mL; 4.541 mmol) was added drop wise to a mixture of Q5 (0.9 g; 3.028 mmol), Z4 (0.54 g; 3.028 mmol) and PPh$_3$ (1.19 g; 4.541 mmol) in THF (45 mL). The mixture was stirred at RT for 2 h. EtOAc and water were added. The layers were decanted. The organic layer was washed with water, dried over MgSO$_4$, filtered and the solvent was evaporated. The crude compound was purified by flash chromatography over silica gel (15-40 μm, 120 g, Heptane-EtOAc 85-15 to 70/30). The pure fractions were collected and evaporated to dryness to give intermediate J7 after crystallization with diisopropyl-ether (520 mg, 38% yield).

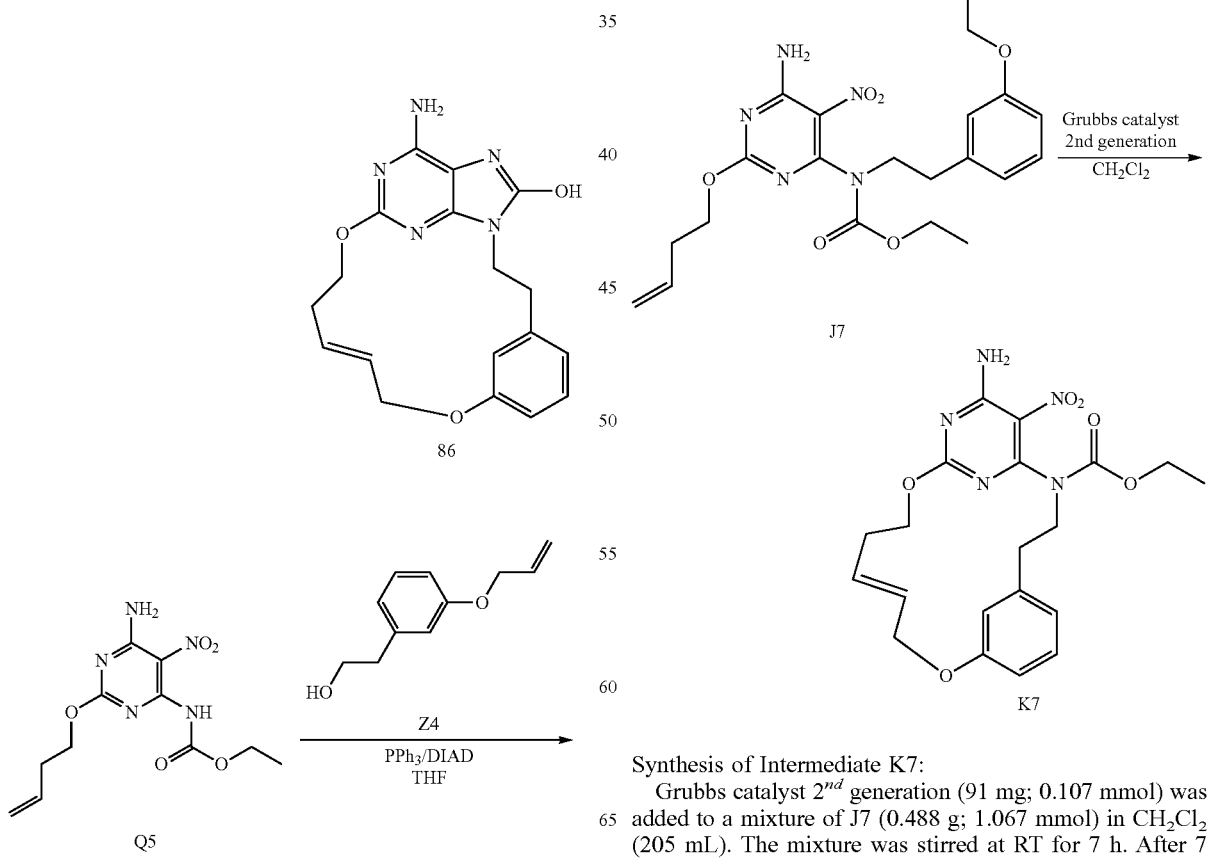

Synthesis of Intermediate K7:

Grubbs catalyst 2$^{nd}$ generation (91 mg; 0.107 mmol) was added to a mixture of J7 (0.488 g; 1.067 mmol) in CH$_2$Cl$_2$ (205 mL). The mixture was stirred at RT for 7 h. After 7 hours SiliaBond® DMT (1.42 g; 0.853 mmol) was added and the mixture was stirred at RT overnight. The reaction was filtered through a pad of Celite®, washed with $CH_2Cl_2$ and the solvent was evaporated. The crude was purified together with another batch (0.12 mmole scale) by flash chromatography over silica gel (15-40 μm, 40 g, $CH_2Cl_2$/ MeOH 99.75/0.25). The pure fractions were collected and evaporated to dryness to give fraction 1; which was then purified by achiral SFC (Stationary phase: Chiralpak IA 5 μm 250*20 mm), Mobile phase: 70% $CO_2$, 30% MeOH) to give 240 mg of intermediate K7 (E isomer, 52% yield).

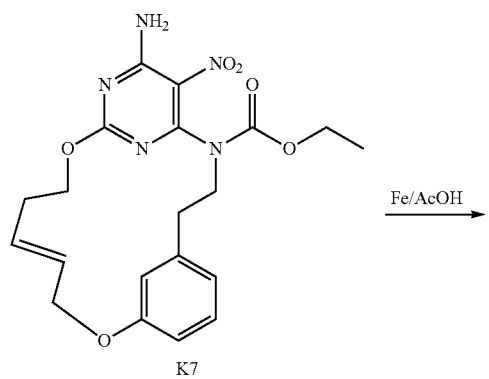

K7

Fe/AcOH →

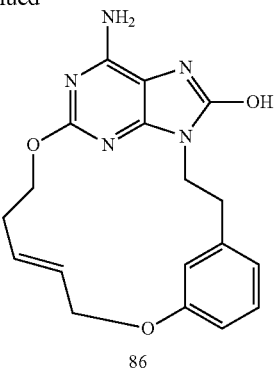

86

Synthesis of Final Compound 86:

Iron (0.52 g; 9.315 mmol) was added to a mixture of K7 (0.2 g; 0.466 mmol) in acetic acid (5.4 mL) and water (550 μL). The mixture was stirred at 50° C. for 5 h. The mixture was filtered through Celite®, washed with AcOH, and then the filtrate was concentrated. The crude compound was dissolved into DMF with 5 g of $SiO_2$ 60-200 μm and the resulting suspension was evaporated until dryness and put on the top of a 25 g column chromatography. Purification was carried out by flash chromatography over silica gel (15-40 μm, 25 g, $CH_2Cl_2/CH_3OH/NH_4OH$: 95/5/0.5 to 90/10/0.5). The pure fractions were collected and evaporated to dryness. This batch was crystallized from $CH_3OH$, the precipitate was filtered off, dried under vacuum at 90° C. to give final compound 86 (68 mg, 41% yield).

OVERALL SCHEME IN THE PREPARATION OF
FINAL PRODUCTS: METHOD 30

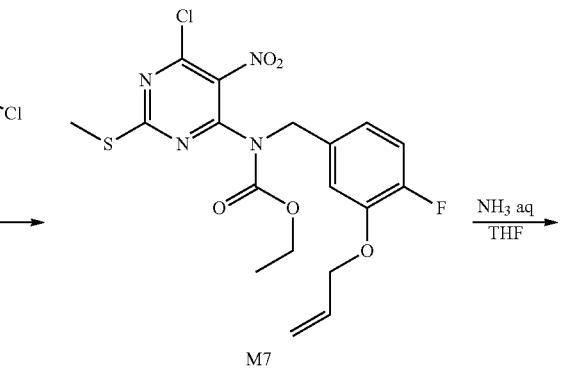

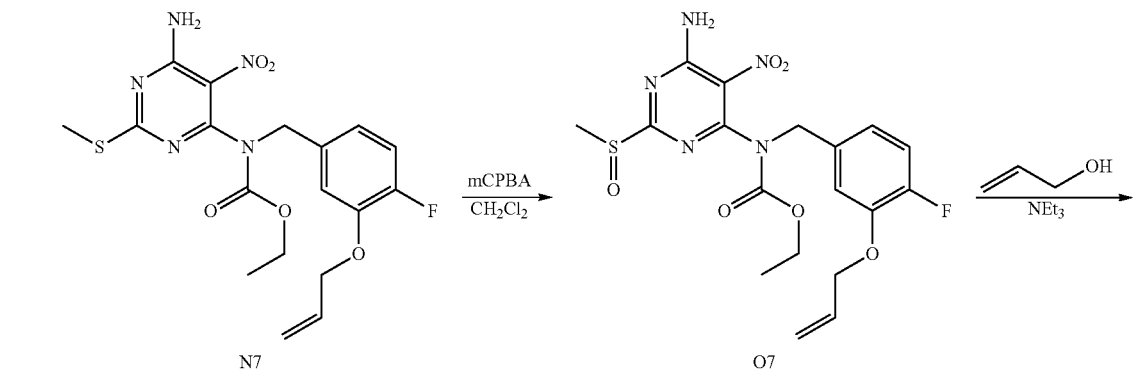

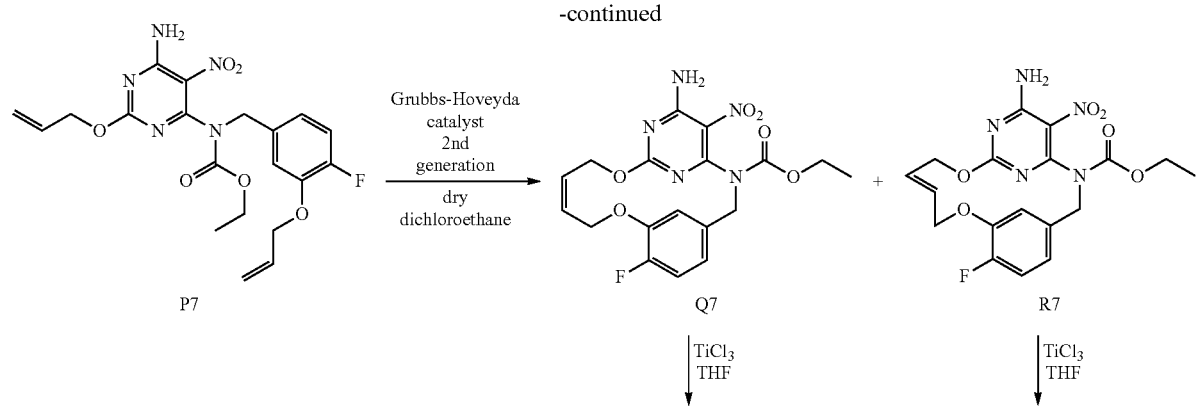

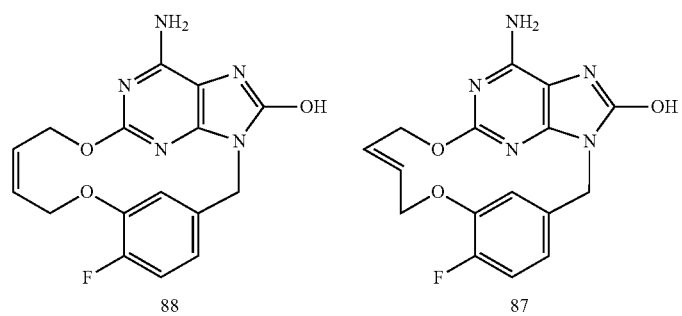

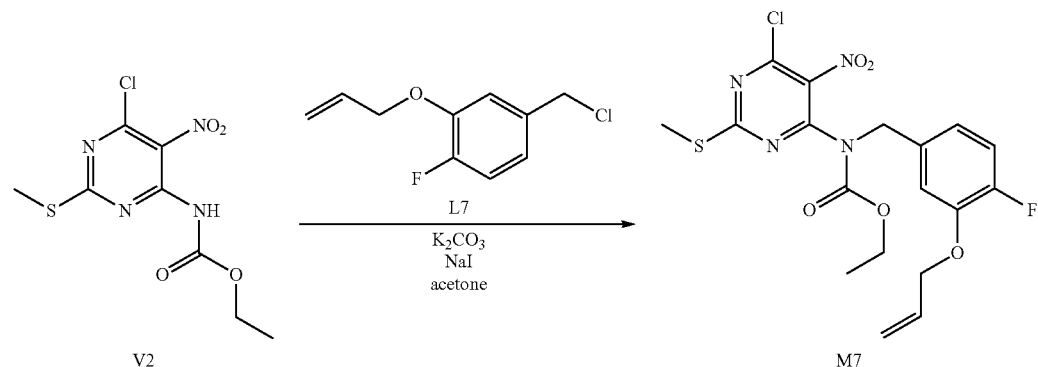

Synthesis of Intermediate M7:

A mixture of V2 (10.0 g; 34.16 mmol), L7 (6.85 g; 34.16 mmol), NaI (5.12 g; 34.16 mmol) and K₂CO₃ (7.08 g; 51.24 mmol) in acetone (370 mL) were stirred at RT for 24 h. The precipitate was filtered off, rinsed with acetone. The filtrate was concentrated under reduced pressure. The crude compound was taken up with CH₂Cl₂, the precipitate (residual intermediate V2) was filtered off, washed with the minimum of CH₂Cl₂ and the filtrate was concentrated to give 16.8 g of intermediate M7, which was directly used in the next step.

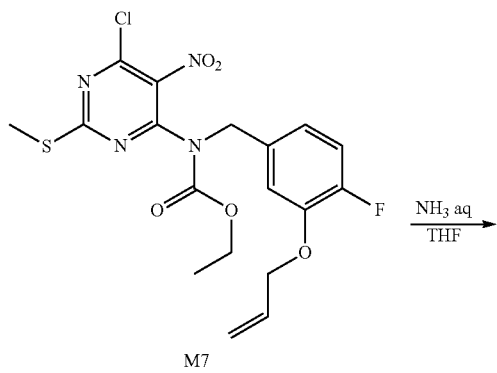

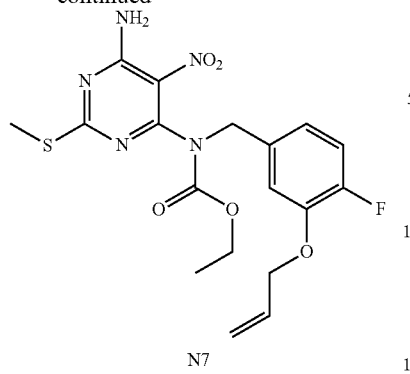

N7

Synthesis of Intermediate N7:

A mixture of M7 (16.8 g, 36.77 mmol) in NH₃ in water (30%) (100 mL) and THF (100 mL) was stirred at RT for 1 h. The mixture was diluted with water and was extracted with EtOAc. The organic layer was washed with brine, dried over MgSO₄, filtered and the solvent was evaporated to give 15.7 g of intermediate N7 (98% yield).

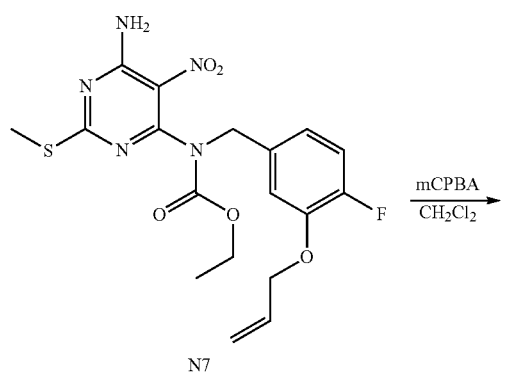

N7

Synthesis of Intermediate O7:

At 0° C., 3-chloroperoxybenzoic acid (8.8 g, 35.66 mmol) in CH₂Cl₂ (100 mL) was added to a mixture of N7 (15.6 g, 35.66 mmol) in CH₂Cl₂ (100 mL). The mixture was stirred at RT for 3 h. An aqueous solution of Na₂S₂O₃ (2 eq) was added to the mixture. The two layers were separated and the aqueous layer was extracted with CH₂Cl₂ (twice). The combined organic layers were washed with a saturated aqueous solution of NaHCO₃, dried over MgSO₄, filtered and the solvent was removed under reduced pressure to afford 16 g of intermediate O7 as a yellow oil (99% yield).

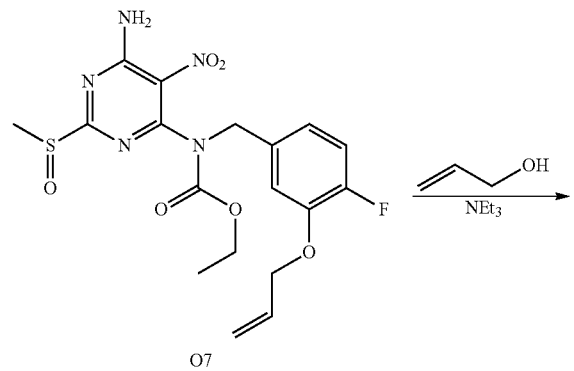

O7

P7

Synthesis of Intermediate P7:

A mixture of O7 (8.0 g, 17.642 mmol) in allyl alcohol (90 mL) and NEt₃ (4.9 mL, 35.285 mmol) was stirred at 90° C. for 1 h. The mixture was evaporated until dryness and purified by flash chromatography over silica gel (15-40 μm, 120 g, CH₂Cl₂/CH₃OH/NH₄OH: 99.5/0.5). The pure fractions were collected and evaporated to dryness to give 6.3 g of intermediate P7 (80% yield).

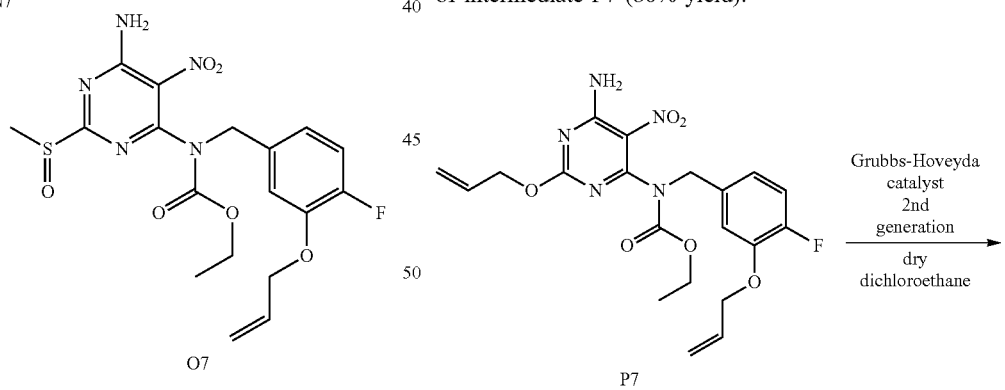

P7

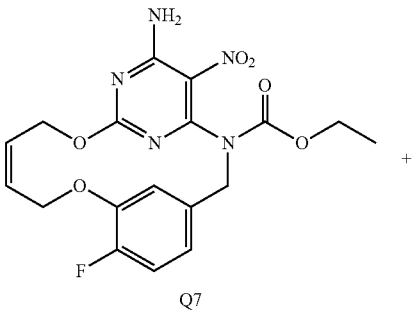

Q7

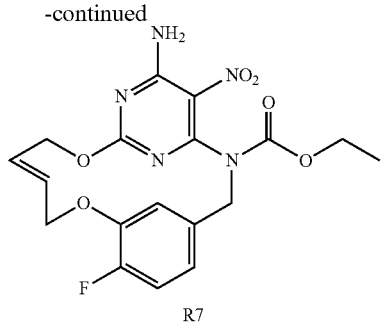

Synthesis of Intermediates Q7 and R7:

The solvent was degassed by bubbling $N_2$ through. Reaction was split into 2 equal portions of 750 mg of P7:

A solution of P7 (750 mg; 1.676 mol) and chlorodicyclohexylborane (1M in hexane) (335 µL; 0.335 µmol) in dry dichloroethane (330 mL) was stirred at 80° C. and under $N_2$ atmosphere for 1 h. 0.033 eq of Grubbs-Hoveyda catalyst $2^{nd}$ generation (35 mg; 56 µmol) was added and the mixture was stirred in sealed tube at 120° C. for 1 h. Then the tube was opened, 0.033 eq of catalyst (35 mg; 56 µmol) was added again and the mixture was stirred in sealed tube at 120° C. for 1 h (sequence repeated two times). SiliaBond® DMT (1.72 g; 0.894 mmol) was added to the mixture, which was stirred at RT overnight. The mixture was filtered through a pad of Celite®, the Celite® was washed with $CH_2Cl_2$ and the filtrate was evaporated. The compound was taken up with $CH_2Cl_2$, the precipitate was filtered off (0.82 g, fraction 1). The filtrate was purified by flash chromatography over silica gel (15-40 µm, 80 g, $CH_2Cl_2/CH_3OH/NH_4OH$: 99.5/0.5/0.5). The pure fractions were collected and evaporated to dryness (0.11 g, fraction 2). Fractions 1 and 2 were combined (0.93 g) and were purified by achiral SFC (Stationary phase: AMINO 6 µm 150×21.2 mm), Mobile phase: 80% $CO_2$, 20% MeOH) to give 0.25 g of intermediate R7 (18% yield, isomer E) and 0.566 g of intermediate Q7 (40% yield, isomer Z).

Synthesis of Final Compound 87:

At 0° C., $TiCl_3$ (10.2 mL; 11.923 mmol) was added dropwise to a mixture of R7 (250 mg; 0.596 mmol) in THF (30 mL). The mixture was stirred at 0° C. for 4 h then at RT overnight. Water was added and the mixture was basified with $K_2CO_3$. The mixture was filtered through a pad of Celite®. The Celite® was washed with $EtOAc/CH_3OH$ 70/30. The layers were decanted and the organic layer was evaporated until dryness. The crude compound was dissolved into DMF then 2 g of $SiO_2$ was added and the resulting mixture was evaporated until dryness. Purification was carried out by flash chromatography over silica gel (solid deposit) (15-40 µm, 25 g, $CH_2Cl_2/CH_3OH/NH_4OH$: 95/5/0.5). The pure fractions were collected and evaporated to dryness to give 20 mg of final compound 87 after crystallization from $CH_3CN$ (17% yield).

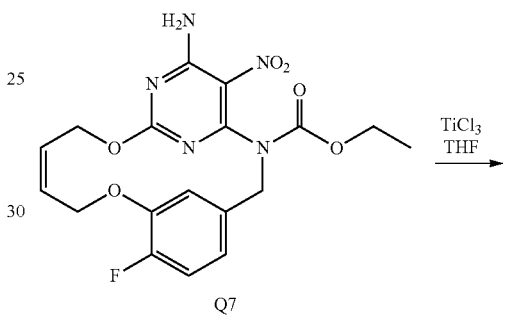

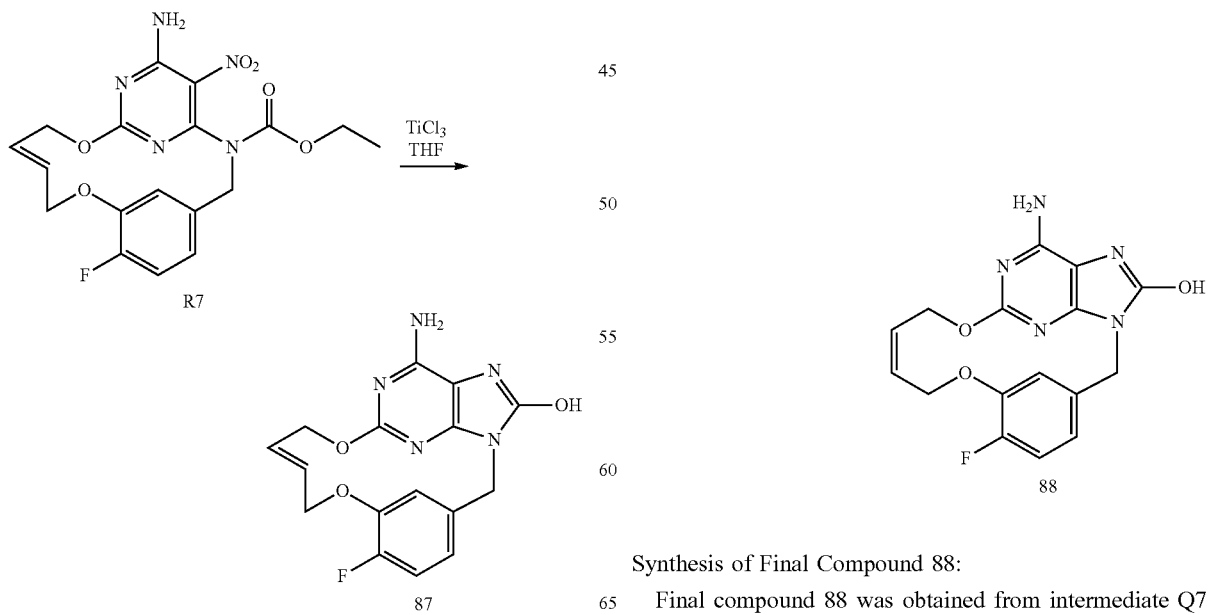

Synthesis of Final Compound 88:

Final compound 88 was obtained from intermediate Q7 (250 mg, 0.596 mmol) with the procedure described for final compound 87, yielding 9 mg (4% yield).

OVERALL SCHEME IN THE PREPARATION OF FINAL PRODUCTS: METHOD 31
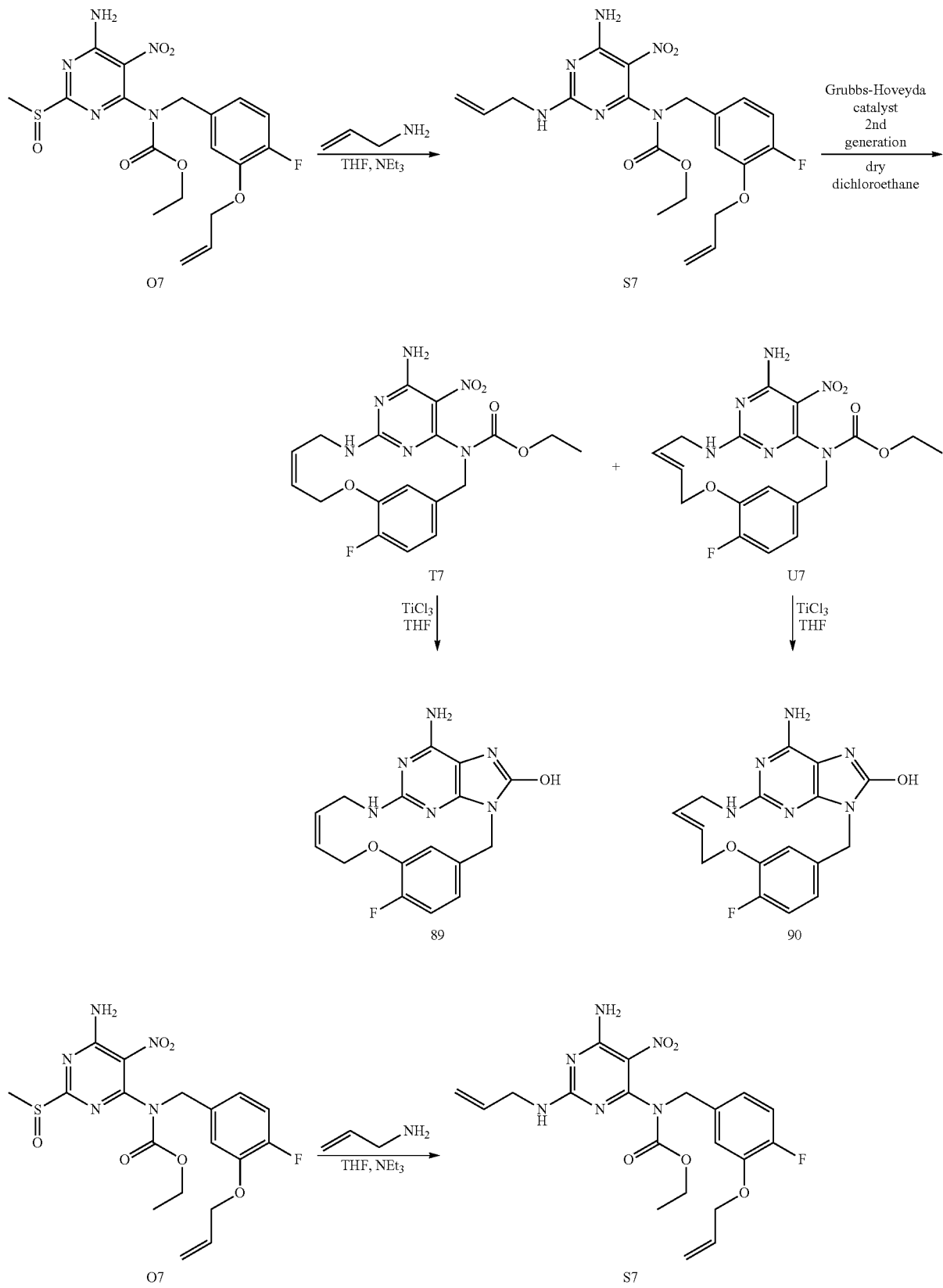

Synthesis of Intermediate S7:

At 0° C., allylamine (1.46 mL, 19.407 mmol) was added drop wise to a mixture of Q7 (8.0 g, 17.642 mmol) and NEt₃ (4.905 mL, 35.285 mmol) in THF (100 mL). The mixture was stirred at RT for 3 h. Water and EtOAc were added. The layers were decanted. The mixture was extracted with EtOAc. The organic layer was dried over MgSO₄, filtered and the solvent was evaporated. The crude was purified by flash chromatography over silica gel (15-40 µm, 120 g, CH₂Cl₂/CH₃OH/NH₄OH: 99.5/0.5). The pure fractions were collected and evaporated to dryness to give 5.8 g of intermediate S7 (74% yield).

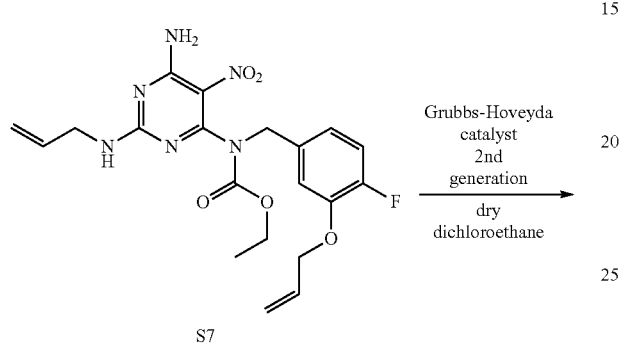

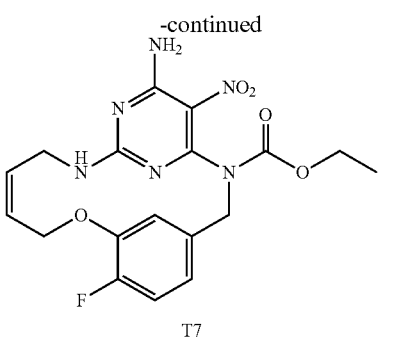

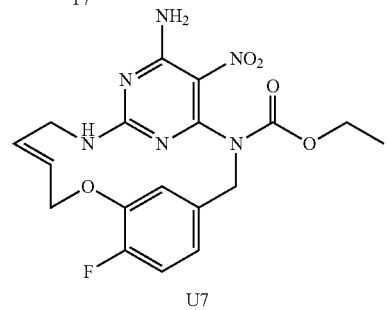

Synthesis of Intermediates T7 and U7:
The intermediates T7 and U7 were synthesized with the method described for intermediates Q7 and R7.

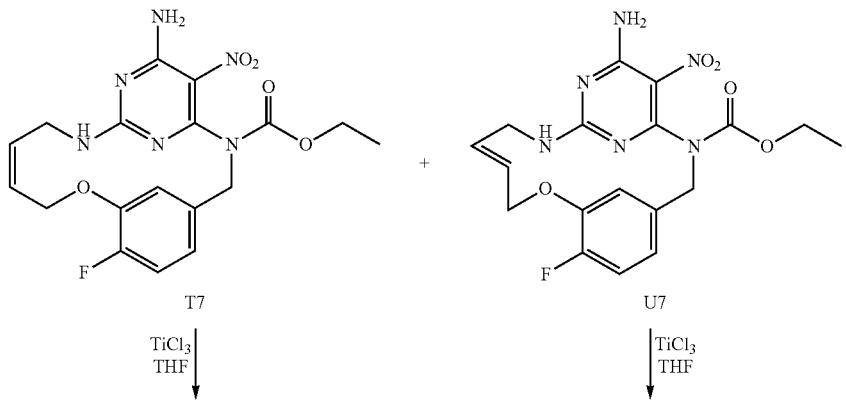

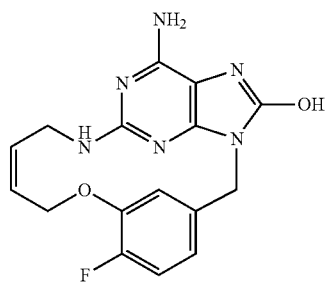

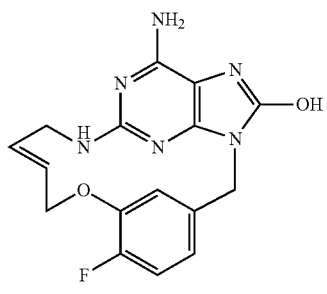

Synthesis of Final Compounds 89 and 90:

Final compounds 89 and 90 were synthesized with the method described for final compounds 87 and 88.

OVERALL SCHEME IN THE PREPARATION OF FINAL PRODUCTS: METHOD 32

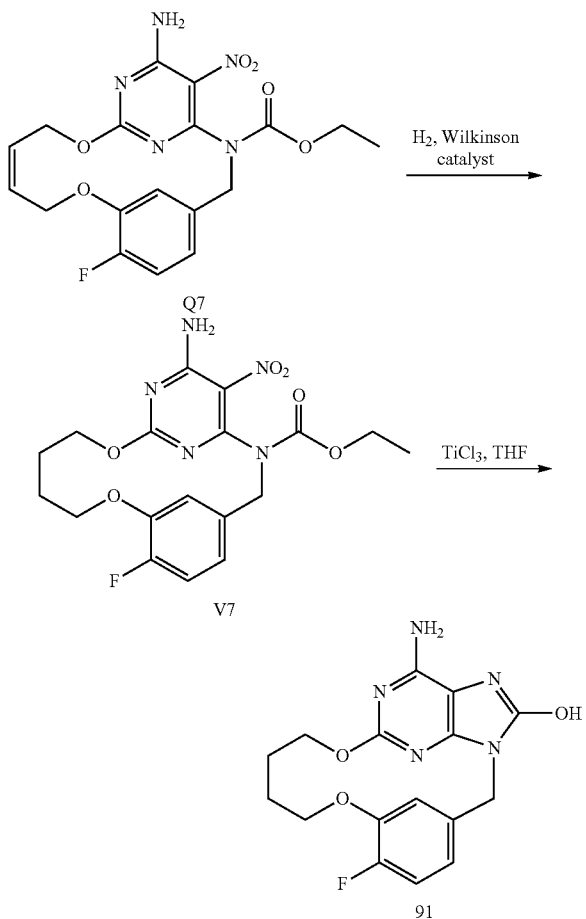

Synthesis of Intermediate V7:

A mixture of Q7 (200 mg, 0.477 mmol) and Wilkinson's catalyst (88.2 mg, 0.0954 mmol) in THF/MeOH (50/50) (30 mL) was stirred at RT under a 8 bar pressure of $H_2$ for 20 h. The mixture was evaporated until dryness to give 0.30 g of intermediate V7 directly used in the next step.

Synthesis of Final Compound 91:

Final compound 91 was synthesized with the method described for final compounds 87 and 88.

Lcms Methods:

General Procedure VDR2 (for Methods V300xV30xx.olp)

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method V3014V3001

In addition to the general procedure VDR2: Reversed phase UPLC was carried out on a Waters HSS (High Strength Silica) T3 column (1.8 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 99% A (hold for 0.5 minutes) to 15% A and 85% B in 4.5 minutes, hold for 2 min and back to the initial conditions in 0.5 min, hold for 1.5 minutes. An injection volume of 2 µL was used. Cone voltage was 20 V for positive and negative ionization mode. Mass spectra were acquired by scanning from 100 to 1000 in 0.2 seconds using an interscan delay of 0.1 seconds.

Method V3018V3001

In addition to the general procedure VDR2: Reversed phase UPLC was carried out on a Waters Acquity BEH (bridged ethylsiloxane/silica hybrid) C18 column (1.7 µm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 µl was used. Cone voltage was 20V for positive and negative ionization mode. Mass spectra were acquired by scanning from 100 to 1000 in 0.2 seconds using an interscan delay of 0.1 seconds.

TABLE 1

Compounds of formula (I).

| # | STRUCTURE | Exact Mass | Mass Found [M + H] | LCMS Ret Time, Method | Synthesis method | NMR |
|---|---|---|---|---|---|---|
| 1 | (structure shown) | 323.1 | 324 | 2.52, V3018V3001 | Method 1 | $^1$H NMR (500 MHz, DMSO-$d_6$) δ (ppm) 9.91 (br. s., 1H), 8.00-8.11 (m, 1H), 7.04-7.24 (m, 3H), 6.43 (s, 2H), 5.36-5.77 (m, 2H), 4.82 (d, J = 4.7 Hz, 2H), 4.63-4.69 (m, 1H), 4.45-4.57 (m, 1H), 3.17-3.32 (m, 2H), 2.34-2.43 (m, 2H) |

TABLE 1-continued

| | | | Mass | LCMS Ret | | |
| | | Exact | Found | Time, | Synthesis | |
| # | STRUCTURE | Mass | [M + H] | Method | method | NMR |
|---|---|---|---|---|---|---|
| 2 | 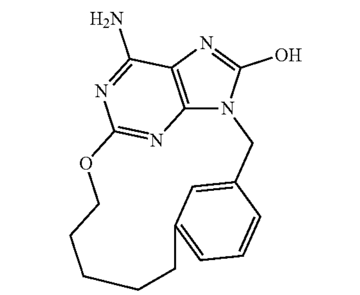 [SMILES: Nc1nc2nc3c1nc(O)n3Cc1cccc(c1)CCCCCO2] | 325.2 | 326 | 2.62, V3018V3001 | Method 2 | $^1$H NMR (500 MHz, DMSO-d$_6$) δ (ppm) 9.93 (s, 1H), 7.57 (s, 1H), 7.14-7.20 (m, 1H), 7.04 (d, J = 7.3 Hz, 1H), 6.93 (d, J = 7.3 Hz, 1H), 6.36 (br. s., 2H), 4.83 (s, 2H), 4.15 (t, J = 6.8 Hz, 2H), 2.60-2.69 (m, 2H), 1.68 (br. s., 2H). 1.18-1.34 (m, 4H) |
| 3 | 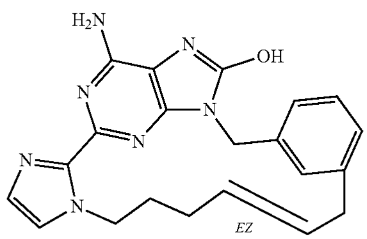 [SMILES: Nc1nc2nc3c1nc(O)n3Cc1cccc(c1)C/C=C/CCCn1ccnc1-2] | 387.2 | 388 | 2.47, V3018V3001 | Method 3 | $^1$H NMR (500 MHz, DMSO-d$_6$) δ (ppm) 9.91-10.50 (m, 1H), 6.91-7.37 (m, 6H), 6.57-6.70 (m, 2H), 5.21-5.54 (m, 2H), 4.82-4.92 (m, 2H), 4.11-4.30 (m, 2H), 3.18-3.32 (m, 2H), 2.03-2.23 (m, 2H), 1.60-1.90 (m, 2H) |
| 4 | 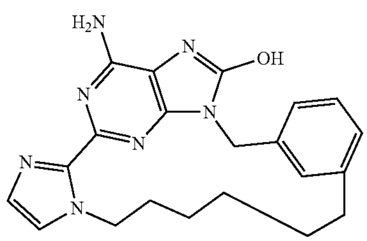 [SMILES: Nc1nc2nc3c1nc(O)n3Cc1cccc(c1)CCCCCCn1ccnc1-2] | 389.2 | 390 | 2.57, V3018V3001 | Method 4 | $^1$H NMR (500 MHz, DMSO-d$_6$) δ (ppm) 11.25 (s, 1H), 7.87 (d, J = 1.3 Hz, 1H), 7.72 (s, 1H), 7.04-7.31 (m, 6H), 4.98 (s, 2H), 4.41-4.49 (m, 2H), 2.58-2.65 (m, 2H), 1.62-1.72 (m, 2H), 1.52-1.61 (m, 2H), 1.13-1.25 (m, 2H), 0.99-1.11 (m, 2H) |
| 5 | 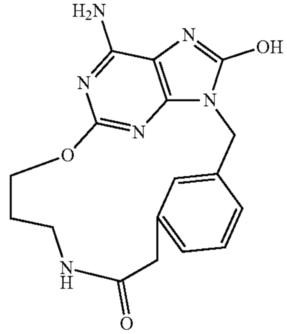 [SMILES: Nc1nc2nc3c1nc(O)n3Cc1cccc(c1)CC(=O)NCCCO2] | 354.1 | 355 | 2.52, V3018V3001 | Method 5 | $^1$H NMR (500 MHz, DMSO-d$_6$) δ (ppm) 10.40-10.67 (m, 1H), 8.25 (t, J = 5.5 Hz, 1H), 7.74 (s, 1H), 6.83-7.27 (m, 5H), 4.79 (s, 2H), 4.53 (t, J = 7.6 Hz, 2H), 3.36 (s, 2H), 3.03-3.13 (m, 2H), 1.66 (s, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 6 | 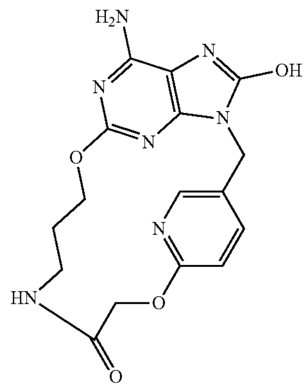 [SMILES: Nc1nc2nc3c1nc(O)n3Cc1ccc(nc1)OCC(=O)NCCCO2] | 371.1 | 372 | 2.40, V3018V3001 | Method 6 | $^1$H NMR (400 MHz, DMSO-d$_6$) δ (ppm) 10.42 (br. s., 1H), 8.31 (s, 1H), 7.59 (t, J = 4.80 Hz, 1H), 7.50 (dd, J = 2.02, 8.59 Hz, 1H), 6.83-7.32 (m, 2H), 6.80 (d, J = 8.59 Hz, 1H), 4.86 (br. s., 2H), 4.67 (br. s., 2H), 3.70 (br. s., 2H), 3.09 (br. s., 2H), 1.72-1.82 (m, 2H) |
| 7 | 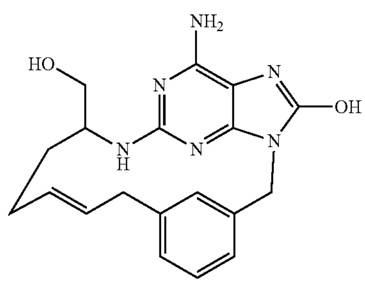 [SMILES: Nc1nc2nc3c1nc(O)n3Cc1cccc(c1)C/C=C/CCC(CO)N2] | 366.2 | 367 | 2.25, V3018V3001 | Method 7 | $^1$H NMR (500 MHz, DMSO-d$_6$) δ (ppm) 9.53 (s, 1H), 7.92 (s, 1H), 7.13-7.22 (m, 2H), 7.07 (d, J = 7.25 Hz, 1H), 5.87 (s, 2H), 5.68 (d, J = 10.09 Hz, 1H), 5.38-5.47 (m, 1H), 5.20-5.30 (m, 1H), 4.77 (d, 1H), 4.66 (d, 1H), 4.57 (t, 1H), 4.25-4.36 (m, 1H), 3.39-3.47 (m, 1H), 3.34-3.39 (m, 1H), 3.18-3.30 (m, 2H), 2.05-2.18 (m, 2H), 1.70-1.80 (m, 1H), 1.40-1.51 (m, 1H) |
| 8 | 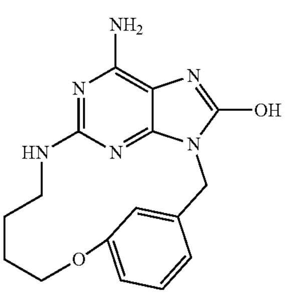 [SMILES: Nc1nc2nc3c1nc(O)n3Cc1cccc(c1)OCCCCN2] | 326.1 | 327 | 2.26, V3018V3001 | Method 8 | $^1$H NMR (500 MHz, DMSO-d$_6$) δ (ppm) 9.64 (br. s., 1H), 9.36 (s, 1H), 7.08 (t, J = 7.70 Hz, 1H), 6.76 (d, J = 7.70 Hz, 1H), 6.71 (s, 1H), 6.62 (dd, J = 1.73, 7.70 Hz, 1H), 6.06 (s, 2H), 4.71 (s, 2H), 3.39 (t, J = 6.46 Hz, 4H), 1.76-1.92 (m, 4H) |
| 9 | 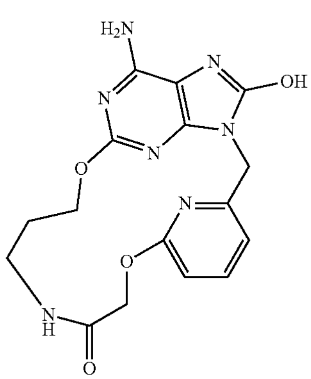 [SMILES: Nc1nc2nc3c1nc(O)n3Cc1cccc(n1)OCC(=O)NCCCO2] | 371.1 | 372 | 2.49, V3018V3001 | Method 9 | $^1$H NMR (500 MHz, DMSO-d$_6$) δ (ppm) 10.00 (br. s., 1H), 7.97 (t, J = 5.83 Hz, 1H), 7.68 (t, J = 7.72 Hz, 1H), 7.00 (d, J = 7.72 Hz, 1H), 6.80 (d, J = 7.72 Hz, 1H), 6.39 (s, 2H), 4.65-4.94 (m, 4H), 4.20 (t, J = 7.72 Hz, 2H), 2.96-3.12 (m, 2H), 1.50-1.73 (m, 2H) |

TABLE 1-continued

| | | | Compounds of formula (I). | | | |
|---|---|---|---|---|---|---|
| # | STRUCTURE | Exact Mass | Mass Found [M + H] | LCMS Ret Time, Method | Synthesis method | NMR |
| 10 | | 368.2 | 369 | 2.33, V3018V3001 | Method 10 | ¹H NMR (500 MHz, DMSO-d₆) δ (ppm) 9.61 (s, 1H), 7.43 (s, 1H), 7.15-7.26 (m, 1H), 7.07-7.14 (m, 1H), 7.02 (d, J = 7.25 Hz, 1H), 5.92 (s, 2H), 5.56 (d, J = 10.09 Hz, 1H), 4.95 (d, J = 14.50 Hz, 1H), 4.47-4.63 (m, 2H), 4.06-4.23 (m, 1H), 3.34-3.39 (m, 1H), 3.22-3.30 (m, 1H), 2.55-2.68 (m, 2H), 1.67-1.84 (m, 1H), 1.46-1.61 (m, 1H), 1.22-1.45 (m, 5H), 0.97-1.14 (m, 1H) |
| 11 | | 327.1 | 328 | 2.23, V3018V3001 | Method 11 | ¹H NMR (500 MHz, DMSO-d₆) δ (ppm) 9.93 (br. s., 1H), 7.92 (s, 1H), 7.15 (t, J = 7.72 Hz, 1H), 6.81 (d, J = 7.72 Hz, 1H), 6.66-6.77 (m, 1H), 6.39 (br. s., 2H), 4.82 (s, 2H), 4.57 (t, J = 5.99 Hz, 2H), 4.27 (t, J = 6.62 Hz, 2H), 1.44-1.73 (m, 4H) |
| 12 | | 343.1 | 344 | 2.12, V3018V3001 | Method 12 | ¹H NMR (500 MHz, DMSO-d₆) δ (ppm) 9.93 (br. s., 1H), 7.72 (s, 1H), 7.16 (t, J = 7.88 Hz, 1H), 6.95 (d, J = 7.88 Hz, 1H), 6.78 (dd, J = 1.89, 7.88 Hz, 1H), 6.43 (br. s., 2H), 4.82 (s, 2H), 4.66 (t, J = 4.57 Hz, 2H), 3.99-4.07 (m, 2H), 3.59 (td, J = 4.57, 12.14 Hz, 4H) |
| 13 | | 342.1 | 343 | 1.97, V3018V3001 | Method 8 | ¹H NMR (500 MHz, DMSO-d₆) δ (ppm) 9.75 (br. s., 1H), 9.36 (br. s., 1H), 7.09 (t, J = 7.88 Hz, 1H), 6.73 (d, J = 7.88 Hz, 1H), 6.68 (s, 1H), 6.62 (d, J = 7.88 Hz, 1H), 6.16 (s, 2H), 4.73 (s, 2H), 3.45-3.69 (m, 8H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 14 | 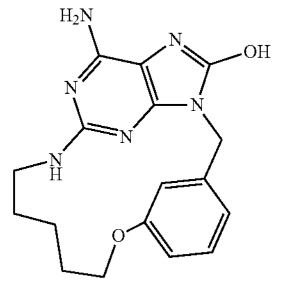 [SMILES: Nc1nc2nc3c1nc(O)n3Cc1cccc(c1)OCCCCCN2] | 340.2 | 341 | 2.37, V3018V3001 | Method 12 | $^1$H NMR (500 MHz, DMSO-$d_6$) δ (ppm) 9.65 (s, 1H), 7.48 (s, 1H), 7.19 (t, J = 7.72 Hz, 1H), 6.90 (d, J = 7.72 Hz, 1H), 6.77 (dd, J = 1.89, 7.72 Hz, 1H), 6.10 (t, J = 6.31 Hz, 1H), 5.99 (s, 2H), 4.75 (s, 2H), 3.87-3.99 (m, 2H), 3.42 (q, J = 6.31 Hz, 2H), 1.60-1.78 (m, 2H), 1.39-1.50 (m, 2H), 1.29-1.39 (m, 2H) |
| 15 | 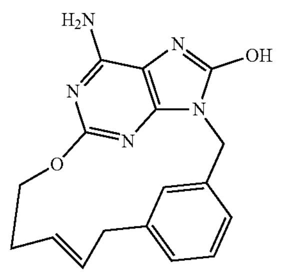 [SMILES: Nc1nc2nc3c1nc(O)n3Cc1cccc(c1)C/C=C/CCO2] | 323.1 | 324 | 2.49, V3018V3001 | Method 14 | $^1$H NMR (500 MHz, DMSO-$d_6$) δ (ppm) 9.76-10.25 (m, 1H), 8.07 (s, 1H), 6.95-7.29 (m, 3H), 6.44 (s, 2H), 5.57-5.81 (m, 1H), 5.29-5.54 (m, 1H), 4.82 (s, 2H), 4.66 (br. s., 2H), 3.20 (d, J = 6.31 Hz, 2H), 2.39 (br. s., 2H) |
| 16 | 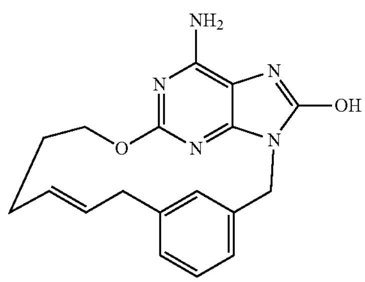 [SMILES: Nc1nc2nc3c1nc(O)n3Cc1cccc(c1)C/C=C/CCCO2] | 337.2 | 338 | 2.65, V3018V3001 | Method 13 | $^1$H NMR (500 MHz, DMSO-$d_6$) δ (ppm) 9.95 (s, 1H), 7.81 (s, 1H), 6.94-7.39 (m, 3H), 6.39 (s, 2H), 5.14-5.62 (m, 2H), 4.78 (s, 2H), 4.54 (s, 2H), 1.59-2.31 (m, 5H), 1.23 (br. s., 1H) |
| 17 | 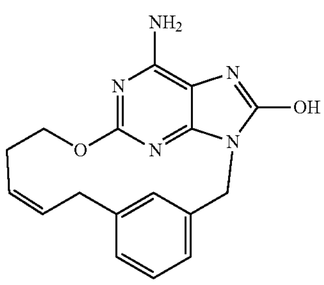 [SMILES: Nc1nc2nc3c1nc(O)n3Cc1cccc(c1)C/C=C\CCO2] | 323.1 | 324 | 2.51, V3018V3001 | Method 14 | $^1$H NMR (500 MHz, DMSO-$d_6$) δ 9.92 (br. s., 1H), 8.03 (br. s., 1H), 7.17-7.25 (m, 1H), 7.08-7.16 (m, 2H), 6.43 (br. s., 2H), 5.68-5.77 (m, 1H), 5.47-5.57 (m, 1H), 4.81 (s, 2H), 4.43-4.53 (m, 2H), 3.28-3.32 (br. s., 2H), 2.34-2.42 (m, 2H) |
| 18 | 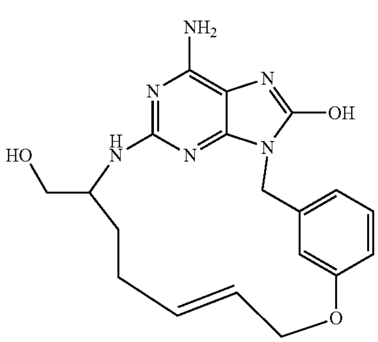 [SMILES: Nc1nc2nc3c1nc(O)n3Cc1cccc(c1)OC/C=C/CCC(CO)N2] | 382.2 | 383 | 2.13, V3018V3001 | Method 15 | $^1$H NMR (500 MHz, DMSO-$d_6$) δ 9.62 (s, 1H), 7.17 (t, J = 8.20 Hz, 1H), 7.11 (s, 1H), 6.99 (d, J = 8.20 Hz, 1H), 6.78 (dd, J = 1.89, 8.20 Hz, 1H), 5.91 (s, 2H), 5.71 (dt, J = 6.50, 15.76 Hz, 1H), 5.58 (d, J = 9.77 Hz, 1H), 5.50 (dt, J = 4.89, 15.76 Hz, 1H), 4.83 (d, J = 9.77 Hz, 1H), 4.48-4.73 (m, |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| | | | | | | 4H), 4.09-4.23 (m, 1H), 3.38-3.48 (m, 2H), 1.97-2.08 (m, 2H), 1.62-1.75 (m, 1H), 1.29-1.40 (m, 1H) |
| 19 | 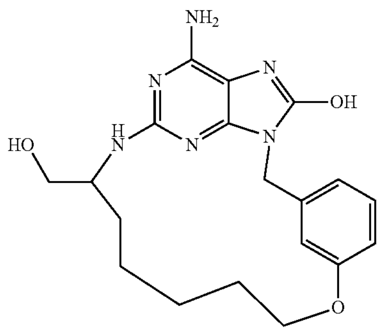 [SMILES: Nc1nc2nc3c1nc(O)n3Cc1cccc(c1)OCCCCCC(CO)N2] | 384.2 | 385 | 2.19, V3018V3001 | Method 10 | $^1$H NMR (500 MHz, DMSO-d$_6$) δ 9.64 (s, 1H), 7.16-7.23 (m, 1H), 7.12 (br. s., 1H), 7.01 (d, J = 7.25 Hz, 1H), 6.80 (dd, J = 1.73, 8.04 Hz, 1H), 5.95 (s, 2H), 5.64 (d, J = 9.14 Hz, 1H), 4.85 (d, J = 14.19 Hz, 1H), 4.52-4.67 (m, 2H), 4.03-4.16 (m, 2H), 3.91-4.03 (m, 1H), 3.37-3.50 (m, 2H), 1.24-1.68 (m, 8H) |
| 20 | 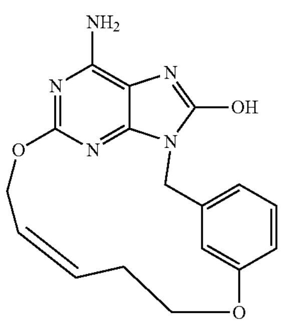 [SMILES: Nc1nc2nc3c1nc(O)n3Cc1cccc(c1)OCC/C=C\CO2] | 339.1 | 340 | 2.37, V3018V3001 | Method 16 | $^1$H NMR (500 MHz, DMSO-d$_6$) δ 9.99 (br. s., 1H), 7.57 (br. s., 1H), 7.21 (t, J = 7.70 Hz, 1H), 6.94 (d, J = 7.70 Hz, 1H), 6.78 (dd, J = 1.58, 7.70 Hz, 1H), 6.49 (br. s., 2H), 5.74-5.85 (m, 1H), 5.59-5.69 (m, 1H), 5.13 (d, J = 7.57 Hz, 2H). 4.85 (s, 2H), 3.90-4.02 (m, 2H), 2.45-2.50 (m, 2H) |
| 21 | 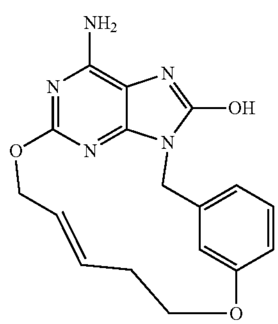 [SMILES: Nc1nc2nc3c1nc(O)n3Cc1cccc(c1)OCC/C=C/CO2] | 339.1 | 340 | 2.32, V3018V3001 | Method 16 | $^1$H NMR (500 MHz, DMSO-d$_6$) δ 9.94 (br. s., 1H), 7.15-7.25 (m, 2H), 6.92 (d, J = 7.57 Hz, 1H), 6.83 (dd, J = 1.73, 7.57 Hz, 1H), 6.44 (br. s., 2H), 5.76 (dt, J = 7.00, 15.61 Hz, 1H), 5.46 (dt, J = 5.12, 15.61 Hz, 1H), 4.76-4.84 (m, 4H), 4.05-4.13 (m, 2H), 2.27-2.38 (m, 2H) |
| 22 | 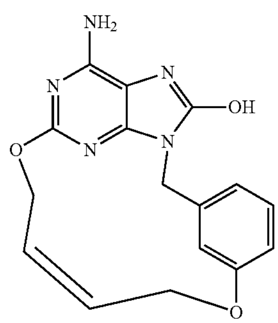 [SMILES: Nc1nc2nc3c1nc(O)n3Cc1cccc(c1)OC/C=C\CO2] | 325.1 | 326 | 2.19, V3018V3001 | Method 16 | $^1$H NMR (500 MHz, DMSO-d$_6$) δ 10.25 (br. s., 1H), 7.91 (br. s., 1H), 7.18 (t, J = 7.25 Hz, 1H), 6.87 (d, J = 7.25 Hz, 1H), 6.79 (d, J = 7.25 Hz, 1H), 6.54 (br. s., 2H), 5.30-5.48 (m, 2H), 5.12 (br. s., 2H), 4.81 (br. s., 2H), 4.76 (br. s., 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 23 | 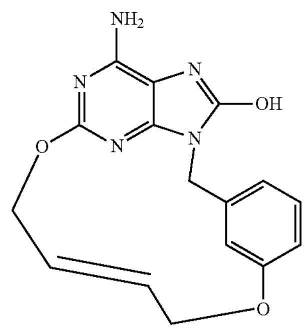 [SMILES: Nc1nc2nc3c1nc(O)n3Cc1cccc(c1)OC/C=C/CO2] | 325.1 | 326 | 2.15, V3018V3001 | Method 16 | $^1$H NMR (500 MHz, DMSO-d$_6$) δ 9.96 (br. s., 1H), 7.55 (s, 1H), 7.16 (t, J = 7.25 Hz, 1H), 6.88 (d, J = 7.25 Hz, 1H), 6.80 (dd, J = 1.73, 7.25 Hz, 1H), 6.44 (br. s., 2H), 5.61-5.77 (m, 2H), 4.78 (s, 4H), 4.56 (d, J = 4.73 Hz, 2H) |
| 24 | 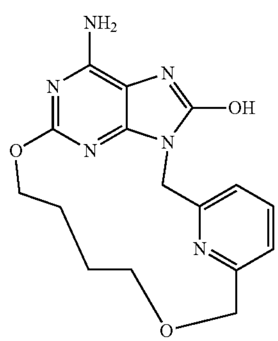 [SMILES: Nc1nc2nc3c1nc(O)n3Cc1cccc(n1)COCCCCO2] | 342.1 | 343 | 1.75, V3018V3001 | Method 17 | $^1$H NMR (500 MHz, DMSO-d$_6$) δ 9.98 (br. s., 1H), 7.73 (t, J = 7.57 Hz, 1H), 7.25 (dd, J = 7.57, 13.24 Hz, 2H), 6.37 (br. s., 2H), 4.99 (s, 2H), 4.41 (s, 2H), 4.21 (t, J = 7.25 Hz, 2H), 3.61 (t, J = 5.83 Hz, 2H), 1.38-1.56 (m, 4H) |
| 25 | 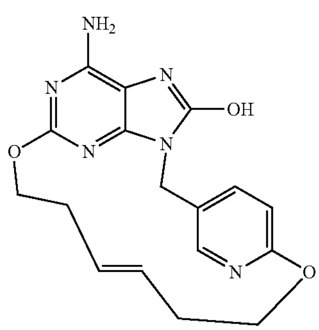 [SMILES: Nc1nc2nc3c1nc(O)n3Cc1ccc(nc1)OCC/C=C/CCO2] | 354.1 | 355 | 2.2, V3018V3001 | Method 16 | $^1$H NMR (500 MHz, DMSO-d$_6$) δ 9.86 (br. s., 1H), 8.19 (d, J = 2.53 Hz, 1H), 7.50 (dd, J = 2.02, 8.59 Hz, 1H), 6.64 (d, J = 8.59 Hz, 1H), 6.14 (s, 2H), 5.17-5.25 (m, 2H), 4.80 (s, 2H), 4.67 (br. s., 2H), 3.80-3.89 (m, 2H), 2.25-2.37 (m, 2H), 1.83-1.91 (m, 2H) |
| 26 | 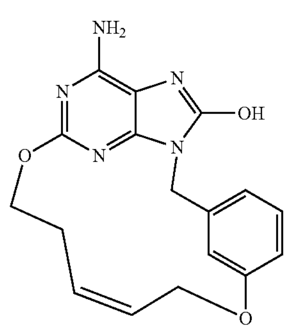 [SMILES: Nc1nc2nc3c1nc(O)n3Cc1cccc(c1)OC/C=C\CCO2] | 339.1 | 340 | 2.37, V3018V3001 | Method 16 | $^1$H NMR (500 MHz, DMSO-d$_6$) δ 9.84 (br. s., 1H), 7.28 (d, J = 1.26 Hz, 1H), 7.16-7.24 (m, 1H), 6.96 (d, J = 7.25 Hz, 1H), 6.76-6.82 (m, 1H), 6.46 (br. s., 2H), 5.38-5.50 (m, 2H), 4.74 (s, 2H), 4.68 (d, J = 3.78 Hz, 2H), 4.57 (t, J = 7.57 Hz, 2H), 2.43-2.53 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 27 | 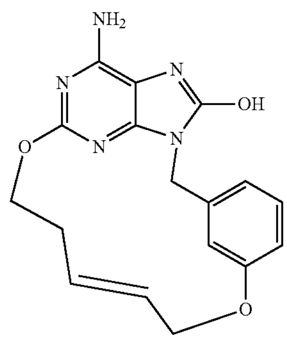 [SMILES: Nc1nc2nc3c1nc(O)n3Cc1cccc(c1)OC/C=C/CCO2] | 339.1 | 340 | 2.35, V3018V3001 | Method 16 | $^1$H NMR (500 MHz, DMSO-$d_6$) δ 9.97 (br. s., 1H), 7.18 (t, J = 7.25 Hz, 1H), 7.03 (s, 1H), 6.93 (d, J = 7.25 Hz, 1H), 6.75 (d, J = 7.25 Hz, 1H), 6.52 (br. s., 2H), 5.43-5.56 (m, 2H), 4.79 (s, 2H), 4.56-4.62 (m, 2H), 4.42-4.47 (m, 2H), 2.32-2.39 (m, 2H) |
| 28 | 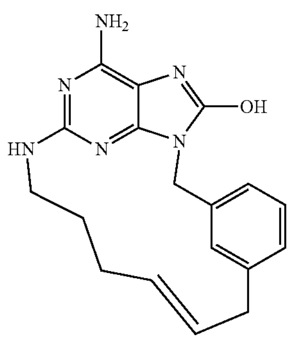 [SMILES: Nc1nc2nc3c1nc(O)n3Cc1cccc(c1)C/C=C/CCCN2] | 336.2 | 337 | 2.59, V3018V3001 | Method 7 | $^1$H NMR (500 MHz, DMSO-$d_6$) δ 9.57 (s, 1H), 7.85 (s, 1H), 7.12-7.24 (m, 2H), 7.08 (d, J = 7.25 Hz, 1H), 5.80-5.99 (m, 3H), 5.44-5.52 (m, 1H), 5.31-5.39 (m, 1H), 4.71 (s, 2H), 3.46-3.54 (m, 2H), 3.27-3.40 (m, 2H), 1.97-2.16 (m, 2H), 1.57 (br. s., 2H) |
| 29 | 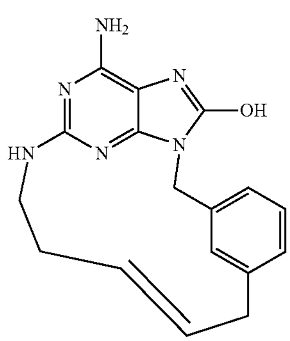 [SMILES: Nc1nc2nc3c1nc(O)n3Cc1cccc(c1)C/C=C/CCN2] | 322.2 | 323 | 2.45, V3018V3001 | Method 7 | $^1$H NMR (500 MHz, DMSO-$d_6$) δ 9.54 (br. s., 1H), 8.19 (br. s., 1H), 6.97-7.24 (m, 3H), 6.27 (br. s., 1H), 5.92 (br. s., 2H), 5.56-5.68 (m, 1H), 5.44-5.56 (m, 1H), 4.75 (s, 2H), 3.25-3.78 (m, 2H), 3.14-3.24 (m, 2H), 2.12-2.24 (m, 2H) |
| 30 | 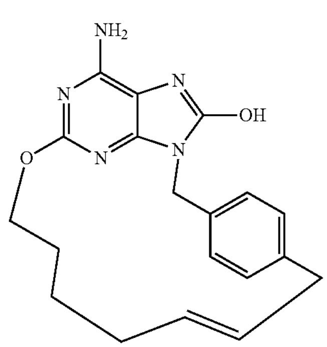 [SMILES: Nc1nc2nc3c1nc(O)n3Cc1ccc(cc1)C/C=C/CCCCO2] | 351.2 | 352 | 2.75, V3018V3001 | Method 14 | $^1$H NMR (500 MHz, DMSO-$d_6$) δ 10.09 (br. s., 1H), 7.05 (s, 4H), 6.37 (br. s., 2H), 5.60-5.73 (m, 1H), 4.83-4.96 (m, 3H), 3.67-3.72 (m, 2H), 3.12-3.17 (m, 2H), 1.91 (br. s., 2H), 1.03-1.19 (m, 4H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 31 | 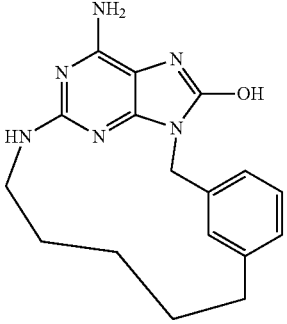 [SMILES: Nc1nc2nc3c1nc(O)n3Cc1cccc(c1)CCCCCN2] | 324.2 | 325 | 2.52, V3018V3001 | Method 10 | ¹H NMR (500 MHz, DMSO-d₆) δ 9.63 (br. s., 1H), 7.63 (s, 1H), 7.10-7.20 (m, 1H), 7.01 (d, J = 7.58 Hz, 1H), 6.95 (d, J = 7.58 Hz, 1H), 6.09 (t, J = 6.06 Hz, 1H), 5.88 (s, 2H), 4.77 (s, 2H), 3.08-3.18 (m, 2H), 2.59-2.70 (m, 2H), 1.69 (br. s., 2H), 1.13-1.31 (m, 4H) |
| 32 | 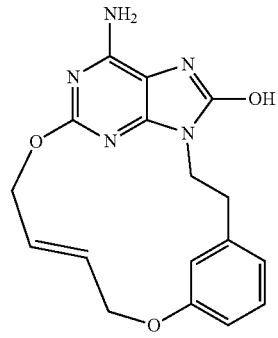 [SMILES: Nc1nc2nc3c1nc(O)n3CCc1cccc(c1)OC/C=C/CO2] | 339.1 | 340 | 2.15, V3018V3001 | Method 18 | ¹H NMR (500 MHz, DMSO-d₆) δ 9.73 (br. s., 1H), 6.85-6.93 (m, 2H), 6.58 (dd, J = 1.58, 8.20 Hz, 1H), 6.37 (d, J = 8.20 Hz, 1H), 6.26 (br. s., 2H), 5.66-5.74 (m, 1H), 5.55 (br. d, J = 16.39 Hz, 1H), 4.63-4.69 (m, 4H), 4.03 (t, J = 5.20 Hz, 2H), 2.97 (t, J = 5.20 Hz, 2H) |
| 33 | 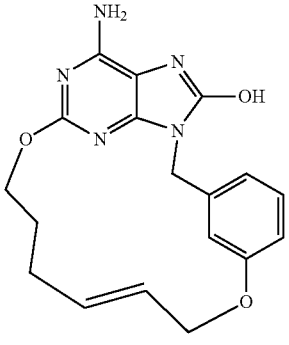 [SMILES: Nc1nc2nc3c1nc(O)n3Cc1cccc(c1)OC/C=C/CCCO2] | 353.1 | 354 | 2.46, V3018V3001 | Method 16 | ¹H NMR (500 MHz, DMSO-d₆) δ 9.97 (br. s., 1H), 7.08-7.21 (m, 2H), 6.85 (d, J = 7.57 Hz, 1H), 6.78 (dd, J = 1.89, 7.57 Hz, 1H), 6.39 (br. s., 2H), 5.75-5.84 (m, 1H), 5.51 (dt, J = 5.24, 15.68 Hz, 1H), 4.74-4.79 (m, 2H), 4.67 (d, J = 4.73 Hz, 2H), 4.21-4.27 (m, 2H), 2.02-2.08 (m, 2H), 1.55-1.66 (m, 2H) |
| 34 | 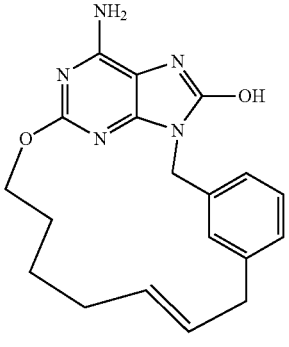 [SMILES: Nc1nc2nc3c1nc(O)n3Cc1cccc(c1)C/C=C/CCCCO2] | 351.2 | 352 | 2.82, V3018V3001 | Method 14 | ¹H NMR (500 MHz, DMSO-d₆) δ 9.94 (br. s., 1H), 7.29 (d, J = 6.94 Hz, 1H), 7.17-7.25 (m, 2H), 7.10 (d, J = 6.94 Hz, 1H), 6.41 (br. s., 2H), 5.42 (br. s., 2H), 4.79 (br. s., 2H), 4.16-4.24 (m, 2H), 3.23 (br. s., 2H), 2.03 (br. s., 2H), 1.77 (br. s., 2H), 1.41 (br. s., 2H) |

TABLE 1-continued

Compounds of formula (I).

| # | STRUCTURE | Exact Mass | Mass Found [M + H] | LCMS Ret Time, Method | Synthesis method | NMR |
|---|-----------|-----------|--------------------|----------------------|------------------|-----|
| 35 | 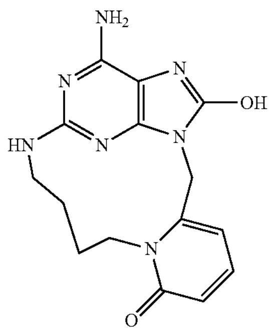 [SMILES: Nc1nc2nc3c1nc(O)n3Cc1cccc(=O)n1CCCCN2] | 327.1 | 328 | 1.81, V3018V3001 | Method 8 | ¹H NMR (500 MHz, DMSO-d₆) δ 11.30 (br. s., 1H), 9.64 (s, 1H), 7.33 (dd, J = 6.9, 8.8 Hz, 1H), 6.24 (d, J = 8.8 Hz, 1H), 5.96 (br. s., 3H), 4.71 (s, 2H), 3.30-3.48 (m, 4H), 1.70-1.94 (m, 4H) |
| 36 | 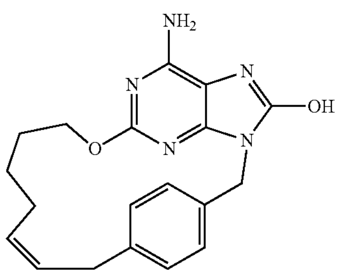 [SMILES: Nc1nc2nc3c1nc(O)n3Cc1ccc(cc1)C/C=C\CCCCO2] | 351.2 | 352 | 2.77, V3018V3001 | Method 14 Method 26 (metathesis reaction) | ¹H NMR (400 MHz, DMSO-d₆) δ 9.99 (br. s., 1H), 7.13 (d, J = 7.6 Hz, 2H), 7.02 (d, J = 7.6 Hz, 2H), 6.34 (br. s., 2H), 5.92 (dt, J = 7.6, 10.1 Hz, 1H), 5.45 (dt, J = 8.0, 10.1 Hz, 1H), 4.87 (s, 2H), 3.82 (t, J = 7.6 Hz, 2H), 3.21-3.29 (m, 2H), 1.59-1.77 (m, 2H), 0.60-0.92 (m, 4H) |
| 37 | 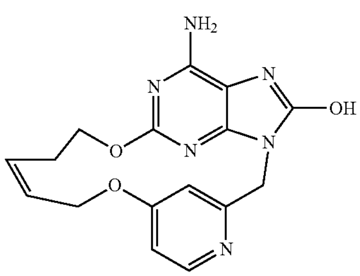 [SMILES: Nc1nc2nc3c1nc(O)n3Cc1cc(ccn1)OC/C=C\CCO2] | 340.1 | 341 | 2.03, V3018V3001 | Method 21 | ¹H NMR (500 MHz, DMSO-d₆) δ 10.21 (br. s., 1H), 8.23 (d, J = 5.6 Hz, 1H), 7.33 (d, J = 1.9 Hz, 1H), 6.81 (dd, J = 1.9, 5.6 Hz, 1H), 6.57 (br. s., 2H), 5.51 (dt, J = 7.6. 10.7 Hz, 1H), 5.42 (dt, J = 5.6, 10.7 Hz, 1H), 4.88 (s, 2H), 4.78 (d, J = 5.6 Hz, 2H), 4.51 (t, J = 7.6 Hz, 2H) |
| 38 | 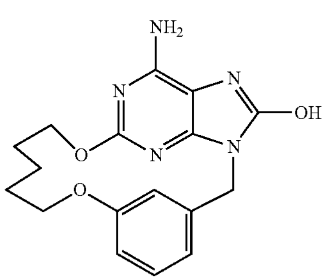 [SMILES: Nc1nc2nc3c1nc(O)n3Cc1cccc(c1)OCCCCCO2] | 341.1 | 342 | 2.4, V3018V3001 | Method 19 | ¹H NMR (500 MHz, DMSO-d₆) δ 9.94 (s, 1H), 7.39 (s, 1H), 7.20 (t, J = 7.7 Hz, 1H), 6.91 (d, J = 7.7 Hz, 1H), 6.81 (d, J = 7.7 Hz, 1H), 6.45 (br. s., 2H), 4.82 (s, 2H), 4.49 (t, J = 6.5 Hz, 2H), 3.98 (t, J = 7.3 Hz, 2H), 1.62-1.76 (m, 2H), 1.50-1.61 (m, 2H), 1.32-1.45 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 39 | 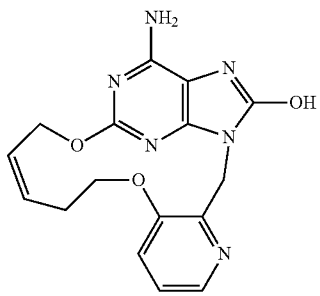 [SMILES: Nc1nc2nc3c1nc(O)n3Cc1ncccc1OCC/C=C\CO2] | 340.1 | 341 | 1.88, V3018V3001 | Method 20 | $^1$H NMR (400 MHz, DMSO-d$_6$) δ 9.85 (br. s., 1H), 7.96 (d, J = 4.6 Hz, 1H), 7.55 (d, J = 8.1 Hz, 1H), 7.21 (dd, J = 4.6, 8.1 Hz, 1H), 6.33 (s, 2H), 5.45 (dt, J = 7.6, 10.6 Hz, 1H), 5.30 (dt, J = 5.6, 10.6 Hz, 1H), 4.88 (s, 2H), 4.32-4.55 (m, 4H), 2.42-2.48 (m, 2H) |
| 40 | 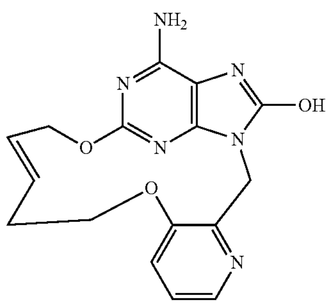 [SMILES: Nc1nc2nc3c1nc(O)n3Cc1ncccc1OCC/C=C/CO2] | 340.1 | 341 | 1.94, V3018V3001 | Method 20 | $^1$H NMR (400 MHz, DMSO-d$_6$) δ 9.77 (br. s., 1H), 7.91 (d, J = 4.0 Hz, 1H), 7.47 (d, J = 8.6 Hz, 1H), 7.18 (dd, J = 4.0, 8.6 Hz, 1H), 6.34 (s, 2H), 5.70 (dt, J = 6.5, 15.4 Hz, 1H), 5.24 (dt, J = 5.5, 15.4 Hz, 1H), 4.93 (s, 2H), 4.56 (d, J = 5.5 Hz, 2H), 4.45 (t, J = 6.5 Hz, 2H), 2.35-2.42 (m, 2H) |
| 41 | 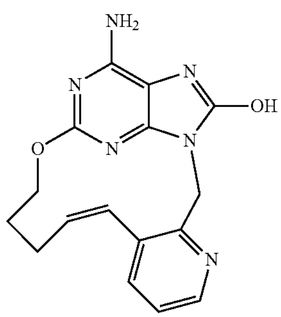 [SMILES: Nc1nc2nc3c1nc(O)n3Cc1ncccc1/C=C\CCCO2] | 324.1 | 325 | 2.06, V3018V3001 | Method 21 | $^1$H NMR (400 MHz, DMSO-d$_6$) δ 9.76 (s, 1H), 8.33 (d, J = 3.5 Hz, 1H), 7.57 (d, J = 7.6 Hz, 1H), 7.20 (dd, J = 3.5, 7.6 Hz, 1H), 6.83 (d, J = 11.6 Hz, 1H), 6.29 (br. s., 2H), 5.79-6.00 (m, 1H), 4.93 (d, J = 13.6 Hz, 1H), 4.81 (d, J = 13.6 Hz, 1H), 4.45-4.67 (m, 1H), 3.78-3.98 (m, 1H), 2.18-2.36 (m, 1H), 2.01-2.14 (m, 1H), 1.54-1.83 (m, 2H) |
| 42 | 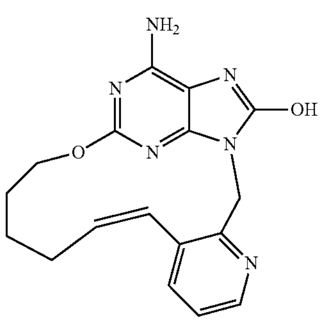 [SMILES: Nc1nc2nc3c1nc(O)n3Cc1ncccc1/C=C\CCCCO2] | 338.1 | 339 | 2.21, V3018V3001 | Method 21 | $^1$H NMR (400 MHz, DMSO-d$_6$) δ 9.85 (br. s., 1H), 8.32 (dd. J = 1.5, 4.6 Hz, 1H), 7.57 (d, J = 7.6 Hz, 1H), 7.25 (dd, J = 4.6, 7.6 Hz, 1H), 6.86 (d, J = 12.1 Hz, 1H), 6.32 (s, 2H), 5.70-5.85 (m, 1H), 5.00 (d, J = 14.7 Hz, 1H), 4.80 (d, J = 14.7 Hz, 1H), 3.75 (dt, J = 4.6, 11.4 Hz, 1H), 3.54 (dt, J = 4.6, 11.4 Hz, 1H), 1.93-2.47 (m, 3H), 1.24-1.65 (m, 3H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 43 | 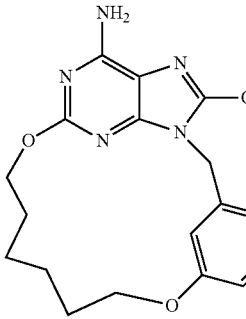 | 355.2 | 356 | 2.53, V3018V3001 | Method 19 | $^1$H NMR (500 MHz, DMSO-d$_6$) δ 9.94 (br. s., 1H), 7.13-7.30 (m, 2H), 6.98 (d, J = 7.3 Hz, 1H), 6.80 (d, J = 7.6 Hz, 1H), 6.41 (br. s., 2H), 4.80 (s, 2H), 4.34 (t, J = 6.8 Hz, 2H), 4.13 (t, J = 6.3 Hz, 2H), 1.56 (m, 4H), 1.42 (m, 4H) |
| 44 | 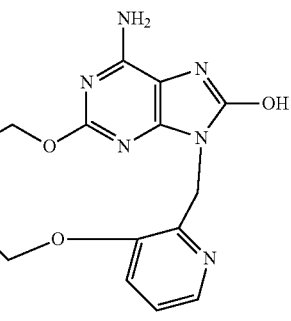 | 340.1 | 341 | 1.85, V3018V3001 | Method 21 | $^1$H NMR (400 MHz, DMSO-d$_6$) δ 9.78 (br. s., 1H), 8.04 (d, J = 4.0 Hz, 1H), 7.43 (d, J = 7.6 Hz, 1H), 7.24 (dd, J = 4.0, 7.6 Hz, 1H), 6.30 (s, 2H), 6.12 (dt, J = 7.0, 15.7 Hz, 1H), 5.54 (dt, J = 5.0, 15.7 Hz, 1H), 5.01 (s, 2H), 4.49 (d, J = 5.0 Hz, 2H), 4.18-4.28 (m, 2H), 2.23-2.36 (m, 2H) |
| 45 | 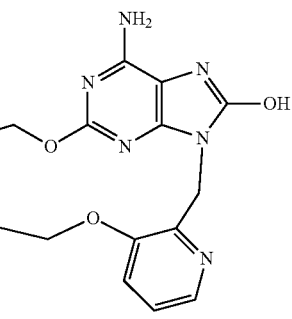 | 340.1 | 341 | 1.99, V3018V3001 | Method 21 | $^1$H NMR (500 MHz, DMF) δ 10.14 (br. s., 1H), 8.29 (d, J = 4.1 Hz, 1H), 7.58 (d, J = 7.9 Hz, 1H), 7.43 (dd, J = 4.1, 7.9 Hz, 1H), 6.66 (br. s., 2H), 6.10 (dt, J = 5.7, 10.4 Hz, 1H), 5.90 (dt, J = 8.4, 10.4 Hz, 1H), 5.29 (s, 2H), 5.13 (d, J = 5.7 Hz, 2H), 3.96-4.18 (m, 2H), 2.58-2.76 (m, 2H) |
| 46 | 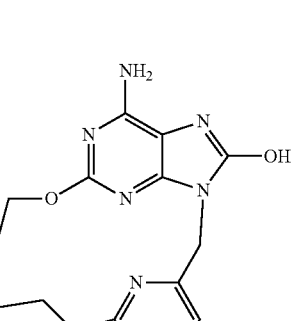 | 338.1 | 339 | 2.09, V3018V3001 | Method 21 | $^1$H NMR (500 MHz, DMSO-d$_6$) δ 10.00 (br. s., 1H), 7.58 (t, J = 7.6 Hz, 1H), 7.11 (d, J = 7.6 Hz, 1H), 6.99 (d, J = 7.6 Hz, 1H), 6.39 (br. s., 2H), 5.39 (dt, J = 7.2, 10.4 Hz, 1H), 5.16 (dt, J = 7.4, 10.4 Hz, 1H), 4.95 (s, 2H), 3.71 (t, J = 7.4 Hz, 2H), 2.63-2.71 (m, 2H), 2.25-2.34 (m, 2H), 1.96-2.06 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 47 | 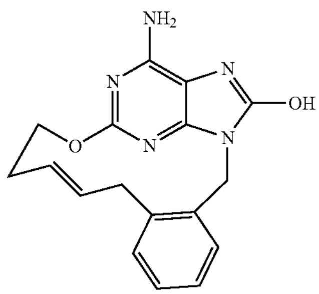 [SMILES: Nc1nc2nc3c1nc(O)n3Cc1ccccc1C/C=C/CCO2] | 323.1 | 324 | 2.44, V3018V3001 | Method 21 | $^1$H NMR (500 MHz, DMSO-d$_6$) δ 10.22 (br. s., 1H), 7.30 (dd, J = 1.9, 7.3 Hz, 1H), 7.12-7.21 (m, 2H), 7.10 (dd, J = 2.2, 7.3 Hz, 1H), 6.47 (br. s., 2H), 5.55 (dt, J = 4.0, 15.7 Hz, 1H), 5.18 (dt, J = 7.2, 15.7 Hz, 1H), 4.89 (s, 2H), 4.07-4.24 (m, 2H), 3.37-3.66 (m, 2H), 2.11-2.33 (m, 2H) |
| 48 | 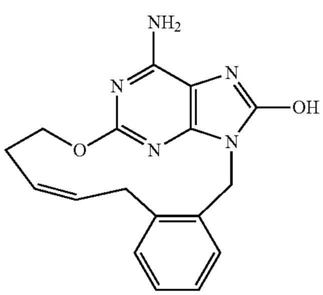 [SMILES: Nc1nc2nc3c1nc(O)n3Cc1ccccc1C/C=C\CCO2] | 323.1 | 324 | 2.52, V3018V3001 | Method 21 | $^1$H NMR (400 MHz, DMSO-d$_6$) δ 10.02 (br. s., 1H), 7.30 (d, J = 7.6 Hz, 1H), 7.03-7.23 (m, 3H), 6.43 (br. s., 2H), 6.16 (dt, J = 8.0, 9.6 Hz, 1H), 5.78 (dt, J = 8.0, 9.6 Hz, 1H), 5.03-5.29 (m, 1H), 4.73-5.01 (m, 2H), 4.07-4.38 (m, 1H), 3.65-4.02 (m, 1H), 2.13-2.31 (m, 2H) |
| 49 | 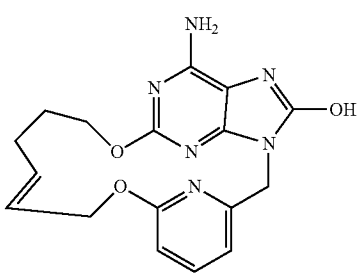 [SMILES: Nc1nc2nc3c1nc(O)n3Cc1cccc(n1)OC/C=C/CCCO2] | 354.1 | 355 | 2.43, V3018V3001 | Method 21 | $^1$H NMR (500 MHz, DMSO-d$_6$) δ 10.00 (br. s., 1H), 7.60 (t, J = 7.7 Hz, 1H), 6.80 (d, J = 7.3 Hz, 1H), 6.65 (d, J = 8.2 Hz, 1H), 6.41 (br. s., 2H), 5.81 (dt, J = 7.7, 15.5 Hz, 1H), 5.58 (dt, J = 5.4, 15.5 Hz, 1H), 4.87 (s, 2H), 4.84 (d, J = 5.4 Hz, 2H), 4.10 (t, J = 7.7 Hz, 2H), 1.90-2.07 (m, 2H), 1.48-1.66 (m, 2H) |
| 50 | 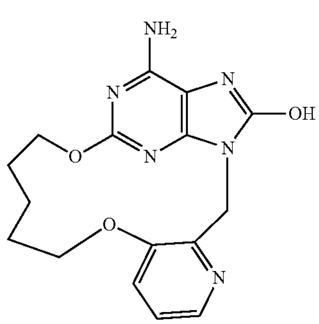 [SMILES: Nc1nc2nc3c1nc(O)n3Cc1ncccc1OCCCCCO2] | 342.1 | 343 | 2.03, V3018V3001 | Method 19 | $^1$H NMR (400 MHz, DMSO-d$_6$) δ 9.80 (br. s., 1H), 8.03 (d, J = 4.6 Hz, 1H), 7.40 (d, J = 8.1 Hz, 1H), 7.24 (dd, J = 4.6, 8.1 Hz, 1H), 6.32 (br. s., 2H), 4.98 (s, 2H), 3.99-4.35 (m, 4H), 1.50-1.86 (m, 6H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 51 | 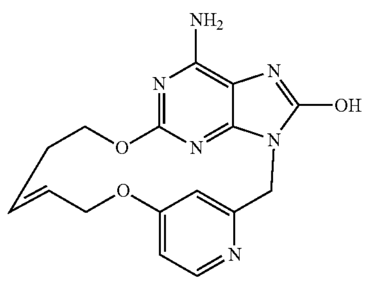 [SMILES: Nc1nc2nc3c1nc(O)n3Cc1cc(ccn1)OC/C=C/CCO2] | 340.1 | 341 | 1.97, V3018V3001 | Method 21 | $^1$H NMR (400 MHz, DMSO-d$_6$) δ 10.05 (br. s., 1H), 8.23 (d, J = 6.1 Hz, 1H), 6.85 (d, J = 2.0 Hz, 1H), 6.76 (dd, J = 2.0, 6.1 Hz, 1H), 6.51 (s, 2H), 5.50 (dt, J = 7.0, 15.7 Hz, 1H), 5.40 (dt, J = 5.6, 15.7 Hz, 1H), 4.90 (s, 2H), 4.59 (d, J = 5.6 Hz, 2H), 4.45-4.56 (m, 2H), 2.19-2.41 (m, 2H) |
| 52 | 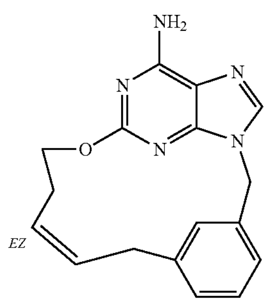 [SMILES: Nc1nc2nc3c1ncn3Cc1cccc(c1)C/C=C\CCO2] | 307.1 | 308 | 2.56, V3018V3001 | Method 22 | $^1$H NMR (500 MHz, DMSO-d$_6$) δ 8.17 (br. s., 1H), 8.07 (s, 0.3H), 8.02 (s, 0.7H), 7.29 (d, J = 7.6 Hz, 0.3H), 7.10-7.25 (m, 4H), 7.07 (d, J = 7.3 Hz, 0.7H), 5.63-5.75 (m, 1H), 5.55 (td, J = 6.6, 10.7 Hz, 0.3H), 5.43 (td, J = 7.5, 15.3 Hz, 0.7H), 5.22 (s, 1.4H), 5.21 (s, 0.6H), 4.64-4.77 (m, 1.4H), 4.49-4.60 (m, 0.6H), 3.30 (d, J = 7.9 Hz, 0.6H), 3.18 (d, J = 7.9 Hz, 1.4H), 2.37-2.45 (m, 2H) |
| 53 | 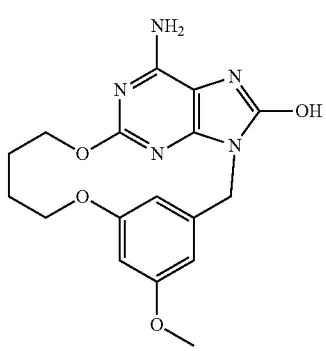 [SMILES: COc1cc2cc(c1)OCCCCOc1nc(N)c3nc(O)n(c3n1)C2] | 357.1 | 358 | 2.23, V3018V3001 | Method 23 | $^1$H NMR (400 MHz, DMSO-d$_6$) δ 9.95 (br. s., 1H), 7.51 (s, 1H), 6.38 (s, 3H), 6.30 (s, 1H), 4.77 (s, 2H), 4.55 (t, J = 6.3 Hz, 2H), 4.24 (t, J = 6.3 Hz, 2H), 3.66 (s, 3H), 1.40-1.73 (m, 4H) |
| 54 | 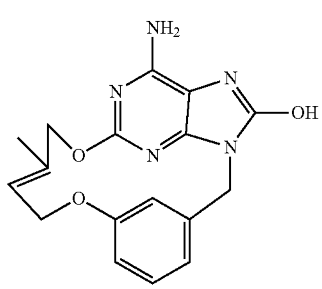 [SMILES: C/C1=C\COc2cccc(c2)Cn2c(O)nc3c(N)nc(nc32)OC1] | 339.1 | 340 | 2.25, V3018V3001 | Method 16 | $^1$H NMR (500 MHz, DMSO-d$_6$) δ 9.98 (br. s., 1H), 7.39 (s, 1H), 7.14 (t, J = 7.6 Hz, 1H), 6.86 (d, J = 7.6 Hz, 1H), 6.79 (dd, J = 1.7, 7.6 Hz, 1H), 6.43 (br. s., 2H), 5.37 (t, J = 5.5 Hz, 1H), 4.77 (s, 2H), 4.65 (d, J = 5.5 Hz, 2H), 4.59 (s, 2H), 1.57 (s, 3H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 55 | 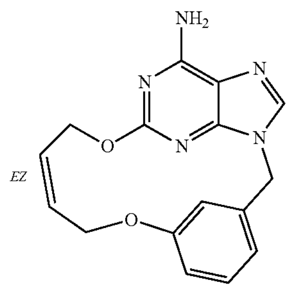 [SMILES: Nc1nc2nc3c1ncn3Cc1cccc(c1)OC/C=C\CO2] | 309.1 | 310 | 2.17, V3018V3001 | Method 22 | $^1$H NMR (400 MHz, DMSO-d$_6$) δ 8.11 (s, 0.5H), 8.08 (s, 0.5H), 8.06 (br. s., 0.5H), 7.64 (s, 0.5H), 7.08-7.24 (m, 3H), 7.05 (d, J = 7.1 Hz, 0.5H), 6.99 (d, J = 7.6 Hz, 0.5H), 6.73-6.86 (m, 1H), 5.70-5.82 (m, 0.5H), 5.63 (dt, J = 3.6, 16.2 Hz, 0.5H), 5.28-5.50 (m, 1H), 5.16 (s, 3H), 4.69-4.92 (m, 2H), 4.54 (d, J = 5.6 Hz, 1H) |
| 56 | 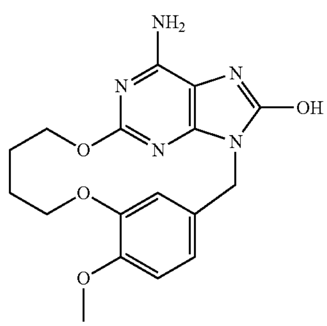 [SMILES: COc1ccc2cc1OCCCCOc1nc(N)c3nc(O)n(c3n1)C2] | 357.1 | 358 | 1.99, V3018V3001 | Method 23 | $^1$H NMR (400 MHz, DMSO-d$_6$) δ 9.85 (br. s, 1H), 7.88 (s, 1H), 6.85 (d, J = 7.6 Hz, 1H), 6.77 (d, J = 7.6 Hz, 1H), 6.35 (br. s., 2H), 4.77 (s, 2H), 4.45-4.63 (m, 2H), 4.08-4.34 (m, 2H), 3.68 (s, 3H), 1.44-1.72 (m, 4H) |
| 57 | 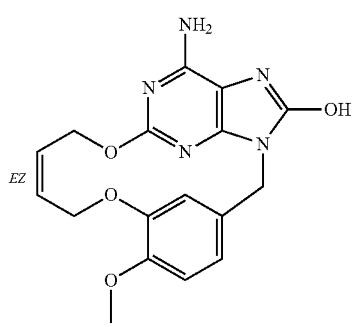 [SMILES: COc1ccc2cc1OC/C=C\COc1nc(N)c3nc(O)n(c3n1)C2] | 355.1 | 356 | 1.94, V3018V3001 | Method 23 | $^1$H NMR (400 MHz, DMSO-d$_6$) δ 9.91 (br. s., 1H), 7.84 (br. s., 1H), 6.65-6.98 (m, 2H), 6.42 (br. s., 2H), 5.26-5.48 (m, 2H), 4.95-5.21 (m, 2H), 4.77-4.90 (m, 2H), 4.71 (br. s., 2H), 3.71 (br. s., 3H) |
| 58 | 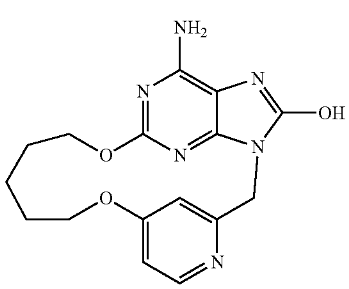 [SMILES: Nc1nc2nc3c1nc(O)n3Cc1cc(ccn1)OCCCCCO2] | 342.1 | 343 | 2.01, V3018V3001 | Method 24 | $^1$H NMR (400 MHz, DMSO-d$_6$) δ 9.88 (br. s, 1H), 8.24 (d, J = 5.6 Hz, 1H), 7.28 (d, J = 1.5 Hz, 1H), 6.79 (dd, J = 1.5, 5.6 Hz, 1H), 6.46 (br. s., 2H), 4.92 (s, 2H), 4.44 (t, J = 6.3 Hz, 2H), 4.05-4.16 (m, 2H), 1.62-1.78 (m, 2H), 1.49-1.63 (m, 2H), 1.19-1.37 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 59 | 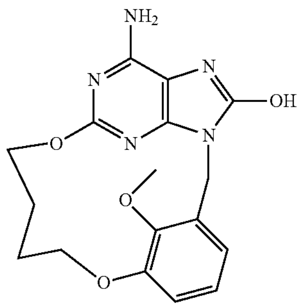 [SMILES: COc1c2cccc1OCCCCOc1nc(N)c3nc(O)n(c3n1)C2] | 357.1 | 358 | 2.2, V3018V3001 | Method 23 Method 25 (metathesis reaction) | $^1$H NMR (500 MHz, DMSO-d$_6$) δ 9.93 (br. s., 1H), 6.98 (d, J = 7.2 Hz, 1H), 6.91 (t, J = 7.2 Hz, 1H), 6.70 (d, J = 7.2 Hz, 1H), 6.31 (br. s., 2H), 4.92 (d, J = 13.5 Hz, 1H), 4.82 (d, J = 13.5 Hz, 1H), 4.47-4.61 (m, 1H), 4.31-4.46 (m, 1H), 3.87-3.98 (m, 1H), 3.83 (s, 3H), 3.46-3.61 (m, 1H), 1.47-1.77 (m, 2H), 1.04-1.36 (m, 2H) |
| 60 | 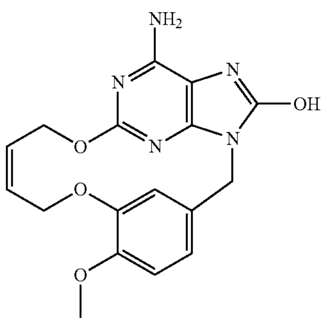 [SMILES: COc1ccc2cc1OC/C=C\COc1nc(N)c3nc(O)n(c3n1)C2] | 355.1 | 356 | 1.93, V3018V3001 | Method 23 | $^1$H NMR (400 MHz, DMSO-d$_6$) δ 9.92 (s, 1H), 7.84 (s, 1H), 6.86 (d, J = 8.0 Hz, 1H), 6.81 (d, J = 8.0 Hz, 1H), 6.41 (br. s., 2H), 5.26-5.47 (m, 2H), 4.99-5.23 (m, 2H), 4.75-4.91 (m, 2H), 4.71 (s, 2H), 3.71 (s, 3H) |
| 61 | 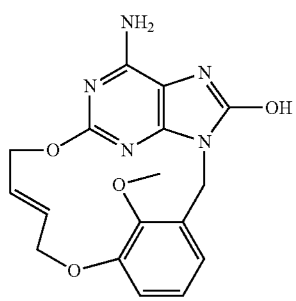 [SMILES: COc1c2cccc1OC/C=C/COc1nc(N)c3nc(O)n(c3n1)C2] | 355.1 | 356 | 2.15, V3018V3001 | Method 25 | $^1$H NMR (400 MHz, DMSO-d$_6$) δ 9.95 (br. s., 1H), 6.80-7.03 (m, 2H), 6.63 (d, J = 6.6 Hz, 1H), 6.33 (br. s., 2H), 5.76-5.90 (m, 1H), 5.04 (dd, J = 5.8, 16.0 Hz, 1H), 4.92 (q, J = 14.1 Hz, 2H), 4.69-4.84 (m, 2H), 4.44 (d, J = 13.6 Hz, 1H), 3.86-3.98 (m, 1H), 3.78 (s, 3H) |
| 62 | 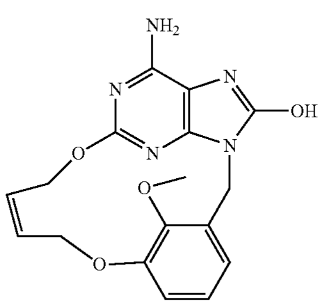 [SMILES: COc1c2cccc1OC/C=C\COc1nc(N)c3nc(O)n(c3n1)C2] | 355.1 | 356 | 2.15, V3018V3001 | Method 25 | $^1$H NMR (400 MHz, DMSO-d$_6$) δ 9.90 (s, 1H), 6.79-6.88 (m, 2H), 6.69-6.77 (m, 1H), 6.31 (s, 2H), 5.60-5.81 (m, 1H), 5.32-5.46 (m, 2H), 5.19-5.31 (m, 1H), 4.92 (d, J = 13.6 Hz, 1H), 4.80 (d, J = 13.6 Hz, 1H), 4.27-4.40 (m, 1H), 4.10-4.26 (m, 1H), 3.83 (s, 3H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 63 | 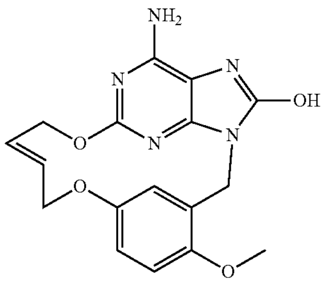 [SMILES: COc1ccc2cc1Cn1c(O)nc3c(N)nc(nc31)OC/C=C/CO2] | 355.1 | 356 | 2.05, V3018V3001 | Method 25 | $^1$H NMR (400 MHz, DMSO-d$_6$) δ 9.91 (br. s., 1H), 6.99 (d, J = 2.5 Hz, 1H), 6.87 (dd, J = 2.5, 9.0 Hz, 1H), 6.82 (d, J = 9.0 Hz, 1H), 6.41 (br. s., 2H), 5.62 (dt, J = 6.6, 16.0 Hz, 1H), 5.34 (dt, J = 3.5, 16.0 Hz, 1H), 4.79 (s, 2H), 4.72 (d, J = 3.5 Hz, 2H), 4.33 (d, J = 6.6 Hz, 2H), 3.68 (s, 3H) |
| 64 | 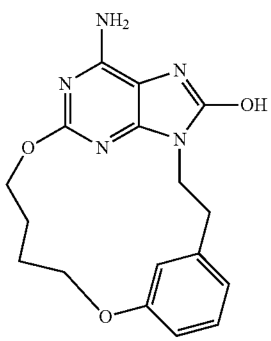 [SMILES: Nc1nc2nc3c1nc(O)n3CCc1cccc(c1)OCCCCO2] | 341.1 | 342 | 2.13, V3018V3001 | Method 18 Method 24 | $^1$H NMR (500 MHz, DMSO-d$_6$) δ 9.79 (br. s, 1H), 7.16 (s, 1H), 6.88 (t, J = 7.7 Hz, 1H), 6.62 (dd, J = 1.9, 7.7 Hz, 1H), 6.36 (d, J = 7.7 Hz, 1H), 6.25 (br. s., 2H); 4.26-4.34 (m, 2H), 4.16-4.25 (m, 2H), 3.97-4.11 (m, 2H), 2.90-3.00 (m, 2H), 1.49-1.70 (m, 4H) |
| 65 | 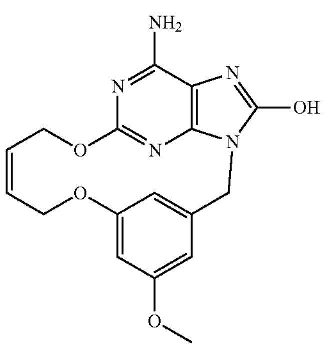 [SMILES: COc1cc2cc(c1)OC/C=C\COc1nc(N)c3nc(O)n(c3n1)C2] | 355.1 | 356 | 2.19, V3018V3001 | Method 25 | $^1$H NMR (400 MHz, DMSO-d$_6$) δ 10.00 (br. s., 1H), 7.52 (s, 1H), 6.43 (s, 3H), 6.35 (s, 1H), 5.25-5.50 (m, 2H), 4.96-5.22 (m, 2H), 4.74-4.85 (m, 2H), 4.72 (s, 2H), 3.68 (s, 3H) |
| 66 | 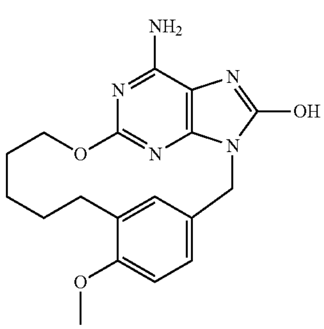 | 355.2 | 356 | 2.58, V3018V3001 | Method 23 | $^1$H NMR (400 MHz, DMSO-d$_6$) δ 9.89 (br. s., 1H), 7.55 (br. s., 1H), 6.96 (d, J = 8.1 Hz, 1H), 6.83 (d, J = 8.1 Hz, 1H), 6.32 (br. s., 2H), 4.78 (s, 2H), 3.97-4.34 (m, 2H), 3.71 (s, 3H), 2.56-2.67 (m, 2H), 1.53-1.82 (m, 2H), 1.14-1.45 (m, 4H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 67 | 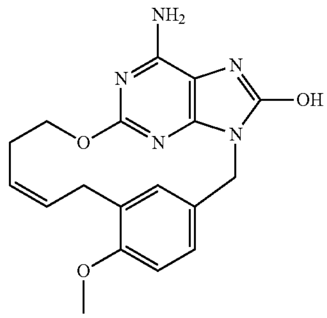 [SMILES: COc1ccc2cc1C/C=C\CCOc1nc(N)c3nc(O)n(c3n1)C2] | 353.1 | 354 | 2.53, V3018V3001 | Method 23 | $^1$H NMR (400 MHz, DMSO-$d_6$) δ 9.88 (br. s., 1H), 7.79 (br. s., 1H), 7.12 (d, J = 8.1 Hz, 1H), 6.87 (d, J = 8.1 Hz, 1H), 6.40 (br. s., 2H), 5.66 (dt, J = 8.0, 10.7 Hz, 1H), 5.57 (dt, J = 7.1, 10.7 Hz, 1H), 4.75 (s, 2H), 4.46 (t, J = 8.0 Hz, 2H), 3.74 (s, 3H), 3.21 (d, J = 7.1 Hz, 2H), 2.16-2.40 (m, 2H) |
| 68 | 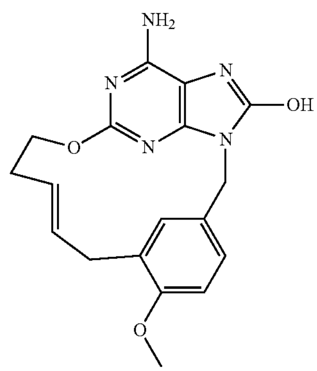 [SMILES: COc1ccc2cc1C/C=C/CCOc1nc(N)c3nc(O)n(c3n1)C2] | 353.1 | 354 | 2.5, V3018V3001 | Method 23 | $^1$H NMR (400 MHz, DMSO-$d_6$) δ 9.83 (br. s., 1H), 8.10 (s, 1H), 7.12 (d, J = 8.1 Hz, 1H), 6.81 (d, J = 8.1 Hz, 1H), 6.38 (br. s., 2H), 5.69 (dt, J = 8.0, 15.7 Hz, 1H), 5.43 (dt, J = 7.1, 15.7 Hz, 1H), 4.76 (s, 2H), 4.62-4.73 (m, 2H), 3.73 (s, 3H), 3.08 (d, J = 7.1 Hz, 2H), 2.36-2.46 (m, 2H) |
| 69 | 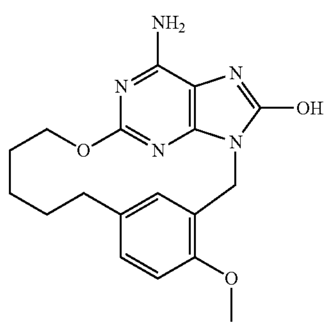 | 355.2 | 356 | 2.53, V3018V3001 | Method 23 | $^1$H NMR (400 MHz, DMSO-$d_6$) δ 9.82 (br. s., 1H), 7.39 (br. s., 1H), 7.03 (d, J = 8.1 Hz, 1H), 6.81 (d, J = 8.1 Hz, 1H), 6.30 (br. s., 2H), 4.83 (s, 2H), 3.87-4.24 (m, 2H), 3.64 (s, 3H), 2.54-2.70 (m, 2H), 1.52-1.78 (m, 2H), 1.10-1.36 (m, 4H) |
| 70 | 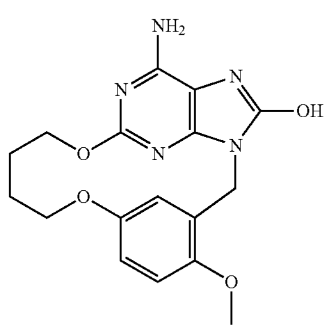 [SMILES: COc1ccc2cc1Cn1c(O)nc3c(N)nc(nc31)OCCCCO2] | 357.1 | 358 | 2.14, V3018V3001 | Method 25 Method 24 | $^1$H NMR (400 MHz, DMSO-$d_6$) δ 9.78 (br. s., 1H), 7.77 (br. s., 1H), 6.84 (d, J = 8.5 Hz, 1H), 6.77 (dd, J = 2.5, 8.5 Hz, 1H), 6.31 (br. s., 2H), 4.85 (s, 2H), 4.38 (t, J = 7.1 Hz, 2H), 4.07-4.27 (m, 2H), 3.66 (s, 3H), 1.57-1.69 (m, 2H), 1.40-1.56 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 71 | 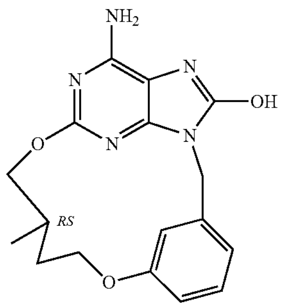 [SMILES: CC1CCOc2cccc(c2)Cn2c(O)nc3c(N)nc(nc32)OC1] | 341.1 | 342 | 2.34, V3018V3001 | Method 16 (metathesis reaction) Method 23 (D6 & 56) | ¹H NMR (500 MHz, DMSO-d$_6$) δ 10.00 (br. s., 1H), 7.91 (s, 1H), 7.14 (t, J = 7.7 Hz, 1H), 6.79 (d, J = 7.7 Hz, 1H), 6.74 (dd, J = 1.9, 7.7 Hz, 1H), 6.44 (br. s., 2H), 4.96 (d, J = 13.9 Hz, 1H), 4.87-4.93 (m, 1H), 4.67 (d, J = 13.9 Hz, 1H), 4.48-4.61 (m, 1H), 4.01-4.15 (m, 1H), 3.78-3.88 (m, 1H), 1.66-1.79 (m, 1H), 1.48-1.61 (m, 2H), 0.85 (d, J = 6.9 Hz, 3H) |
| 72 | 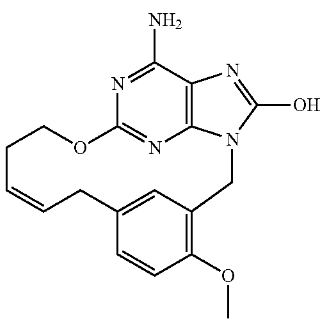 [SMILES: COc1ccc2cc1Cn1c(O)nc3c(N)nc(nc31)OCC/C=C\C2] | 353.1 | 354 | 2.47, V3018V3001 | Method 23 | ¹H NMR (400 MHz, DMSO-d$_6$) δ 9.85 (br. s., 1H), 7.92 (d, J = 2.0 Hz, 1H), 7.07 (dd, J = 2.0, 8.1 Hz, 1H), 6.86 (d, J = 8.1 Hz, 1H), 6.38 (s, 2H), 5.71 (dt, J = 8.0, 10.7 Hz, 1H), 5.39 (dt, J = 7.6, 10.7 Hz, 1H), 4.88 (s, 2H), 4.25-4.39 (m, 2H), 3.73 (s, 3H), 3.24 (d, J = 7.6 Hz, 2H), 2.25-2.40 (m, 2H) |
| 73 | 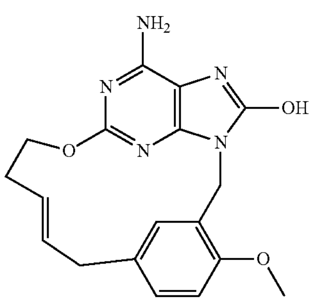 [SMILES: COc1ccc2cc1Cn1c(O)nc3c(N)nc(nc31)OCC/C=C/C2] | 353.1 | 354 | 2.48, V3018V3001 | Method 23 | ¹H NMR (400 MHz, DMSO-d$_6$) δ 9.95 (br. s., 1H), 7.61 (d, J = 2.0 Hz, 1H), 7.01 (dd, J = 2.0, 8.1 Hz, 1H), 6.84 (d, J = 8.1 Hz, 1H), 6.43 (br. s., 2H), 5.56 (dt, J = 7.0, 15.7 Hz, 1H), 5.28 (dt, J = 6.6, 15.7 Hz, 1H), 4.89 (s, 2H), 4.41-4.59 (m, 2H), 3.78 (s, 3H), 3.07 (d, J = 6.6 Hz, 2H), 2.22-2.37 (m, 2H) |
| 74 | 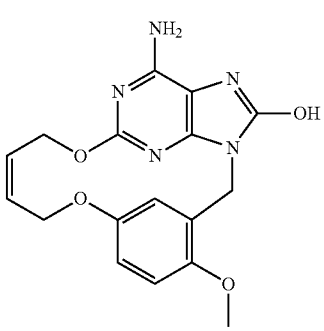 [SMILES: COc1ccc2cc1Cn1c(O)nc3c(N)nc(nc31)OC/C=C\CO2] | 355.1 | 356 | 2.11, V3018V3001 | Method 25 | ¹H NMR (400 MHz, DMSO-d$_6$) δ 9.85 (br. s., 1H), 7.81 (br. s., 1H), 6.83 (d, J = 8.6 Hz, 1H), 6.78 (d, J = 8.6 Hz, 1H), 6.38 (br. s., 2H), 5.29-5.49 (m, 2H), 4.95-5.15 (m, 2H), 4.82 (br. s., 2H), 4.65-4.78 (m, 2H), 3.68 (s, 3H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 75 | 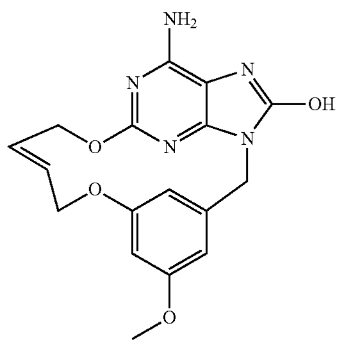 [SMILES: COc1cc2cc(c1)OC/C=C/COc1nc(N)c3nc(O)n(c3n1)C2] | 355.1 | 356 | 2.16, V3018V3001 | Method 25 | ¹H NMR (400 MHz, DMSO-d$_6$) δ 9.97 (br. s., 1H), 7.17 (s, 1H), 6.49 (br. s., 2H), 6.42 (s, 1H), 6.37 (s, 1H), 5.63-5.71 (m, 2H), 4.75-4.80 (m, 2H), 4.73 (s, 2H), 4.56 (d, J = 4.6 Hz, 2H), 3.65 (s, 3H) |
| 76 | 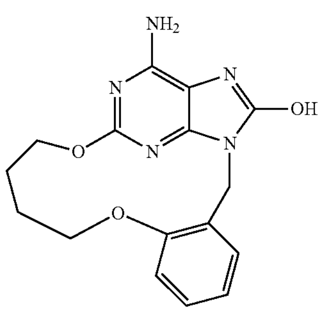 [SMILES: Nc1nc2nc3c1nc(O)n3Cc1ccccc1OCCCCO2] | 327.1 | 328 | 2.33, V3018V3001 | Method 23 (D6 & 56) | ¹H NMR (400 MHz, DMSO-d$_6$) δ 9.86 (br. s., 1H), 7.49 (dd, J = 1.5, 7.6 Hz, 1H), 7.24 (t, J = 7.6 Hz, 1H), 6.96 (d, J = 7.6 Hz, 1H), 6.88 (t, J = 7.6 Hz, 1H), 6.34 (s, 2H), 4.88 (br. s., 2H), 4.14-4.30 (m, 2H), 4.02-4.13 (m, 2H), 1.77-2.16 (m, 4H) |
| 77 | 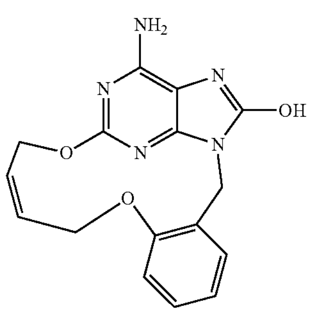 [SMILES: Nc1nc2nc3c1nc(O)n3Cc1ccccc1OC/C=C\CO2] | 325.1 | 326 | 2.19, V3018V3001 | Method 25 | ¹H NMR (400 MHz, DMSO-d$_6$) δ 9.90 (br. s., 1H), 7.35 (dd, J = 1.5, 7.6 Hz, 1H), 7.22 (t, J = 7.6 Hz, 1H), 7.13 (d, J = 7.6 Hz, 1H), 6.89 (t, J = 7.6 Hz, 1H), 6.34 (s, 2H), 6.04 (dt, J = 8.0, 10.7 Hz, 1H), 5.66 (dt, J = 7.0, 10.7 Hz, 1H), 4.83 (br. s., 6H) |
| 78 | 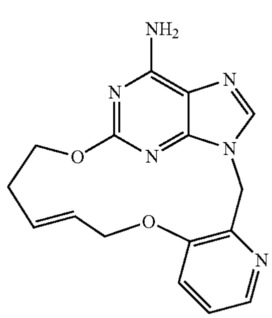 [SMILES: Nc1nc2nc3c1ncn3Cc1ncccc1OC/C=C/CCO2] | 324.1 | 325 | 2.03, V3018V3001 | Method 26 | ¹H NMR (400 MHz, DMSO-d$_6$) δ 8.15 (d, J = 4.0 Hz, 1H), 7.81 (s, 1H), 7.41 (d, J = 8.0 Hz, 1H), 7.34 (dd, J = 4.0, 8.0 Hz, 1H), 7.02 (s, 2H), 6.3 (dt, J = 7.0, 15.7 Hz, 1H), 5.65 (dt, J = 5.1, 15.7 Hz, 1H), 5.40 (s, 2H), 4.42-4.57 (m, 2H), 4.37 (d, J = 5.1 Hz, 2H), 2.35-2.45 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 79 | 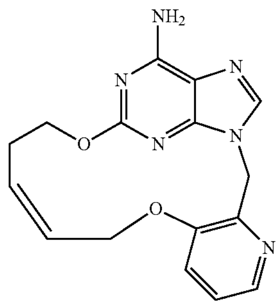 [SMILES: Nc1nc2nc3c1ncn3Cc1ncccc1OC/C=C\CCO2] | 324.1 | 325 | 2.11, V3018V3001 | Method 26 | $^1$H NMR (500 MHz, DMSO-d$_6$) δ 8.15 (d, J = 4.1 Hz, 1H), 8.11 (s, 1H), 7.52 (d, J = 8.2 Hz, 1H), 7.30 (dd, J = 4.1, 8.2 Hz, 1H), 7.14 (br. s., 2H), 5.95 (dt, J = 7.0, 10.7 Hz, 1H), 5.80 (dt, J = 7.6, 10.7 Hz, 1H), 5.40 (br. s., 2H), 4.59 (d, J = 7.0 Hz, 2H), 4.24 (t, J = 7.6 Hz, 2H), 2.55-2.62 (m, 2H) |
| 80 | 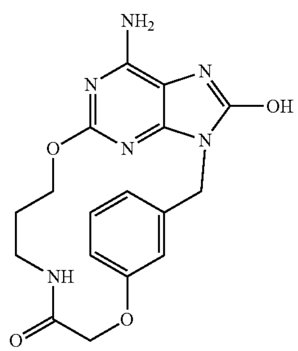 [SMILES: Nc1nc2nc3c1nc(O)n3Cc1cccc(c1)OCC(=O)NCCCO2] | 370.1 | 371 | 2.03, V3018V3001 | Method 27 | $^1$H NMR (500 MHz, DMSO-d$_6$) δ 10.48 (br. s., 1H), 7.34-7.72 (m, 2H), 7.26 (t, J = 7.3 Hz, 1H), 7.07 (d, J = 7.3 Hz, 1H), 6.98 (s, 1H), 6.90 (dd, J = 2.5, 7.3 Hz, 1H), 4.87 (s, 2H), 4.75 (s, 2H), 4.21-4.14 (m, 2H), 3.41-3.50 (m, 2H), 1.75-1.90 (m, 2H) |
| 81 | 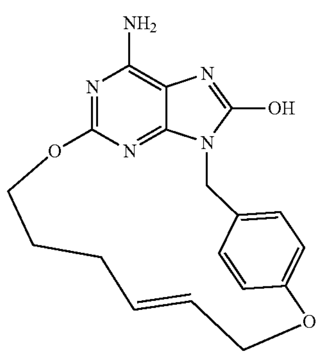 [SMILES: Nc1nc2nc3c1nc(O)n3Cc1ccc(cc1)OC/C=C/CCCO2] | 353.1 | 354 | 2.31, V3018V3001 | Method 16 (O4) Method 23 (metathesis reaction & final cyclisation) | $^1$H NMR (500 MHz, DMSO-d$_6$) δ 9.95 (br. s., 1H), 7.12 (d, J = 8.2 Hz, 2H), 6.83 (d, J = 8.2 Hz, 2H), 6.29 (br. s., 2H), 5.53 (dt, J = 6.6, 15.7 Hz, 1H), 5.27 (dt, J = 5.4, 15.7 Hz, 1H), 4.87 (s, 2H), 4.67 (d, J = 5.4 Hz, 2H), 3.59 (t, J = 6.6 Hz, 2H), 1.90-2.10 (m, 2H), 1.53-1.71 (m, 2H) |
| 82 | 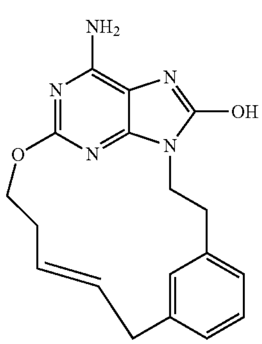 [SMILES: Nc1nc2nc3c1nc(O)n3CCc1cccc(c1)C/C=C/CCO2] | 337.2 | 338 | 2.45, V3018V3001 | Method 18 (D5) Method 14 (15) | $^1$H NMR (500 MHz, DMSO-d$_6$) δ 9.81 (br. s., 1H), 7.12 (s, 1H), 6.99 (t, J = 7.2 Hz, 1H), 6.84 (d, J = 7.2 Hz, 1H), 6.76 (d, J = 7.2 Hz, 1H), 6.29 (br. s., 2H), 5.52 (dt, J = 5.7, 15.5 Hz, 1H), 5.15 (dt, J = 4.9, 15.5 Hz, 1H), 4.45 (t, J = 4.9 Hz, 2H), 4.04 (t, J = 5.7 Hz, 2H), 3.07-3.2 (m, 4H), 2.15-2.41 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 83 | 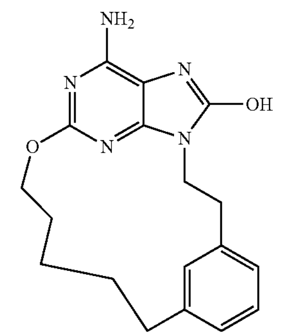 [SMILES: Nc1nc2nc3c1nc(O)n3CCc1cccc(c1)CCCCCO2] | 339.2 | 340 | 2.57, V3018V3001 | Method 24 | $^1$H NMR (500 MHz, DMSO-d$_6$) δ 9.85 (br. s., 1H), 7.23 (s, 1H), 6.79-6.91 (m, 2H), 6.42-6.53 (m, 1H), 6.24 (br. s., 2H), 4.08 (t, J = 6.5 Hz, 2H), 3.91-4.01 (m, 2H), 2.85-2.97 (m, 2H), 2.53-2.60 (m, 2H), 1.66 (quin, J = 6.8 Hz, 2H), 1.28 (quin, J = 6.8 Hz, 2H), 1.12 (quin, J = 6.8 Hz, 2H) |
| 84 | 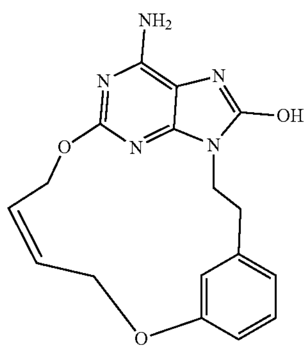 [SMILES: Nc1nc2nc3c1nc(O)n3CCc1cccc(c1)OC/C=C\CO2] | 339.1 | 340 | 2.28, V3018V3001 | Method 18 | $^1$H NMR (500 MHz, DMSO-d$_6$) δ 10.09 (br. s, 1H), 7.42 (s, 1H), 7.07 (t, J = 7.6 Hz, 1H), 6.63-6.77 (m, 2H), 6.55 (br. s., 2H), 5.64 (dt, J = 4.7, 11.5 Hz, 1H), 5.54 (dt, J = 5.7, 11.5 Hz, 1H), 4.89-5.12 (m, 2H), 4.75 (d, J = 5.7 Hz, 2H), 3.94 (t, J = 6.8 Hz, 2H), 2.85 (t, J = 6.8 Hz, 2H) |
| 85 | 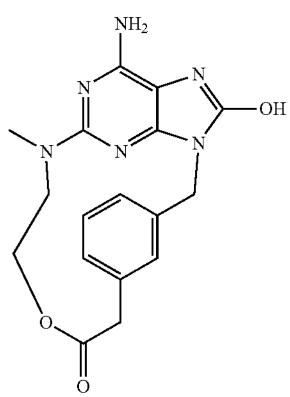 [SMILES: CN1CCOC(=O)Cc2cccc(c2)Cn2c(O)nc3c(N)nc1nc32] | 354.1 | 355 | 2.2, V3018V3001 | Method 28 | $^1$H NMR (500 MHz, DMSO-d$_6$) δ 9.63 (s, 1H), 8.04 (s, 1H), 7.22 (t, J = 7.2 Hz, 1H), 7.16 (d, J = 7.2 Hz, 1H), 7.10 (d, J = 7.2 Hz, 1H), 6.07 (br. s., 2H), 4.79 (s, 2H), 4.25-4.31 (m, 2H), 3.76-4.19 (m, 2H), 3.63 (s, 2H), 3.00 (s, 3H) |
| 86 | 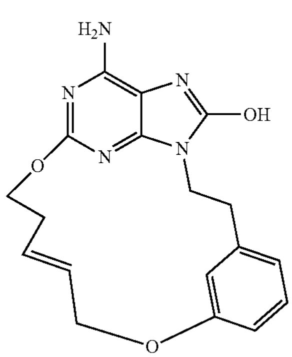 [SMILES: Nc1nc2nc3c1nc(O)n3CCc1cccc(c1)OC/C=C/CCO2] | 353.1 | 354 | 2.2, V3018V3001 | Method 29 | $^1$H NMR (500 MHz, DMSO-d$_6$) δ 9.71 (s, 1H), 6.86 (t, J = 7.7 Hz, 1H), 6.77 (s, 1H), 6.62 (dd, J = 1.9, 7.7 Hz, 1H), 6.33 (d, J = 7.7 Hz, 1H), 6.21 (s, 2H), 5.63 (dt, J = 6.3, 15.4 Hz, 1H), 5.55 (dt, J = 4.4, 15.4 Hz, 1H), 4.57 (d, J = 4.4 Hz, 2H), 4.32 (t, J = 5.20 Hz, 2H), 3.97 (t, J = 6.0 Hz, 2H), 2.96 (t, J = 6.0 Hz, 2H), 2.22-2.40 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 87 | 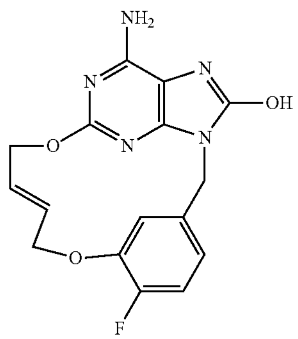 [SMILES: Nc1nc2nc3c1nc(O)n3Cc1ccc(F)c(c1)OC/C=C/CO2] | 343.1 | 344 | 2.18, V3018V3001 | Method 30 | $^1$H NMR (500 MHz, DMSO-d$_6$) δ 9.99 (br. s., 1H), 7.63 (dd, J = 1.9, 8.2 Hz, 1H), 7.11 (dd, J = 8.2, 11.0 Hz, 1H), 6.70-6.96 (m, 1H), 6.46 (br. s., 2H), 5.76 (dt, J = 6.3, 16.1 Hz, 1H), 5.65 (dt, J = 3.8, 16.1 Hz, 1H), ), 4.78-4.85 (m, 2H), 4.77 (s, 2H), 4.57 (d, J = 6.3 Hz, 2H) |
| 88 | 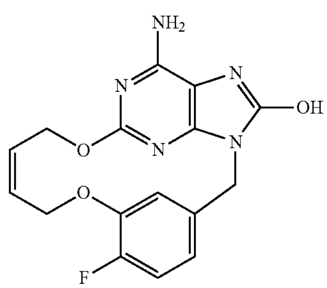 [SMILES: Nc1nc2nc3c1nc(O)n3Cc1ccc(F)c(c1)OC/C=C\CO2] | 343.1 | 344 | 2.18, V3018V3001 | Method 30 | $^1$H NMR (500 MHz, DMSO-d$_6$) δ 10.02 (br. s., 1H), 8.05 (d, J = 8.2 Hz, 1H), 7.11 (dd, J = 8.2, 11.2 Hz, 1H), 6.72-6.93 (m, 1H), 6.48 (br. s., 2H), 5.32-5.50 (m, 2H), 4.98-5.28 (m, 2H), 4.81-4.97 (m, 2H), 4.79 (s, 2H) |
| 89 | 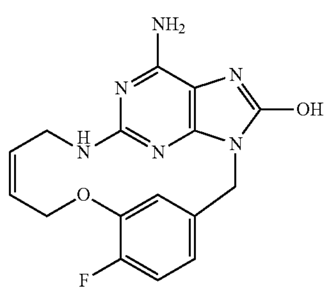 [SMILES: Nc1nc2nc3c1nc(O)n3Cc1ccc(F)c(c1)OC/C=C\CN2] | 342.1 | 343 | 2.14, V3018V3001 | Method 31 | $^1$H NMR (500 MHz, DMSO-d$_6$) δ 9.66 (br. s., 1H), 8.10 (d, J = 8.2 Hz, 1H), 7.09 (dd, J = 8.2, 11.2 Hz, 1H), 6.62-6.90 (m, 1H), 6.29 (t, J = 6.8 Hz, 1H), 6.02 (br. s., 2H), 5.12-5.45 (m, 2H), 4.77-5.06 (m, 2H), 4.70 (s, 2H), 3.52-4.32 (m, 2H) |
| 90 | 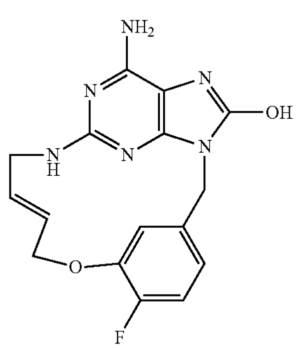 [SMILES: Nc1nc2nc3c1nc(O)n3Cc1ccc(F)c(c1)OC/C=C/CN2] | 342.1 | 343 | 2.13, V3018V3001 | Method 31 | $^1$H NMR (500 MHz, DMSO-d$_6$) δ 9.64 (br. s., 1H), 7.75 (dd, J = 1.7, 8.4 Hz, 1H), 7.07 (dd, J = 8.4, 11.2 Hz, 1H), 6.72-6.93 (m, 1H), 6.48 (t, J = 5.5 Hz, 1H), 5.98 (s, 2H), 5.68 (dt, J = 6.0, 15.8 Hz, 1H), 5.59 (dt, J = 3.8, 15.8 Hz, 1H), 4.70 (s, 2H), 4.59 (d, J = 6.0 Hz, 2H), 3.63-3.86 (m, 2H) |

TABLE 1-continued

Compounds of formula (I).

| # | STRUCTURE | Exact Mass | Mass Found [M + H] | LCMS Ret Time, Method | Synthesis method | NMR |
|---|---|---|---|---|---|---|
| 91 | (structure: purine with NH₂, O-linked propyl chain to phenyl ring with F, OH on imidazole) | 345.1 | 346 | 2.21, V3018V3001 | Method 32 | $^1$H NMR (500 MHz, DMSO-$d_6$) δ 9.92 (br. s., 1H), 8.08 (d, J = 8.2 Hz, 1H), 7.09 (dd, J = 8.2, 11.7 Hz, 1H), 6.62-6.91 (m, 1H), 6.41 (br. s., 2H), 4.81 (s, 2H), 4.57 (t, J = 6.5 Hz, 2H), 4.35 (t, J = 6.8 Hz, 2H), 1.62-1.74 (m, 2H), 1.50-1.60 (m, 2H) |
| 92 | (structure: purine with NH₂, NH-linked propyl chain to phenyl ring with F, OH on imidazole) | 344.1 | 345 | 2.2, V3018V3001 | Method 32 | $^1$H NMR (500 MHz, DMSO-$d_6$) δ 9.58 (s, 1H), 8.16 (d, J = 8.5 Hz, 1H), 7.08 (dd, J = 8.5, 11.7 Hz, 1H), 6.59-6.88 (m, 1H), 6.23 (t, J = 6.5 Hz, 1H), 5.94 (s, 2H), 4.74 (s, 2H), 4.29 (t, J = 7.3 Hz, 2H), 3.38-3.57 (m, 2H), 1.53-1.72 (m, 2H), 1.26-1.47 (m, 2H) |

Biological Activity of Compounds of Formula (I)
Description of Biological Assays
Assessment of TLR7 and TLR8 Activity The ability of compounds to activate human TLR7 and TLR8 was assessed in a cellular reporter assay using HEK293 cells transiently transfected with a TLR7 or TLR8 expression vector and NFκB-luc reporter construct. Briefly, HEK293 cells were grown in culture medium (DMEM supplemented with 10% FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated 48 hours at 37° C. in a humidified 5% $CO_2$ atmosphere. Transfected cells were then detached with Trypsin-EDTA, washed in PBS and resuspended in medium to a density of $1.67 \times 10^5$ cells/mL. Thirty microliters of cells were then dispensed into each well in 384-well plates, where 10 μL of compound in 4% DMSO was already present. Following 6 hours incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

In parallel, a similar dilution series of compound was used (10 μL of compound in 4% DMSO) with 30 μL per well of cells transfected with NFκB-luc reporter construct alone ($1.67 \times 10^5$ cells/mL). Six hours after incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Counterscreen data is reported as LEC.

Measurement of Interferon Production in Human PBMC

Activation of human TLR7 results in robust production of interferon by plasmacytoid dendritic cells present in human blood. The potential of compounds to induce interferon was evaluated by determination of interferon in the conditioned media from peripheral blood mononuclear cells (PBMC). The presence of interferon in the samples was determined, using an interferon reporter cell line stably expressing an interferon-stimulated responsive elements (ISRE)-luc reporter construct. The ISRE element with sequence GAAACTGAAACT (SEQ ID: 1) is highly responsive to the STAT1-STAT2-IRF9 transcription factor, which becomes activated upon binding of IFN-I to the IFN receptor. Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume). After overnight incubation of the PBMCs with the compounds, 10 μL of supernatant was transferred to 384-well plates containing $5 \times 10^3$ HEK-ISRE-luc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISRE-luc cells was reported as LEC. The LEC in turn indicates the degree of ISRE activation on transfer of a defined amount of PBMC culture medium. Recombinant interferon alfa-2a (Roferon-A) was used as a standard control compound.

The LEC values for the compounds in table 2 on HEK293 TLR8-NFκB-luc were >10 μM for compound 6, 20.46 μM for compound 39, >19.49 μM for compound 40, 11.16 μM for compound 41, >10 μM for compound 44, 5.48 μM for compound 47, >10 μM for compound 63, 0.27 μM for compound 75 and >25 μM for all other compounds.

The LEC values for the compounds in table 2 on HEK293 NFκB-luc were greater than the highest tested concentration (>10 μM for compounds 6, 44 and 63, and >25 μM for all other compounds).

TABLE 2

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 1 | 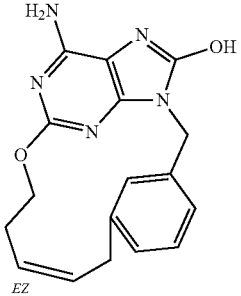 [SMILES: Nc1nc2nc3c1nc(O)n3Cc1cccc(c1)C/C=C\CCO2] | 0.154 | 5 | 0.081 | 5 |
| 2 | 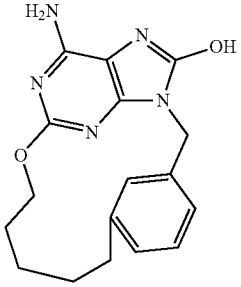 [SMILES: Nc1nc2nc3c1nc(O)n3Cc1cccc(c1)CCCCCO2] | 0.51 | 1 | 0.22 | 2 |
| 3 | 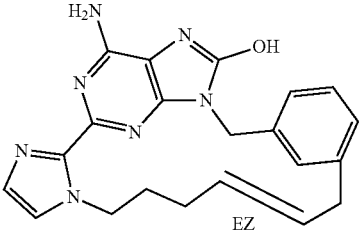 [SMILES: Nc1nc2nc3c1nc(O)n3Cc1cccc(c1)C/C=C/CCCn1ccnc1-2] | 1.05 | 1 | 0.14 | 1 |
| 4 | 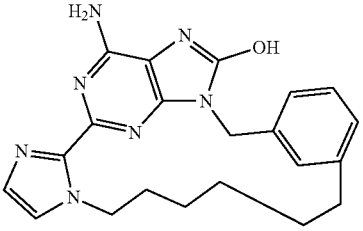 [SMILES: Nc1nc2nc3c1nc(O)n3Cc1cccc(c1)CCCCCCn1ccnc1-2] | 3.27 | 1 | 0.64 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 5 | 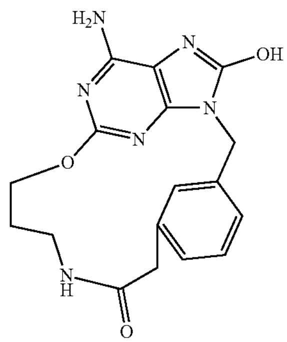 [SMILES: Nc1nc2nc3c1nc(O)n3Cc1cccc(c1)CC(=O)NCCCO2] | 0.24 | 1 | 0.044 | 2 |
| 6 | 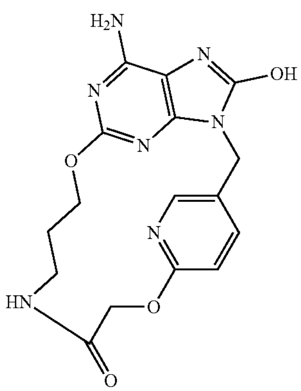 [SMILES: Nc1nc2nc3c1nc(O)n3Cc1ccc(nc1)OCC(=O)NCCCO2] | >10 | 1 | 1.73 | 2 |
| 7 | 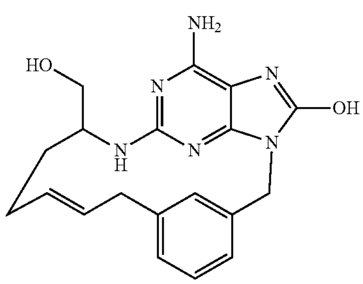 [SMILES: Nc1nc2nc3c1nc(O)n3Cc1cccc(c1)C/C=C/CCC(CO)N2] | 0.87 | 1 | 0.31 | 2 |
| 8 | 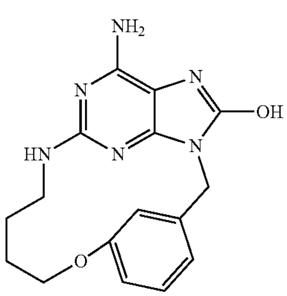 [SMILES: Nc1nc2nc3c1nc(O)n3Cc1cccc(c1)OCCCCN2] | 2.42 | 1 | 0.68 | 4 |

TABLE 2-continued
Compounds of formula (I)
| # | STRUCTURE | HEK293 TLR7-NFκB-luc (LEC; μM) | n | PBMC HEK-ISRE-luc (LEC; μM) | n |
|---|---|---|---|---|---|
| 9 | 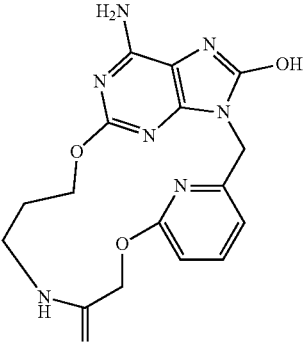 | 0.30 | 1 | 0.098 | 2 |
| 10 | 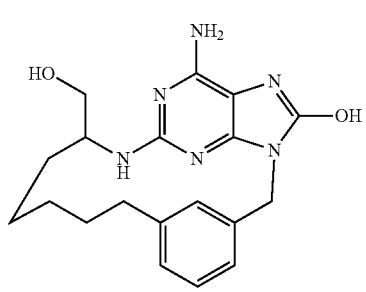 | 5.26 | 1 | 0.53 | 2 |
| 11 | 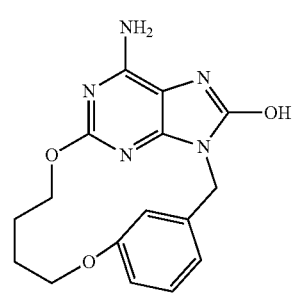 [SMILES: Nc1nc2nc3c1nc(O)n3Cc1cccc(c1)OCCCCO2] | 0.050 | 2 | 0.022 | 4 |
| 12 | 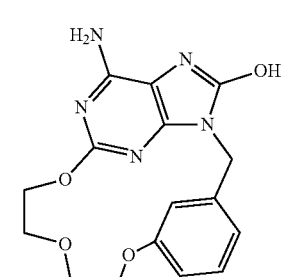 | 0.39 | 1 | 0.043 | 4 |
| 13 | 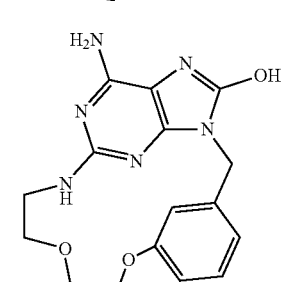 | 14.69 | 1 | 4.7 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 14 | 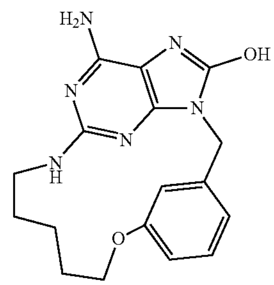 [SMILES: Nc1nc2nc3c1nc(O)n3Cc1cccc(c1)OCCCCCN2] | 1.68 | 1 | 0.51 | 3 |
| 15 | 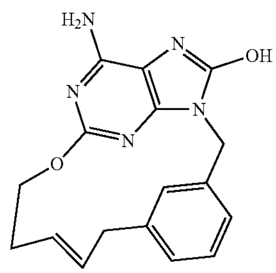 [SMILES: Nc1nc2nc3c1nc(O)n3Cc1cccc(c1)C/C=C/CCO2] | 0.12 | 6 | 0.016 | 11 |
| 16 | 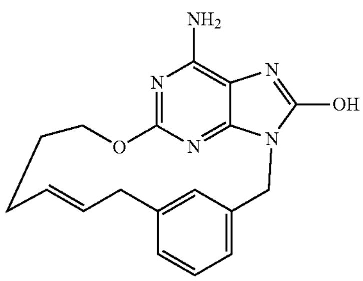 [SMILES: Nc1nc2nc3c1nc(O)n3Cc1cccc(c1)C/C=C/CCCO2] | 0.375 | 12 | 0.11 | 7 |
| 17 | 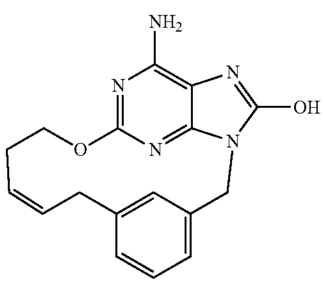 [SMILES: Nc1nc2nc3c1nc(O)n3Cc1cccc(c1)C/C=C\CCO2] | 0.067 | 4 | 0.013 | 6 |
| 18 | 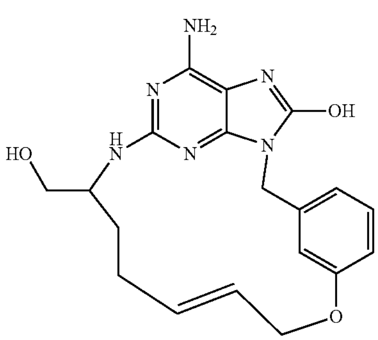 [SMILES: Nc1nc2nc3c1nc(O)n3Cc1cccc(c1)OC/C=C/CCC(CO)N2] | 0.82 | 1 | 0.056 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 19 | 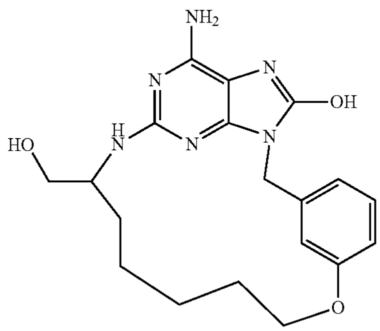 [SMILES: Nc1nc2nc3c1nc(O)n3Cc1cccc(c1)OCCCCCC(CO)N2] | 2.24 | 1 | 0.14 | 2 |
| 20 | 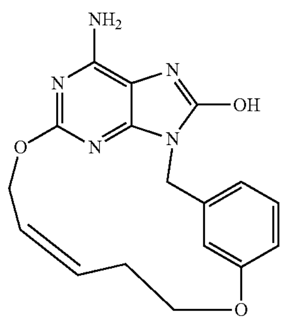 [SMILES: Nc1nc2nc3c1nc(O)n3Cc1cccc(c1)OCC/C=C\CO2] | 0.74 | 1 | 0.15 | 2 |
| 21 | 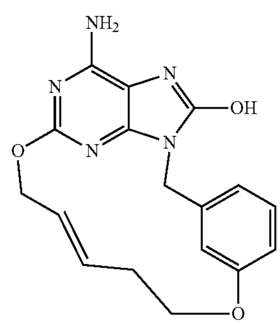 [SMILES: Nc1nc2nc3c1nc(O)n3Cc1cccc(c1)OCC/C=C/CO2] | 0.3 | 1 | 0.05 | 2 |
| 22 | 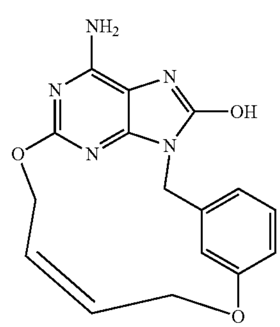 [SMILES: Nc1nc2nc3c1nc(O)n3Cc1cccc(c1)OC/C=C\CO2] | 0.12 | 1 | 0.054 | 4 |

TABLE 2-continued
| | | Compounds of formula (I) | | | |
|---|---|---|---|---|---|
| # | STRUCTURE | HEK293 TLR7-NFκB-luc (LEC; μM) | n | PBMC HEK-ISRE-luc (LEC; μM) | n |
| 23 | 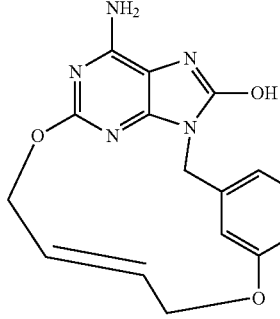 | 0.043 | 1 | 0.012 | 2 |
| 24 | 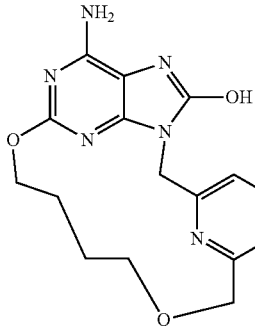 | 1.05 | 1 | 0.15 | 2 |
| 25 | 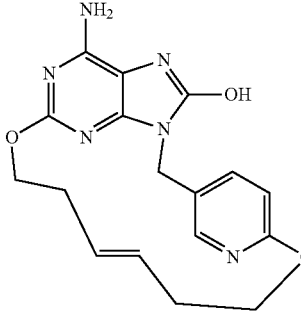 | 20.22 | 1 | 3.61 | 4 |
| 26 | 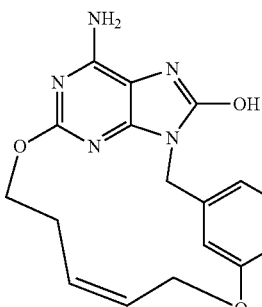 | 0.027 | 1 | 0.093 | 4 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 27 | 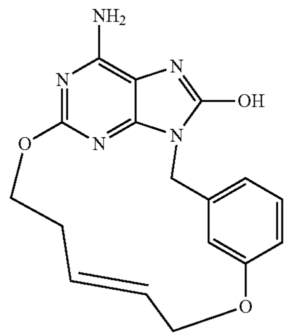 [SMILES: Nc1nc2nc3c1nc(O)n3Cc1cccc(c1)OC/C=C/CCO2] | 1.31 | 6 | 0.11 | 6 |
| 28 | 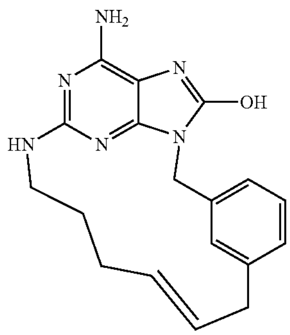 [SMILES: Nc1nc2nc3c1nc(O)n3Cc1cccc(c1)C/C=C/CCCN2] | 0.77 | 1 | 0.26 | 4 |
| 29 | 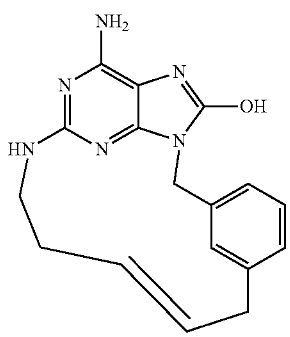 [SMILES: Nc1nc2nc3c1nc(O)n3Cc1cccc(c1)C/C=C/CCN2] | 0.81 | 1 | 0.15 | 2 |
| 30 | 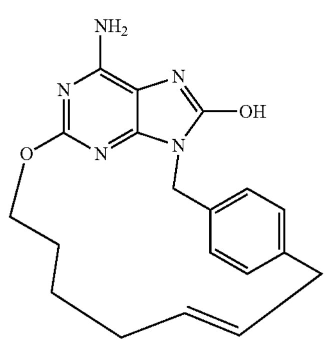 [SMILES: Nc1nc2nc3c1nc(O)n3Cc1ccc(cc1)C/C=C/CCCCO2] | 0.87 | 1 | 0.56 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 31 | 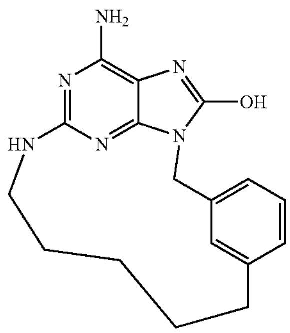 [SMILES: Nc1nc2nc3c1nc(O)n3Cc1cccc(c1)CCCCCN2] | 1.36 | 2 | 0.263 | 6 |
| 32 | 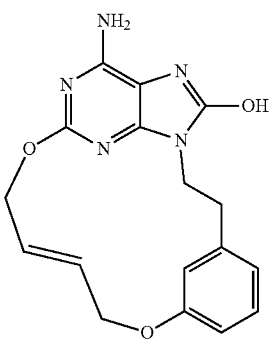 [SMILES: Nc1nc2nc3c1nc(O)n3CCc1cccc(c1)OC/C=C/CO2] | 0.92 | 2 | 0.12 | 4 |
| 33 | 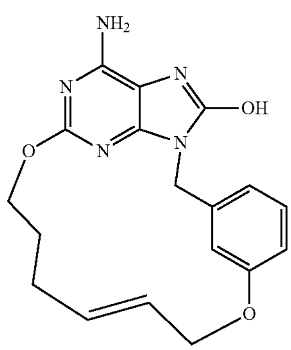 [SMILES: Nc1nc2nc3c1nc(O)n3Cc1cccc(c1)OC/C=C/CCCO2] | 0.17 | 2 | 0.11 | 4 |
| 34 | 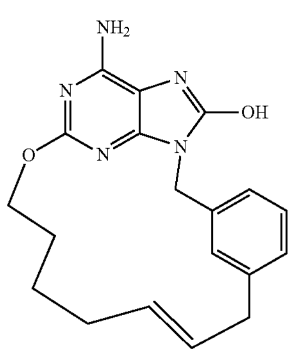 [SMILES: Nc1nc2nc3c1nc(O)n3Cc1cccc(c1)C/C=C/CCCCO2] | 9.81 | 1 | 0.032 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 35 | 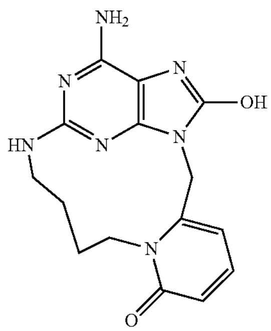 [SMILES: Nc1nc2nc3c1nc(O)n3Cc1cccc(=O)n1CCCCN2] | 1.68 | 1 | 0.41 | 2 |
| 36 | 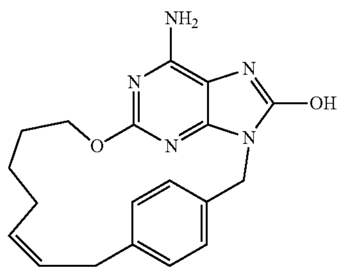 [SMILES: Nc1nc2nc3c1nc(O)n3Cc1ccc(cc1)C/C=C\CCCCO2] | 12.45 | 1 | 0.68 | 2 |
| 37 | 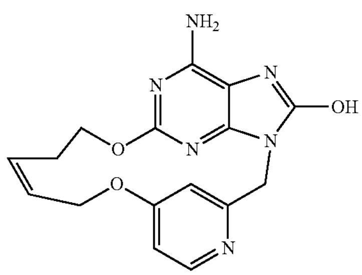 [SMILES: Nc1nc2nc3c1nc(O)n3Cc1cc(ccn1)OC/C=C\CCO2] | 0.8 | 1 | 0.12 | 2 |
| 38 | 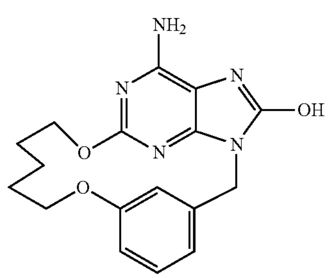 [SMILES: Nc1nc2nc3c1nc(O)n3Cc1cccc(c1)OCCCCCO2] | 0.53 | 3 | 0.027 | 2 |
| 39 | 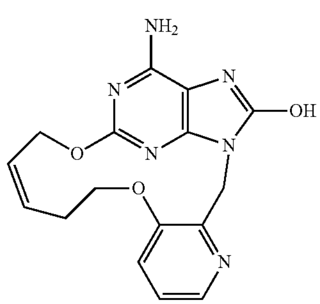 [SMILES: Nc1nc2nc3c1nc(O)n3Cc1ncccc1OCC/C=C\CO2] | 1.16 | 2 | 0.22 | 4 |

TABLE 2-continued
| | | Compounds of formula (I) | | | |
|---|---|---|---|---|---|
| # | STRUCTURE | HEK293 TLR7-NFκB-luc (LEC; μM) | n | PBMC HEK-ISRE-luc (LEC; μM) | n |
| 40 | 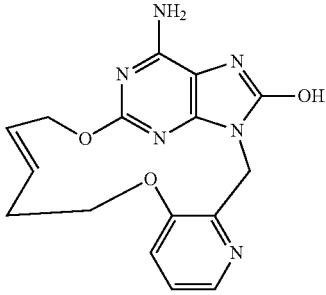 [SMILES: Nc1nc2nc3c1nc(O)n3Cc1ncccc1OCC/C=C/CO2] | 1.3 | 3 | 0.15 | 4 |
| 41 | 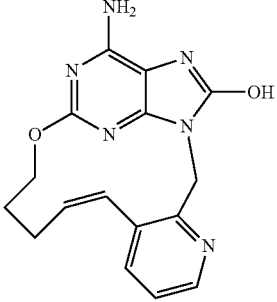 [SMILES: Nc1nc2nc3c1nc(O)n3Cc1ncccc1/C=C\CCCO2] | 1.93 | 2 | 0.48 | 4 |
| 42 | 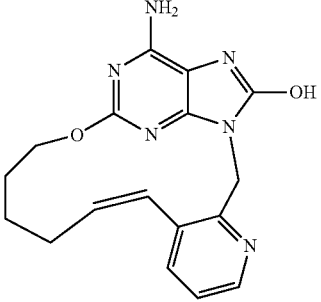 [SMILES: Nc1nc2nc3c1nc(O)n3Cc1ncccc1/C=C\CCCCO2] | 2.28 | 2 | 0.5 | 4 |
| 43 | 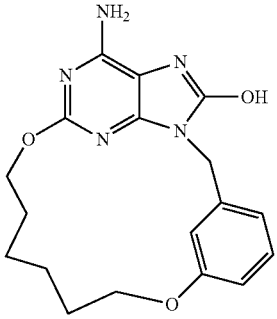 [SMILES: Nc1nc2nc3c1nc(O)n3Cc1cccc(c1)OCCCCCCO2] | 0.11 | 2 | 0.034 | 4 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 44 | 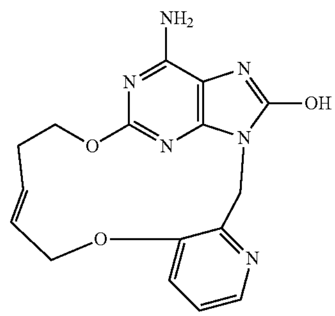 [SMILES: Nc1nc2nc3c1nc(O)n3Cc1ncccc1OC/C=C/CCO2] | 5.77 | 2 | 0.62 | 2 |
| 45 | 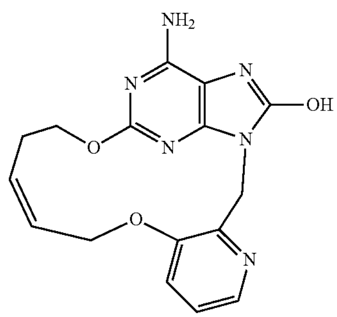 [SMILES: Nc1nc2nc3c1nc(O)n3Cc1ncccc1OC/C=C\CCO2] | 0.108 | 2 | 0.01 | 6 |
| 46 | 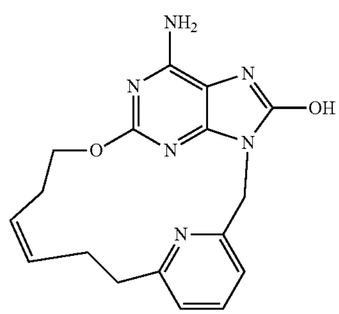 [SMILES: Nc1nc2nc3c1nc(O)n3Cc1cccc(n1)CC/C=C\CCO2] | 6.49 | 1 | 1.13 | 2 |
| 47 | 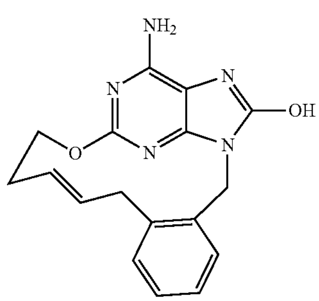 [SMILES: Nc1nc2nc3c1nc(O)n3Cc1ccccc1C/C=C/CCO2] | 3.43 | 3 | 2.34 | 4 |
| 48 | 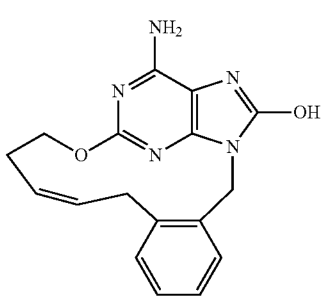 [SMILES: Nc1nc2nc3c1nc(O)n3Cc1ccccc1C/C=C\CCO2] | 0.64 | 1 | 2.04 | 2 |

TABLE 2-continued
Compounds of formula (I)
| # | STRUCTURE | HEK293 TLR7-NFκB-luc (LEC; μM) | n | PBMC HEK-ISRE-luc (LEC; μM) | n |
|---|---|---|---|---|---|
| 49 | 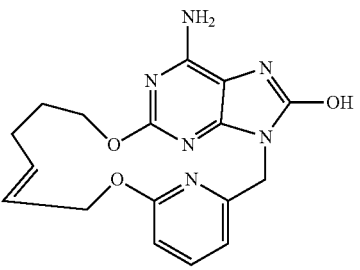 [SMILES: Nc1nc2nc3c1nc(O)n3Cc1cccc(n1)OC/C=C/CCCO2] | 0.21 | 1 | 0.16 | 2 |
| 50 | 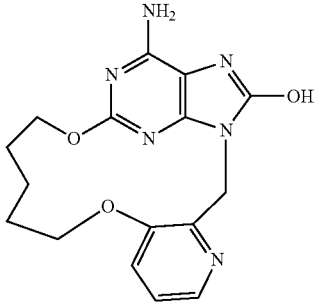 [SMILES: Nc1nc2nc3c1nc(O)n3Cc1ncccc1OCCCCCO2] | 1.19 | 1 | 0.24 | 2 |
| 51 | 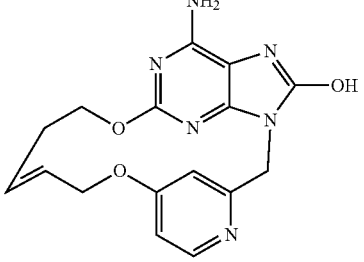 | 0.74 | 1 | 0.069 | 2 |
| 52 | 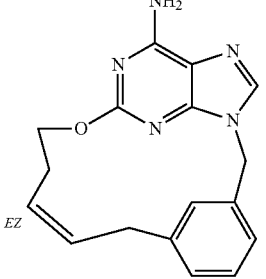 | 7.96 | 1 | 4.8 | 2 |
| 53 | 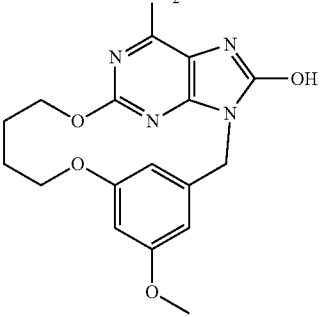 | 0.029 | 1 | 0.01 | 2 |

TABLE 2-continued
Compounds of formula (I)
| # | STRUCTURE | HEK293 TLR7-NFκB-luc (LEC; μM) | n | PBMC HEK-ISRE-luc (LEC; μM) | n |
|---|---|---|---|---|---|
| 54 | 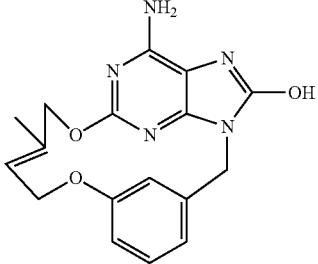 [SMILES: C/C1=C\COc2cccc(c2)Cn2c(O)nc3c(N)nc(nc32)OC1] | 0.041 | 2 | 0.026 | 4 |
| 55 | 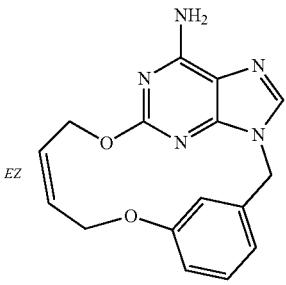 [SMILES: Nc1nc2nc3c1ncn3Cc1cccc(c1)OC/C=C\CO2] | >25 | 1 | 15.31 | 2 |
| 56 | 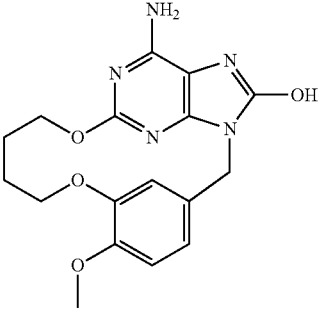 [SMILES: COc1ccc2cc1OCCCCOc1nc(N)c3nc(O)n(c3n1)C2] | 0.056 | 2 | 0.01 | 4 |
| 57 | 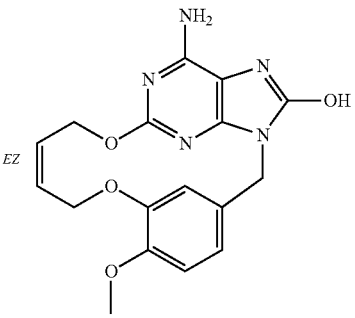 [SMILES: COc1ccc2cc1OC/C=C\COc1nc(N)c3nc(O)n(c3n1)C2] | 0.08 | 1 | 0.021 | 2 |
| 58 | 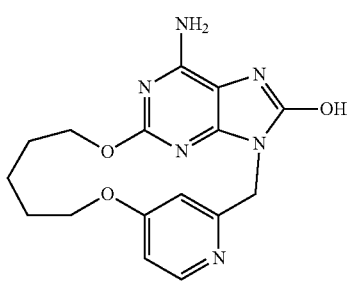 [SMILES: Nc1nc2nc3c1nc(O)n3Cc1cc(ccn1)OCCCCCO2] | 0.63 | 3 | 0.086 | 4 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 59 | 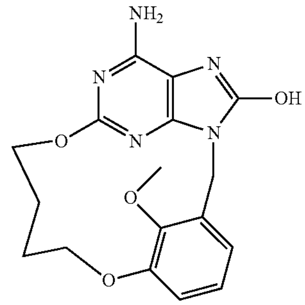 [SMILES: COc1c2cccc1OCCCCOc1nc(N)c3nc(O)n(c3n1)C2] | 4.41 | 1 | 1.92 | 2 |
| 60 | 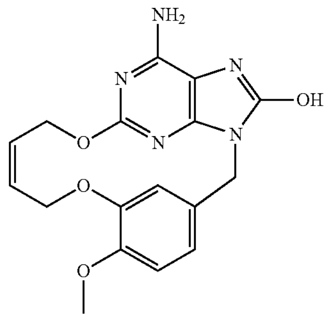 [SMILES: COc1ccc2cc1OC/C=C\COc1nc(N)c3nc(O)n(c3n1)C2] | 0.088 | 1 | 0.033 | 2 |
| 61 | 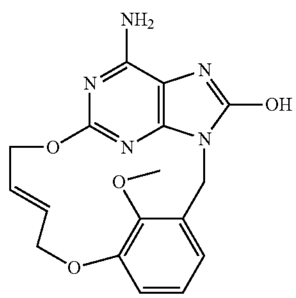 [SMILES: COc1c2cccc1OC/C=C/COc1nc(N)c3nc(O)n(c3n1)C2] | 4.7 | 1 | 4.98 | 2 |
| 62 | 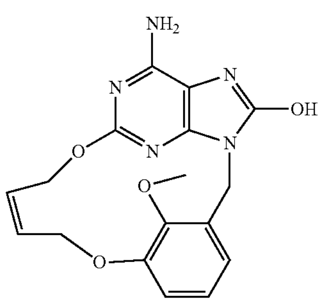 [SMILES: COc1c2cccc1OC/C=C\COc1nc(N)c3nc(O)n(c3n1)C2] | 7.26 | 1 | 2.03 | 2 |
| 63 | 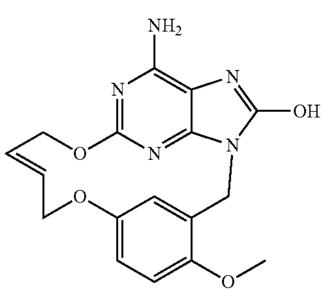 [SMILES: COc1ccc2cc1Cn1c(O)nc3c(N)nc(nc31)OC/C=C/CO2] | 0.12 | 1 | 0.031 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 64 | 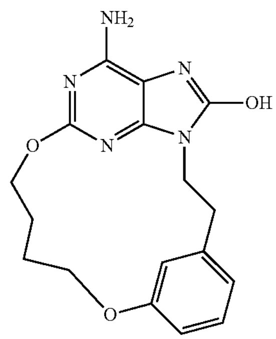 [SMILES: Nc1nc2nc3c1nc(O)n3CCc1cccc(c1)OCCCCO2] | 1.49 | 1 | 0.5 | 2 |
| 65 | 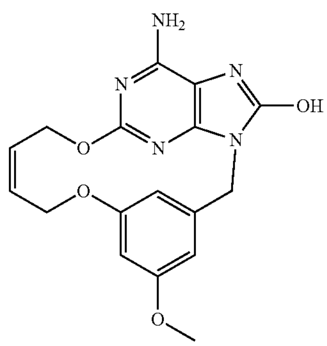 [SMILES: COc1cc2cc(c1)OC/C=C\COc1nc(N)c3nc(O)n(c3n1)C2] | 0.038 | 2 | 0.03 | 2 |
| 66 | 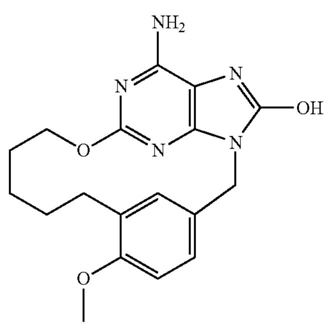 [SMILES: COc1ccc2cc1CCCCCOc1nc(N)c3nc(O)n(c3n1)C2] | 0.032 | 1 | 0.018 | 2 |
| 67 | 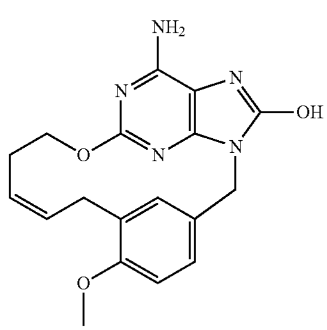 [SMILES: COc1ccc2cc1C/C=C\CCOc1nc(N)c3nc(O)n(c3n1)C2] | 0.0024 | 1 | 0.0028 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 68 | 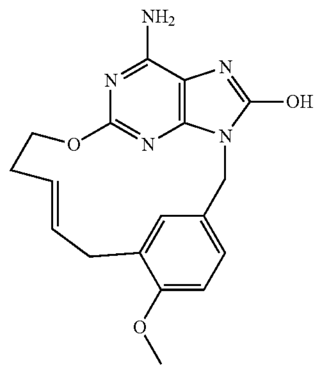 [SMILES: COc1ccc2cc1C/C=C/CCOc1nc(N)c3nc(O)n(c3n1)C2] | 0.006 | 1 | 0.0057 | 2 |
| 69 | 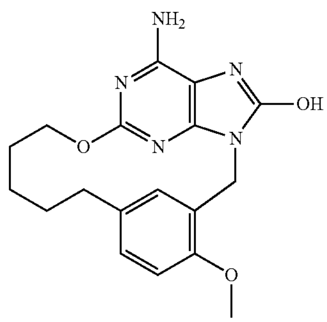 [SMILES: COc1ccc2cc1Cn1c(O)nc3c(N)nc(nc31)OCCCCC2] | 0.2 | 1 | 0.039 | 2 |
| 70 | 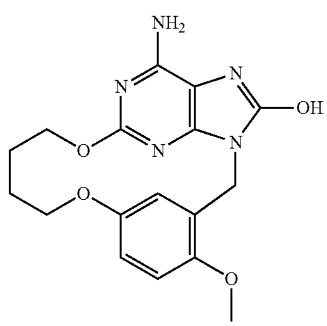 [SMILES: COc1ccc2cc1Cn1c(O)nc3c(N)nc(nc31)OCCCCO2] | 0.15 | 1 | 0.04 | 2 |
| 71 | 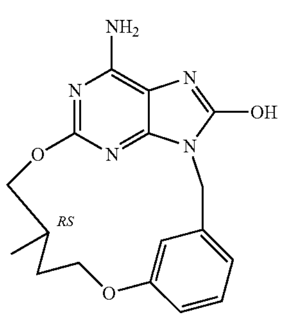 [SMILES: CC1CCOc2cccc(c2)Cn2c(O)nc3c(N)nc(nc32)OC1] | 0.12 | 1 | 0.04 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 72 | 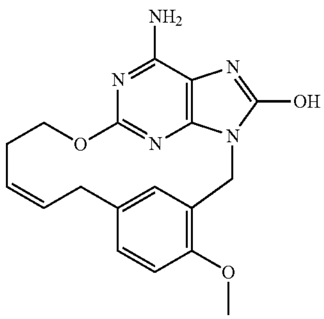 [SMILES: COc1ccc2cc1Cn1c(O)nc3c(N)nc(nc31)OCC/C=C\C2] | 0.018 | 1 | 0.0029 | 2 |
| 73 | 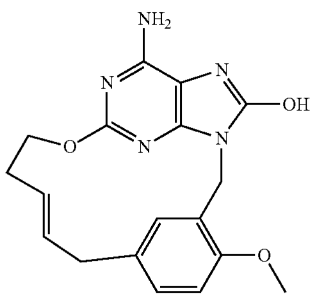 [SMILES: COc1ccc2cc1Cn1c(O)nc3c(N)nc(nc31)OCC/C=C/C2] | 0.045 | 1 | 0.01 | 2 |
| 74 | 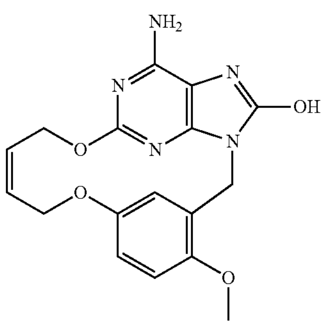 [SMILES: COc1ccc2cc1Cn1c(O)nc3c(N)nc(nc31)OC/C=C\CO2] | 0.1 | 1 | 0.044 | 2 |
| 75 | 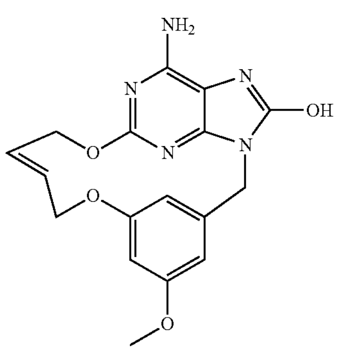 [SMILES: COc1cc2cc(c1)OC/C=C/COc1nc(N)c3nc(O)n(c3n1)C2] | 0.0068 | 1 | 0.0026 | 2 |

TABLE 2-continued
Compounds of formula (I)
| # | STRUCTURE | HEK293 TLR7-NFκB-luc (LEC; μM) | n | PBMC HEK-ISRE-luc (LEC; μM) | n |
|---|---|---|---|---|---|
| 76 | 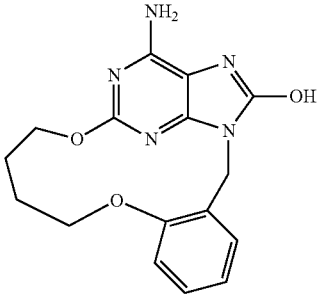 [SMILES: Nc1nc2nc3c1nc(O)n3Cc1ccccc1OCCCCO2] | 0.12 | 1 | 0.064 | 2 |
| 77 | 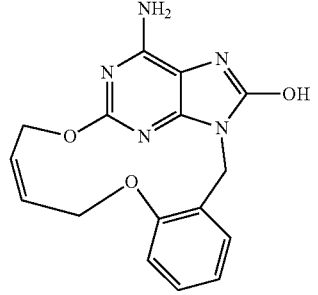 [SMILES: Nc1nc2nc3c1nc(O)n3Cc1ccccc1OC/C=C\CO2] | 0.53 | 1 | 0.1 | 2 |
| 78 | 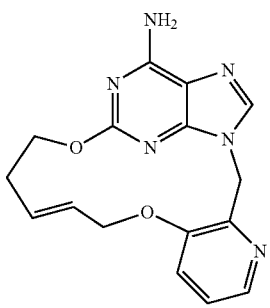 [SMILES: Nc1nc2nc3c1ncn3Cc1ncccc1OC/C=C/CCO2] | 9.68 | 1 | 2 >25 | |
| 79 | 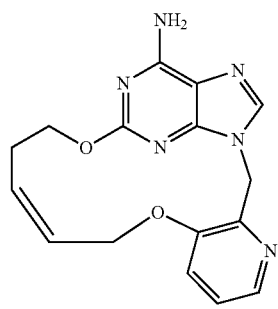 [SMILES: Nc1nc2nc3c1ncn3Cc1ncccc1OC/C=C\CCO2] | 2.34 | 1 | 1.78 | 2 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 80 | 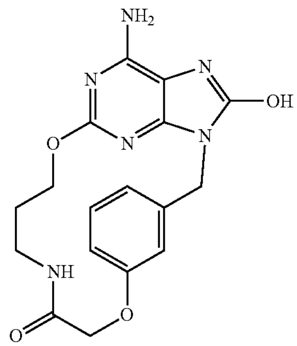 [SMILES: Nc1nc2nc3c1nc(O)n3Cc1cccc(c1)OCC(=O)NCCCO2] | 0.041 | 3 | 0.087 | 4 |
| 81 | 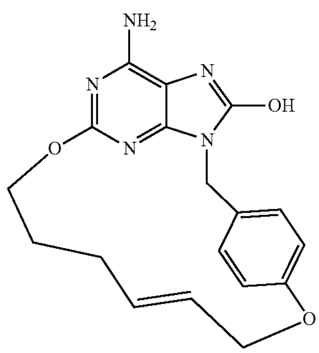 [SMILES: Nc1nc2nc3c1nc(O)n3Cc1ccc(cc1)OC/C=C/CCCO2] | 4.59 | 1 | 0.63 | 2 |
| 82 | 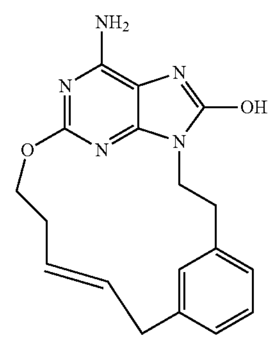 [SMILES: Nc1nc2nc3c1nc(O)n3CCc1cccc(c1)C/C=C/CCO2] | 3.95 | 1 | | |
| 83 | 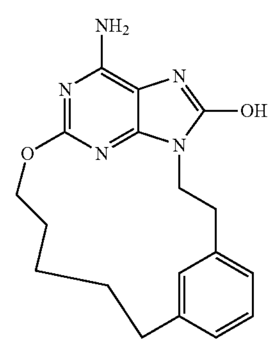 [SMILES: Nc1nc2nc3c1nc(O)n3CCc1cccc(c1)CCCCCO2] | >25 | 1 | 2.66 | 4 |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 84 | 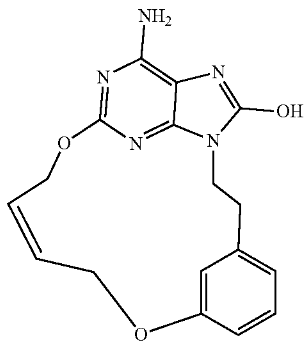 [SMILES: Nc1nc2nc3c1nc(O)n3CCc1cccc(c1)OC/C=C\CO2] | 3.4 | 1 | 0.51 | 2 |
| 85 | 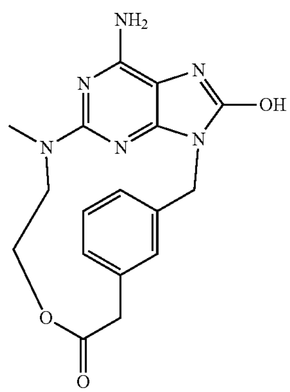 [SMILES: CN1CCOC(=O)Cc2cccc(c2)Cn2c(O)nc3c(N)nc1nc32] | 0.33 | 2 | 12.48 | 4 |
| 86 | 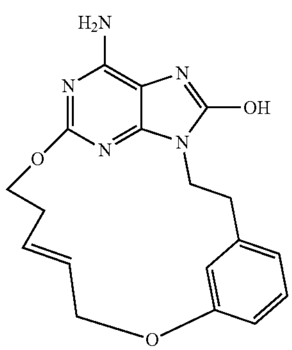 [SMILES: Nc1nc2nc3c1nc(O)n3CCc1cccc(c1)OC/C=C/CCO2] | 7.91 | 1 | 2.43 | 2 |
| 87 | 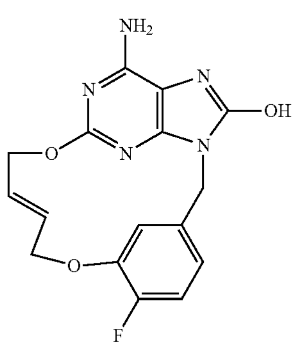 [SMILES: Nc1nc2nc3c1nc(O)n3Cc1ccc(F)c(c1)OC/C=C/CO2] | 0.034 | 1 | | |

TABLE 2-continued

Compounds of formula (I)

| # | STRUCTURE | HEK293 TLR7-NFκB-luc (LEC; μM) | n | PBMC HEK-ISRE-luc (LEC; μM) | n |
|---|---|---|---|---|---|
| 88 | 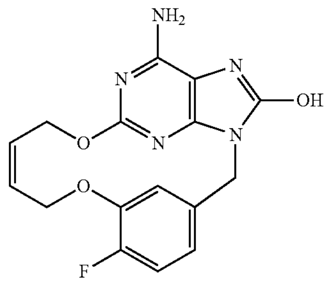 [SMILES: Nc1nc2nc3c1nc(O)n3Cc1ccc(F)c(c1)OC/C=C\CO2] | 0.11 | 1 | | |
| 89 | 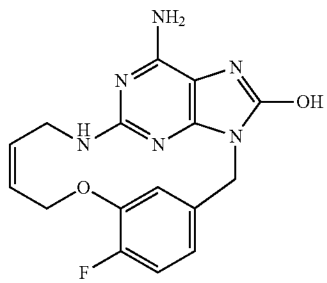 [SMILES: Nc1nc2nc3c1nc(O)n3Cc1ccc(F)c(c1)OC/C=C\CN2] | 0.4 | 1 | | |
| 90 | 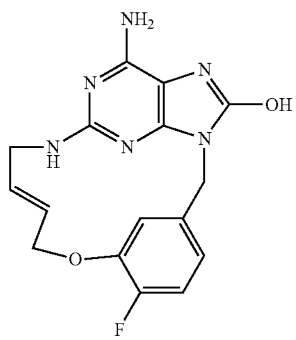 [SMILES: Nc1nc2nc3c1nc(O)n3Cc1ccc(F)c(c1)OC/C=C/CN2] | 0.063 | 1 | | |
| 91 | 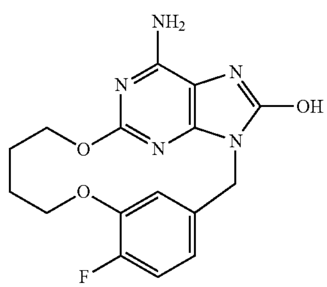 [SMILES: Nc1nc2nc3c1nc(O)n3Cc1ccc(F)c(c1)OCCCCO2] | 0.14 | 1 | | |
| 92 | | 0.47 | 1 | | | n represents the number of experiments performed.

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaactgaaa ct                                                       12

Column 269, Claim 2, Line 60, change 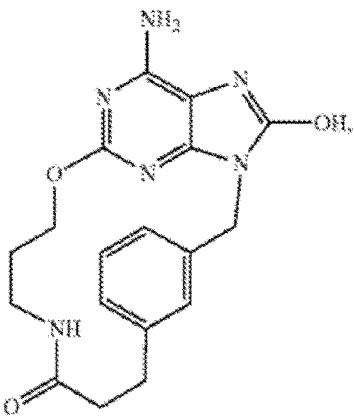 to 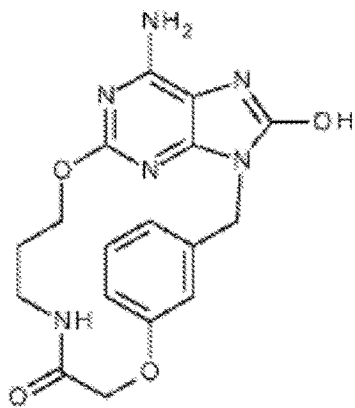

The invention claimed is:

1. A compound of formula (I):

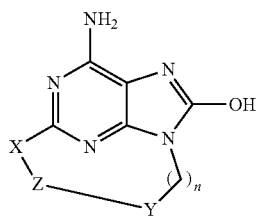

(I)

n = 1 to 3 or a pharmaceutically acceptable salt thereof;
wherein:
X is selected from the group consisting of oxygen, NH, or

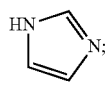

Y is phenyl or pyridyl, optionally substituted by one or more substituents independently selected from $C_{1-6}$alkyl, $C_{1-4}$alkoxy, trifluoromethyl or halogen;

Z is selected from the group consisting of $C_{1-10}$alkyl, —$C_{1-6}$alkyl-NH—C(O)—$C_{1-6}$alkyl-O—, —$C_{1-10}$alkyl-O—, —$C_{1-6}$alkyl-O—$C_{1-6}$alkyl-, and —$C_{1-6}$alkyl-O—$C_{1-6}$alkyl-O—, wherein alkyl is unsaturated or saturated and can optionally be substituted by an alkyl or alkylhydroxyl.

2. The compound of claim 1 selected from the group consisting of:

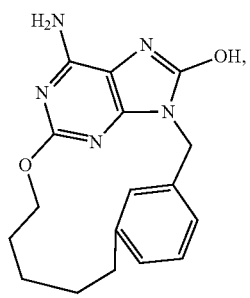

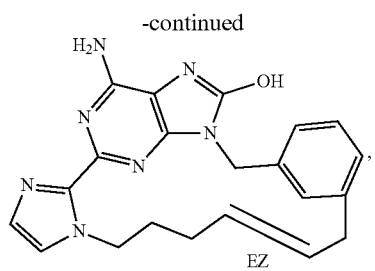

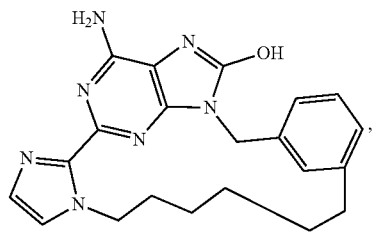

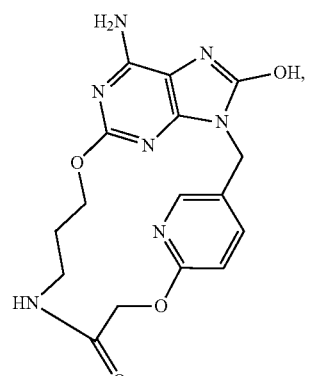

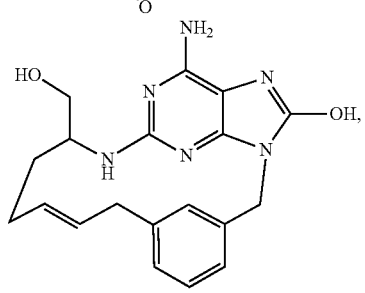

259
-continued
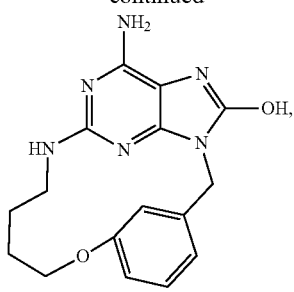
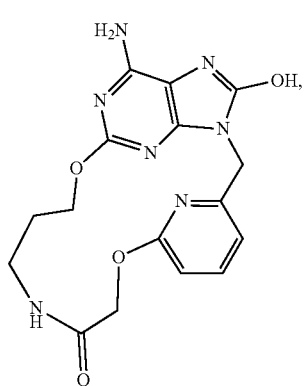
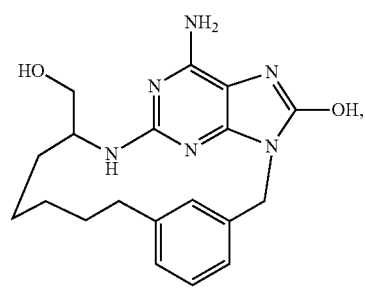
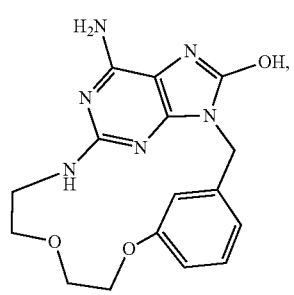
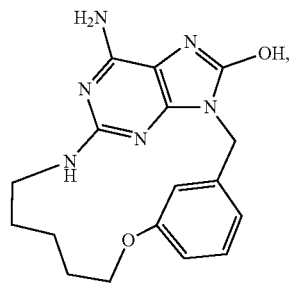
260
-continued
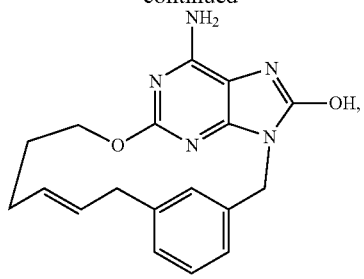
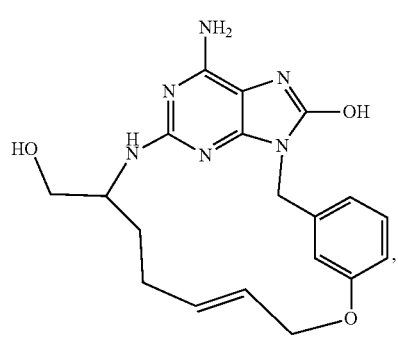
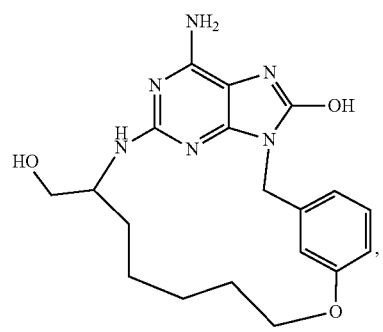
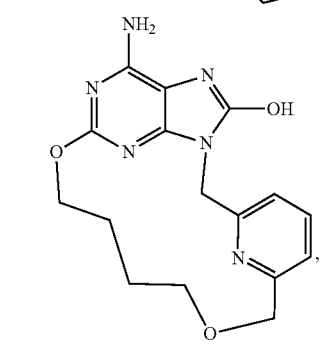
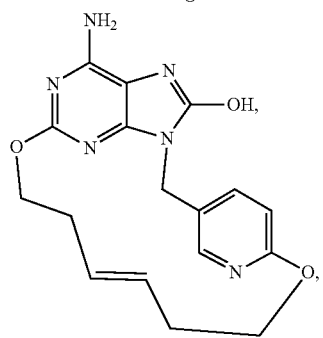

261
-continued
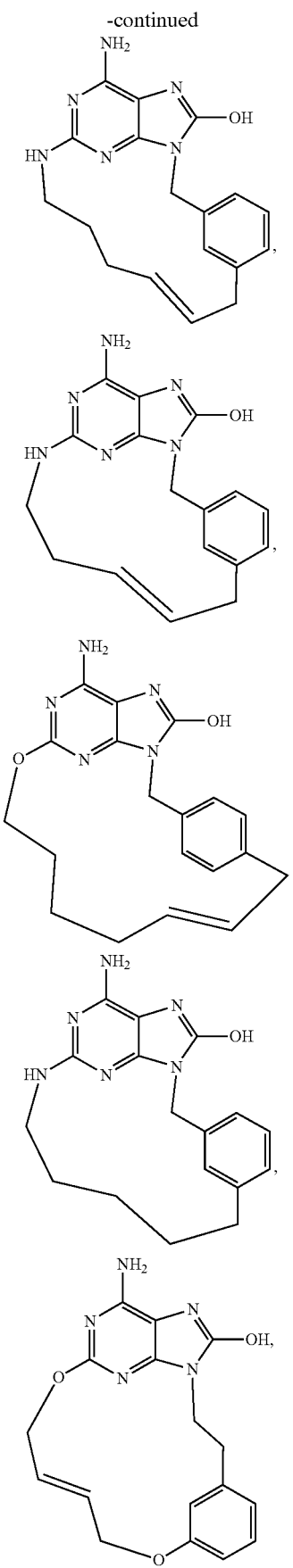
262
-continued
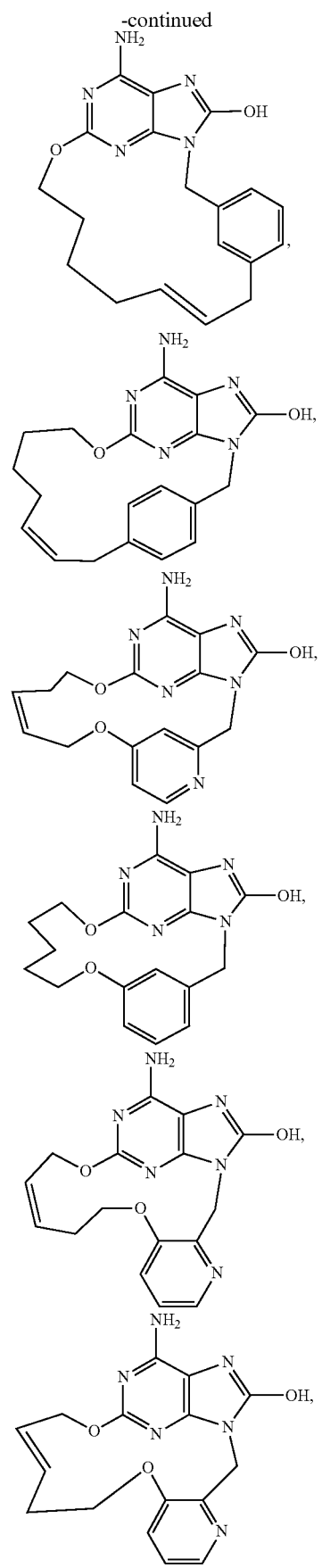

263
-continued
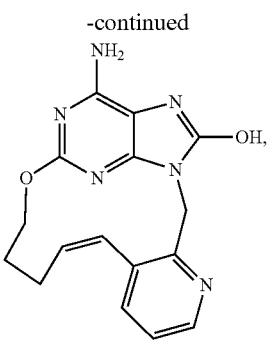
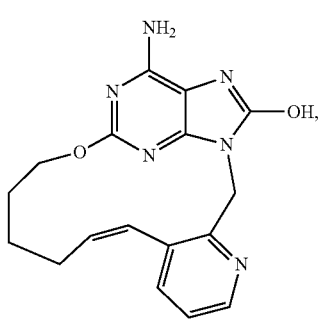
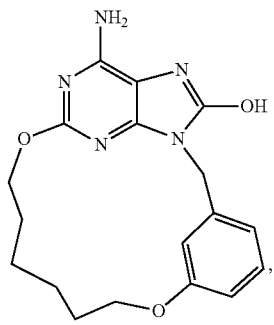
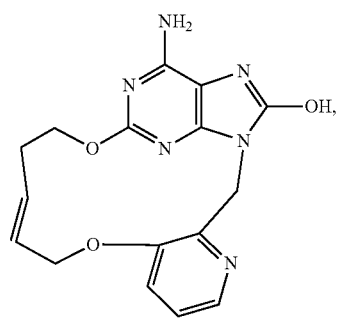
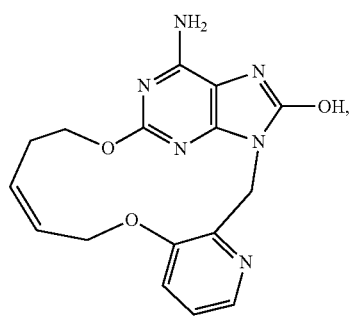
264
-continued
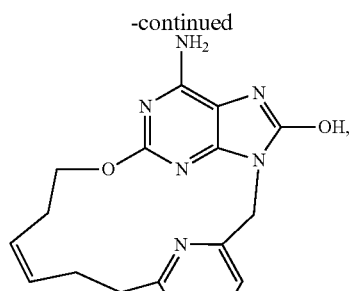
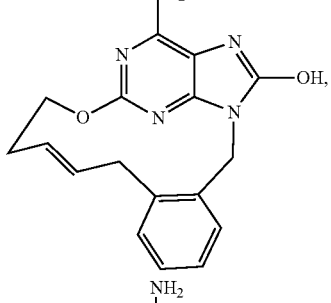
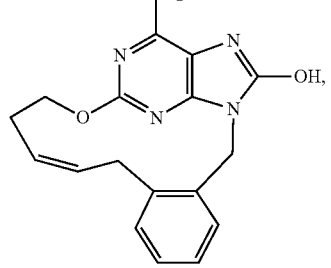
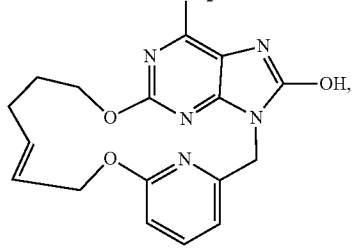
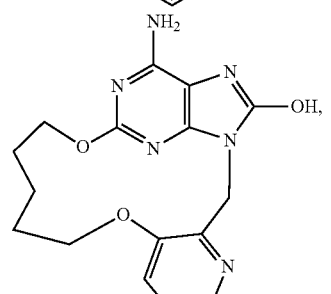
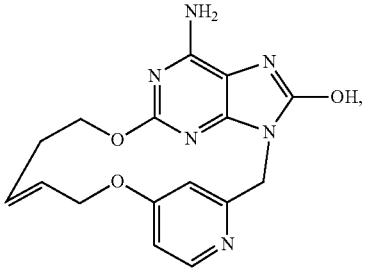

-continued
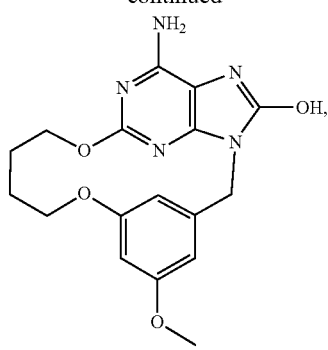
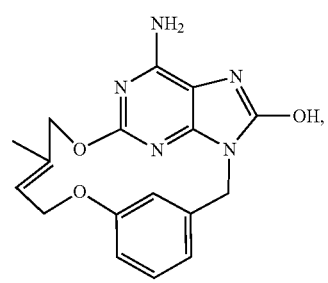
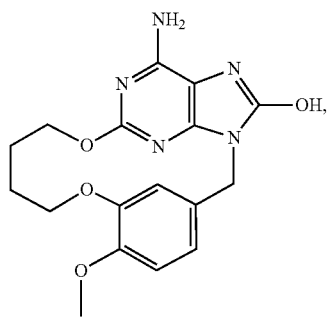
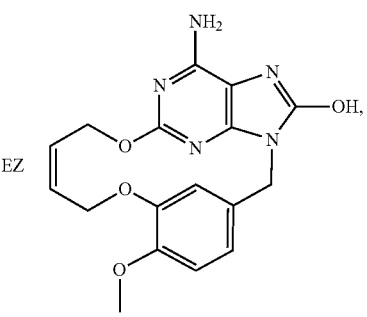
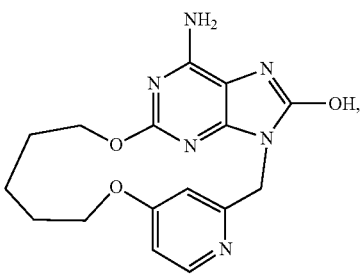
-continued
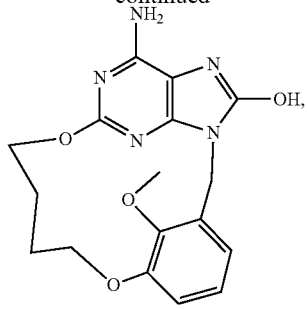
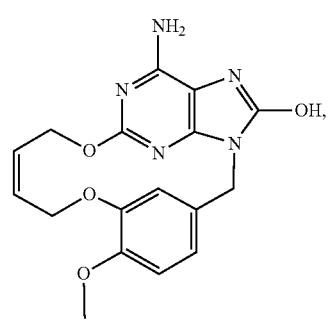
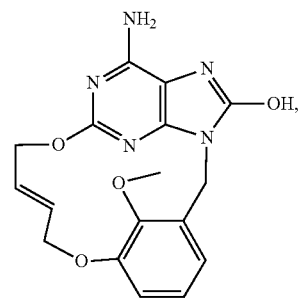
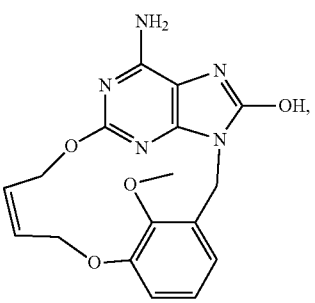
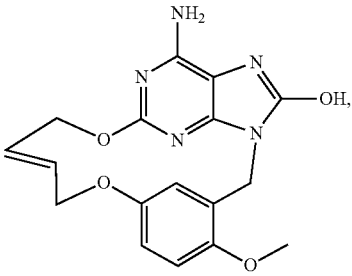

267
-continued
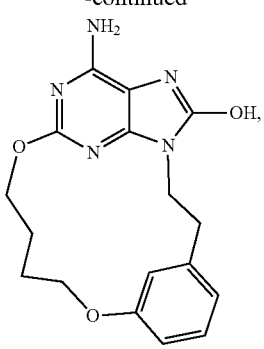
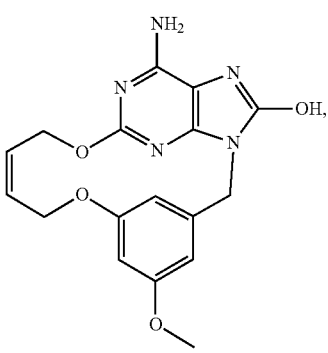
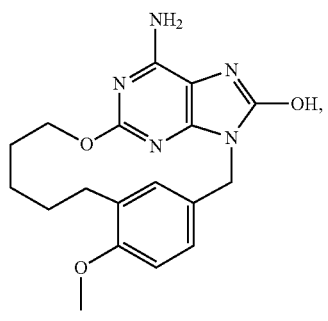
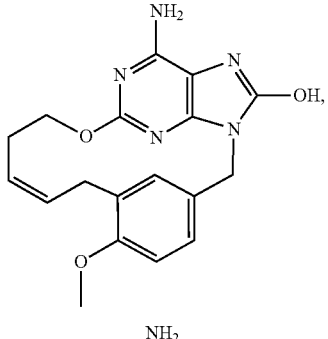
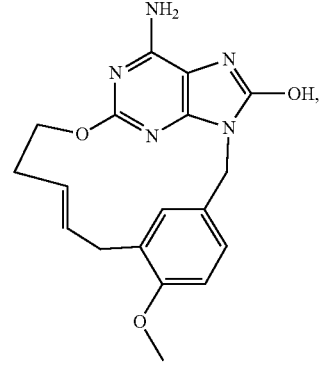
268
-continued
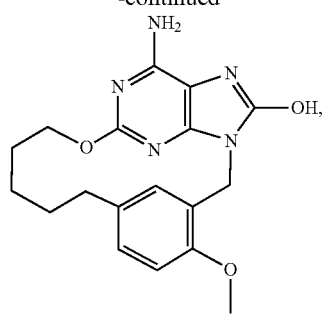
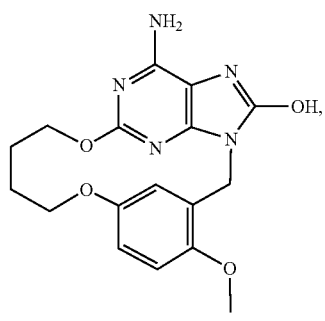
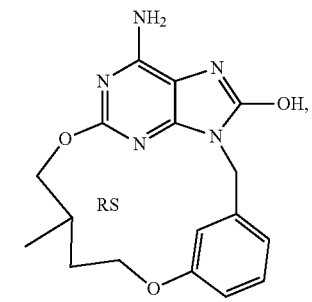
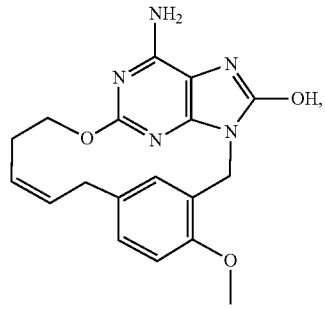
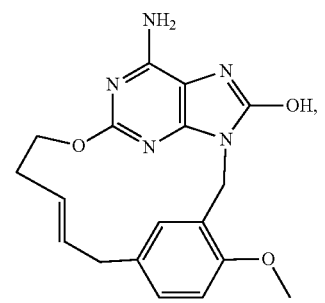

269
-continued
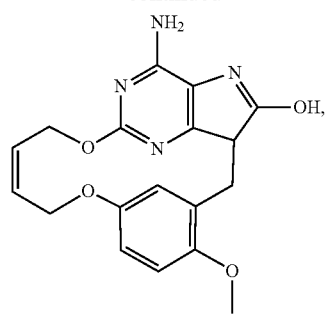
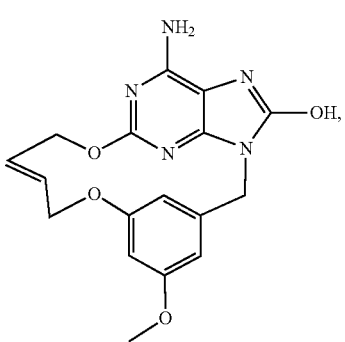
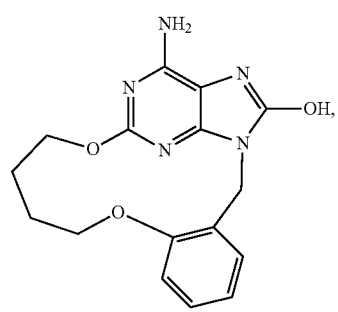
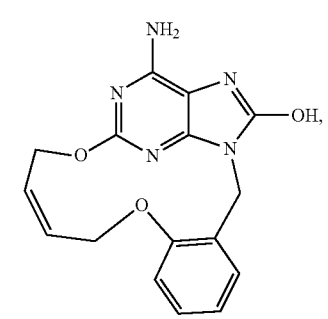
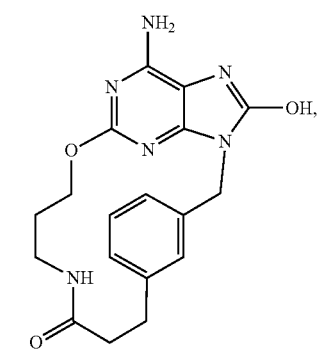
270
-continued
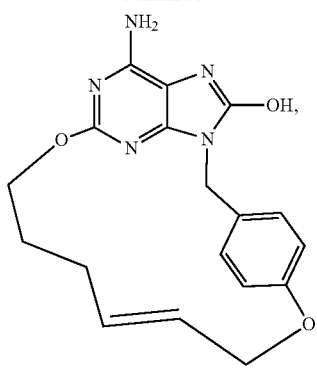
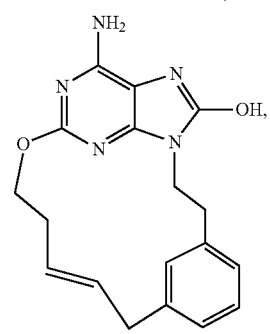
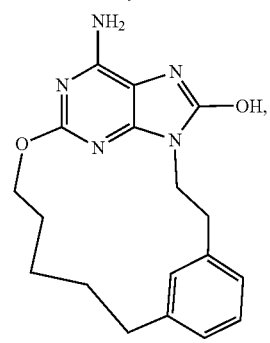
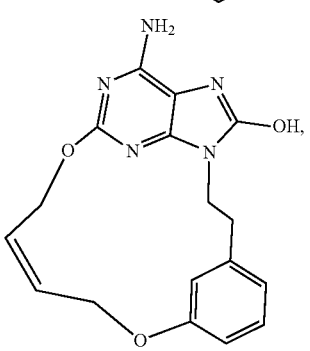
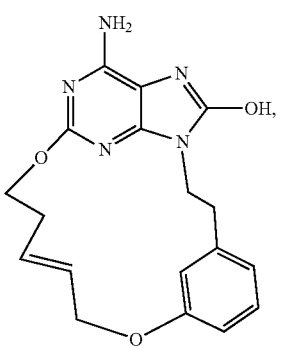

271

-continued

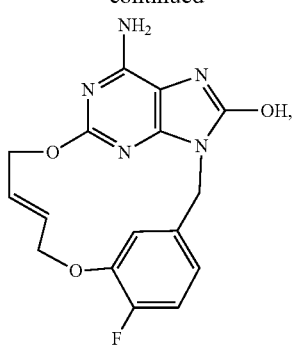

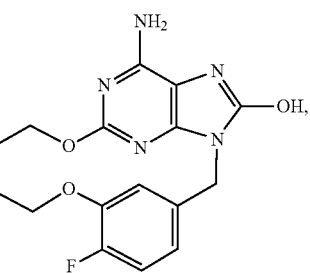

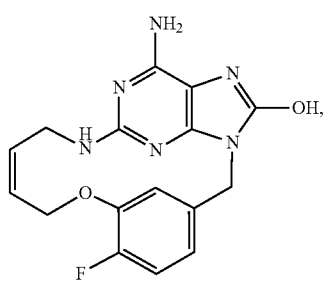

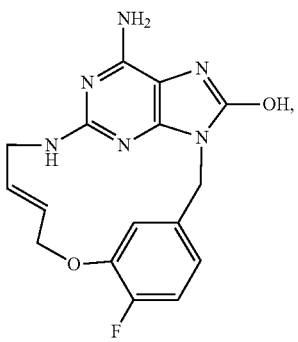

272

-continued

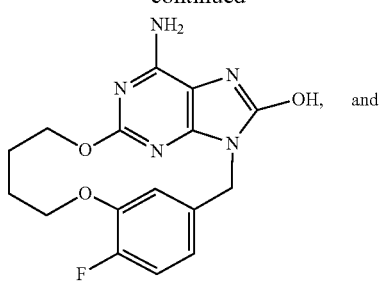    and

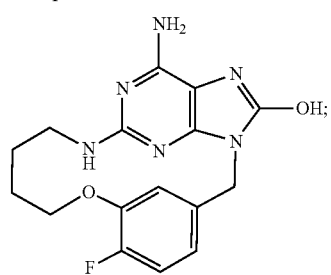

or a pharmaceutically acceptable salt thereof.

3. A pharmaceutical composition comprising a compound of claim 1, or a pharmaceutically acceptable salt thereof, together with one or more pharmaceutically acceptable excipients, diluents, or carriers.

4. A method of activating TLR7 in a subject, comprising administering a compound of formula (I) or a pharmaceutically acceptable salt thereof according to claim 1.

5. A method for inducing interferon production in a subject comprising administering to said subject a therapeutically effective amount of a compound of claim 1.

6. A compound selected from the group consisting of:

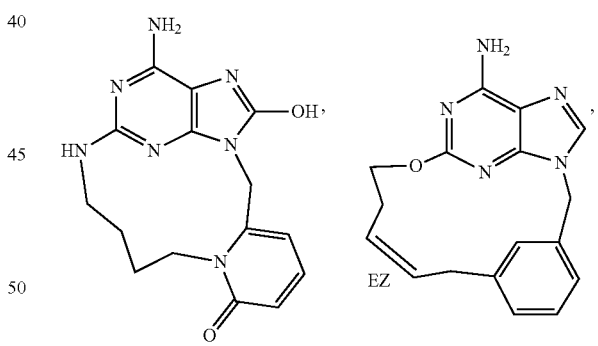

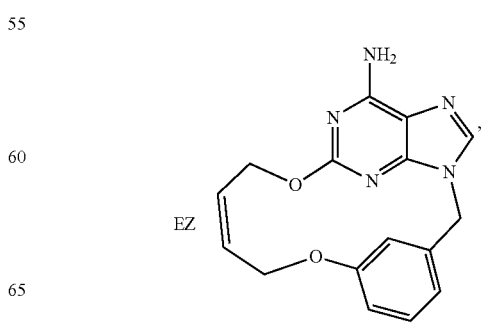

273
-continued

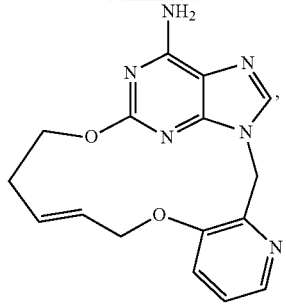

274
-continued

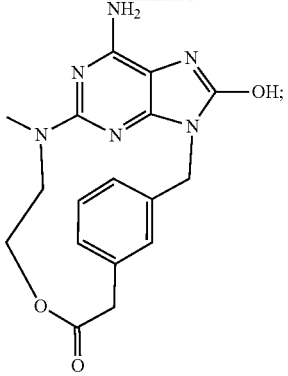

or a pharmaceutically acceptable salt thereof.

7. A pharmaceutical composition comprising a compound of claim 6, or a pharmaceutically acceptable salt thereof, together with one or more pharmaceutically acceptable excipients, diluents, or carriers.

8. A method of activating TLR7 in a subject, comprising administering a compound of formula (I) or a pharmaceutically acceptable salt thereof according to claim 6.

9. A method for inducing interferon production in a subject comprising administering to said subject a therapeutically effective amount of a compound of claim 6.

* * * * *

UNITED STATES PATENT AND TRADEMARK OFFICE
CERTIFICATE OF CORRECTION

PATENT NO. : 10,822,349 B2  Page 1 of 2
APPLICATION NO. : 16/404638
DATED : November 3, 2020
INVENTOR(S) : Jean-François Bonfanti It is certified that error appears in the above-identified patent and that said Letters Patent is hereby corrected as shown below:

In the Claims

Column 269, Claim 2, Line 5, change 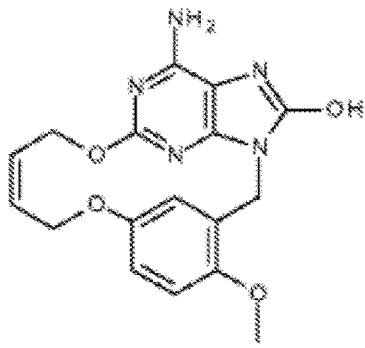 to 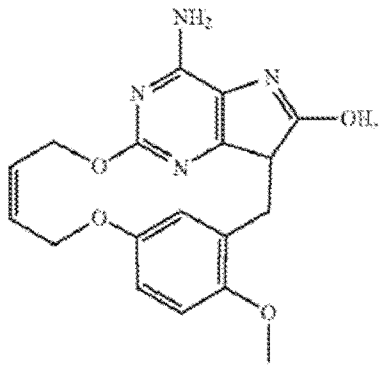

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,822,349 B2